(12) United States Patent (10) Patent No.: US 7,838,254 B2
Chu et al. (45) Date of Patent: Nov. 23, 2010

(54) METHODS OF USING GPR119 TO IDENTIFY PEPTIDE YY (PYY) SECRETAGOGUES AND COMPOUNDS USEFUL IN THE TREATMENT OF CONDITIONS MODULATED BY PYY

(75) Inventors: Zhi-Liang Chu, San Diego, CA (US); James N Leonard, San Diego, CA (US); Robert M Jones, San Diego, CA (US)

(73) Assignee: Arena Pharmaceuticals, Inc., San Diego, CA (US)

( * ) Notice: Subject to any disclaimer, the term of this patent is extended or adjusted under 35 U.S.C. 154(b) by 0 days.

(21) Appl. No.: 12/391,097

(22) Filed: Feb. 23, 2009

(65) Prior Publication Data

US 2009/0253153 A1 Oct. 8, 2009

Related U.S. Application Data

(60) Provisional application No. 61/123,273, filed on Apr. 7, 2008.

(51) Int. Cl.
*G01N 33/53* (2006.01)
*G01N 33/567* (2006.01)
*C12P 21/06* (2006.01)
*C12N 1/20* (2006.01)
*C12N 15/74* (2006.01)

(52) U.S. Cl. ............... 435/7.2; 435/7.21; 435/69.1; 435/252.3; 435/471

(58) Field of Classification Search .............. None
See application file for complete search history.

(56) References Cited

U.S. PATENT DOCUMENTS

| | | | |
|---|---|---|---|
| 4,166,452 A | 9/1979 | Generales, Jr. |
| 4,256,108 A | 3/1981 | Teeuwes et al. |
| 4,265,874 A | 5/1981 | Bonsen et al. |
| 4,704,362 A | 11/1987 | Itakura et al. |
| 5,462,856 A | 10/1995 | Lerner et al. |
| 5,922,576 A | 7/1999 | He et al. |
| 6,040,145 A | 3/2000 | Huber |
| 6,051,386 A | 4/2000 | Lerner et al. |
| 6,100,042 A | 8/2000 | Fowlkes et al. |
| 6,100,234 A | 8/2000 | Huber |
| 6,166,063 A | 12/2000 | Villhauer |
| 6,183,974 B1 | 2/2001 | Bringhurst et al. |
| 6,221,660 B1 | 4/2001 | Bonini et al. |
| 6,242,422 B1 | 6/2001 | Karanewsky |
| 6,303,661 B1 | 10/2001 | Demuth et al. |
| 6,380,398 B2 | 4/2002 | Kanstrup et al. |
| 6,395,767 B2 | 5/2002 | Robl et al. |
| 6,410,508 B1 | 6/2002 | Isales et al. |
| 6,432,969 B1 | 8/2002 | Villhauer et al. |
| 6,468,756 B1 | 10/2002 | Bonini et al. |
| 6,573,287 B2 | 6/2003 | Sulsky et al. |
| 6,617,340 B1 | 9/2003 | Villhauer et al. |
| 6,645,995 B2 | 11/2003 | Kanstrup et al. |
| 6,653,064 B1 | 11/2003 | Jochum et al. |
| 6,699,871 B2 | 3/2004 | Edmondson et al. |
| 6,706,742 B2 | 3/2004 | de Nanteuil et al. |
| 6,710,040 B1 | 3/2004 | Hulin et al. |
| 6,716,843 B2 | 4/2004 | de Nanteuil et al. |
| 6,727,261 B2 | 4/2004 | Gobbi et al. |
| 6,800,650 B2 | 10/2004 | Boehringer et al. |
| 6,803,357 B1 | 10/2004 | Bachovchin et al. |
| 6,812,350 B2 | 11/2004 | Hulin et al. |
| 6,844,316 B2 | 1/2005 | Niestroj et al. |
| 6,849,622 B2 | 2/2005 | Yasuda et al. |
| 6,861,440 B2 | 3/2005 | Boehringer et al. |
| 6,867,205 B2 | 3/2005 | Boehringer et al. |
| 6,869,947 B2 | 3/2005 | Kanstrup et al. |
| 6,897,222 B2 | 5/2005 | Gobbi et al. |
| 6,946,480 B2 | 9/2005 | Demuth et al. |
| 6,949,515 B2 | 9/2005 | Demuth et al. |
| 6,995,183 B2 | 2/2006 | Hamann et al. |
| 7,008,957 B2 | 3/2006 | Wagner et al. |
| 7,022,718 B2 | 4/2006 | Boehringer et al. |
| 7,026,316 B2 | 4/2006 | Ashton et al. |
| 7,053,055 B2 | 5/2006 | Demuth et al. |
| 7,060,722 B2 | 6/2006 | Kitajima et al. |
| 7,074,794 B2 | 7/2006 | Kitajima et al. |
| 7,074,798 B2 | 7/2006 | Yoshikawa et al. |
| 7,083,933 B1 | 8/2006 | Griffin et al. |
| 7,084,120 B2 | 8/2006 | Demuth et al. |
| 7,094,800 B2 | 8/2006 | Schoenafinger et al. |
| 7,122,555 B2 | 10/2006 | Boehringer et al. |
| 7,132,426 B2 | 11/2006 | Jones et al. |
| 7,217,711 B2 | 5/2007 | Eckhardt et al. |
| 7,238,670 B2 | 7/2007 | Natarajan et al. |
| 7,238,671 B2 | 7/2007 | Natarajan et al. |
| 7,470,699 B2 | 12/2008 | Jones et al. |

(Continued)

FOREIGN PATENT DOCUMENTS

CA 2 123 128 5/1993

(Continued)

OTHER PUBLICATIONS

U.S. Appl. No. 60/486,728, filed Jul. 11, 2003, Jones et al.

(Continued)

*Primary Examiner*—Robert Landsman
(74) *Attorney, Agent, or Firm*—Fish & Richardson P.C.

(57) ABSTRACT

The present invention relates to methods of using GPR119 receptor to identify peptide YY (PYY) secretagogues and compounds useful in the treatment of conditions modulated by PYY, such as conditions modulated by stimulation of NPY Y2 receptor (Y2R). Agonists of GPR119 receptor are useful as therapeutic agents for treating or preventing a condition modulated by PYY, such as a condition modulated by stimulation of Y2R. Conditions modulated by PYY such as may be a condition modulated by stimulation of Y2R include bone-related conditions, metabolic disorders, angiogenesis-related conditions, ischemia-related conditions, convulsive disorders, malabsorptive disorders, cancers, and inflammatory disorders.

27 Claims, 3 Drawing Sheets

U.S. PATENT DOCUMENTS

| | | |
|---|---|---|
| 7,495,002 B2 | 2/2009 | Langkopf et al. |
| 7,501,426 B2 | 3/2009 | Himmelsbach et al. |
| 7,550,455 B2 | 6/2009 | Himmelsbach et al. |
| 7,645,763 B2 | 1/2010 | Himmelsbach et al. |
| 2002/0006899 A1 | 1/2002 | Pospisilk et al. |
| 2002/0049164 A1 | 4/2002 | Demuth et al. |
| 2002/0103384 A1 | 8/2002 | Kanstrup et al. |
| 2002/0183367 A1 | 12/2002 | Sulsky et al. |
| 2002/0198205 A1 | 12/2002 | Himmelsbach et al. |
| 2003/0078247 A1 | 4/2003 | DeNanteuil et al. |
| 2003/0087950 A1 | 5/2003 | DeNanteuil et al. |
| 2003/0100563 A1 | 5/2003 | Edmondson et al. |
| 2003/0105077 A1 | 6/2003 | Kanstrup et al. |
| 2003/0119738 A1 | 6/2003 | Niestroj et al. |
| 2003/0119750 A1 | 6/2003 | Demuth et al. |
| 2003/0125304 A1 | 7/2003 | Demuth et al. |
| 2003/0125539 A1 | 7/2003 | Bonini et al. |
| 2003/0130199 A1 | 7/2003 | Von Hoersten et al. |
| 2003/0130281 A1 | 7/2003 | Boehringer et al. |
| 2003/0134802 A1 | 7/2003 | Demuth et al. |
| 2003/0162820 A1 | 8/2003 | Demuth et al. |
| 2003/0195188 A1 | 10/2003 | Boehringer et al. |
| 2003/0199528 A1 | 10/2003 | Kanstrup et al. |
| 2003/0216382 A1 | 11/2003 | Boehringer et al. |
| 2003/0216450 A1 | 11/2003 | Evans et al. |
| 2003/0225102 A1 | 12/2003 | Sankaranarayanan et al. |
| 2003/0232788 A1 | 12/2003 | Karanewsky et al. |
| 2004/0034014 A1 | 2/2004 | Kanstrup et al. |
| 2004/0063935 A1 | 4/2004 | Yasuda et al. |
| 2004/0072892 A1 | 4/2004 | Fukushima et al. |
| 2004/0077645 A1 | 4/2004 | Himmelsbach et al. |
| 2004/0082570 A1 | 4/2004 | Yoshikawa et al. |
| 2004/0087587 A1 | 5/2004 | Himmelsbach et al. |
| 2004/0097510 A1 | 5/2004 | Himmelsbach et al. |
| 2004/0106656 A1 | 6/2004 | Ashton et al. |
| 2004/0110817 A1 | 6/2004 | Hulin et al. |
| 2004/0116328 A1 | 6/2004 | Yoshikawa et al. |
| 2004/0138214 A1 | 7/2004 | Himmelsbach et al. |
| 2004/0176406 A1 | 9/2004 | Gobbi et al. |
| 2004/0180925 A1 | 9/2004 | Matsuno et al. |
| 2004/0229926 A1 | 11/2004 | Yasuda et al. |
| 2004/0242898 A1 | 12/2004 | Hulin et al. |
| 2004/0254226 A1 | 12/2004 | Feng et al. |
| 2004/0259883 A1 | 12/2004 | Sakashita et al. |
| 2004/0259902 A1 | 12/2004 | Boehringer et al. |
| 2004/0259903 A1 | 12/2004 | Boehringer et al. |
| 2005/0004205 A1 | 1/2005 | Evans et al. |
| 2005/0032804 A1 | 2/2005 | Cypes et al. |
| 2005/0038020 A1 | 2/2005 | Hamann et al. |
| 2005/0043292 A1 | 2/2005 | Parker et al. |
| 2005/0059650 A1 | 3/2005 | Jones et al. |
| 2005/0059724 A1 | 3/2005 | Schoenafinger et al. |
| 2005/0070562 A1 | 3/2005 | Jones et al. |
| 2006/0014764 A1 | 1/2006 | Feng et al. |
| 2006/0024313 A1 | 2/2006 | Chen et al. |
| 2006/0039974 A1 | 2/2006 | Akiyama et al. |
| 2006/0040963 A1 | 2/2006 | Mathvink et al. |
| 2006/0046978 A1 | 3/2006 | Pierau et al. |
| 2006/0052382 A1 | 3/2006 | Duffy et al. |
| 2006/0069116 A1 | 3/2006 | Ashton et al. |
| 2006/0074087 A1 | 4/2006 | Ashton et al. |
| 2006/0111336 A1 | 5/2006 | Duffy et al. |
| 2006/0135512 A1 | 6/2006 | Boehringer et al. |
| 2006/0135767 A1 | 6/2006 | Feng et al. |
| 2006/0142262 A1 | 6/2006 | Jones et al. |
| 2006/0142576 A1 | 6/2006 | Meng et al. |
| 2006/0154866 A1 | 7/2006 | Chu et al. |
| 2006/0217379 A1 | 9/2006 | Jones et al. |
| 2007/0032420 A1 | 2/2007 | Polidori et al. |
| 2007/0066590 A1 | 3/2007 | Jones et al. |
| 2007/0072803 A1 | 3/2007 | Chu et al. |
| 2007/0072804 A1 | 3/2007 | Chu et al. |
| 2007/0072844 A1 | 3/2007 | Jones et al. |
| 2007/0078150 A1 | 4/2007 | Jones et al. |
| 2007/0082874 A1 | 4/2007 | Jones et al. |
| 2007/0155763 A1 | 7/2007 | Jones et al. |
| 2007/0167473 A1 | 7/2007 | Jones et al. |
| 2007/0287670 A1 | 12/2007 | Natarajan et al. |
| 2008/0058339 A1 | 3/2008 | Brandt et al. |
| 2009/036434 A1 | 2/2009 | Jones et al. |
| 2009/0253153 A1 | 10/2009 | Chu et al. |

FOREIGN PATENT DOCUMENTS

| | | |
|---|---|---|
| CA | 2 289 124 | 11/1998 |
| CA | 2 289 125 | 11/1998 |
| CA | 2 339 537 | 3/2000 |
| CA | 2 433 090 | 7/2002 |
| CA | 2 466 870 | 6/2003 |
| DE | 296075 | 11/1991 |
| DE | 19616486 | 10/1997 |
| DE | 19823831 | 12/1999 |
| DE | 19828113 | 1/2000 |
| DE | 19834591 | 2/2000 |
| DE | 10143840 | 3/2003 |
| DE | 10238243 | 3/2004 |
| DE | 10238470 | 3/2004 |
| DE | 10238477 | 3/2004 |
| DE | 10251927 | 5/2004 |
| DE | 10256264 | 6/2004 |
| DE | 10327439 | 1/2005 |
| DE | 10333935 | 2/2005 |
| DE | 200410032263 | 1/2006 |
| EP | 0 995 440 | 4/2000 |
| EP | 1 043 328 | 10/2000 |
| EP | 1 050 540 | 11/2000 |
| EP | 1 092 727 | 4/2001 |
| EP | 1 215 207 | 6/2002 |
| EP | 1 228 061 | 8/2002 |
| EP | 1 245 568 | 10/2002 |
| EP | 1 248 604 | 10/2002 |
| EP | 1 258 476 | 11/2002 |
| EP | 1 280 797 | 2/2003 |
| EP | 1 296 974 | 4/2003 |
| EP | 1 301 187 | 4/2003 |
| EP | 1 323 710 | 7/2003 |
| EP | 1 333 025 | 8/2003 |
| EP | 1 338 651 | 8/2003 |
| EP | 1338 592 | 8/2003 |
| EP | 1 354 882 | 10/2003 |
| EP | 1 304 327 | 4/2004 |
| EP | 1 426 366 | 4/2004 |
| EP | 1 465 891 | 10/2004 |
| EP | 1 469 873 | 10/2004 |
| EP | 1 489 088 | 12/2004 |
| EP | 1 490 335 | 12/2004 |
| EP | 1 538 217 | 6/2005 |
| EP | 1 624 874 | 2/2006 |
| EP | 1 627 870 | 2/2006 |
| EP | 1 659 123 | 5/2006 |
| EP | 1 664 031 | 6/2006 |
| EP | 1 671 649 | 6/2006 |
| EP | 1 287 133 | 12/2006 |
| EP | 1 902 730 | 3/2008 |
| FR | 2822826 | 10/2002 |
| FR | 2824825 | 11/2002 |
| JP | 1998081666 | 3/1998 |
| JP | 1998182613 | 7/1998 |
| JP | 2000191616 | 7/2000 |
| JP | 2000511559 | 9/2000 |
| JP | 2000327689 | 11/2000 |
| JP | 2001510442 | 7/2001 |
| JP | 2002265439 | 9/2002 |
| JP | 2002356471 | 12/2002 |

| | | | | | | |
|---|---|---|---|---|---|---|
| JP | 2002356472 | 12/2002 | | WO | WO 03/000250 | 1/2003 |
| JP | 2002363157 | 12/2002 | | WO | WO 03/002530 | 1/2003 |
| JP | 2003238566 | 8/2003 | | WO | WO 03/002531 | 1/2003 |
| JP | 2003300977 | 10/2003 | | WO | WO 03/002553 | 1/2003 |
| JP | 2003327532 | 11/2003 | | WO | WO 03/002593 | 1/2003 |
| JP | 2004002367 | 1/2004 | | WO | WO 03/002595 | 1/2003 |
| JP | 2004002368 | 1/2004 | | WO | WO 03/002596 | 1/2003 |
| JP | 2004026678 | 1/2004 | | WO | WO 03/004496 | 1/2003 |
| JP | 2004026820 | 1/2004 | | WO | WO 03/004498 | 1/2003 |
| JP | 2004035574 | 2/2004 | | WO | WO 03/015775 | 2/2003 |
| JP | 2004043429 | 2/2004 | | WO | WO 03/022871 | 3/2003 |
| JP | 2004244412 | 9/2004 | | WO | WO 03/024942 | 3/2003 |
| JP | 2004269468 | 9/2004 | | WO | WO 03/024965 | 3/2003 |
| JP | 2004269469 | 9/2004 | | WO | WO 03/026661 | 4/2003 |
| JP | 2004315496 | 11/2004 | | WO | WO 03/035057 | 5/2003 |
| JP | 2005023038 | 1/2005 | | WO | WO 03/035067 | 5/2003 |
| WO | WO 91/16339 | 10/1991 | | WO | WO 03/037327 | 5/2003 |
| WO | WO 93/08259 | 4/1993 | | WO | WO 03/038123 | 5/2003 |
| WO | WO 93/10127 | 5/1993 | | WO | WO 03/040174 | 5/2003 |
| WO | WO 95/15309 | 6/1995 | | WO | WO 03/045228 | 6/2003 |
| WO | WO 95/29691 | 11/1995 | | WO | WO 03/045977 | 6/2003 |
| WO | WO 97/40832 | 11/1997 | | WO | WO 03/055881 | 7/2003 |
| WO | WO 98/18763 | 5/1998 | | WO | WO 03/057144 | 7/2003 |
| WO | WO 98/19998 | 5/1998 | | WO | WO 03/057666 | 7/2003 |
| WO | WO 98/50046 | 11/1998 | | WO | WO 03/068748 | 8/2003 |
| WO | WO 98/50066 | 11/1998 | | WO | WO 03/068757 | 8/2003 |
| WO | WO 99/14344 | 3/1999 | | WO | WO 03/072528 | 9/2003 |
| WO | WO 99/16864 | 4/1999 | | WO | WO 03/072556 | 9/2003 |
| WO | WO 99/25719 | 5/1999 | | WO | WO 03/074500 | 9/2003 |
| WO | WO 99/38501 | 8/1999 | | WO | WO 03/080633 | 10/2003 |
| WO | WO 99/56753 | 11/1999 | | WO | WO 03/082817 | 10/2003 |
| WO | WO 99/61431 | 12/1999 | | WO | WO 03/084940 | 10/2003 |
| WO | WO 99/62914 | 12/1999 | | WO | WO 03/095425 | 11/2003 |
| WO | WO 99/67278 | 12/1999 | | WO | WO 03/099279 | 12/2003 |
| WO | WO 00/10549 | 3/2000 | | WO | WO 03/101448 | 12/2003 |
| WO | WO 00/12704 | 3/2000 | | WO | WO 03/101958 | 12/2003 |
| WO | WO00/22129 | 4/2000 | | WO | WO 03/104229 | 12/2003 |
| WO | WO 00/23421 | 4/2000 | | WO | WO 03/105763 | 12/2003 |
| WO | WO 00/31258 | 6/2000 | | WO | WO 03/106456 | 12/2003 |
| WO | WO 00/34241 | 6/2000 | | WO | WO 2004/000327 | 12/2003 |
| WO | WO 00/50562 | 8/2000 | | WO | WO 2004/004661 | 1/2004 |
| WO | WO 00/53171 | 9/2000 | | WO | WO 2004/007446 | 1/2004 |
| WO | WO 00/56296 | 9/2000 | | WO | WO 2004/007468 | 1/2004 |
| WO | WO 00/56297 | 9/2000 | | WO | WO 2004/009544 | 1/2004 |
| WO | WO 00/69868 | 11/2000 | | WO | WO 2004/014860 | 2/2004 |
| WO | WO 00/71135 | 11/2000 | | WO | WO 2004/018467 | 3/2004 |
| WO | WO 01/34594 | 5/2001 | | WO | WO 2004/018468 | 3/2004 |
| WO | WO 01/52825 | 7/2001 | | WO | WO 2004/018469 | 3/2004 |
| WO | WO 01/55105 | 8/2001 | | WO | WO 2004/020407 | 3/2004 |
| WO | WO 01/68603 | 9/2001 | | WO | WO 2004/024943 | 3/2004 |
| WO | WO 01/81304 | 11/2001 | | WO | WO 2004/032836 | 4/2004 |
| WO | WO 01/81337 | 11/2001 | | WO | WO 2004/033455 | 4/2004 |
| WO | WO 01/87929 | 11/2001 | | WO | WO 2004/037169 | 5/2004 |
| WO | WO 01/96295 | 12/2001 | | WO | WO 2004/037181 | 5/2004 |
| WO | WO 01/97808 | 12/2001 | | WO | WO 2004/041795 | 5/2004 |
| WO | WO 02/02560 | 1/2002 | | WO | WO 2004/041820 | 5/2004 |
| WO | WO 02/14271 | 2/2002 | | WO | WO 2004/043940 | 5/2004 |
| WO | WO 02/30890 | 4/2002 | | WO | WO 2004/046106 | 6/2004 |
| WO | WO 02/30891 | 4/2002 | | WO | WO 2004/048379 | 6/2004 |
| WO | WO 02/34900 | 5/2002 | | WO | WO 2004/050022 | 6/2004 |
| WO | WO 02/38541 | 5/2002 | | WO | WO 2004/050658 | 6/2004 |
| WO | WO 02/42461 | 5/2002 | | WO | WO 2004/052362 | 6/2004 |
| WO | WO 02/44362 | 6/2002 | | WO | WO 2004/052850 | 6/2004 |
| WO | WO 02/49648 | 6/2002 | | WO | WO 2004/058266 | 7/2004 |
| WO | WO 02/051836 | 7/2002 | | WO | WO 2004/064778 | 8/2004 |
| WO | WO 02/055088 | 7/2002 | | WO | WO 2004/065380 | 8/2004 |
| WO | WO 02/062764 | 8/2002 | | WO | WO 2004/067509 | 8/2004 |
| WO | WO 02/068420 | 9/2002 | | WO | WO 2004/069162 | 8/2004 |
| WO | WO 02/076450 | 10/2002 | | WO | WO 2004/071454 | 8/2004 |
| WO | WO 02/083109 | 10/2002 | | WO | WO 2004/076413 | 9/2004 |
| WO | WO 02/083128 | 10/2002 | | WO | WO 2004/076433 | 9/2004 |
| WO | WO 03/000180 | 1/2003 | | WO | WO 2004/076434 | 9/2004 |
| WO | WO 03/000181 | 1/2003 | | WO | WO 2004/085378 | 10/2004 |

| | | |
|---|---|---|
| WO | WO 2004/085661 | 10/2004 |
| WO | WO 2004/087053 | 10/2004 |
| WO | WO 2004/087650 | 10/2004 |
| WO | WO 2004/092128 | 10/2004 |
| WO | WO 2004/096806 | 11/2004 |
| WO | WO 2004/099134 | 11/2004 |
| WO | WO 2004/103276 | 12/2004 |
| WO | WO 2004/103993 | 12/2004 |
| WO | WO 2004/104215 | 12/2004 |
| WO | WO 2004/104216 | 12/2004 |
| WO | WO 2004/108730 | 12/2004 |
| WO | WO 2004/110375 | 12/2004 |
| WO | WO 2004/110436 | 12/2004 |
| WO | WO 2004/111041 | 12/2004 |
| WO | WO 2004/111051 | 12/2004 |
| WO | WO 2004/112701 | 12/2004 |
| WO | WO 2005/000846 | 1/2005 |
| WO | WO 2005/000848 | 1/2005 |
| WO | WO 2005/003135 | 1/2005 |
| WO | WO 2005/007647 | 1/2005 |
| WO | WO 2005/007658 | 1/2005 |
| WO | WO 2005/009956 | 2/2005 |
| WO | WO 2005/011581 | 2/2005 |
| WO | WO 2005/012249 | 2/2005 |
| WO | WO 2005/012308 | 2/2005 |
| WO | WO 2005/012312 | 2/2005 |
| WO | WO 2005/019168 | 3/2005 |
| WO | WO 2005/020920 | 3/2005 |
| WO | WO 2005/021536 | 3/2005 |
| WO | WO 2005/023762 | 3/2005 |
| WO | WO 2005/025554 | 3/2005 |
| WO | WO 2005/026148 | 3/2005 |
| WO | WO 2005/030127 | 4/2005 |
| WO | WO 2005/030751 | 4/2005 |
| WO | WO 2005/032590 | 4/2005 |
| WO | WO 2005/033099 | 4/2005 |
| WO | WO 2005/034940 | 4/2005 |
| WO | WO 2005/037779 | 4/2005 |
| WO | WO 2005/037828 | 4/2005 |
| WO | WO 2005/040095 | 5/2005 |
| WO | WO 2005/042488 | 5/2005 |
| WO | WO 2005/042533 | 5/2005 |
| WO | WO 2005/044195 | 5/2005 |
| WO | WO 2005/047297 | 5/2005 |
| WO | WO 2005/049022 | 6/2005 |
| WO | WO 2005/051950 | 6/2005 |
| WO | WO 2005/058849 | 6/2005 |
| WO | WO 2005/058901 | 6/2005 |
| WO | WO 2005/061489 | 7/2005 |
| WO | WO 2005/063750 | 7/2005 |
| WO | WO 2005/072530 | 8/2005 |
| WO | WO 2005/075426 | 8/2005 |
| WO | WO 2005/079795 | 9/2005 |
| WO | WO 2005/082348 | 9/2005 |
| WO | WO 2005/082849 | 9/2005 |
| WO | WO 2005/082906 | 9/2005 |
| WO | WO 2005/085246 | 9/2005 |
| WO | WO 2005/087235 | 9/2005 |
| WO | WO 2005/094323 | 10/2005 |
| WO | WO 2005/095339 | 10/2005 |
| WO | WO 2005/095381 | 10/2005 |
| WO | WO 2005/100334 | 10/2005 |
| WO | WO 2005/106011 | 11/2005 |
| WO | WO 2005/108382 | 11/2005 |
| WO | WO 2005/115982 | 12/2005 |
| WO | WO 2005/116014 | 12/2005 |
| WO | WO 2005/116029 | 12/2005 |
| WO | WO 2005/118555 | 12/2005 |
| WO | WO 2005/120494 | 12/2005 |
| WO | WO 2005/121089 | 12/2005 |
| WO | WO 2005/121121 | 12/2005 |
| WO | WO 2005/121131 | 12/2005 |
| WO | WO 2005/123685 | 12/2005 |
| WO | WO 2006/000576 | 1/2006 |
| WO | WO 2006/009886 | 1/2006 |
| WO | WO 2006/011035 | 2/2006 |
| WO | WO 2006/012395 | 2/2006 |
| WO | WO 2006/012441 | 2/2006 |
| WO | WO 2006/013104 | 2/2006 |
| WO | WO 2006/015691 | 2/2006 |
| WO | WO 2006/015699 | 2/2006 |
| WO | WO 2006/020017 | 2/2006 |
| WO | WO 2006/023750 | 3/2006 |
| WO | WO 2006/027204 | 3/2006 |
| WO | WO 2006/029769 | 3/2006 |
| WO | WO 2006/030847 | 3/2006 |
| WO | WO 2006/033848 | 3/2006 |
| WO | WO 2006/039325 | 4/2006 |
| WO | WO 2006/040625 | 4/2006 |
| WO | WO 2006/040966 | 4/2006 |
| WO | WO 2006/043490 | 4/2006 |
| WO | WO 2006/047248 | 5/2006 |
| WO | WO 2006/058064 | 6/2006 |
| WO | WO 2006/058628 | 6/2006 |
| WO | WO 2006/067531 | 6/2006 |
| WO | WO 2006/067532 | 6/2006 |
| WO | WO 2006/068163 | 6/2006 |
| WO | WO 2006/068978 | 6/2006 |
| WO | WO 2006/070208 | 6/2006 |
| WO | WO 2006/070208 | 7/2006 |
| WO | WO 2006/071752 | 7/2006 |
| WO | WO 2006/071762 | 7/2006 |
| WO | WO 2006/076231 | 7/2006 |
| WO | WO 2006/083491 | 8/2006 |
| WO | WO 2006/086727 | 8/2006 |
| WO | WO 2007/003960 | 1/2007 |
| WO | WO 2007/003961 | 1/2007 |
| WO | WO 2007/003962 | 1/2007 |
| WO | WO 2007/003964 | 1/2007 |
| WO | WO 2007/035355 | 3/2007 |
| WO | WO 2007/116229 | 10/2007 |
| WO | WO 2007/116230 | 10/2007 |
| WO | WO 2007/120689 | 10/2007 |
| WO | WO 2007/120702 | 10/2007 |
| WO | WO 2007/138362 | 12/2007 |
| WO | WO 2008/005569 | 1/2008 |
| WO | WO 2008/005576 | 1/2008 |
| WO | WO 2008/008895 | 1/2008 |
| WO | WO 2008/025798 | 3/2008 |
| WO | WO 2008/025799 | 3/2008 |
| WO | WO 2008/025800 | 3/2008 |
| WO | WO 2008/070692 | 6/2008 |
| WO | WO 2008/076243 | 6/2008 |
| WO | WO 2010/001166 | 1/2010 |

OTHER PUBLICATIONS

U.S. Appl. No. 60/487,443, filed Jul. 14, 2003, Jones et al.
U.S. Appl. No. 60/577,354, filed Jun. 4, 2004, Jones et al.
U.S. Appl. No. 60/643,086, filed Jan. 10, 2005, Chu.
American Diabetes Association, "Implications of the United Kingdom Prospective Diabetes Study," *Diabetes Care*, 25 (Suppl 1), Jan. 2002, 5 pages.
Ammala et al., "GPR119 dependent hormone secretion: Insulin, GLP-1 and more," Keystone Symposia, Islet and Beta Cell Biology, Poster Presentation, Poster Session 1, Apr. 7, 2008.
Ammala et al., "GPR119 dependent hormone secretion: Insulin, GLP-1 and more," Abstract 102, Keystone Symposia, Islet and Beta Cell Biology, conference held Apr. 6-11, 2008 at Snowbird, Utah (according to conference organizers, the abstract was made available to attendees in an abstract book distributed at the conference).
Balkan et al., "Inhibition of dipeptidyl peptidase IV with NVP-DPP728 increases plasma GLP-1 (7-36 amide) concentrations and improves oral glucose tolerance in obese Zucker rats," *Diabetologia*, 42(11):1324-1331 (1999).

Balkan, "Effects of glucagon-like peptide-1 (GLP-1) on glucose homeostasis and food intake," *Appetite*, 35(3):269-270 (2000).
Charpentier, "Oral combination therapy for type 2 diabetes," *Diabetes Metab. Res. Rev.*, 18:S70-S76 (2002).
Deacon et al., "Preservation of active incretin hormones by inhibition of dipeptidyl peptidase IV suppresses meal-induced incretin secretion in dogs," *J. Endocrinol.*, 172(2):355-362 (2002).
Deacon et al., "Inhibitors of dipeptidyl peptidase IV: a novel approach for the prevention and treatment of Type 2 diabetes?," *Expert Opin. Investig. Drugs*, 13(9):1091-1102 (2004).
Declaration of James N. Leonard, dated Dec. 12, 2008, 13 pages.
Drucker, "Therapeutic potential of dipeptidyl peptidase IV inhibitors for the treatment of type 2 diabetes," *Expert Opin. Investig. Drugs*, 12(1):87-100 (2003).
Duffy et al., "Effects of antidiabetic drugs on dipeptidyl peptidase IV activity: nateglinide is an inhibitor of DPP IV and augments the antidiabetic activity of glucagon-like peptide-1," *Eur. J. Pharmacol.*, 568:278-286 (2007).
Evans, "Dipeptidyl peptidase IV inhibitors," *IDrugs*, 5(6):577-585 (2002).
Findlay et al., "Mechanisms of bone loss in rheumatoid arthritis," *Mod. Rheumatol.*, 15:232-240 (2005).
Holst et al., "Inhibition of the Activity of Dipeptidyl-Peptidase IV as a Treatment for Type 2 Diabetes," *Diabetes*, 47:1663-1670 (1998).
Holst, "Treatment of Type 2 diabetes mellitus with agonists of the GLP-1 receptor or DPP-IV inhibitors," *Expert Opinion on Emerging Drugs*, 9(1):155-166 (2004).
Hughes et al., "NVP-DPP728 (1-[[[2-[(5-cyanopyridin-2-yl)amino]ethyl]amino]acetyl]-2-cyano-(S)-pyrrolidine), a slow-binding inhibitor of dipeptidyl peptidase IV," *Biochemistry*, 38(36):11597-11603 (1999).
Inzucchi, "Oral Antihyperglycemic Therapy for Type 2 Diabetes," *JAMA*, 287:360-372 (2002).
Jones et al., "GPR 119 agonists for the treatment of type 2 diabetes," *Expert Opinion Therapeutic Patents*, 19(10):1339-1359 (2009).
Kim et al.,"(2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine: a potent, orally active dipeptidyl peptidase IV inhibitor for the treatment of type 2 diabetes," *J. Med. Chem.*, 48:141-151 (2005).
Lankas et al., "Dipeptidyl Peptidase IV Inhibition for the Treatment of Type 2 Diabetes," *Diabetes*, 54:2988-2994 (2005).
Mitani et al., "Dipeptidyl peptidase IV inhibition improves impaired glucose tolerance in high-fat diet-fed rats: study using a Fischer 344 rat substrain deficient in its enzyme activity," *Jpn. J. Pharmacol.*, 88(4):442-450 (2002).
Ning et al., "Endogenous and synthetic agonists of GPR119 differ in signaling pathways and their effects on insulin secretion in MIN6c4 insulinoma cells," *Brit. J Pharmacol.*, 155:1056-1065 (2008).
Pei et al., "Discovery and Structure—Activity Relationships of Piperidinone- and Piperidine-Constrained Phenethylamines as Novel, Potent, and Selective Dipeptidyl Peptidase IV Inhibitors," *J. Med. Chem.*, 50:1983-1987 (2007).
Reimer et al., "Long-term inhibition of dipeptidyl peptidase IV improves glucose tolerance and preserves islet function in mice," *Eur. J Endocrinol.*, 146(5):717-727 (2002).
Rendell, "Advances in diabetes for the millennium: drug therapy of type 2 diabetes," *MedGenMed.*, 6(3 Suppl):9 (2004).
Riddle, "Oral pharmacologic management of type 2 diabetes," *Am. Fam. Physician*, 60(9):2613-2620 (1999).
Semple et al., "Discovery of the First Potent and Orally Efficacious Agonist of the Orphan G-Protein Coupled Receptor 119," *J. Med. Chem.*, 51:5172-5175 (2008).
Sudre et al., "Chronic inhibition of circulating dipeptidyl peptidase IV by FE 999011 delays the occurrence of diabetes in male zucker diabetic fatty rats," *Diabetes*, 51(5):1461-1469 (2002).
Takasaki et al., "K579, a slow-binding inhibitor of dipeptidyl peptidase IV, is a long-acting hypoglycemic agent," *Eur. J. Pharmacol.*, 486:335-342 (2004).
Wiedeman et al., "Dipeptidyl peptidase IV inhibitors for the treatment of impaired glucose tolerance and type 2 diabetes," *Curr. Opin. Investig. Drugs*, 4(4):412-420 (2003).
U.S. Appl. No. 60/342,015, filed Oct. 18, 2001, Natarajan et al.

Abe et al., "First synthesis and determination of the absolute configuration of sulphostin, a novel inhibitor of dipeptidyl peptidase IV," *J Nat Prod.*,67:99-1004 (2004).
Abramowicz et al., "Drugs for diabetes," *Treatment Guidelines from the Medical Letter*, 3(36):57-62 (2005).
Abbott et al., "Blockade of the neuropeptide Y Y2 receptor with the specific antagonist BIIE0246 attenuates the effect of endogenous and exogenous peptide $YY_{(3-36)}$ on food intake," *Brain Res.*, 1043:139-144 (2005).
Adachi et al., "Free fatty acids administered into the colon promote the secretion of glucagon-like peptide-1 and insulin," *Biochem. Biophys. Res. Commun.*, 340:332-337 (2006).
Adler, Bone Diseases, Springer-Verlag, Germany (2000).
Adrian et al., "Human distribution and release of a putative new gut hormone, peptide YY," *Gastroenterology*, 89:1070-1077 (1985).
Adult Treatment Panel III (ATP III: National Institutes of Health: Third Report of the National Cholesterol Education Program Expert Panel on Detection, Evaluation, and Treatment of High Blood Cholesterol in Adults (Adult Treatment Panel IIIJ), Executive Summary, Bethesda, MD., National Institutes of Health, National Heart, Lung and Blood Institute (NIH pub. No. 01-3670) (2001).
Ahren et al., "Inhibition of Dipeptidyl Peptidase-4 Augments Insulin Secretion in Response to Exogenously Administered Glucagon-Like Peptide-1, Glucose-Dependent Insulinotropic Polypeptide, Pituitary Adenylate Cyclase-Activating Polypeptide, and Gastrin-Releasing Peptide in Mice," *Endocrinology*, 146(4):2055-2059 (2005).
Ahren et al., "Inhibition of dipeptidyl peptidase-4 reduces glycemia, sustains insulin levels, and reduces glucagon levels in type 2 diabetes," *J .Clin. Endocrinol. Metab.*, 89:2078-2084 (2004).
Ahren et al., "Inhibition of dipeptidyl peptidase IV improves metabolic control over a 4-week study period in type 2 diabetes," *Diabetes Care*, 25:869-875 (2002).
Anini et al., "Role of leptin in the regulation of glucagon-like peptide-1 secretion," *Diabetes*, 52:252-259 (2003).
Altschul et al., "Basic Local Alignment Search Tool," *J. Mol. Biol.*, 215:403-410 (1990).
Altschul et al., "Gapped BLAST and PSI-BLAST: a new generation of protein database search programs," *Nucleic Acids Research*, 25:3389-3402 (1997).
Arehart et al., "Acceleration of cardiovascular disease by a dysfunctional prostacyclin receptor mutation: potential implications for cyclooxygenase-2 inhibition," *Circ. Res.*, 102(8):986-993 (2008).
Atik et al., "Burden of osteoporosis", *Clinical Orthopaedics and Related Research*, 443:19-24 (2006).
Ausubel et al., Short Protocols in Molecular Biology, 3$^{rd}$ Edition, Wiley & Sons (1995).
Bak et al., "The effect of aging on fracture healing in the rat," *Calcified Tissue International*, 45:292-297 (1989).
Balasubramaniam et al., "Structure-activity studies including a □(CH-NH) scan of peptide YY (PYY) active site, PYY(22-36), for interaction with rat intestinal PYY receptors: development of analogues with potent in vivo activity in the intestine," *J. Med. Chem.*, 43:3420-3427 (2000).
Balasubramaniam et al., "Neuropeptide Y (NPY) $Y_2$ receptor-selective agonist inhibits food intake and promotes fat metabolism in mice: combined anorectic effects of $Y_2$ and $Y_4$ receptor-selective agonists," *Peptides*, 28:235-240 (2007).
Balena et al., "Eight Weeks of Treatment with the Long Acting, Human GLP-1 Analogue R1583 Improves Glycemic Control and Lowers Body Weight in Subjects with Type 2 Diabetes Mellitus (T2DM) Treated with Metformin: A Double-Blind Placebo-Controlled Phase 2 Study," *Diabetes* Abstract ADA08L-1604: contact View, [108-OR] (2008).
Barrish et al., "The use of stable isotope labeling and liquid chromatography/tandem mass spectrometry techniques to study the pharmacokinetics and bioavailability of the antimigraine drug, MK-0462 (rizatriptan) in dogs," *Rapid Commun. Mass Spectrom.*, 10:1033-1037 (1996).
Batterham et al., "Gut hormone $PYY_{3-36}$ physiologically inhibits food intake," *Nature*, 418:650-654 (2002).

Bas et al., "Radioiodinated Analogs of EP 00652218 for the Exploration of the Tachykinin NK1 Receptor by Spect," *J. Labelled Compd. Radiopharm.*, 44:S280-S282 (2001).

Beers et al., "The Merck Manual of Diagnosis and Therapy Seventeenth Edition," *Merck Research Laboratories*, Whitehouse Station, NJ, 469-471 (1999).

Behre, "Adiponectin, obesity and atherosclerosis," *Scand. J. Clin. Lab. Invest.*, 67:449-458 (2007).

Benoist et al., "In vivo sequence requirements of the SV40 early promotor region," *Nature*, 290:304-310 (1981).

Berge et al., "Pharmaceutical salts," *Journal of Pharmaceutical Sciences*, 66:1-19 (1977).

Bilchik et al., "Peptide YY is a physiological regulator of water and electrolyte absorption in the canine small bowel in vivo," *Gastroenterology*, 105:1441-1448 (1993).

Bilchik et al., "Peptide YY augments postprandial small intestinal absorption in the conscious dog," *Am. J. Surg.*, 167:570-574 (1994).

Boey et al., "Peptide YY ablation in mice leads to the development of hyperinsulinaemia and obesity," *Diabetologia*, 49:1360-1370 (2006).

Boey et al., "PYY transgenic mice are protected against diet-induced and genetic obesity," *Neuropeptides*, 42:19-30 (2008).

Bollag et al., "Osteoblast-derived cells express functional glucose-dependent insulinotropic peptide receptors," *Endocrinology*, 141:1228-1235 (2000).

Bollag et al., "Glucose-dependent insulinotropic peptide is an integrative hormone with osteotropic effects," *Molecular and Cellular Endocrinology*, 177:35-41 (2001).

Bose et al., "Glucagon-like peptide 1 can directly protect the heart against ischemia/reperfusion injury," *Diabetes*, 54:146-151 (2005).

Bradley, "TNF-mediated inflammatory disease," *J. Pathol.*, 214:149-160 (2008).

Brubaker et al., "Regulation of glucagon-like peptide-1 synthesis and secretion in the GLUTag enteroendoctrine cell line," *Endocrinology*, 139:4108-4114 (1998).

Brutlag et al., "Improved sensitivity of biological sequence database searches," *Cabios Comput Appl. Biosci.*, 6(3):237-245 (1990).

Buchan et al., "Clinical pharmacokinetics of frovatriptan," *Headache Suppl.*, 42(suppl. 2):S54-S62 (2002).

Caldwell et al., "Fluoropyrrolidine amides as dipeptidyl peptidase IV inhibitors," *Biorg. Med. Chem. Lett.*, 14(5):1265-1268 (2004).

Campbell et al., "Selective $A_1$-adenosine receptor antagonists identified using yeast *saccharomyces cerevisiae* functional assays," *Bioorganic & Medical Chemistry Letters*, 9:2413-2418 (1999).

Carpenter et al., "The in vitro and in vivo effects of a GPR119 agonist," Poster, *Diabetes Mellitus, Insulin Action and Resistance*, Keystone Symposia, Breckenridge, Colorado (Jan. 22, 2008-Jan. 27, 2008).

Cello et al., "Chemical synthesis of poliovirus cDNA: generation of infectious virus in the absence of natural template," *Science*, 297:1016-1018 (2002).

Center WatchSM, "Clinical Trial Result Information," dated May 7, 2007 [online]. Retrieved on Feb. 5, 2009]. Retrieved from the Internet: http://www.centerwatch.com/clinical-trials/results/db/stur10066.html.

Chavez-Eng et al., "High-performance liquid chromatographic-tandem mass spectrometric evaluation and determination of stable isotope labeled analogs of rofecoxib in human plasma samples from oral bioavailability studies," *J. Chromatogr. B. Analyt. Technol. Biomed. Life. Sci.*, 767:117-129 (2002).

Chaudhri et al., "Gastrointestinal satiety signals," *Annu. Rev. Physiol.*, 70:239-255 (2008).

Chen et al., "CD26," *J. Biol. Regul. Homest. Agents*, 8:47-54 (2004).

Chen et al., "Glucose responsiveness of a reporter gene transduced into hepatocytic cells using a retroviral vector," *FEBS Letters*, 365:223-226 (1995).

Childs, "Diabetes medications update," *The Kansas Nurse*, 79(5):4-6 (2004).

Chu et al., "A role for intestinal endocrine cell-expressed, GPR119 in glycemic control by enhancing GLP-1 and GIP release," *Endocrinology*, 149(5):2038-2047 (2008).

Chu et al., "A role for β-cell-expressed G protein-coupled receptor 119 in glycemic control by enhancing glucose-dependent insulin release," *Endocrinology*, 148:2601-2609 (2007).

Chu et al., "Agonists of the orphan GPCR 19AJ promote insulin secretion by stimulating both GLP-1—producing endocrine cells and pancreatic β-cells," Abstract #112, p. 42, *Diabetes Mellitus: Molecular Mechanisms, Genetics and New Therapies*, Keystone Symposia, Keystone, Colorado (Jan. 27, 2005-Feb. 2, 2005).

Chu et al., "AR231453 mediates improved glycemic control exclusively via GDIR/GPR119," Abstract # 117 & Poster, *Diabetes: Molecular Genetics, Signaling Pathways and Integrated Physiology*, Keystone Symposia, Keystone, Colorado (Jan. 14, 2007-Jan. 19, 2007).

Chu et al., "Identification of an orphan, β-cell-specific GPCR that enhances glucose-dependent insulin release," Abstract #107, p. 56, *Toward Understanding Islet Biology*, Keystone Symposia, Keystone, Colorado (Jan. 21, 2003-Jan. 26, 2003).

Chu et al., "Novel lipid amide activators of GDIR/GPR119 and their role in glucose homeostasis," Abstract # 230 & Poster, *Diabetes: Molecular Genetics, Signaling Pathways and Integrated Physiology*, Keystone Symposia, Keystone, Colorado (Jan. 14, 2007-Jan. 19, 2007).

Chu et al., "Transgenic mice with β-cell-targeted expression of the human orphan GPCR 19AJ are resistant to high fat diet-induced hyperglycemia," Abstract #228, p. 54, *Diabetes Mellitus: Molecular Mechanisms, Genetics and New Therapies*, Keystone Symposia, Keystone, Colorado (Jan. 27, 2005-Feb. 2, 2005).

Collier et al., "Radiosynthesis and in-vivo evaluation of the pseudopeptide σ-opioid anatagonist $[I^{125}]$-ITIPP(ψ)," *J. Labelled Comd Radiopharm.*, 42: S264-S266 (1999).

ConjuChem Press Release Dec. 3, 2008 (3 pages).

Cox, "Peptide YY: a neuroendocrine neighbor of note," *Peptides*, 28:345-351 (2007).

Crespo et al., "Morphometric and mechanical properties of femora in young adult male turkeys with and without femoral fractures," *Poultry Science*, 79:602-608 (2000).

Cruze et al., "The $Y_2$ receptor mediates increases in collateral-dependent blood flow in a model of peripheral arterial insufficiency," *Peptides*, 28:269-280 (2007).

Deacon et al., "Degradation of endogenous and exogenous gastric inhibitory polypeptide in healthy and in type 2 diabetic subjects as revealed using a new assay for the intact peptide," *The Journal of Clinical Endocrinology & Metabolism*, 85:3575-3581 (2000).

Deacon et al., "Dipeptidyl peptidase IV inhibition potentiates the insulinotropic effect of glucagon-like peptide 1 in the anesthetized pig," *Diabetes*, 47(5):764-769 (1998).

Deacon, "What do we know about the secretion and degradation of incretin hormones," *Regulatory Peptides*, 128:117-124 (2005).

D'Alessio et al., "Glucagon-like peptide 1: evolution of an incretin into a treatment for diabetes," *Am. J. Physiol. Endocrinol. Metab.*, 286(6):E882-E890 (2004).

Ding et al., "Impact of glucose-dependent peptide on age-induced bone loss," *Journal of Bone and Mineral Research* (published online Dec. 10, 2007).

Drucker, "The biology of incretin hormones", *Cell Metabolism*, 3:153-165, (2006).

Drucker, "Enhancing incretin action for the treatment of type 2 diabetes," *Diabetes Care*, 26(10):2929-2940 (2003).

During et al., "Glucagon-like peptide-1 receptor is involved in learning and neuroprotection," *Nat Med.*, 9:1173-1179 (2003).

E-mail communication, Deno Dialynas and Kellie McConnell (Aug. 14, 2006).

Eberlein et al., "A new molecular form of PYY: structural characterization of human $PYY_{3-36}$ and $PYY_{1-36}$," *Peptides*, 10:797-803 (1989).

Ekstrand et al., "Deletion of neuropeptide Y (NPY) 2 receptor in mice results in blockage of NPY-induced angiogenesis and delayed wound healing," *Proc. Natl. Acad. Sci. USA*, 100:6033-6038 (2003).

Edmondson et al., "Potent and selective proline derived dipeptidyl peptidase IV inhibitors," *Bioorg Med Chem Lett.*,14:5151-5155 (2004).

Ekblad et al., "Distribution of pancreatic polypeptide and peptide YY," *Peptides*, 23:251-261 (2002).

El Bahh et al., "The anti-epileptic actions of neuropeptide Y in the hippocampus are mediated by $Y_2$ and not $Y_5$ receptors," *Eur. J. Neurosci.*, 22:1417-1430 (2005).

Engelstoft et al., "A gut feeling for obesity: 7TM sensors on enteroendocrine cells," *Cell Metabolism*, 8(6):447-449 (2008).

Felig et al., Eds., Endocrinology and Metabolism 4th Edition, McGraw-Hill Book Company (2001).

Fayad et al., "Noninvasive In vivo high-resolution magnetic resonance imaging of atherosclerotic lesions in genetically engineered mice," *Circulation*, 98:1541-1547 (1998).

Fredriksson R. et al., "Seven evolutionarily conserved human rhodopain G protein-coupled receptors lacking close relatives," *FEBS Lett.*, 554(3):381-388 (2003).

Fyfe et al., "GPR119 Agonists are Potential Novel Oral Agents for the Treatment of Diabesity", *Diabetes* (2007) 56 (Supplement 1):A142, (Abstract #532-P; American Diabetes Association).

Fyfe et al., "Synthesis, SAR, and in vivo efficacy of novel GPR119 agonists with a 4-[3-(4-methanesulfinylphenoxy)propyl]-1-Boc-piperidine core," Abstract # MEDI 62, Division of Medicinal Chemistry, 234th ACS National Meeting, Boston, MA (Aug. 19-23, 2007).

Fyfe et al., "Discovery of novel, orally active, synthetic GPR119 agonists as potential agents for treatment of obesity and associated metabolic disorders," *Diabetes*, 55 (Suppl. 1):p. A81 (Jun. 2006).

Fyfe et al., "New nonpeptide-binding GPCRs as targets for diabetes and the metabolic syndrome," *Ann. Rep. Med Chem.*, 42:129-145 (2007).

GenBank ® Accession No. AAN95195, rat G Protein-coupled receptor 119 (Gpr119) protein (date of last modification: Dec. 20, 2002).

GenBank ® Accession No. AY288423, Mus musculus G Protein-coupled receptor 119 (Gpr119) mRNA, complete cds. (date of last modification: Dec. 8, 2003).

GenBank ® Accession No. AAP72125, G Protein-coupled receptor 119 [homo sapiens] (date of last modification: Dec. 8, 2003).

Gish et al., "Identification of protein coding regions by database similarity search," *Nature Genet,*, 3:266-272 (1993).

Greig et al., "New therapeutic strategies and drug candidates for neurodegenerative diseases: p53 and TNF-alpha inhibitors, and GLP-1 receptor agonists," *Ann NY Acad Sci*,1035:290-315 (2004).

Gomez et al., "Intestinal peptide YY: ontogeny of gene expression in rat bowel and trophic actions on rat and mouse bowel," *Am. J. Physiol.*, 268:G71-G81 (1995).

Gong et al., "An antagonist of monocyte chemoattractant protein 1 (MCP-1) inhibits arthritis in the MRL-1pr mouse model," *J. Exp. Med.*, 186:131-137 (1997).

Graham et al., "Characteristics of a human cell line transformed by DNA from human adenovirus type 5," *J. Gen Virol.*, 36:59 (1977).

Grandt et al., "Two molecular forms of peptide YY (PYY) are abundant in human blood: characterization of a radioimmunoassay recognizing PYY 1-36 and PYY 3-36," *Regul. Pept.*, 51:151-159 (1994).

Grise et al., "Peptide YY inhibits growth of human breast cancer in vitro and in vivo," *J. Surg. Res.*, 82:151-155 (1999).

Guerre-Millo, "Adiponectin: an update," *Diabetes & Metab.*, 34:12-18 (2008).

Gulyas et al., "Drug distribution in man: a positron emission tomography study after oral administration of the labelled neuroprotective drug vinpocetine," *Eur. J. Nucl. Med. Mol. Imaging*, 29:1031-1038 (2002).

Hamer et al., "Regulation in vivo of a cloned mammalian gene: cadmium induces the transcription of a mouse metallothionein gene in SV40 vectors," *J. Mol. Appl. Gen.*,1(4):273-288 (1982).

Handbook of Pharmaceutical Excipients (Rowe et al., eds), 4th Edition, 2003, Pharmaceutical Press.

Hansmann et al., "Pulmonary arterial hypertension is linked to insulin resistance and reversed by peroxisome proliferator-activated receptor-γ activation," *Circulation*, 115:1275-1284 (2007).

Hara et al., "Measurement of the high-molecular weight form of adiponectin in plasma is useful for the prediction of insulin resistance and metabolic syndrome," *Diabetes Care*, 29:1357-1362 (2006).

Hay et al., "Inflammatory bowel disease: costs-of-illness," *J. Clin. Gastroenterol.*, 14:309-317 (1992).

He et al., "A simplified system for generating recombinant adenoviruses," *Proc. Natl. Acad. Sci. USA*, 95:2509-2514 (1998).

Hirasawa et al., "Free fatty acids regulate gut incretin glucagon-like peptide 1 secretion through GPR 120," *Nature Medicine*, 11(1):90-98 (2005).

Holz et al., "Glucagon-like peptide-1 synthetic analogs: new therapeutic agents for use in the treatment of diabetes mellitus," *Curr. Med. Chem.*, 10(22):2471-2483 (2003).

Irwin et al., "Comparison of the metabolic effects of Gip receptor antagonism and PYY(3-36) receptor activation in high fat fed mice," *Peptides*, 28(11):2192-2198 (2007).

Jee et al., "Overview: animal models of osteopenia and osteoporosis," *J. Musculoskel. Neuron. Interact.*, 1(3):193-207 (2001).

Jetter et al., "Effects of grapefruit juice on the pharmacokinetics of sildenafil," *Clin. Pharmacol. Ther.*, 71:21-29 (2002).

Johnston et al., "Isolation of the yeast regulatory gene GAL4 and analysis of its dosage effects on the galactose/melibiose regulon," *Proc. Natl. Acad. Sci. USA*, 79:6971-6975 (1982).

Karlin et al., "Methods for assessing the statistical significance of molecular sequence features by using general scoring schemes," *Proc. Natl. Acad. Sci. USA*, 87:2264-2268 (1990).

Keighley et al., "Inflammatory bowel disease," *Ailment Pharmacol. Ther.*, 18:Suppl 3:66-70 (2003).

Keire et al., "Primary structures of PYY, [Pro[34]]PYY, and PYY-(3-36) confer different conformations and receptor selectivity," *Am. J. Physiol. Gastrointest. Liver Physiol.*, 279:G126-G131 (2000).

Kenakin, "Are receptors promiscuous? Intrinsic efficacy as a transduction phenomenon," *Life Sciences*, 43:1095-1101 (1988).

King et al. "Control of yeast mating signal transduction by a mammalian beta 2-adrenergic receptor and Gs alpha subunit," *Science*, New Series, 250(4977):121-123 (1990).

Kopelman P.G., "Obesity as a medical problem," *Nature*, 404(6778):635-643 (2000).

Kubota et al., "Disruption of adiponectin causes insulin resistance and neointimal formation," *J. Biol. Chem.*, 277:25863-25866 (2002).

Lumb et al., "Novel selective neuropeptide Y2 receptor PEGylated peptide agonists reduce food intake and body weight in mice," *J Med. Chem.*, 50:2264-2268 (2007).

Lauffer et al., "GPR119: "double-dipping" for better glycemic control," *Endocrinology*, 149(5) 2035-2037 (2008).

Le Bas et al., "Radioiodinated analogs of EP 00652218 for the exploration of the tachykinin NKI receptor by spect," *J. Labelled Compd Radiopharm.*, 44:S280-S282 (2001).

Lee et al., "Impaired angiogenesis in neuropeptide Y (NPY)-Y2 receptor knockout mice," *Peptides*, 24:99-106 (2003).

Lee et al., "Neuropeptide Y induces ischemic angiogenesis and restores function of ischemic skeletal muscles, " *J. Clin. Invest.*, 111:1853-1862 (2003).

Leiting et al., "Catalytic properties and inhibition of proline-specific dipeptidyl peptidases II, IV and VII," *Biochem. J.*, 371:525-532 (2003).

Leonard, "GPR119—Overseer of Gut and Pancreatic Endocrine Systems in Glucose Homeostasis," 68th *Scientific Sessions, American Diabetes Association* (2008).

Lippincott Williams & Wilkins; and Handbook of Pharmaceutical Excipients (Rowe et al., eds), 4th Edition, *Pharmaceutical Press* (2003).

Liu et al., "Pancreatic peptide YY mRNA levels increase during adaptation after small intestinal resection," *J. Surg. Res.*, 58:6-11 (1995).

Liu et al., "Y2 receptors decrease human pancreatic cancer growth and intracellular cyclic adenosine monophosphate levels," *Surgery*, 118:229-236 (1995).

Liu et al., "Peptide YY: a potential proabsorptive hormone for the treatment of malabsorptive disorders," *Am. Surg.*, 62:232-236 (1996).

Lundberg et al., "Localization of peptide YY (PYY) in gastrointestinal endocrine cells and effects on intestinal blood flow and motility," *Proc. Natl. Acad. Sci. USA*, 79:4471-4475 (1982).

Maeda et al. "Diet-induced insulin resistance in mice lacking adiponectin/ACRP30," *Nat. Med.*, 8:731-737 (2002).

Marsh et al., "Role of the Y5 neuropeptide Y receptor in limbic seizures," *Proc. Natl. Acad. Sci. USA*, 96:13518-13523 (1999).

Marso et al., "Low adiponectin levels are associated with atherogenic dyslipidemia and lipid-rich plaque in nondiabetic coronary arteries," *Diabetes Care*, 31(5):989-994 (2008).

Mather, "Establishment and characterization of two distinct mouse testicular epithelial cell lines," *Biol. Reprod.*, 23:243-251 (1980).

Mather et al., "Culture of testicular cells in hormone-supplemented serum-free medium," *Ann. N.Y. Acad. Sci.*, 383:44-68 (1982).

Matsuda et al., "Role of adiponectin in preventing vascular stenosis. The missing link of adipo-vascular axis," *J. Biol. Chem.*, 277:37487-37491 (2002).

Mayet et al., *Diabetologia*, 48(Suppl.):A166, Abstract (2005).

McCormack, ((OSI)™ Pharmaceuticals Inc. ), "Update on PSN821," SEC File No. 0-15190; Accession No. 950123-7-16093 (Nov. 29 2007).

McFadden et al., "Peptide YY inhibits the growth of Barrett's esophageal adenocarcinoma in vitro," *Am. J Surg.*, 188:516-519 (2004).

McGinnis et al., "Actual causes of death in the United States," *JAMA*, 270:2207-2212 (1993).

McIntosh et al., "Dipeptidyl peptidase IV inhibitors: How do they work as new antidiabetic agents?," *Regulatory Peptides*, 128:159-165 (2005).

Mclean et al., "Visualizing Differences in Ligand Regulation of Wild-Type and Constitutively Active Mutant $\beta_2$—Adrenoceptor-Green Fluorescent Protein Fusion Proteins," *Molecular Pharmacology*, 56:1182-1191 (1999).

McKnight, "Functional relationships between transcriptional control signals of the thymidine kinase gene of herpes simplex virus," *Cell*, 31:355-365 (1982).

Mentlein, "Therapeutic assessment of glucagon-like peptide-1 agonists compared with dipeptidyl peptidase IV inhibitors as potential antidiabetic drugs," *Expert Opin. Investig. Drugs*, 14:57-64 (2005).

Merck Sante S.A.S., "Glucovance, film-coted tablets," *Pediatric Public Assessment Report EU Work Sharing Procedure-Assessment of Pediatric data*, 1-8 (2008).

Milligan et al., "Chimaeric G alpha proteins: their potential use in drug discovery," *Trends in Pharmaceutical Sciences*, 20:118-24 (1999).

Miret et al. "Functional Expression of Heteromeric Calcitonin Gene-related Peptide and Adrenomedullin Receptors in Yeast," *The Journal of Biological Chemistry*, 277(9):6881-6887 (2002).

Morley et al., "An investigation of tolerance to the actions of leptogenic and anorexigenic drugs in mice," *Life Sci.*, 41:2157-2165 (1987).

Morris et al., "Hapten-induced model of chronic inflammation and ulceration in the rat colon," *Gastroenterology*, 96:795-803 (1989).

Mosekilde et al., "The effects of growth hormone on fracture healing in rats: a histological description," *Bone*, 14:19-27 (1993).

Mulcahy et al., "Sustained Glycaemic Control over 6 Years in a Large Outpatient Cohort Using a Repeatedly Implemented Aggressive Treatment Protocol," Abstract No. 531-P In Diabetes, Abstract Book, 67th Scientific Sessions, Friday, Jun. 22-Tuesday, Jun. 26, 2007, Chicago, IL, vol. 56, supplement 1, p. A142 (Jun. 2007).

Potenza et al., "A rapid quantitative bioassay for evaluating the effects of ligands upon receptors that modulate cAMP levels in a melanophere cell line," *Pigment Cell Research*, 5(6)-372-378 (1992).

Prevention and Management of Osteoporosis, World Health Organization Technical Report Series, 921, Geneva (2003).

Raisz, "Pathogenesis of osteoporosis: concepts, conflicts, and prospects," *The Journal of Clinical Investigation*, 115(12):3318-3325 (2005).

Ramsay et al., "Detection of receptor ligands by monitoring slecctive stabilization of a *Renilla* luciferase-tagged, constitutively active mutant, G-protein-coupled receptor," *British Journal of Pharmacology*, 315-323 (2001).

Remington: The Science and Practice of Pharmacy, (A.R. Gennaro, ed.), 20th Edition, 2000, Lippincott Williams & Wilkins.

Rendell et al., "Combination therapy with pioglitazone plus metformin or sulfonylurea in patients with Type 2 diabetes influence of prior antidiabetic drug regimen," *Journal of Diabetes and Its Complications*, 17:211-217 (2003).

Renshaw et al., "Peptide YY: a potential therapy for obesity," *Curr. Drug Targets*, 6:171-179 (2005).

Ruggeri, "Platelets in atherothrombosis," *Nat. Med.*, 8:1227-1234 (2002).

Sakamoto et al., "Expression and distribution of Gpr119 in the pancreatic islets of mice and rats: predominant localization in pancreatic polypeptide-secreting PP-cells," *Biochem. Biophys. Res. Commun.*, 351:474-480 (Dec. 2006).

Sambrook et al., Molecular Cloning: A Laboratory Manual, Second Edition, Cold-Spring Harbor, N.Y. (1989).

Sambrook et al., Molecular Cloning: A Laboratory Manual, Third Edition, Cold-Spring Harbor, N.Y. (2001).

Sanofi Aventis *AVE0010—R&D Meeting* (Sep. 17, 2007).

Schwartz et al., "Safety profile and metabolic effects of 14 days of treatment with DIO-902: results of a phase IIa multicenter, randomized, double-blind, placebo-controlled, parallel-group trial in patients with type 2 diabetes mellitus," *Clin. Ther.*, 30(6):1081-1088 (2008).

Shibata et al., "Adiponectin stimulates angiogenesis in response to tissue ischemia through stimulation of amp-activated protein kinase signaling," *J. Biol. Chem.*, 279:28670-28674 (2004).

Shibata et al., "Adiponectin stimulates angiogenesis in response to tissue ischemia through stimulation of amp-activated protein kinase signaling," *Nat. Med.*, 11:1096-1103 (2005).

Shibata et al., "Adiponectin protects against the development of systolic dysfunction following myocardial infarction," *J. Mol. Cell. Cardiol.*, 42:1065-1074 (2007).

Shore et al., "Adiponectin attenuates allergen-induced airway inflammation and hyperresponsiveness in mice," *J. Allergy Clin. Immunol.*, 118:389-395 (2006).

Sierra-Ascencio et al., "Exenatide: use in humans," *Gas Med Mex.*, 142(6):483-491 (2006) (Abstract).

Silver et al., "Amino terminus of the yeast GAL4 gene product is sufficient for nuclear localization," *Proc. Natl. Acad. Sci. USA*, 81:5951-5955 (1984).

Soga et al., "Lysophosphatidylcholine enhances glucose-dependent insulin secretion via an orphan G-protein-coupled receptor," *Biochemical and Biophysical Research Communications*, 326:744-751 (2005).

Sondhi et al., "cDNA array reveals increased expression of glucose-dependent insulinotropic polypeptide following chronic clozapine treatment: role in atypical antipsychotic drug-induced adverse metabolic effects," *The Pharmacogenomics Journal*, 6:131-140 (2006).

Souli et al., "Several receptors mediate the antisecretory effect of peptide YY, neuropeptide Y, and pancreatic polypeptide on VIP-induced fluid secretion in the rat jejunum in vivo," *Peptides*, 18:551557 (1997).

Stewart et al., Pharmacokinetics, Safety, and Tolerability of Albiglutide (Syncria®), a Long-Acting GLP-1 Mimetic, in Healthy Volunteers, Abstract ADA08L__1316: Contact View, [522-P] (2008).

Summer et al., "Alveolar macrophage activation and an emphysema-like phenotype in adiponectin-deficient mice," *Am. J. Physiol. Lung Cell Mol. Physiol.*, 294(6):L1035-L1042 (Epub. Mar. 7, 2008).

Suzuki et al., "Regulatable promoters for use in gene therapy applications: modification of the 5'-flanking region of the CFTR gene with multiple cAMP response elements to support basal, low-level gene expression that can be upregulated by exogenous agents that raise intracellular levels of cAMP," *Hum. Gene Ther.*, 7:1883-1893 (1996).

Tao et al., "Adiponectin cardioprotection after myocardial ischemia/reperfusion involves the reduction of oxidative/nitrative stress," *Circulation*, 115:1408-1416 (2007).

Takasaki et al., "Effects of combination treatment with dipeptidyl peptidase IV inhibitor and sulfonylurea on glucose levels in rats," *J Pharmacol Sciences*, 95(2):291-293 (2004).

Tatemoto et al., "Isolation of two novel candidate hormones using a chemical method for finding naturally occurring polypeptides," *Nature*, 285:417-418 (1980).

Tilg et al., "Adipocytokines: mediators linking adipose tissue, inflammation and immunity," *Nat. Rev. Immunol.*, 6:772-783 (2006).

Traynor et al., "Modulation by μ-Opioid Agonists of Guanosine-5'-O-(3-[35]thio)triphosphate Binding to membranes from Human Neuroblastoma SH-SY5Y Cells," *Molecular Pharmacology*, 47:848-854 (1995).

Trümper et al., "Glucose-Dependent Insulinotropic Polypeptide is a Growth Factor for β (INS-1) Cells by Pleiotropic Signaling," *Mol. Endocrinol.*, 15(9):1559-1570 (2001).

Tseng et al., "Peptide YY and cancer: current findings and potential clinical applications," *Peptides*, 23:389-395 (2002).

Tsukiyama et al., "Gastric Inhibitory Polypeptide as an endogenous Factor Promoting New bone Formation after Food Ingestion," *Molecular Endocrinology*, 20(7):1644-1651 (2006).

Ueno et al., "The role of PYY in feeding regulation," *Regul. Pept.*, 145:12-16 (2008).

Urlaub and Chasin, "Isolation of Chinese hamster cell mutants deficient in dihydrofolate reductase activity," *Proc. Natl. Acad. Sci. (USA)*, 77:4216 (1980).

Uttenthal, "The anorectic gut hormones: GLP-1 and co-secreted peptides," *CLI*, 4 pages (2007).

Villhauer et al.,"1-AA(3-hydroxy-l-adamantyl)amino]acetyl-2-cyano-(S)-pyrrolidine: a potent, selective, and orally bioavailable dipeptidyl peptidase IV inhibitor with antihyperglycemic properties," *J Med. Chem.* 46: 2774-2789 (2003).

Villhauer et al., 1-A2-A(5-Cyanopyridin-2-y1) aminolethylamino]acetyl-2-(S)- pyrrolidinecarbonitrile; a potent, selective and orally bioavailable dipeptidyl peptidase JV inhibitor with antihyperglycemic properties, *J Med Chem.*, 45:2362-2365 (2002).

Vona-Davis et al., "PYY and the pancreas: inhibition of tumor growth and inflammation," *Peptides*, 28:334-338 (2007).

Wang Y. et al., "BI-1356. Dipeptidyl-Peptidase IV Inhibitor, Antidiabetic Agent," *Drugs of the Future*, 33(6):473-477 (2008).

Weber, "Dipeptidyl peptidase IV inhibitors for the treatment of diabetes," *J. Med. Chem.*, 47(17):4135-4141 (2004).

Weber et al., "MK-0431 is a potent, selective, dipeptidyl peptidase IV inhibitor for the treatment of type 2 diabetes," *Diabetes*, 53(Suppl. 2):A151, 633-P (Abstract) (2004).

Williams Textbook of Endocrinology, 10th Edition, Larsen et al., Eds., W.B. Saunders Company (2002).

Woldbye et al., "Differential suppression of seizures via Y2 and Y5 neuropeptide Y receptors," *Neurobiology of Dis.*, 20:760-772 (2005).

Wise et al., "The identification of ligands at orphan G-protein coupled receptors," *Annu. Rev. Pharmacol. Toxicol.*, 44:43-66 (2004).

Wong et al., "Nonpeptide factor Xa inhibitors: DPC423, a highly potent and orally bioavailable pyrazole antithrombotic agent," *Cardiovasc. Drug Rev.*, 20:137-52 (2002).

Wortley et al., "Peptide YY regulates bone turnover in rodents," *Gastroenterology*, 133:1534-1543 (2007).

Yamada et al., *Endocrinology & Diabetology*, 23:237-243 (Sep. 2006) (Translation).

Yamamoto et al., "Correlation of the adipocyte-derived protein adiponectin with insulin resistance index and serum high-density lipoprotein-cholesterol, independent of body mass index, in the Japanese population," *Clin. Sci. (Lond)*, 103:137-142 (2002).

Yang et al., "Efficacy and specificity of bFGF increased collateral flow in experimental peripheral arterial insufficiency," *Am. J Physiol. Heart Circ. Physiol.*, 278:H1966-H1973 (2000).

Yasuda et al., "Metformin causes reduction of food intake and body weight gain and improvement of glucose intolerance in combination with dipeptidyl peptidase IV inhibitor in Zucker fa/fa rats," *J Pharmacol. Exp. Ther.*, 310(2): 614-619 (2004).

Yasuda et al., "Enhanced secretion of glucagon-like peptide 1 by biguanide compounds," *Biochem. Biophys. Res. Commun.*, 298:779-784 (2002).

Yokota et al., "Adiponectin, a new member of the family of soluble defense collagens, negatively regulates the growth of myelomonocytic progenitors and the functions of macrophages," *Blood*, 96:1723-1732 (2000).

Xie et al., "Glucose-dependent insulinotropic peptide-overexpressing transgenic mice have increased bone mass," *Bone XX* (2007).

Xie et al., "Glucose-dependent insulinotropic polypeptide receptor knockout mice have altered bone turnover," *Bone*, 37:759-769 (2005).

Xu, "Metabolic Disease Drug Discovery-Strategic Research Institute's Third International World Summit, Dipeptidyl peptidase-IV inhibitors," *IDrugs*, 7(9):839-840 (2004).

Zander et al., "Effect of 6-week course of glucagon-like peptide 1 on glycaemic control, insulin sensitivity, and beta-cell function in type 2 diabetes: a parallel-group study," *Lancet*, 359:824-830 (2002).

Zhong et al., "Effects of glucose-dependent insulinotropic peptide on osteoclast function," *Am. J Physiol. Endocrinol. Metab.*, 292:E543-E548 (2007).

Zhu et al., "Synthesis and mode of action of (125)I and (3)H-labeled thieno [2,3-c] pyridine antagonists of cell adhesions molecule expressions," *J Org. Chem.*, 67(3):943-948 (2002).

Zimmerman et al., "The effect of a high-fat meal on the oral bioavailability of the immunosuppressant sirolimus (rapamycin)," *J. Clin. Pharmacol.*, 39:1155-1161 (1999).

Cox et al., "Peptide YY Is Critical for Acylethanolamine Receptor Gpr119-Induced Activation of Gastrointestinal Mucosal Responses," *Cell Metabolism*, 11:532-421 (2010).

Schwartz et al., "An Enteroendocrine Full Package Solution," *Cell Metabolism*, 11:445-447 (2010).

Nauck et al., "Incretins and their analogues as new antidiabetic drugs," *Drug News Perspect.*, 16:413-422 (2003).

Nauck et al., "Gastric inhibitory polypeptide and glucagon-like peptide-1 in the pathogenesis of type 2 diabetes," *Diabetes*, 53(Suppl 3):S190-196 (2004).

Nichols et al., eds. Sinauer Associates, Inc., "Indirect Mechanisms of Synaptic Transmission," Chapter 8, *Neuron to Brain* (3rd Ed.) (1992).

Nightingale et al., "Gastrointestinal hormones in short bowel syndrome. Peptide YY may be the 'colonic brake' to gastric emptying," *Gut*, 39:267-272 (1996).

Nishimura et al., "Adiponectin prevents cerebral ischemic injury through endothelial nitric oxide synthase dependent mechanisms," *Circulation*, 117:216-223 (2008).

Offermanns et al., "G alpha 15 and G alpha 16 couple a wide variety of receptors to phosphollpase C." *J. Biol. Chem.*, 270:15175-80 (1995).

Ohashi et al., "Adiponectin replenishment ameliorates obesity-related hypertension," *Hypertension*, 47:1108-1116 (2006).

Okada et al., "Program & Abstracts," *The Endocrine Society*, Supplement 180 (1993).

Okamoto et al., "Adiponectin reduces atherosclerosis in apolipoprotein E-deticient mice," *Circulation*, 106:2767-2770 (2002).

Oku et al., "Adiponectin deficiency suppresses ABCA1 expression and ApoA-I synthesis in the liver," *FEBS Lett.*, 581:5029-5033 (2007).

Ortiz et al., "A novel long-acting selective neuropeptide Y2 receptor polyethylene glycol-conjugated peptide agonist reduces food intake and body weight and improves glucose metabolism in rodents," *J. Pharmacol. Exp. Ther.*, 323:692-700 (2007).

Ouchi et al., "Novel modulator for endothelial adhesion molecules: adipocyte-derived plasma protein adiponectin," *Circulation*, 100:2473-2476 (1999).

Ouchi et al., "Adiponectin as an anti-inflammatory factor," *Clin. Chim. Acta.*, 380:24-30 (2007).

Overton et al., "Deorphanization of a G protein-coupled receptor for oleoylethanolamide and its use in the discovery of small-molecule hypophagic agents", *Cell Metabolism*, 3:167-175 (2006).

Overton et al., "GPR119, a novel G protein-coupled receptor target for the treatment of type 2 diabetes and obesity," *Br. J. Pharmacol.*, 1-6 (2007).

Overton et al.,"GPR119, a novel G protein-coupled receptor target for the treatment of type 2 diabetes and obesity," *Br. J. Pharmacol.*, 153:S76-S81 (2008).

Parker et al., "Neuropeptide Y Y2 receptor in health and disease," *Br. J. Pharmacol.*, 153:420-431 (2008).

Pearson, "Inflammatory bowel disease," *Nurs. Times*, 100:86-90 (2004).

Pederson et al., "Improved glucose tolerance in Zucker fatty rats by oral administration of the dipeptidyl peptidase IV inhibitor isoleucine thiazolidide," *Diabetes*, 47(8):1253-1258 (1998).

Peters et al., "Aminomethyl-pyrimidines as novel DPP-IV inhibitors: a 10(5)-fold activity increase by optimization of aromatic substituents," *Bioorg. Med. Chem. Lett.*, 14:1491-1493 (2004).

Pittner et al., "Effects of PYY[3-36] in rodent models of diabetes and obesity," *Int. J. Obes. Relat. Metab. Disord.*, 28:963-971 (2004).

Polymorphism in Pharmaceutical Solids (1999) Britain, ed., Marcel Dekker, Inc.

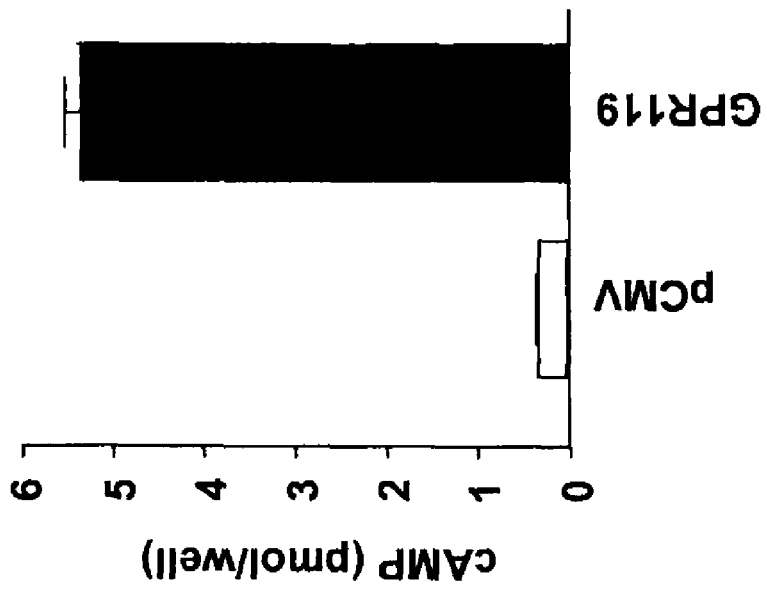
Figure 1. GPR119 Receptor Exhibits Constitutive Activity for Increasing cAMP Accumulation in Transfected HEK293 Cells

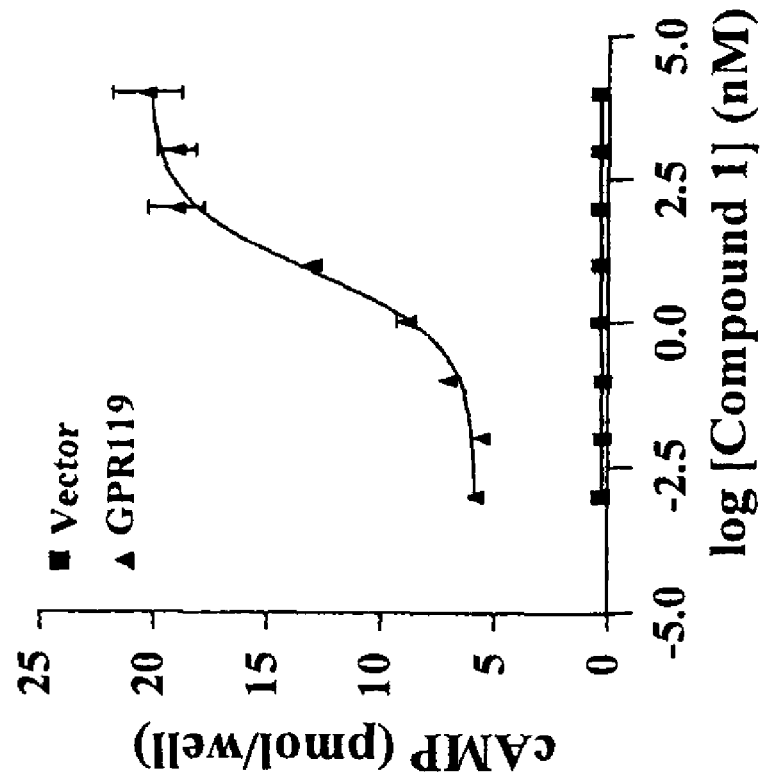

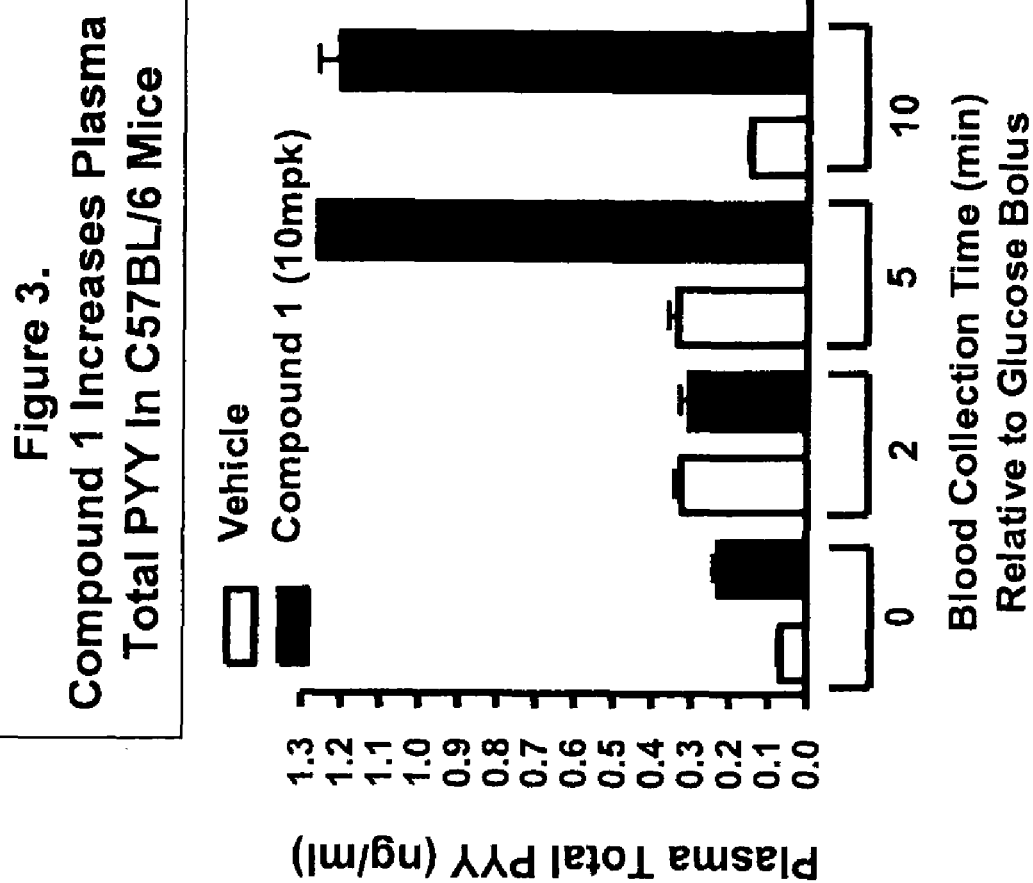

SEQUENCE LISTING

<160> NUMBER OF SEQ ID NOS: 4

<210> SEQ ID NO 1
<211> LENGTH: 1008
<212> TYPE: DNA
<213> ORGANISM: Homo sapien

<400> SEQUENCE: 1

```
atggaatcat ctttctcatt tggagtgatc cttgctgtcc tggcctccct catcattgct      60
actaacacac tagtggctgt ggctgtgctg ctgttgatcc acaagaatga tggtgtcagt     120
ctctgcttca ccttgaatct ggctgtggct gacaccttga ttggtgtggc catctctggc     180
ctactcacag accagctctc cagcccttct cggcccacac agaagaccct gtgcagcctg     240
cggatggcat ttgtcacttc ctccgcagct gcctctgtcc tcacggtcat gctgatcacc     300
tttgacaggt accttgccat caagcagccc ttccgctact tgaagatcat gagtgggttc     360
gtggccgggg cctgcattgc cgggctgtgg ttagtgtctt acctcattgg cttcctccca     420
ctcggaatcc ccatgttcca gcagactgcc tacaaagggc agtgcagctt ctttgctgta     480
tttcaccctc acttcgtgct gacccctctcc tgcgttggct tcttcccagc catgctcctc     540
tttgtcttct tctactgcga catgctcaag attgcctcca tgcacagcca gcagattcga     600
aagatggaac atgcaggagc catggctgga ggttatcgat ccccacggac tcccagcgac     660
```

-continued

```
ttcaaagctc tccgtactgt gtctgttctc attgggagct ttgctctatc ctggaccccc    720
ttccttatca ctggcattgt gcaggtggcc tgccaggagt gtcacctcta cctagtgctg    780
gaacggtacc tgtggctgct cggcgtgggc aactccctgc tcaacccact catctatgcc    840
tattggcaga aggaggtgcg actgcagctc taccacatgg ccctaggagt gaagaaggtg    900
ctcacctcat tcctcctctt tctctcggcc aggaattgtg gcccagagag gcccagggaa    960
agttcctgtc acatcgtcac tatctccagc tcagagtttg atggctaa               1008
```

<210> SEQ ID NO 2
<211> LENGTH: 335
<212> TYPE: PRT
<213> ORGANISM: Homo sapien

<400> SEQUENCE: 2

```
Met Glu Ser Ser Phe Ser Phe Gly Val Ile Leu Ala Val Leu Ala Ser
1               5                   10                  15

Leu Ile Ile Ala Thr Asn Thr Leu Val Ala Val Ala Val Leu Leu Leu
            20                  25                  30

Ile His Lys Asn Asp Gly Val Ser Leu Cys Phe Thr Leu Asn Leu Ala
        35                  40                  45

Val Ala Asp Thr Leu Ile Gly Val Ala Ile Ser Gly Leu Leu Thr Asp
    50                  55                  60

Gln Leu Ser Ser Pro Ser Arg Pro Thr Gln Lys Thr Leu Cys Ser Leu
65                  70                  75                  80

Arg Met Ala Phe Val Thr Ser Ser Ala Ala Ala Ser Val Leu Thr Val
                85                  90                  95

Met Leu Ile Thr Phe Asp Arg Tyr Leu Ala Ile Lys Gln Pro Phe Arg
            100                 105                 110

Tyr Leu Lys Ile Met Ser Gly Phe Val Ala Gly Ala Cys Ile Ala Gly
        115                 120                 125

Leu Trp Leu Val Ser Tyr Leu Ile Gly Phe Leu Pro Leu Gly Ile Pro
    130                 135                 140

Met Phe Gln Gln Thr Ala Tyr Lys Gly Gln Cys Ser Phe Phe Ala Val
145                 150                 155                 160

Phe His Pro His Phe Val Leu Thr Leu Ser Cys Val Gly Phe Phe Pro
                165                 170                 175

Ala Met Leu Leu Phe Val Phe Phe Tyr Cys Asp Met Leu Lys Ile Ala
            180                 185                 190

Ser Met His Ser Gln Gln Ile Arg Lys Met Glu His Ala Gly Ala Met
        195                 200                 205

Ala Gly Gly Tyr Arg Ser Pro Arg Thr Pro Ser Asp Phe Lys Ala Leu
    210                 215                 220

Arg Thr Val Ser Val Leu Ile Gly Ser Phe Ala Leu Ser Trp Thr Pro
225                 230                 235                 240

Phe Leu Ile Thr Gly Ile Val Gln Val Ala Cys Gln Glu Cys His Leu
                245                 250                 255

Tyr Leu Val Leu Glu Arg Tyr Leu Trp Leu Leu Gly Val Gly Asn Ser
            260                 265                 270

Leu Leu Asn Pro Leu Ile Tyr Ala Tyr Trp Gln Lys Glu Val Arg Leu
        275                 280                 285

Gln Leu Tyr His Met Ala Leu Gly Val Lys Lys Val Leu Thr Ser Phe
    290                 295                 300

Leu Leu Phe Leu Ser Ala Arg Asn Cys Gly Pro Glu Arg Pro Arg Glu
305                 310                 315                 320
```

```
Ser Ser Cys His Ile Val Thr Ile Ser Ser Ser Glu Phe Asp Gly
            325                 330                 335

<210> SEQ ID NO 3
<211> LENGTH: 22
<212> TYPE: DNA
<213> ORGANISM: Artificial Sequence
<220> FEATURE:
<223> OTHER INFORMATION: Primer

<400> SEQUENCE: 3
gtcctgccac ttcgagacat gg                                    22

<210> SEQ ID NO 4
<211> LENGTH: 23
<212> TYPE: DNA
<213> ORGANISM: Artificial Sequence
<220> FEATURE:
<223> OTHER INFORMATION: Primer

<400> SEQUENCE: 4
gaaacttctc tgcccttacc gtc                                   23
```

METHODS OF USING GPR119 TO IDENTIFY PEPTIDE YY (PYY) SECRETAGOGUES AND COMPOUNDS USEFUL IN THE TREATMENT OF CONDITIONS MODULATED BY PYY

CROSS-REFERENCE TO RELATED APPLICATIONS

This application claims priority to U.S. Provisional Application No. 61/123,273, filed on Apr. 7, 2008, the disclosure of which is incorporated by reference in its entirety in this application.

FIELD OF THE INVENTION

The present invention relates to methods of using GPR119 receptor to identify peptide YY (PYY) secretagogues and compounds useful in the treatment of conditions modulated by PYY, such as conditions modulated by stimulation of NPY Y2 receptor (Y2R). Agonists of GPR119 receptor are useful as therapeutic agents for treating or preventing a condition modulated by PYY, such as a condition modulated by stimulation of Y2R. Conditions modulated by PYY such as may be a condition modulated by stimulation of Y2R include bone-related conditions, metabolic disorders, angiogenesis-related conditions, ischemia-related conditions, convulsive disorders, malabsorptive disorders, cancers, and inflammatory disorders.

BACKGROUND OF THE INVENTION

The following discussion is intended to facilitate the understanding of the invention, but is not intended nor admitted to be prior art to the invention.

A. Osteoporosis

Osteoporosis is a disabling disease characterized by the loss of bone mass and microarchitectural deterioration of skeletal structure leading to compromised bone strength, which predisposes a patient to increased risk of fragility fractures. Osteoporosis affects more than 75 million people in Europe, Japan and the United States, and causes more than 2.3 million fractures in Europe and the United States alone. In the United States, osteoporosis affects at least 25% of all post-menopausal white women, and the proportion rises to 70% in women older than 80 years. One in three women older than 50 years will have an osteoporotic fracture that causes a considerable social and financial burden on society. The disease is not limited to women; older men also can be affected. By 2050, the worldwide incidence of hip fracture in men is projected to increase by 310% and 240% in women. The combined lifetime risk for hip, forearm, and vertebral fractures presenting clinically is around 40%, equivalent to the risk for cardiovascular disease. Osteoporotic fractures therefore cause substantial mortaility, morbidity, and economic cost. With an ageing population, the number of osteoporotic fractures and their costs will at least double in the next 50 years unless effective preventive strategies are developed. (See, e.g., Atik et al., Clin Orthop Relat Res (2006) 443:19-24; Raisz, J Clin Invest (2005) 115:3318-3325; and World Health Organization Technical Report Series 921 (2003), Prevention and Management of Osteoporosis.)

B. Obesity and Diabetes

Obesity is a major public health concern because of its increasing prevalence and associated health risks. Moreover, obesity may affect a person's quality of life through limited mobility and decreased physical endurance as well as through social, academic and job discrimination.

Obesity and being overweight are generally defined by body mass index (BMI), which is correlated with total body fat and serves as a measure of the risk of certain diseases. BMI is calculated by weight in kilograms divided by height in meters squared ($kg/m^2$). Overweight is typically defined as a BMI of 25-29.9 $kg/m^2$, and obesity is typically defined as a BMI of 30 $kg/m^2$ or higher. See, e.g., National Heart, Lung, and Blood Institute, Clinical Guidelines on the Identification, Evaluation, and Treatment of Overweight and Obesity in Adults, The Evidence Report, Washington, D.C.: U.S. Department of Health and Human Services, NIH publication no. 98-4083 (1998).

Recent studies have found that obesity and its associated health risks are not limited to adults, but also affect children and adolescents to a startling degree. According to the Center for Disease Control, the percentage of children and adolescents who are defined as overweight has more than doubled since the early 1970s, and about 15 percent of children and adolescents are now overweight. Risk factors for heart disease, such as high cholesterol and high blood pressure, occur with increased frequency in overweight children and adolescents compared with normal-weight subjects of similar age. Also, type 2 diabetes, previously considered an adult disease, has increased dramatically in children and adolescents. Overweight conditions and obesity are closely linked to type 2 diabetes. It has recently been estimated that overweight adolescents have a 70% chance of becoming overweight or obese adults. The probability increases to about 80% if at least one parent is overweight or obese. The most immediate consequence of being overweight as perceived by children themselves is social discrimination.

Overweight or obese individuals are at increased risk for ailments such as hypertension, dyslipidemia, type 2 (non-insulin dependent) diabetes, insulin resistance, glucose intolerance, hyperinsulinemia, coronary heart disease, angine pectoris, congestive heart failure, stroke, gallstones, cholescystitis, cholelithiasis, gout, osteoarthritis, obstructive sleep apnea and respiratory problems, gall bladder disease, certain forms of cancer (e.g., endometrial, breast, prostate, and colon) and psychological disorders (such as depression, eating disorders, distorted body image and low self esteem). The negative health consequences of obesity make it the second leading cause of preventable death in the United States and impart a significant economic and psychosocial effect on society. See, e.g., McGinnis et al, JAMA (1993) 270:2207-2212.

Obesity is now recognized as a chronic disease that requires treatment to reduce its associated health risks. Although weight loss is an important treatment outcome, one of the main goals of obesity management is to improve cardiovascular and metabolic values to reduce obesity-related morbidity and mortality. It has been shown that 5-10% loss of body weight can substantially improve metabolic values, such as blood glucose, blood pressure, and lipid concentrations. Hence, it is believed that a 5-10% reduction in body weight may reduce morbidity and mortality.

Currently available prescription drugs for managing obesity generally reduce weight by decreasing dietary fat absorption, as with orlistat, or by creating an energy deficit be reducing food intake and/or increasing energy expenditure, as seen with sibutramine. The search for alternatives to presently available antiobesity agents has taken several paths one of which has focused on certain gut peptides that have been implicated in modulating satiety such as peptide YY (PYY) (Chaudhri et al, Annu Rev Physiol (2008) 70:239-255).

C. Atherosclerosis

Atherosclerosis is a complex disease characterized by inflammation, lipid accumulation, cell death and fibrosis. Atherosclerosis is characterized by cholesterol deposition and monocyte infiltration into the subendothelial space, resulting in foam cell formation. Thrombosis subsequent to atherosclerosis leads to myocardial infarction and stroke. Atherosclerosis is the leading cause of mortality in many countries, including the United States. (See, e.g., Ruggeri, Nat Med (2002) 8:1227-1234; Arehart et al, Circ Res, Mar. 6, 2008, Epub ahead of print.)

D. Inflammatory Bowel Disease (IBD)

Inflammatory bowel disease (IBD) is the general name for diseases that cause inflammation in the intestines and includes, e.g. Crohn's disease, ulcerative colitis, ulcerative proctitis. U.S. medical costs of inflammatory bowel disease for 1990 have been estimated to be $1.4 to $1.8 billion. Lost productivity has been estimated to have added an additional $0.4 to $0.8 billion, making the estimated cost of inflammatory bowel disease $1.8 to $2.6 billion. (See, e.g., Pearson, Nursing Times (2004) 100:86-90; Hay et al, J Clin Gastroenterol (1992) 14:309-317; Keighley et al, Ailment Pharmacol Ther (2003) 18:66-70.)

Enteritis refers to inflammation of the intestine, especially the small intestine, a general condition that can have any of numerous different causes. Enterocolitis refers to inflammation of the small intestine and colon.

Crohn's disease (CD) is an inflammatory process that can affect any portion of the digestive tract, but is most commonly seen in the last part of the small intestine otherwise called the (terminal) ileum and cecum. Altogether this area is also known as the ileocecal region. Other cases may affect one or more of: the colon only, the small bowel only (duodenum, jejunum and/or ileum), the anus, stomach or esophagus. In contrast with ulcerative colitis, CD usually does not affect the rectum, but frequently affects the anus instead. The inflammation extends deep into the lining of the affected organ. The inflammation can cause pain and can make the intestines empty frequently, resulting in diarrhea. Crohn's disease may also be called enteritis. Granulomatous colitis is another name for Crohn's disease that affects the colon. Ileitis is CD of the ileum which is the third part of the small intestine. Crohn's colitis is CD affecting part or all of the colon.

Ulcerative colitis (UC) is an inflammatory disease of the large intestine, commonly called the colon. UC causes inflammation and ulceration of the inner lining of the colon and rectum. The inflammation of UC is usually most severe in the rectal area with severity diminishing (at a rate that varies from patient to patient) toward the cecum, where the large and small intestine join. Inflammation of the rectum is called proctitis. Inflammation of the sigmoid colon (located just above the rectum) is called sigmoiditis. Inflammation involving the entire colon is termed pancolitis. The inflammation causes the colon to empty frequently resulting in diarrhea. As the lining of the colon is destroyed ulcers form releasing mucus, pus and blood. Ulcerative proctitis is a form of UC that affects only the rectum.

E. Peptide YY (PYY)

Peptide YY (PYY) is a 36 amino acid peptide originally isolated in 1980 from porcine intestine (Tatemoto et al, Nature (1980) 285:417-418). PYY is secreted from enteroendocrine L-cells within both the large and small intestine. It has been shown that in rat and human gut concentrations of immunoreactive PYY are low in duodenum and jenunum, high in ileum and colon, and highest in rectum (Lundberg et al, PNAS USA (1982) 79:4471-4475; Adrian et al, Gastroenterol (1985) 89:1070-1077; Ekblad et al, Peptides (2002) 23:251-261; Ueno et al, Regul Pept (2008) 145:12-16). (PYY expression in rat been reported to also extend to alpha cells of the islets of Langerhans and to cells in the medulla oblongata (Ekblad et al, Peptides (2002) 23:251-261; PYY is released into the circulation as $PYY_{1-36}$ and $PYY_{3-36}$ (Eberlein et al, Peptides (1989) 10:797-803). $PYY_{3-36}$ is generated from $PYY_{1-36}$ by cleavage of the N-terminal Tyr and Pro residues by dipeptidyl peptidase IV. $PYY_{3-36}$ is the predominant form of PYY in human postprandial plasma (Grandt et al, Regul Pept (1994) 51:151-159). $PYY_{1-36}$ and $PYY_{3-36}$ have been reported to have comparable agonist activity at NPY Y2 receptor (Y2R), a G protein-coupled receptor (Parker et al, Br J Pharmacol (2008) 153:420-431); however, $PYY_{3-36}$ has been reported to be a high-affinity Y2R selective agonist (Keire et al, Am J Physiol Gastrointest Liver Physiol (2000) 279:G126-G131). PYY was subsequently reported to reduce high-fat food intake in rats after peripheral administration (Okada et al, Endocrinology Supplement (1993) 180) and to cause weight loss in mice after peripheral administration (Morley et al, Life Sciences (1987) 41:2157-2165).

Peripheral administration of PYY3-36 has been reported to markedly reduce food intake and weight gain in rats, to decrease appetite and food intake in humans, and to decrease food intake in mice, but not in Y2R-null mice, which was said to suggest that the food intake effect requires the Y2R. In human studies, infusion of $PYY_{3-36}$ was found to significantly decrease appetite and reduce food intake by 33% over 24 hours. Infusion of $PYY_{3-36}$ to reach the normal postprandial circulatory concentrations of the peptide led to peak serum levels of $PYY_{3-36}$ within 15 minutes, followed by a rapid decline to basal levels within 30 minutes. It was reported that there was significant inhibition of food intake in the 12-hour period following the PYY3-36 infusion, but was essentially no effect on food intake in the 12-hour to 24-hour period. In a rat study, repeated administration of $PYY_{3-36}$ intraperitoneally (injections twice daily for 7 days) reduced cumulative food intake (Batterham et al, Nature (2002) 418: 650-654; Renshaw et al, Current Drug Targets (2005) 6:171-179).

Peripheral administration of $PYY_{3-36}$ has been reported to reduce food intake, body weight gain and glycemic indices in diverse rodent models of metabolic diseases of both sexes (Pittner et al, Int J Obes Relat Metab Disord (2004) 28:963-971). It has been reported that blockade of Y2R with the specific antagonist BIIE-246 attenuates the effect of peripherally administered endogenous and exogenous $PYY_{3-36}$ for reducing food intake (Abbott et al, Brain Res (2005) 1043: 139-144). It has been reported that peripheral administration of a novel long-acting selective Y2R polyethylene glycol-conjugated peptide agonist reduces food intake and improves glucose metabolism (glucose disposal, plasma insulin and plasma glucose) in rodents (Ortiz et al, JPET (2007) 323:692-700; Lamb et al, J Med Chem (2007) 50:2264-2268). It has been reported that PYY ablation in mice leads to the development of hyperinsulinemia and obesity (Boey et al, Diabetologia (2006) 49: 1360-1370). It has been reported that peripheral administration of a long-acting, potent and highly selective Y2R agonist inhibits food intake and promotes fat metabolism in mice (Balasubramaniam et al, Peptides (2007) 28:235-240).

There is evidence that agents which stimulate PYY synthesis in vivo can confer protection against diet-induced and genetic obesity and can improve glucose tolerance (Boey et al, Neuropeptides (2008) 42:19-30).

It has been reported that Y2R agonists such as $PYY_{1-36}$ and $PYY_{3-36}$ can confer protection against epileptic seizures, such as against kainate seizures (El Bahh et al, Eur J Neurosci (2005) 22:1417-1430; Woldbye et al, Neurobiology of Disease (2005) 20:760-772).

It has been reported that Y2R agonists such as $PYY_{1-36}$ and $PYY_{3-36}$ act as proabsorbtive (or anti-secretory) hormones, increasing upon intravenous administration the absorption of both water and sodium in various parts of the bowel (Bilchik et al, Gastroenterol (1993) 105:1441-1448; Liu et al, J Surg Res (1995) 58:6-11; Nightingale et al, Gut (1996) 39:267-272; Liu et al, Am Surg (1996) 62:232-236; Balasubramaniam et al, J Med Chem (2000) 43:3420-3427). It has been reported that Y2R agonists such as PYY analogues inhibit secretion and promote absorption and growth in the intestinal epithelium (Balasubramaniam et al, J Med Chem (2000) 43:3420-3427). It has been reported that PYY promotes intestinal growth in normal rats (Gomez et al, Am J Physiol (1995) 268:G71-G81). It has been reported that Y2R agonists such as $PYY_{1-36}$ and $PYY_{3-36}$ inhibit bowel motility and work to prevent diarrhea (EP1902730; also see Cox, Peptides (2007) 28:345-351).

It has been reported that Y2R agonists such as $PYY_{1-36}$ and $PYY_{3-36}$ can confer protection against inflammatory bowel disease such as ulcerative colitis and Crohn's disease (WO 03/105763). It has been reported that PYY-deficient mice exhibit an osteopenic phenotype, i.e. that PYY can increase bone mass and/or can confer protection against loss of bone mass (e.g., decreases loss of bone mass) (Wortley et al, Gastroenterol (2007) 133:1534-1543). It has been reported that $PYY_{3-36}$ can confer protection in rodent models of pancreatitis (Vona-Davis et al, Peptides (2007) 28:334-338).

It has been reported that angiogenesis is impaired in Y2R-deficient mice (Lee et al, Peptides (2003) 24:99-106), i.e. that agonists of Y2R such as $PYY_{1-36}$ and $PYY_{3-36}$ promote angiogenesis. has been reported that would healing is impaired in Y2R-deficient mice (Ekstrand et al, PNAS USA (2003) 100:6033-6038), i.e. that agonists of Y2R such as $PYY_{1-36}$ and $PYY_{3-36}$ promote wound healing. It has been reported that ischemic angiogenesis is impaired in Y2R-deficient mice (Lee et al, J Clin Invest (2003) 111:1853-1862), i.e. that agonists of Y2R such as $PYY_{1-36}$ and $PYY_{3-36}$ promotes revascularization and restoration of function of ischemic tissue. It has been reported that agonists of Y2R such as $PYY_{1-36}$ and $PYY_{3-36}$ mediate increases in collateral-dependent blood flow in a rat model of peripheral arterial disease (Cruze et al, Peptides (2007) 28:269-280).

It has been reported that PYY and Y2R agonists such as $PYY_{3-36}$ can suppress tumor growth in the cases of, e.g., pancreatic cancer such as pancreatic ductal adenocarcinoma, breast cancer such as breast infiltrative ductal adenocarcinoma, colon cancer such as colon adenocarcinoma and Barrett's adenocarcinoma (Liu et al, Surgery (1995) 118:229-236; Liu et al, J Surg Res (1995) 58:707-712; Grise et al, J Surg Res (1999) 82:151-155; Tseng et al, Peptides (2002) 23:389-395; McFadden et al, Am J Surg (2004) 188:516-519).

It has been reported that stimulation of Y2R such as by $PYY_{3-36}$ leads to an increase in plasma adiponectin (Ortiz et al, JPET (2007) 323:692-700). Adiponectin is an adipokine with potent anti-inflammatory properties (Ouchi et al, Clin Chim Acta (2007) 380:24-30; Tilg et al, Nat Rev Immunol (2006) 6:772-783). Adiponectin exerts anti-atherogenic effects by targeting vascular endothelial cells and macrophages and insulin-sensitizing effects, predominantly in muscle and liver (Kubota et al, J Biol Chem (2002) 277:25863-25866; Maeda et al, Nat Med (2002) 8:731-737). Low adiponectin levels have been reported to be associated with atherogenic lipoproteins in dyslipidemia (elevated triglycerides, small dense LDL cholesterol, low HDL cholesterol) (Marso et al, Diabetes Care (2008) February 5 Epub ahead of print). Adiponectin has been implicated in high density lipoprotein (HDL) assembly (Oku et al, FEBS Letters (2007) 581:5029-5033). Adiponectin has been found to ameliorate the abnormalities of metabolic syndrome, including insulin resistance, hyperglycemia, and dyslipidemia, in a mouse model of obesity-linked metabolic syndrome associated with decreased adiponectin levels (Hara et al, Diabetes Care (2006) 29:1357-1362). Adiponectin has been reported to stimulate angiogenesis in response to tissue ischemia (Shibata et al, J Biol Chem (2004) 279:28670-28674). Adiponectin has been reported to prevent cerebral ischemic injury through endothelial nitric oxide synthase-dependent mechanisms (Nishimura et al, Circulation (2008) 117:216-223). Adiponectin has been reported to confer protection against myocardial ischemia-reperfusion injury (Shibata et al, Nat Med (2005) 11:1096-1103; Tao et al, Circulation (2007) 115: 1408-1416). Adiponectin has been reported to confer protection against myocardial ischaemia-reperfusion injury via AMP-activated protein kinase, Akt, and nitric oxide (Gonon et al, Cardiovasc Res (2008) 78:116-122). Adiponectin has been reported to confer protection against the development of systolic dysfunction following myocardial infarction, through its abilities to suppress cardiac hypertrophy and interstitial fibrosis, and protect against myocyte and capillary loss (Shibata et al, J Mol Cell Cardiol (2007) 42:1065-1074). Adiponectin has been reported to confer protection against inflammatory lung disease; adiponectin-deficient mice exhibit an emphysema-like phenotype (Summer et al, Am J Physiol Lung Cell Mol Physiol (Mar. 7, 2008)). Adiponectin has been reported to confer protection against allergic airway inflammation and airway hyperresponsiveness such as may be associated with asthma (Shore et al, J Allergy Clin Immunol (2006) 118:389-395). Adiponectin has been suggested to confer protection against pulmonary arterial hypertension by virtue of its insulin-sensitizing effects (Hansmann et al, Circulation (2007) 115:1275-1284). Adiponectin has been reported to ameliorate obesity-related hypertension, with said amelioration of hypertension being associated in part with upregulated prostacyclin expression (Ohashi et al, Hypertension (2006) 47:1108-1116). Adiponectin has been reported to decrease tumor necrosis factor (TNF)-α-induced expression of the adhesion molecules VCAM-1, E-selectin and ICAM-1 in human aortic endothelial cells (HAECs) (Ouchi et al, Circulation (1999) 100:2473-2476) and to inhibit production of TNF-α in macrophages (Yokota et al, Blood (2000) 96:1723-1732). Adiponectin has been reported to confer protection against restenosis after vascular intervention (Matsuda et al, J Biol Chem (2002) 277:37487-37491). The central role of TNF-α in inflammation has been demonstrated by the ability of agents that block the action of TNF-α to treat a range of inflammatory conditions. TNF-α-mediated inflammatory conditions encompass rheumatoid arthritis, inflammatory bowel disease such as Crohn's disease, ankylosing spondylitis, psoriasis, ischemic brain injury, cardiac allograft rejection, asthma, and the like (Bradley, J Pathol (2008) 214:149-160). See, e.g., Yamamoto et al, Clinical Science (2002) 103: 137-142; Behre, Scand J Clin Lab Invest (2007) 67:449-458; Guerre-Millo, Diabetes & Metabolism (2008) 34:12-18; Parker et al, Br J Pharmacol (2008) 153:420-431.

F. Treatment of Conditions Modulated by PYY

An attractive alternative approach for treatment of conditions modulated by PYY is to develop an orally active composition for increasing an endogenous level of PYY in an individual, such as an endogenous level of plasma PYY, such as by stimulation of PYY secretion in gut enteroendocrine cells.

G. GPR119

GPR119 is a G protein-coupled receptor (GPR119; e.g., human GPR119, GenBank® Accession No. AAP72125 and alleles thereof; e.g., mouse GPR119, GenBank® Accession No. AY288423 and alleles thereof). GPR119 stimulation as by an agonist leads to elevation of the level of intracellular cAMP, consistent with GPR119 being coupled to Gs. In the patent literature, GPR119 has been referred to as RUP3 (e.g., WO 00/31258); GPR119 has also been referred to as Glucose-Dependent Insulinotropic Receptor (GDIR).

H. G Protein-Coupled Receptors

Although a number of receptor classes exist in humans, by far the most abundant and therapeutically relevant is represented by the G protein-coupled receptor (GPCR) class. It is estimated that there are some 30,000-40,000 genes within the human genome, and of these, approximately 2% are estimated to code for GPCRs.

GPCRs represent an important area for the development of pharmaceutical products. Drugs active at GPCRs have therapeutic benefit across a broad spectrum of human diseases as diverse as pain, cognitive dysfunction, hypertension, peptic ulcers, rhinitis, and asthma. Of the approximately 500 clinically marketed drugs, greater than 30% are modulators of GPCR function. These drugs exert their activity at approximately 30 well-characterized GPCRs. (See, e.g., Wise et al, Annu Rev Pharmacol Toxicol (2004) 44:43-66.)

GPCRs share a common structural motif, having seven sequences of between 22 to 24 hydrophobic amino acids that form seven alpha helices, each of which spans the membrane (each span is identified by number, i.e., transmembrane-1 (TM-1), transmembrane-2 (TM-2), etc.). The transmembrane helices are joined by strands of amino acids between transmembrane-2 and transmembrane-3, transmembrane-4 and transmembrane-5, and transmembrane-6 and transmembrane-7 on the exterior, or "extracellular" side, of the cell membrane (these are referred to as "extracellular" regions 1, 2 and 3 (EC-1, EC-2 and EC-3), respectively). The transmembrane helices are also joined by strands of amino acids between transmembrane-1 and transmembrane-2, transmembrane-3 and transmembrane-4, and transmembrane-5 and transmembrane-6 on the interior, or "intracellular" side, of the cell membrane (these are referred to as "intracellular" regions 1, 2 and 3 (IC-1, IC-2 and IC-3), respectively). The "carboxy" ("C") terminus of the receptor lies in the intracellular space within the cell, and the "amino" ("N") terminus of the receptor lies in the extracellular space outside of the cell.

Generally, when a ligand binds with the receptor (often referred to as "activation" of the receptor), there is a change in the conformation of the receptor that facilitates coupling between the intracellular region and an intracellular "G-protein." It has been reported that GPCRs are "promiscuous" with respect to G proteins, i.e., that a GPCR can interact with more than one G protein. See, Kenakin, Life Sciences (1988) 43:1095-1101. Although other G proteins exist, currently, Gq, Gs, Gi, Gz and Go are G proteins that have been identified. Ligand-activated GPCR coupling with the G-protein initiates a signaling cascade process (referred to as "signal transduction"). Under normal conditions, signal transduction ultimately results in cellular activation or cellular inhibition. Although not wishing to be bound to theory, it is thought that the IC-3 loop as well as the carboxy terminus of the receptor interact with the G protein.

There are also promiscuous G proteins, which appear to couple several classes of GPCRs to the phospholipase C pathway, such as G15 or G16 (Offermanns & Simon, J Biol Chem (1995) 270:15175-80), or chimeric G proteins designed to couple a large number of different GPCRs to the same pathway, e.g. phospholipase C (Milligan & Rees, Trends in Pharmaceutical Sciences (1999) 20:118-24).

Under physiological conditions, GPCRs exist in the cell membrane in equilibrium between two different conformations: an "inactive" state and an "active" state. A receptor in an inactive state is unable to link to the intracellular signaling transduction pathway to initiate signal transduction leading to a biological response. Changing the receptor conformation to the active state allows linkage to the transduction pathway (via the G-protein) and produces a biological response.

A receptor may be stabilized in an active state by a ligand or a compound such as a drug. Recent discoveries, including but not exclusively limited to modifications to the amino acid sequence of the receptor, provide means other than ligands or drugs to promote and stabilize the receptor in the active state conformation. These means effectively stabilize the receptor in an active state by simulating the effect of a ligand binding to the receptor. Stabilization by such ligand-independent means is termed "constitutive receptor activation."

SUMMARY OF THE INVENTION

The present invention relates to the unexpected discovery by Applicant that administration of a GPR119 agonist to an individiual, such as by oral administration, can act to increase plasma total PYY in the individual. The present invention features methods relating to GPR119 for identifying PYY secretagogues, compounds useful for treatment or prevention of a condition modulated by PYY, and compounds useful for a modulation of a PYY-related activity in an individual. A GPR119 agonist is useful for increasing plasma total PYY in an individual. In certain embodiments, the individual is a human.

Nucleotide sequence encoding human GPR119 polypeptide is given in SEQ ID NO: 1. The amino acid sequence of said encoded human GPR119 polypeptide is given in SEQ ID NO: 2.

In a first aspect, the invention features a method for identifying PYY secretagogues, compounds useful for treatment or prevention of a condition modulated by PYY, or compounds useful for a modulation of a PYY-related activity in an individual, comprising the steps of:

(a) contacting a test compound with a host cell or with membrane of a host cell comprising a G protein-coupled receptor, wherein the G protein-coupled receptor comprises an amino acid sequence selected from the group consisting of:

(i) amino acids 1-335 of SEQ ID NO:2;

(ii) amino acids 2-335 of SEQ ID NO:2;

(iii) an amino acid sequence comprising the amino acid sequence of a polypeptide derived from (i) by substitution, deletion or addition of one or several amino acids in the amino acid sequence defined in (i);

(iv) the amino acid sequence of a G protein-coupled receptor encoded by a polynucleotide hybridizing under stringent conditions to the complement of SEQ ID NO:1;

(v) a variant of SEQ ID NO: 2 when selected from the group consisting of:

(a') the amino acid sequence of a G protein-coupled receptor having at least about 80% identity to SEQ ID NO: 2; and (b') an amino acid sequence of a G protein-coupled receptor comprising at least 20 contiguous amino acids of SEQ ID NO: 2;
(vi) the amino acid sequence of a constitutively active version of a G protein-coupled receptor having SEQ ID NO: 2; and
(vii) a biologically active fragment of any one of (i) to (vi); and
(b) determining the ability of the test compound to stimulate functionality of the G protein-coupled receptor;

wherein the ability of the test compound to stimulate functionality of the G protein-coupled receptor is indicative of the test compound being a PYY secretagogue, a compound useful for treatment or prevention of a condition modulated by PYY, or a compound useful for a modulation of a PYY-related activity in an individual.

In certain embodiments, the G protein-coupled receptor comprises the amino acid sequence of a G protein-coupled receptor having at least about 80% identity to SEQ ID NO: 2.

In certain embodiments, the G protein-coupled receptor comprises the amino acid sequence of SEQ ID NO: 2.

In certain embodiments, the variant of SEQ ID NO: 2 is an allele of SEQ ID NO: 2.

In certain embodiments, the variant of SEQ ID NO: 2 is an ortholog of SEQ ID NO: 2. In certain embodiments, the variant of SEQ ID NO: 2 is a mammalian ortholog of SEQ ID NO: 2.

In certain embodiments, the G protein-coupled receptor is recombinant.

In certain embodiments, the method is a method for identifying PYY secretagogues.

In certain embodiments, the method comprises identifying an agonist of the receptor.

In certain embodiments, the method comprises identifying a partial agonist of the receptor.

In certain embodiments, the method is a method for identifying compounds useful for treatment or prevention of a condition modulated by PYY.

In certain embodiments, the method is a method for identifying compounds useful for a modulation of a PYY-related activity in an individual.

The invention additionally features a method for identifying PYY secretagogues, compounds useful for treatment or prevention of a condition modulated by PYY, or compounds useful for a modulation of a PYY-related activity in an individual, comprising steps (a) and (b) of this first aspect, and further comprising:
(c) optionally synthesizing a compound which stimulates the functionality of the receptor in step (b);
(d) contacting a compound which stimulates functionality of the receptor in step (b) in vitro with a vertebrate enteroendocrine cell or with a cell capable of secreting PYY; and
(e) determining whether the compound stimulates PYY secretion from the vertebrate enteroendocrine cell or from the cell capable of secreting PYY;

wherein the ability of the test compound to stimulate PYY secretion from the vertebrate enteroendocrine cell or from the cell capable of secreting PYY is further indicative of the test compound being a PYY secretagogue, a compound useful for treatment or prevention of a condition modulated by PYY, or a compound useful for a modulation of a PYY-related activity in an individual.

In certain embodiments, the vertebrate enteroendocrine cell is a mammalian enteroendocrine cell. In certain embodiments, the enteroendocrine cell is an L cell. In certain embodiments, the enteroendocrine cell is comprised by or derived from tissue obtained from the small or large intestine. In certain embodiments, the enteroendocrine cell is comprised by or derived from tissue obtained from an L cell-containing region of small or large intestine. In certain embodiments, the enteroendocrine cell is comprised by or derived from duodenum, jejunum, ileum, colon or rectum tissue (see, e.g., Lundberg et al, PNAS USA (1982) 79:4471-4475; Adrian et al, Gastroenterol (1985) 89:1070-1077; Ekblad et al, Peptides (2002) 23:251-261; Ueno et al, Regul Pept (2008) 145:12-16). In certain embodiments, the enteroendocrine cell is an enteroendocrine cell line. In certain embodiments, the cell capable of secreting PYY is a cell comprised by or derived from the islets of Langerhans. In certain embodiments, the cell capable of secreting PYY is a neuronal cell. In certain embodiments, the cell capable of secreting PYY is a recombinant cell engineered to be capable of secreting PYY.

The invention additionally features a method for identifying PYY secretagogues, compounds useful for treatment or prevention of a condition modulated by PYY, or compounds useful for a modulation of a PYY-related activity in an individual, comprising steps (a) and (b) of this first aspect, and further comprising:
(c) optionally synthesizing a compound which stimulates functionality of the receptor in step (b);
(d) administering a compound which stimulates functionality of the receptor in step (b) to a vertebrate; and
(e) determining whether the compound increases a PYY level in the vertebrate;

wherein the ability of the test compound to increase a PYY level in the vertebrate is further indicative of the test compound being a PYY secretagogue, a compound useful for treatment or prevention of a condition modulated by PYY, or a compound useful for a modulation of a PYY-related activity in an individual.

In certain embodiments, the PYY level is blood or plasma concentration of total PYY. In certain embodiments, the PYY level is blood or plasma concentration of $PYY_{3-36}$.

In certain embodiments, the vertebrate is a mammal. In certain embodiments, the vertebrate is a non-human vertebrate. In certain embodiments, the vertebrate is a non-human mammal. In certain embodiments, the mammal is a non-human mammal.

In certain embodiments, the vertebrate or the mammal is a human. In certain embodiments, the human is a participant in a study reviewed by a governmental agency charged with marketing approval for a drug. In certain embodiments, the study is a clinical trial. In certain embodiments, the governmental agency is the Food and Drug Administration of the United States.

In certain embodiments, the human is an individual or a patient enrolled or undergoing treatment in a clinical trial.

The invention additionally features a method for identifying PYY secretagogues, compounds useful for treatment or prevention of a condition modulated by PYY, or compounds useful for a modulation of a PYY-related activity in an individual, comprising steps (a) and (b) of this first aspect, and further comprising:
(c) optionally synthesizing a compound which stimulates functionality of the receptor in step (b); and
(d) determining whether the compound increases a PYY level in a sample, said sample having been obtained from a vertebrate previously administered with a compound which stimulates functionality of the receptor in step (b);

wherein the ability of the test compound to increase a PYY level in the vertebrate is further indicative of the test compound being a PYY secretagogue, a compound useful for treatment or prevention of a condition modulated by PYY, or a compound useful for a modulation of a PYY-related activity in an individual.

In certain embodiments, the vertebrate is a mammal. In certain embodiments, the vertebrate is a non-human vertebrate. In certain embodiments, the vertebrate is a non-human mammal. In certain embodiments, the mammal is a non-human mammal.

In certain embodiments, the vertebrate or the mammal is a human. In certain embodiments, the human is a participant in a study reviewed by a governmental agency charged with marketing approval for a drug. In certain embodiments, the study is a clinical trial. In certain embodiments, the governmental agency is the Food and Drug Administration of the United States.

The invention additionally features a method for identifying PYY secretagogues, compounds useful for treatment or prevention of a condition modulated by PYY, or compounds useful for a modulation of a PYY-related activity in an individual, comprising steps (a) and (b) of this first aspect, and further comprising:
(c) optionally synthesizing a compound which stimulates functionality of the receptor in step (b);
(d) optionally providing a compound which stimulates functionality of the receptor in step (b);
(e) contacting a compound which stimulates functionality of the receptor in step (b) in vitro with a vertebrate enteroendocrine cell or with a cell capable of secreting PYY; and
(f) determining whether the compound stimulates PYY secretion from the vertebrate enteroendocrine cell or from the cell capable of secreting PYY;

wherein the ability of the test compound to stimulate PYY secretion from the vertebrate enteroendocrine cell or from the cell capable of secreting PYY is further indicative of the test compound being a PYY secretagogue, a compound useful for treatment or prevention of a condition modulated by PYY, or a compound useful for a modulation of a PYY-related activity in an individual.

In certain embodiments, the vertebrate enteroendocrine cell is a mammalian enteroendocrine cell. In certain embodiments, the enteroendocrine cell is an L cell. In certain embodiments, the enteroendocrine cell is comprised by or derived from tissue obtained from the small or large intestine. In certain embodiments, the enteroendocrine cell is comprised by or derived from tissue obtained from an L cell-containing region of small or large intestine. In certain embodiments, the enteroendocrine cell is comprised by or derived from duodenum, jejunum, ileum, colon or rectum tissue (see, e.g., Lundberg et al, PNAS USA (1982) 79:4471-4475; Adrian et al, Gastroenterol (1985) 89:1070-1077; Ekblad et al, Peptides (2002) 23:251-261; Ueno et al, Regul Pept (2008) 145:12-16). In certain embodiments, the enteroendocrine cell is an enteroendocrine cell line. In certain embodiments, the cell capable of secreting PYY is a cell comprised by or derived from the islets of Langerhans. In certain embodiments, the cell capable of secreting PYY is a neuronal cell. In certain embodiments, the cell capable of secreting PYY is a recombinant cell engineered to be capable of secreting PYY.

The invention additionally features a method for identifying PYY secretagogues, compounds useful for treatment or prevention of a condition modulated by PYY, or compounds useful for a modulation of a PYY-related activity, comprising steps (a) and (b) of this first aspect, and further comprising:
(c) optionally synthesizing a compound which stimulates functionality of the receptor in step (b);
(d) optionally providing a compound which stimulates functionality of the receptor in step (b);
(e) administering a compound which stimulates functionality of the receptor in step (b) to a vertebrate; and
(f) determining whether the compound increases a PYY level in the vertebrate;

wherein the ability of the test compound to increase a PYY level in the vertebrate is further indicative of the test compound being a PYY secretagogue, a compound useful for treatment or prevention of a condition modulated by PYY, or a compound useful for a modulation of a PYY-related activity in an individual.

In certain embodiments, the PYY level is blood or plasma concentration of total PYY. In certain embodiments, the PYY level is blood or plasma concentration of $PYY_{3-36}$.

In certain embodiments, the vertebrate is a mammal. In certain embodiments, the vertebrate is a non-human vertebrate. In certain embodiments, the vertebrate is a non-human mammal. In certain embodiments, the mammal is a non-human mammal.

In certain embodiments, the vertebrate or the mammal is a human. In certain embodiments, the human is a participant in a study reviewed by a governmental agency charged with marketing approval for a drug. In certain embodiments, the study is a clinical trial. In certain embodiments, the governmental agency is the Food and Drug Administration of the United States.

The invention additionally features a method for identifying PYY secretagogues, compounds useful for treatment or prevention of a condition modulated by PYY, or compounds useful for a modulation of a PYY-related activity, comprising steps (a) and (b) of this first aspect, and further comprising:
(c) optionally synthesizing a compound which stimulates functionality of the receptor in step (b);
(d) optionally providing a compound which stimulates functionality of the receptor in step (b); and
(e) determining whether the compound increases a PYY level in a sample, said sample having been obtained from a vertebrate previously administered with a compound which stimulates functionality of the receptor in step (b);

wherein the ability of the test compound to increase a PYY level in the vertebrate is further indicative of the test compound being a PYY secretagogue, a compound useful for treatment or prevention of a condition modulated by PYY, or a compound useful for a modulation of a PYY-related activity in an individual.

In certain embodiments, the vertebrate is a mammal. In certain embodiments, the vertebrate is a non-human vertebrate. In certain embodiments, the vertebrate is a non-human mammal. In certain embodiments, the mammal is a non-human mammal.

In certain embodiments, the vertebrate or the mammal is a human. In certain embodiments, the human is a participant in a study reviewed by a governmental agency charged with marketing approval for a drug. In certain embodiments, the study is a clinical trial. In certain embodiments, the governmental agency is the Food and Drug Administration of the United States.

In certain embodiments, the identified PYY secretagogue, or the identified compound useful for treatment or prevention of a condition modulated by PYY, or the identified compound useful for a modulation of a PYY-related activity is an agonist of the receptor. In some embodiments, the identified PYY secretagogue, or the identified compound useful for treatment or prevention of a condition modulated by PYY, or the identified compound useful for a modulation of a PYY-related activity is a partial agonist of the receptor.

In certain embodiments, the G protein-coupled receptor is coupled to a G protein. In certain embodiments, stimulation of the G protein-coupled receptor increases a level of intracellular cAMP accumulation. In certain embodiments, the G protein is Gs.

In some embodiments, a G protein-coupled receptor of the invention is SEQ ID NO:2 or an allele thereof. In some embodiments, a G protein-coupled receptor of the invention is an allele of SEQ ID NO:2. In some embodiments, a G protein-coupled receptor of the invention is an ortholog of SEQ ID NO:2.

In some embodiments, a G protein-coupled receptor of the invention is a G protein-coupled receptor which specifically binds (2-Fluoro-4-methanesulfonyl-phenyl)-{6-[4-(3-isopropyl-[1,2,4]oxadiazol-5-yl)-piperidin-1-yl]-5-nitro-pyrimidin-4-yl}-amine. In some embodiments, a G protein-coupled receptor of the invention is a G protein-coupled receptor for which (2-Fluoro-4-methanesulfonyl-phenyl)-{6-[4-(3-isopropyl-[1,2,4]oxadiazol-5-yl)-piperidin-1-yl]-5-nitro-pyrimidin-4-yl}-amine is a ligand. In some embodiments, a G protein-coupled receptor of the invention is a G protein-coupled receptor for which (2-Fluoro-4-methanesulfonyl-phenyl)-{6-[4-(3-isopropyl-[1,2,4]oxadiazol-5-yl)-piperidin-1-yl]-5-nitro-pyrimidin-4-yl}-amine is an agonist. In some embodiments, a G protein-coupled receptor of the invention exhibits a detectable level of constitutive activity. In some embodiments, the constitutive activity is for increasing a level of intracellular cAMP accumulation. In some embodiments, the constitutive activity is for causing melanophore cells to undergo pigment dispersion.

In certain embodiments, stringent hybridization conditions comprise hybridization at 42° C. in a solution comprising 50% formamide, 5×SSC (1×SSC=150mM NaCl, 15 mM trisodium citrate), 50 mM sodium phosphate (pH 7.6), 5×Denhardt's solution, 10% dextran sulfate, and 20 μg/ml denatured, sheared salmon sperm DNA, followed by washing at 65° C. in a solution comprising 0.1×SSC. Hybridization techniques are well known to the skilled artisan.

In certain embodiments, the GPCR encoded by a polynucleotide hybridizing under stringent conditions to the complement of SEQ ID NO: 1 is SEQ ID NO:2 or an allele thereof. In certain embodiments, the GPCR encoded by a polynucleotide hybridizing under stringent conditions to the complement of SEQ ID NO: 1 is an allele of SEQ ID NO:2. In certain embodiments, the GPCR encoded by a polynucleotide hybridizing under stringent conditions to the complement of SEQ ID NO: 1 is an ortholog of SEQ ID NO:2. In certain embodiments, the GPCR encoded by a polynucleotide hybridizing under stringent conditions to the complement of SEQ ID NO: 1 specifically binds (2-Fluoro-4-methanesulfonyl-phenyl)-{6-[4-(3-isopropyl-[1,2,4]oxadiazol-5-yl)-piperidin-1-yl]-5-nitro-pyrimidin-4-yl}-amine. In certain embodiments, the GPCR encoded by a polynucleotide hybridizing under stringent conditions to the complement of SEQ ID NO: 1 is a receptor for which (2-Fluoro-4-methanesulfonyl-phenyl)-{6-[4-(3-isopropyl-[1,2,4]oxadiazol-5-yl)-piperidin-1-yl]-5-nitro-pyrimidin-4-yl}-amine is an agonist. In some embodiments, the GPCR encoded by a polynucleotide hybridizing under stringent conditions to the complement of SEQ ID NO: 1 exhibits a detectable level of constitutive activity. In some embodiments, the constitutive activity is for increasing a level of intracellular cAMP accumulation. In some embodiments, the constitutive activity is for causing melanophore cells to undergo pigment dispersion.

In certain embodiments, the variant of SEQ ID NO:2 is a G protein-coupled receptor having at least about 80% identity to SEQ ID NO:2. In certain embodiments, the variant of SEQ ID NO:2 is a G protein-coupled receptor comprising at least 20 contiguous amino acids of SEQ ID NO:2. In certain embodiments, the variant of SEQ ID NO:2 which is a G protein-coupled receptor is an endogenous G protein-coupled receptor. In certain embodiments, the variant of SEQ ID NO:2 which is a G protein-coupled receptor is a non-endogenous G protein-coupled receptor.

In certain embodiments, the G protein-coupled receptor which has at least about 80% identity to SEQ ID NO: 2 is SEQ ID NO: 2 or an allele thereof. In certain embodiments, the G protein-coupled receptor which has at least about 80% identity to SEQ ID NO: 2 is an allele of SEQ ID NO: 2. In certain embodiments, the G protein-coupled receptor which has at least about 80% identity to SEQ ID NO: 2 is an ortholog of SEQ ID NO: 2. In certain embodiments, the G protein-coupled receptor which has at least about 80% identity to SEQ ID NO: 2 specifically binds (2-Fluoro-4-methanesulfonyl-phenyl)-{6-[4-(3-isopropyl-[1,2,4]oxadiazol-5-yl)-piperidin-1-yl]-5-nitro-pyrimidin-4-yl}-amine. In certain embodiments, the G protein-coupled receptor which has at least about 80% identity to SEQ ID NO: 2 is a receptor for which (2-Fluoro-4-methanesulfonyl-phenyl)-{6-[4-(3-isopropyl-[1,2,4]oxadiazol-5-yl)-piperidin-1-yl]-5-nitro-pyrimidin-4-yl}-amine is an agonist. In some embodiments, the G protein-coupled receptor which has at least about 80% identity to SEQ ID NO: 2 exhibits a detectable level of constitutive activity. In some embodiments, the constitutive activity is for increasing a level of intracellular cAMP. In some embodiments, the constitutive activity is for causing melanophore cells to undergo pigment dispersion.

In certain embodiments, the G protein-coupled receptor which comprises at least 20 contiguous amino acids of SEQ ID NO: 2 is SEQ ID NO: 2 or an allele of SEQ ID NO: 2. In certain embodiments, the G protein-coupled receptor which comprises at least 20 contiguous amino acids of SEQ ID NO: 2 is an allele of SEQ ID NO: 2. In certain embodiments, the G protein-coupled receptor which comprises at least 20 contiguous amino acids of SEQ ID NO: 2 is an ortholog of SEQ ID NO: 2. In certain embodiments, the G protein-coupled receptor which comprises at least 20 contiguous amino acids of SEQ ID NO: 2 specifically binds (2-Fluoro-4-methanesulfonyl-phenyl)-{6-[4-(3-isopropyl-[1,2,4]oxadiazol-5-yl)-piperidin-1-yl]-5-nitro-pyrimidin-4-yl}-amine. In certain embodiments, the G protein-coupled receptor which comprises at least 20 contiguous amino acids of SEQ ID NO: 2 is a receptor for which (2-Fluoro-4-methanesulfonyl-phenyl)-{6-[4-(3-isopropyl-[1,2,4]oxadiazol-5-yl)-piperidin-1-yl]-5-nitro-pyrimidin-4-yl}-amine is an agonist. In some embodiments, the G protein-coupled receptor which comprises at least 20 contiguous amino acids of SEQ ID NO: 2 exhibits a detectable level of constitutive activity. In some embodiments, the constitutive activity is for increasing a level of intracellular cAMP. In some embodiments, the constitutive activity is for causing melanophore cells to undergo pigment dispersion.

In some embodiments, the G protein-coupled receptor is part of a fusion protein comprising a G protein. Techniques for making a GPCR:G fusion construct are well known to the skilled artisan (see, e.g., International Application WO 02/42461).

In certain embodiments, the host cell comprises an expression vector, said expression vector comprising a polynucleotide encoding the G protein-coupled receptor. An exemplary suitable expression vector is pCMV. Other suitable expression vectors will be readily apparent to those of ordinary skill in the art, and a wide variety of expression vectors are commercially available (e.g., from Clontech, Palo Alto, Calif.; Stratagene, La Jolla, Calif.; and Invitrogen, Carlsbad, Calif.).

In some embodiments, the host cell is a vertebrate cell. In some embodiments, the host cell is a mammalian cell. In some embodiments, the mammalian host cell is selected from the group consisting of a 293 cell, a 293T cell, a CHO cell, an MCB3901 cell, and a COS-7 cell. In some embodiments, the host cell is a yeast cell. In some embodiments, the host cell is a melanophore cell. Other suitable host cells will be readily apparent to those of ordinary skill in the art, and a wide variety of cell lines are available from the American Type Culture Collection, 10801 University Boulevard, Manassas, Va. 20110-2209.

In certain embodiments, said determining is consistent with the G protein-coupled receptor being a Gs-coupled receptor.

In some embodiments, said determining is consistent with the G protein-coupled receptor being coupled through a promiscuous G protein, such as $G\alpha 15$ or $G\alpha 16$, to the phopholipase C pathway. Promiscuous G proteins are well known to the skilled artisan (see, e.g., Offermanns et al., J Biol Chem (1995) 270:15175-15180). In some embodiments, said determining is consistent with the G protein-coupled receptor being coupled through a chimeric G protein, e.g. to the phospholipase C pathway. Chimeric G proteins are well known to the skilled artisan (see, e.g., Milligan et al., Trends in Pharmaceutical Sciences (1999) 20:118-124; and WO 02/42461).

In some embodiments, said determining is through the measurement of a level of a second messenger.

In some embodiments, said determining is through the measurement of a level of a second messenger selected from the group consisting of cyclic AMP (cAMP), cyclic GMP (cGMP), inositol 1,4,5-triphosphate ($IP_3$), diacylglycerol (DAG), MAP kinase activity, MAPK/ERK kinase kinase-1 (MEKK1) activity, and $Ca^{2+}$. In some preferred embodiments, the second messenger is cAMP. In certain embodiments, a level of intracellular cAMP is increased.

In certain embodiments, said determining is carried out using isolated membrane comprising the G protein-coupled receptor.

In certain embodiments, said determining is through the use of a melanophore assay. In certain embodiments, a level of pigment dispersion is increased.

In some embodiments, said determining is through a reporter assay. In some embodiments, said reporter assay is CRE-Luc reporter assay.

In some embodiments, said determining is through the measurement of an activity mediated by increasing a level of intracellular cAMP.

In some embodiments, said determining is through CRE-Luc reporter assay. In certain embodiments, a level of luciferase activity is increased.

In some embodiments, said determining is through the measurement of GTPγS binding to membrane comprising the G protein-coupled receptor. In certain embodiments, said GTPγS is labeled with [$^{35}$S]. In certain embodiments, said GTPγS binding to membrane comprising the GPCR is increased.

In some embodiments, the test compound is a small molecule. In some embodiments, the test compound is a small molecule, with the proviso that the small molecule is not a polypeptide. In some embodiments, the test compound is a small molecule, with the proviso that the small molecule is not an antibody or an antigen-binding fragment thereof. In some embodiments, the test compound is a small molecule, with the proviso that the small molecule is not a lipid. In some embodiments, the test compound is a small molecule, with the proviso that the small molecule is not a polypeptide or a lipid. In some embodiments, the test compound is a polypeptide. In some embodiments, the test compound is a polypeptide, with the proviso that the polypeptide is not an antibody or an antigen-binding fragment thereof. In some embodiments, the test compound is a lipid. In some embodiments, the test compound is not an antibody or an antigen-binding fragment thereof. In some embodiments, the test compound is an antibody or an antigen-binding fragment thereof.

In some embodiments, the method further comprises the step of optionally determining the structure of the PYY secretagogue, the compound useful for treatment or prevention of a condition modulated by PYY, or the compound useful for a modulation of a PYY-related activity in an individual.

In some embodiments, the method further comprises the step of optionally providing the name or structure of the PYY secretagogue, the compound useful for treatment or prevention of a condition modulated by PYY, or the compound useful for a modulation of a PYY-related activity in an individual.

In some embodiments, said method further comprises the step of optionally producing or synthesizing the PYY secretagogue, the compound useful for treatment or prevention of a condition modulated by PYY, or the compound useful for a modulation of a PYY-related activity in an individual.

In some embodiments, said method further comprises the step of formulating the PYY secretagogue, the compound useful for treatment or prevention of a condition modulated by PYY, or the compound useful for a modulation of a PYY-related activity in an individual as a pharmaceutical.

In some embodiments, said method further comprises evaluating the bioavailability of the PYY secretagogue, the compound useful for treatment or prevention of a condition modulated by PYY, or the compound useful for a modulation of a PYY-related activity.

In some embodiments, said method further comprises the step of formulating the PYY secretagogue, the compound useful for treatment or prevention of a condition modulated by PYY, or the compound useful for a modulation of a PYY-related activity in an individual into a pharmaceutical composition.

In certain embodiments, the condition modulated by PYY is a bone-related condition.

In certain embodiments, the bone-related condition is a condition characterized by low bone mass. In certain embodiments, the condition characterized by low bone mass is selected from the group consisting of osteopenia, osteoporosis, rheumatoid arthritis, osteoarthritis, periodontal disease, alveolar bone loss, osteotomy bone loss, childhood idiopathic bone loss, Paget's disease, bone loss due to metastatic cancer, osteolytic lesions, curvature of the spine, and loss of height.

In certain embodiments, the bone-related condition is a bone fracture. In certain embodiments, the bone fracture is selected from the group consisting of a traumatic bone fracture, a long-term bone fracture, and an osteoporotic bone fracture.

In certain embodiments, the bone-related condition is a bone disease. In certain embodiments, the bone disease is selected from the group consisting of osteopenia, osteoporosis, rheumatoid arthritis, osteoarthritis, periodontal disease, alveolar bone loss, osteotomy bone loss, childhood idiopathic bone loss, Paget's disease, bone loss due to metastatic cancer, osteolytic lesions, curvature of the spine, and loss of height.

In certain embodiments, the bone-related condition is enhanced bone healing or bone growth, wherein said enhanced bone healing or bone growth is selected from the group consisting of enhanced bone healing following facial reconstruction, maxillary reconstruction, mandibular reconstruction, periodontal disease or tooth extraction, enhanced long bone extension, enhanced prosthetic ingrowth, and increased bone synostosis.

In certain embodiments, the condition modulated by PYY is a metabolic disorder.

In certain embodiments, the metabolic disorder is selected from the group consisting of overweight, obesity, hyperphagia, diabetes (inclusive of type 1 diabetes and type 2 diabetes), type 2 diabetes, impaired glucose tolerance, insulin resistance, hyperinsulinemia, dyslipidemia, hypertension and metabolic syndrome.

In certain embodiments, the condition modulated by PYY is an angiogenesis-related condition.

In certain embodiments, the angiogeneisis-related condition is selected from the group consisting of peripheral arterial disease, wound healing and ischemia.

In certain embodiments, the condition modulated by PYY is an ischemia-related condition.

In certain embodiments, the ischemia-related condition is selected from the group consisting of ischemic stroke, ischemic heart disease, myocardial infarction, ischemia-reperfusion injury, post-myocardial infarction remodeling, heart failure, and congestive heart failure.

In certain embodiments, the condition modulated by PYY is a malabsorptive disorder.

In certain embodiments, the malabsorptive disorder is selected from the group consisting of short bowel syndrome, enterocolitis, Crohn's disease, ulcerative colitis, irritable bowel syndrome, cholera, and a disorder accompanied by diarrhea.

In certain embodiments, the condition modulated by PYY is a convulsive disorder.

In certain embodiments, the convulsive disorder is epilepsy.

In certain embodiments, the condition modulated by PYY is a cancer.

In certain embodiments, the cancer is selected from the group consisting of pancreatic cancer, breast cancer, colon cancer, and Barrett's adenocarcinoma.

In certain embodiments, the condition modulated by PYY is an inflammatory disorder.

In certain embodiments, the inflammatory disorder is selected from the group consisting of atherosclerosis, atherothrombosis, insulin resistance, diabetes (inclusive of type 1 diabetes and type 2 diabetes), type 1 diabetes, ischemic stroke, pancreatitis, restenosis, an inflammatory lung disease, and an inflammatory bowel disease. In certain embodiments, the inflammatory lung disease is selected from the group consisting of asthma, emphysema, and pulmonary arterial hypertension. In certain embodiments, the inflammatory bowel disease is selected from the group consisting of enteritis, enterocolitis, Crohn's disease, granulomatous colitis, ileitis, Crohn's colitis, ulcerative colitis, sigmoiditis, pancolitis, and ulcerative proctitis.

In certain embodiments, the modulation of a PYY-related activity is selected from the group consisting of:
(a) increasing plasma PYY;
(b) increasing bone mass;
(c) decreasing loss of bone mass;
(d) increasing bone formation;
(e) decreasing food uptake;
(f) decreasing body weight;
(g) increasing satiety;
(h) increasing glucose disposal;
(i) decreasing plasma glucose;
(j) increasing angiogenesis;
(k) decreasing secretion in intestinal epithelium;
(l) increasing absorption in intestinal epithelium; and
(m) increasing plasma adiponectin The invention additionally features a process comprising performing a method according to this first aspect.

In a second aspect, the invention features a method for identifying PYY secretagogues, compounds useful for treatment or prevention of a condition modulated by PYY, or compounds useful for a modulation of a PYY-related activity, comprising the steps of:
(a) contacting a compound in vitro with a vertebrate enteroendocrine cell or with a cell capable of secreting PYY, said compound having been identified by a method according to the first aspect; and
(b) determining whether the compound stimulates PYY secretion from the vertebrate enteroendocrine cell or from the cell capable of secreting PYY;

wherein the ability of the test compound to stimulate PYY secretion from the vertebrate enteroendocrine cell or from the cell capable of secreting PYY is further indicative of the test compound being a PYY secretagogue, a compound useful for treatment or prevention of a PYY-related condition, or a compound useful for a modulation of a PYY-related activity.

In certain embodiments, the vertebrate enteroendocrine cell is a mammalian enteroendocrine cell. In certain embodiments, the enteroendocrine cell is an L cell. In certain embodiments, the enteroendocrine cell is comprised by or derived from tissue obtained from the small or large intestine. In certain embodiments, the enteroendocrine cell is comprised by or derived from tissue obtained from an L cell-containing region of small or large intestine. In certain embodiments, the enteroendocrine cell is comprised by or derived from duodenum, jejunum, ileum, colon or rectum tissue (see, e.g., Lundberg et al, PNAS USA (1982) 79:4471-4475; Adrian et al, Gastroenterol (1985) 89:1070-1077; Ekblad et al, Peptides (2002) 23:251-261; Ueno et al, Regul Pept (2008) 145:12-16). In certain embodiments, the enteroendocrine cell is an enteroendocrine cell line. In certain embodiments, the cell capable of secreting PYY is a cell comprised by or derived from the islets of Langerhans. In certain embodiments, the cell capable of secreting PYY is a neuronal cell. In certain embodiments, the cell capable of secreting PYY is a recombinant cell engineered to be capable of secreting PYY.

The invention additionally features a method for identifying PYY secretagogues, compounds useful for treatment or prevention of a condition modulated by PYY, or compounds useful for a modulation of a PYY-related activity in an individual, comprising the steps of:
(a) administering a compound to a vertebrate, said compound having been identified by a method according to the first aspect; and
(b) determining whether the compound increases a PYY level in the vertebrate;

wherein the ability of the test compound to increase a PYY level in the vertebrate is further indicative of the test compound being a PYY secretagogue, a compound useful for treatment or prevention of a PYY-related condition, or a compound useful for a modulation of a PYY-related activity in an individual.

In certain embodiments, the PYY level is blood or plasma concentration of total PYY. In certain embodiments, the PYY level is blood or plasma concentration of PYY3-36.

In certain embodiments, the vertebrate is a mammal. In certain embodiments, the vertebrate is a non-human vertebrate. In certain embodiments, the vertebrate is a non-human mammal. In certain embodiments, the mammal is a non-human mammal.

In certain embodiments, the vertebrate or the mammal is a human. In certain embodiments, the human is a participant in a study reviewed by a governmental agency charged with marketing approval for a drug. In certain embodiments, the study is a clinical trial. In certain embodiments, the governmental agency is the Food and Drug Administration of the United States.

The invention additionally features a method for identifying PYY secretagogues, compounds useful for treatment or prevention of a condition modulated by PYY, or compounds useful for a modulation of a PYY-related activity in an individual, comprising the steps of:

(a) determining whether the compound increases a PYY level in a sample, said sample having been obtained from a vertebrate previously administered with a compound which stimulates functionality of the receptor in step (b);

wherein the ability of the test compound to increase a PYY level in the vertebrate is further indicative of the test compound being a PYY secretagogue, a compound useful for treatment or prevention of a condition modulated by PYY, or a compound useful for a modulation of a PYY-related activity in an individual.

In certain embodiments, the PYY level is blood or plasma concentration of total PYY. In certain embodiments, the PYY level is blood or plasma concentration of $PYY_{3-36}$.

In certain embodiments, the vertebrate is a mammal. In certain embodiments, the vertebrate is a non-human vertebrate. In certain embodiments, the vertebrate is a non-human mammal. In certain embodiments, the mammal is a non-human mammal.

In certain embodiments, the vertebrate is a mammal. In certain embodiments, the vertebrate is a non-human vertebrate. In certain embodiments, the vertebrate is a non-human mammal.

In certain embodiments, the vertebrate or the mammal is a human. In certain embodiments, the human is a participant in a study reviewed by a governmental agency charged with marketing approval for a drug. In certain embodiments, the study is a clinical trial. In certain embodiments, the governmental agency is the Food and Drug Administration of the United States.

In some embodiments, the test compound is a small molecule. In some embodiments, the test compound is a small molecule, with the proviso that the small molecule is not a polypeptide. In some embodiments, the test compound is a small molecule, with the proviso that the small molecule is not an antibody or an antigen-binding fragment thereof. In some embodiments, the test compound is a small molecule, with the proviso that the small molecule is not a lipid. In some embodiments, the test compound is a small molecule, with the proviso that the small molecule is not a polypeptide or a lipid. In some embodiments, the test compound is a polypeptide. In some embodiments, the test compound is a polypeptide, with the proviso that the polypeptide is not an antibody or an antigen-binding fragment thereof. In some embodiments, the test compound is a lipid. In some embodiments, the test compound is not an antibody or an antigen-binding fragment thereof. In some embodiments, the test compound is an antibody or an antigen-binding fragment thereof.

In some embodiments, the method further comprises the step of optionally determining the structure of the PYY secretagogue, the compound useful for treatment or prevention of a condition modulated by PYY, or the compound useful for a modulation of a PYY-related activity in an individual.

In some embodiments, the method further comprises the step of optionally providing the name or structure of the PYY secretagogue, the compound useful for treatment or prevention of a condition modulated by PYY, or the compound useful for a modulation of a PYY-related activity in an individual.

In some embodiments, said method further comprises the step of optionally producing or synthesizing the PYY secretagogue, the compound useful for treatment or prevention of a condition modulated by PYY, or the compound useful for a modulation of a PYY-related activity in an individual.

In some embodiments, said method further comprises the step of formulating the PYY secretagogue, the compound useful for treatment or prevention of a condition modulated by PYY, or the compound useful for a modulation of a PYY-related activity in an individual as a pharmaceutical.

In some embodiments, said method further comprises evaluating the bioavailability of the PYY secretagogue, the compound useful for treatment or prevention of a condition modulated by PYY, or the compound useful for a modulation of a PYY-related activity.

In some embodiments, said method further comprises the step of formulating the PYY secretagogue, the compound useful for treatment or prevention of a condition modulated by PYY, or the compound useful for a modulation of a PYY-related activity in an individual into a pharmaceutical composition.

The invention additionally features a process comprising performing a method according to this second aspect.

In a third aspect, the invention features a method for identifying PYY secretagogues, compounds useful for treatment or prevention of a condition modulated by PYY, or compounds useful for a modulation of a PYY-related activity in an individual, comprising the steps of:

(a) contacting a GPR119 agonist in vitro with a vertebrate enteroendocrine cell or with a cell capable of secreting PYY; and (b) determining whether the GPR119 agonist stimulates PYY secretion from the vertebrate enteroendocrine cell or from the cell capable of secreting PYY;

wherein the ability of the GPR119 agonist to stimulate PYY secretion from the vertebrate enteroendocrine cell or from the cell capable of secreting PYY is indicative of the GPR119 agonist being a PYY secretagogue, a compound useful for treatment or prevention of a condition modulated by PYY, or a compound useful for a modulation of a PYY-related activity in an individual.

In certain embodiments, the vertebrate enteroendocrine cell is a mammalian enteroendocrine cell. In certain embodiments, the enteroendocrine cell is an L cell. In certain embodiments, the enteroendocrine cell is comprised by or derived from tissue obtained from the small or large intestine. In certain embodiments, the enteroendocrine cell is comprised by or derived from tissue obtained from an L cell-containing region of small or large intestine. In certain embodiments, the enteroendocrine cell is comprised by or derived from duodenum, jejunum, ileum, colon or rectum tissue (see, e.g., Lundberg et al, PNAS USA (1982) 79:4471-4475; Adrian et al, Gastroenterol (1985) 89:1070-1077;

Ekblad et al, Peptides (2002) 23:251-261; Ueno et al, Regul Pept (2008) 145:12-16). In certain embodiments, the enteroendocrine cell is an enteroendocrine cell line. In certain embodiments, the cell capable of secreting PYY is a cell comprised by or derived from the islets of Langerhans. In certain embodiments, the cell capable of secreting PYY is a neuronal cell. In certain embodiments, the cell capable of secreting PYY is a recombinant cell engineered to be capable of secreting PYY.

The invention additionally features a method for identifying PYY secretagogues, compounds useful for treatment or prevention of a condition modulated by PYY, or compounds useful for a modulation of a PYY-related activity in an individual, comprising the steps of:

(a) administering a GPR119 agonist to a vertebrate; and
(b) determining whether the GPR119 agonist increases a PYY level in the vertebrate;

wherein the ability of the GPR119 agonist to increase a PYY level in the vertebrate is indicative of the GPR119 agonist being a PYY secretagogue, a compound useful for treatment or prevention of a condition modulated by PYY, or a compound useful for a modulation of a PYY-related activity in an individual.

In certain embodiments, the PYY level is blood or plasma concentration of total PYY. In certain embodiments, the PYY level is blood or plasma concentration of $PYY_{3-36}$.

In certain embodiments, the vertebrate is a mammal. In certain embodiments, the vertebrate is a non-human vertebrate. In certain embodiments, the vertebrate is a non-human mammal. In certain embodiments, the mammal is a non-human mammal.

In certain embodiments, the vertebrate or the mammal is a human. In certain embodiments, the human is a participant in a study reviewed by a governmental agency charged with marketing approval for a drug. In certain embodiments, the study is a clinical trial. In certain embodiments, the governmental agency is the Food and Drug Administration of the United States.

The invention additionally features a method for identifying PYY secretagogues, compounds useful for treatment or prevention of a condition modulated by PYY, or compounds useful for a modulation of a PYY-related activity in an individual, comprising the steps of:

(a) determining whether the compound increases a PYY level in a sample, said sample having been obtained from a vertebrate previously administered with a GPR119 agonist; administering a GPR119 agonist to a vertebrate;

wherein the ability of the GPR119 agonist to increase a PYY level in the vertebrate is indicative of the GPR119 agonist being a PYY secretagogue, a compound useful for treatment or prevention of a condition modulated by PYY, or a compound useful for a modulation of a PYY-related activity in an individual.

In certain embodiments, the PYY level is blood or plasma concentration of total PYY. In certain embodiments, the PYY level is blood or plasma concentration of $PYY_{3-36}$.

In certain embodiments, the vertebrate is a mammal. In certain embodiments, the vertebrate is a non-human vertebrate. In certain embodiments, the vertebrate is a non-human mammal. In certain embodiments, the mammal is a non-human mammal.

In certain embodiments, the vertebrate or the mammal is a human. In certain embodiments, the human is a participant in a study reviewed by a governmental agency charged with marketing approval for a drug. In certain embodiments, the study is a clinical trial. In certain embodiments, the governmental agency is the Food and Drug Administration of the United States.

In certain embodiments, the GPR119 agonist is an agonist of an endogenous GPR119.

In certain embodiments, the GPR119 agonist is an agonist of human GPR119.

In certain embodiments, the GPR119 agonist is a GPR119 partial agonist.

In certain embodiments, the GPR119 agonist is a selective GPR119 agonist.

In certain embodiments, the GPR119 agonist is a small molecule. In some embodiments, the small molecule is not a polypeptide. In some embodiments, the small molecule is not an antibody or an antigen-binding fragment thereof. In some embodiments, the small molecule is not a lipid. In some embodiments, the small molecule is not a polypeptide or a lipid.

In certain embodiments, the GPR119 agonist is orally available.

In certain embodiments, the GPR119 agonist has an $EC_{50}$ value of less than about 10 µM, less than about 1 µM, less than about 100 nM, less than about 75 nM, less than about 50 nM, less than about 25 nM, less than about 15 nM, less than about 10 nM, less than about 5 nM, less than about 4 nM, less than about 3 nM, less than about 2 nM, or less than about 1 nM. In certain embodiments, the GPR119 agonist has an $EC_{50}$ value of less than about 10 µM, less than about 1 µM, less than about 100 nM, less than about 75 nM, less than about 50 nM, less than about 25 nM, less than about 15 nM, less than about 10 nM, less than about 5 nM, less than about 4 nM, less than about 3 nM, less than about 2 nM, or less than about 1 nM at human GPR119 having SEQ ID NO: 2. In certain embodiments, the GPR119 agonist has an $EC_{50}$ value of less than about 10 µM, less than about 1 µM, less than about 100 nM, less than about 75 nM, less than about 50 nM, less than about 25 nM, less than about 15 nM, less than about 10 nM, less than about 5 nM, less than about 4 nM, less than about 3 nM, less than about 2 nM, or less than about 1 nM at human GPR119 having SEQ ID NO: 2 in adenylyl cyclase assay (exemplary adenylyl cyclase assay is provided in Example 9, Example 10 and in Example 11, infra). In certain embodiments, the GPR119 agonist has an $EC_{50}$ value of less than about 10 µM, less than about 1 µM, less than about 100 nM, less than about 75 nM, less than about 50 nM, less than about 25 nM, less than about 15 nM, less than about 10 nM, less than about 5 nM, less than about 4 nM, less than about 3 nM, less than about 2 nM, or less than about 1 nM at human GPR119 having SEQ ID NO: 2 in melanophore assay (exemplary melanophore assay is provided in Example 12, infra).

Exemplary GPR119 agonists are disclosed, e.g., in International Application No. PCT/US2004/001267 (published as WO 04/065380); International Application No. PCT/US2004/005555 (published as WO 04/076413); International Application No. PCT/US2004/022327 (published as WO 05/007647); International Application No. PCT/US2004/022417 (published as WO 05/007658); International Application No. PCT/US2005/019318 (published as WO 2005/121121); International Application No. PCT/GB2004/050046 (published as WO 2005/061489); International Application No. PCT/US06/00567 (published as WO 2006/083491); International Application No. PCT/GB2005/050264 (published as WO 2006/067531); International Application No. PCT/GB2005/050265 (published as WO 2006/067532); International Application No. PCT/GB2005/050266 (published as WO 2006/070208); International Application No. PCT/JP02/09350 (published as WO 03/026661); International Application No. PCT/JP2005/018412 (published as WO 06/040966); International Application No. PCT/JP2005/019000 (published as WO 2006/043490); International Application No. PCT/GB2006/050176 (published as WO 2007/003960); International Application No. PCT/GB2006/050177 (published as WO 2007/003961); International Application No. PCT/GB2006/050178 (published as WO 2007/003962); International Application No. PCT/GB2006/050182 (published as WO 2007/003964); International Application No. PCT/JP02/09350 (published as WO 03/026661); International Application No. PCT/GB2007/050183 (published as WO 2007/116229); International Application No. PCT/GB2007/050190 (published as WO 2007/116230); International Application No. PCT/US2007/073364 (published as WO 2008/008895); International Application No. PCT/EP2007/058991 (published as WO 2008/025798); International Application No. PCT/EP2007/058993 (published as WO 2008/025799); and International Application No. PCT/EP2007/058995 (published as WO 2008/025800).

In certain embodiments, the method comprises providing the GPR119 agonist.

In certain embodiments, the GPR119 agonist is identifiable by a method according to the first aspect.

In certain embodiments, the method comprises carrying out a method according to the first aspect to identify the GPR119 agonist.

In certain embodiments, the method comprises having identified the GPR119 agonist by a method according to the first aspect.

In some embodiments, the method further comprises the step of optionally determining the structure of the PYY secretagogue, the compound useful for treatment or prevention of a condition modulated by PYY, or the compound useful for a modulation of a PYY-related activity in an individual.

In some embodiments, the method further comprises the step of optionally providing the name or structure of the PYY secretagogue, the compound useful for treatment or prevention of a condition modulated by PYY, or the compound useful for a modulation of a PYY-related activity in an individual.

In some embodiments, said method further comprises the step of optionally producing or synthesizing the PYY secretagogue, the compound useful for treatment or prevention of a condition modulated by PYY, or the compound useful for a modulation of a PYY-related activity in an individual.

In some embodiments, said method further comprises the step of formulating the PYY secretagogue, the compound useful for treatment or prevention of a condition modulated by PYY, or the compound useful for a modulation of a PYY-related activity in an individual as a pharmaceutical.

In some embodiments, said method further comprises evaluating the bioavailability of the PYY secretagogue, the compound useful for treatment or prevention of a condition modulated by PYY, or the compound useful for a modulation of a PYY-related activity.

In some embodiments, said method further comprises the step of formulating the PYY secretagogue, the compound useful for treatment or prevention of a condition modulated by PYY, or the compound useful for a modulation of a PYY-related activity in an individual into a pharmaceutical composition.

The invention additionally features a process comprising performing a method according to this third aspect.

In a fourth aspect, the invention features a method for identifying PYY secretagogues, compounds useful for treatment or prevention of a condition modulated by PYY, or compounds useful for a modulation of a PYY-related activity in an individual, comprising the steps of:

(a) contacting a G protein-coupled receptor with an optionally labeled known ligand for the receptor in the presence or absence of a test compound, wherein a ligand for the receptor is a ligand for GPR119 and wherein the G protein-coupled receptor comprises an amino acid sequence selected from the group consisting of:
 (i) amino acids 1-335 of SEQ ID NO:2;
 (ii) amino acids 2-335 of SEQ ID NO:2;
 (iii) an amino acid sequence comprising the amino acid sequence of a polypeptide derived from (i) by substitution, deletion or addition of one or several amino acids in the amino acid sequence defined in (i);
 (iv) the amino acid sequence of a G protein-coupled receptor encoded by a polynucleotide hybridizing under stringent conditions to the complement of SEQ ID NO:1;
 (v) a variant of SEQ ID NO: 2 when selected from the group consisting of:
  (a') the amino acid sequence of a G protein-coupled receptor having at least about 80% identity to SEQ ID NO: 2; and
  (b') the amino acid sequence of a G protein-coupled receptor comprising at least 20 contiguous amino acids of SEQ ID NO: 2;
 (vi) the amino acid sequence of a constitutively active version of a G protein-coupled receptor having SEQ ID NO: 2; and
 (vii) a biologically active fragment of any one of (i) to (vi); and
(b) detecting the complex between said known ligand and said receptor; and
(c) determining whether less of said complex is formed in the presence of the test compound than in the absence of the test compound;

wherein said determination is indicative of the test compound being a PYY secretagogue, a compound useful for treatment or prevention of a condition modulated by PYY, or a compound useful for a modulation of a PYY-related activity in an individual.

In certain embodiments, the G protein-coupled receptor comprises the amino acid sequence of a G protein-coupled receptor having at least about 80% identity to SEQ ID NO: 2.

In certain embodiments, the receptor comprises the amino acid sequence of SEQ ID NO: 2.

In certain embodiments, the variant of SEQ ID NO: 2 is an allele of SEQ ID NO: 2.

In certain embodiments, the variant of SEQ ID NO: 2 is an ortholog of SEQ ID NO: 2. In certain embodiments, the variant of SEQ ID NO: 2 is a mammalian ortholog of SEQ ID NO: 2.

In certain embodiments, the G protein-coupled receptor is recombinant.

In certain embodiments, the method is a method for identifying PYY secretagogues.

In certain embodiments, the method is a method for identifying compounds useful for treatment or prevention of a condition modulated by PYY.

In certain embodiments, the method is a method for identifying compounds useful for a modulation of a PYY-related activity in an individual.

In certain embodiments, the ligand for GPR119 is a GPR119 agonist. In certain embodiments, the ligand for GPR119 or the GPR119 agonist is a ligand or agonist of an endogenous vertebrate, mammalian or human GPR119 receptor. In certain embodiments, the ligand for GPR119 or the GPR119 agonist is a ligand or agonist of an endogenous human GPR119 receptor. In certain embodiments, the ligand for GPR119 or the GPR119 agonist is identical to a compound disclosed in, e.g., in International Application No. PCT/US2004/001267 (published as WO 04/065380); International Application No. PCT/US2004/005555 (published as WO 04/076413); International Application No. PCT/US2004/022327 (published as WO 05/007647); International Application No. PCT/US2004/022417 (published as WO 05/007658); International Application No. PCT/US2005/019318 (published as WO 2005/121121); International Application No. PCT/GB2004/050046 (published as WO 2005/061489); International Application No. PCT/US06/00567 (published as WO 2006/083491); International Application No. PCT/GB2005/050264 (published as WO 2006/067531); International Application No. PCT/GB2005/050265 (published as WO 2006/067532); International Application No. PCT/GB2005/050266 (published as WO 2006/070208); International Application No. PCT/JP02/09350 (published as WO 03/026661); International Application No. PCT/JP2005/018412 (published as WO 06/040966); International Application No. PCT/JP2005/019000 (published as WO 2006/043490); International Application No. PCT/GB2006/050176 (published as WO 2007/003960); International Application No. PCT/GB2006/050177 (published as WO 2007/003961); International Application No. PCT/GB2006/050178 (published as WO 2007/003962); International Application No. PCT/GB2006/050182 (published as WO 2007/003964); International Application No. PCT/JP02/09350 (published as WO 03/026661); International Application No. PCT/GB2007/050183 (published as WO 2007/116229); International Application No. PCT/GB2007/050190 (published as WO 2007/116230); International Application No. PCT/US2007/073364 (published as WO 2008/008895); International Application No. PCT/EP2007/058991 (published as WO 2008/025798); International Application No. PCT/EP2007/058993 (published as WO 2008/025799); or International Application No. PCT/EP2007/058995 (published as WO 2008/025800). In certain embodiments, the ligand for GPR119 or the GPR119 agonist is (2-Fluoro-4-methanesulfonyl-phenyl)-{6-[4-(3-isopropyl-[1,2,4]oxadiazol-5-yl)-piperidin-1-yl]-5-nitro-pyrimidin-4-yl}-amine. In certain embodiments, the ligand for GPR119 is an endogenous ligand of an endogenous vertebrate, mammalian, or human GPR119 receptor.

In certain embodiments, the optionally labeled known ligand is a labeled known ligand. In certain embodiments, the labeled known ligand is a radiolabeled known ligand. Techniques for radiolabeling a compound, such as for labeling a known ligand of a G protein-coupled receptor of the invention, are well known to the skilled artisan. See, e.g., International Application WO 04/065380. Also see, e.g., Example 14, infra.

Techniques for detecting the complex between a G protein-coupled receptor and a compound known to be a ligand for the G protein-coupled receptor are well known to the skilled artisan. See, e.g., International Application WO 04/065380. Also see, e.g., Example 15, infra.

The invention additionally features a method for identifying PYY secretagogues, compounds useful for treatment or prevention of a condition modulated by PYY, or compounds useful for a modulation of a PYY-related activity in an individual, comprising steps (a) to (c) of this fourth aspect, and further comprising:
(d) optionally synthesizing a compound in the presence of which less of said complex is formed in step (c);

(e) contacting a compound in the presence of which less of said complex is formed in step (c) in vitro with a vertebrate enteroendocrine cell or with a cell capable of secreting PYY; and
(f) determining whether the compound stimulates PYY secretion from the vertebrate enteroendocrine cell or from the cell capable of secreting PYY;

wherein the ability of the test compound to stimulate PYY secretion from the vertebrate enteroendocrine cell or from the cell capable of secreting PYY is further indicative of the test compound being a PYY secretagogue, a compound useful for treatment or prevention of a condition modulated by PYY, or a compound useful for a modulation of a PYY-related activity in an individual.

In certain embodiments, the vertebrate enteroendocrine cell is a mammalian enteroendocrine cell. In certain embodiments, the enteroendocrine cell is an L cell. In certain embodiments, the enteroendocrine cell is comprised by or derived from tissue obtained from the small or large intestine. In certain embodiments, the enteroendocrine cell is comprised by or derived from tissue obtained from an L cell-containing region of small or large intestine. In certain embodiments, the enteroendocrine cell is comprised by or derived from duodenum, jejunum, ileum, colon or rectum tissue (see, e.g., Lundberg et al, PNAS USA (1982) 79:4471-4475; Adrian et al, Gastroenterol (1985) 89:1070-1077; Ekblad et al, Peptides (2002) 23:251-261; Ueno et al, Regul Pept (2008) 145:12-16). In certain embodiments, the enteroendocrine cell is an enteroendocrine cell line. In certain embodiments, the cell capable of secreting PYY is a cell comprised by or derived from the islets of Langerhans. In certain embodiments, the cell capable of secreting PYY is a neuronal cell. In certain embodiments, the cell capable of secreting PYY is a recombinant cell engineered to be capable of secreting PYY.

The invention additionally features a method for identifying PYY secretagogues, compounds useful for treatment or prevention of a condition modulated by PYY, or compounds useful for a modulation of a PYY-related activity in an individual, comprising steps (a) to (c) of this fourth aspect, and further comprising:
(d) optionally synthesizing a compound in the presence of which less of said complex is formed in step (c);
(e) administering a compound in the presence of which less of said complex is formed in step (c) to a vertebrate; and
(f) determining whether the compound increases a PYY level in the vertebrate;

wherein the ability of the test compound to increase a PYY level in the vertebrate is further indicative of the test compound being a PYY secretagogue, a compound useful for treatment or prevention of a condition modulated by PYY, or a compound useful for a modulation of a PYY-related activity in an individual.

In certain embodiments, the vertebrate is a mammal. In certain embodiments, the vertebrate is a non-human vertebrate. In certain embodiments, the vertebrate is a non-human mammal. In certain embodiments, the mammal is a non-human mammal.

In certain embodiments, the vertebrate or the mammal is a human. In certain embodiments, the human is a participant in a study reviewed by a governmental agency charged with marketing approval for a drug. In certain embodiments, the study is a clinical trial. In certain embodiments, the governmental agency is the Food and Drug Administration of the United States.

The invention additionally features a method for identifying PYY secretagogues, compounds useful for treatment or prevention of a condition modulated by PYY, or compounds useful for a modulation of a PYY-related activity in an individual, comprising steps (a) to (c) of this fourth aspect, and further comprising:
- (d) optionally synthesizing a compound in the presence of which less of said complex is formed in step (c); and
- (e) determining whether the compound increases a PYY level in a sample obtained from a vertebrate, said vertebrate having been administered with a compound in the presence of which less of said complex is formed in step (c);

wherein the ability of the test compound to increase a PYY level in the vertebrate is indicative of the test compound being PYY secretagogue, a compound useful for treatment or prevention of a condition modulated by PYY, or a compound useful for a modulation of a PYY-related activity in an individual.

In certain embodiments, the vertebrate is a mammal. In certain embodiments, the vertebrate is a non-human vertebrate. In certain embodiments, the vertebrate is a non-human mammal. In certain embodiments, the mammal is a non-human mammal.

In certain embodiments, the vertebrate or the mammal is a human. In certain embodiments, the human is a participant in a study reviewed by a governmental agency charged with marketing approval for a drug. In certain embodiments, the study is a clinical trial. In certain embodiments, the governmental agency is the Food and Drug Administration of the United States.

The invention additionally features a method for identifying PYY secretagogues, compounds useful for treatment or prevention of a condition modulated by PYY, or compounds useful for a modulation of a PYY-related activity in an individual, comprising steps (a) to (c) of this fourth aspect, and further comprising:
- (d) optionally synthesizing a compound in the presence of which less of said complex is formed according to step (c);
- (e) optionally providing a compound in the presence of which less of said complex is formed according to step (c);
- (f) contacting a compound in the presence of which less of said complex is formed according to step (c) in vitro with a vertebrate enteroendocrine cell or with a cell capable of secreting PYY; and
- (g) determining whether the compound stimulates PYY secretion from the vertebrate enteroendocrine cell or from the cell capable of secreting PYY;

wherein the ability of the test compound to stimulate PYY secretion from the vertebrate enteroendocrine cell or from the cell capable of secreting PYY is further indicative of the test compound being a PYY secretagogue, a compound useful for treatment or prevention of a condition modulated by PYY, or a compound useful for a modulation of a PYY-related activity in an individual.

In certain embodiments, the vertebrate enteroendocrine cell is a mammalian enteroendocrine cell. In certain embodiments, the enteroendocrine cell is an L cell. In certain embodiments, the enteroendocrine cell is comprised by or derived from tissue obtained from the small or large intestine. In certain embodiments, the enteroendocrine cell is comprised by or derived from tissue obtained from an L cell-containing region of small or large intestine. In certain embodiments, the enteroendocrine cell is comprised by or derived from duodenum, jejunum, ileum, colon or rectum tissue (see, e.g., Lundberg et al, PNAS USA (1982) 79:4471-4475; Adrian et al, Gastroenterol (1985) 89:1070-1077; Ekblad et al, Peptides (2002) 23:251-261; Ueno et al, Regul Pept (2008) 145:12-16). In certain embodiments, the enteroendocrine cell is an enteroendocrine cell line. In certain embodiments, the cell capable of secreting PYY is a cell comprised by or derived from the islets of Langerhans. In certain embodiments, the cell capable of secreting PYY is a neuronal cell. In certain embodiments, the cell capable of secreting PYY is a recombinant cell engineered to be capable of secreting PYY.

The invention additionally features a method for identifying PYY secretagogues, compounds useful for treatment or prevention of a condition modulated by PYY, or compounds useful for a modulation of a PYY-related activity in an individual, comprising steps (a) to (c) of this fourth aspect, and further comprising:
- (d) optionally synthesizing a compound in the presence of which less of said complex is formed according to step (c);
- (e) optionally providing a compound in the presence of which less of said complex is formed according to step (c);
- (f) administering a compound in the presence of which less of said complex is formed in step (c) to a vertebrate; and
- (g) determining whether the compound increases a PYY level in the vertebrate;

wherein the ability of the test compound to increase a PYY level in the vertebrate is further indicative of the test compound being a PYY secretagogue, a compound useful for treatment or prevention of a condition modulated by PYY, or a compound useful for a modulation of a PYY-related activity in an individual.

In certain embodiments, the vertebrate is a mammal. In certain embodiments, the vertebrate is a non-human vertebrate. In certain embodiments, the vertebrate is a non-human mammal. In certain embodiments, the mammal is a non-human mammal.

In certain embodiments, the vertebrate or the mammal is a human. In certain embodiments, the human is a participant in a study reviewed by a governmental agency charged with marketing approval for a drug. In certain embodiments, the study is a clinical trial. In certain embodiments, the governmental agency is the Food and Drug Administration of the United States.

The invention additionally features a method for identifying PYY secretagogues, compounds useful for treatment or prevention of a condition modulated by PYY, or compounds useful for a modulation of a PYY-related activity in an individual, comprising steps (a) to (c) of this fourth aspect, and further comprising:
- (d) optionally synthesizing a compound in the presence of which less of said complex is formed according to step (c);
- (e) optionally providing a compound in the presence of which less of said complex is formed according to step (c); and
- (f) determining whether the compound increases a PYY level in a sample obtained from a vertebrate, said vertebrate having been administered with a compound in the presence of which less of said complex is formed in step (c);

wherein the ability of the test compound to increase a PYY level in the vertebrate is further indicative of the test compound being a PYY secretagogue, a compound useful for treatment or prevention of a condition modulated by PYY, or a compound useful for a modulation of a PYY-related activity in an individual.

In certain embodiments, the vertebrate is a mammal. In certain embodiments, the vertebrate is a non-human vertebrate. In certain embodiments, the vertebrate is a non-human mammal. In certain embodiments, the mammal is a non-human mammal.

In certain embodiments, the vertebrate or the mammal is a human. In certain embodiments, the human is a participant in a study reviewed by a governmental agency charged with marketing approval for a drug. In certain embodiments, the study is a clinical trial. In certain embodiments, the governmental agency is the Food and Drug Administration of the United States.

In some embodiments, a G protein-coupled receptor of the invention is SEQ ID NO:2 or an allele thereof. In some embodiments, a G protein-coupled receptor of the invention is an allele of SEQ ID NO:2. In some embodiments, a G protein-coupled receptor of the invention is an ortholog of SEQ ID NO:2.

In some embodiments, a G protein-coupled receptor of the invention is a G protein-coupled receptor which specifically binds (2-Fluoro-4-methanesulfonyl-phenyl)-{6-[4-(3-isopropyl-[1,2,4]oxadiazol-5-yl)-piperidin-1-yl]-5-nitro-pyrimidin-4-yl}-amine. In some embodiments, a G protein-coupled receptor of the invention is a G protein-coupled receptor for which (2-Fluoro-4-methanesulfonyl-phenyl)-{6-[4-(3-isopropyl-[1,2,4]oxadiazol-5-yl)-piperidin-1-yl]-5-nitro-pyrimidin-4-yl}-amine is a ligand. In some embodiments, a G protein-coupled receptor of the invention is a G protein-coupled receptor for which (2-Fluoro-4-methanesulfonyl-phenyl)-{6-[4-(3-isopropyl-[1,2,4]oxadiazol-5-yl)-piperidin-1-yl]-5-nitro-pyrimidin-4-yl}-amine is an agonist. In some embodiments, a G protein-coupled receptor of the invention exhibits a detectable level of constitutive activity. In some embodiments, the constitutive activity is for increasing a level of intracellular cAMP accumulation. In some embodiments, the constitutive activity is for causing melanophore cells to undergo pigment dispersion.

In certain embodiments, stringent hybridization conditions comprise hybridization at 42° C. in a solution comprising 50% formamide, 5×SSC (1×SSC=150 mM NaCl, 15 mM trisodium citrate), 50 mM sodium phosphate (pH 7.6), 5×Denhardt's solution, 10% dextran sulfate, and 20 µg/ml denatured, sheared salmon sperm DNA, followed by washing at 65° C. in a solution comprising 0.1×SSC. Hybridization techniques are well known to the skilled artisan.

In certain embodiments, the GPCR encoded by a polynucleotide hybridizing under stringent conditions to the complement of SEQ ID NO: 1 is SEQ ID NO:2 or an allele thereof. In certain embodiments, the GPCR encoded by a polynucleotide hybridizing under stringent conditions to the complement of SEQ ID NO: 1 is an allele of SEQ ID NO:2. In certain embodiments, the GPCR encoded by a polynucleotide hybridizing under stringent conditions to the complement of SEQ ID NO: 1 is an ortholog of SEQ ID NO:2. In certain embodiments, the GPCR encoded by a polynucleotide hybridizing under stringent conditions to the complement of SEQ ID NO: 1 specifically binds (2-Fluoro-4-methanesulfonyl-phenyl)-{6-[4-(3-isopropyl-[1,2,4]oxadiazol-5-yl)-piperidin-1-yl]-5-nitro-pyrimidin-4-yl}-amine. In certain embodiments, the GPCR encoded by a polynucleotide hybridizing under stringent conditions to the complement of SEQ ID NO: 1 is a receptor for which (2-Fluoro-4-methanesulfonyl-phenyl)-{6-[4-(3-isopropyl-[1,2,4]oxadiazol-5-yl)-piperidin-1-yl]-5-nitro-pyrimidin-4-yl}-amine is a ligand. In certain embodiments, the GPCR encoded by a polynucleotide hybridizing under stringent conditions to the complement of SEQ ID NO: 1 is a receptor for which (2-Fluoro-4-methanesulfonyl-phenyl)-{6-[4-(3-isopropyl-[1,2,4]oxadiazol-5-yl)-piperidin-1-yl]-5-nitro-pyrimidin-4-yl}-amine is an agonist. In some embodiments, the GPCR encoded by a polynucleotide hybridizing under stringent conditions to the complement of SEQ ID NO: 1 exhibits a detectable level of constitutive activity. In some embodiments, the constitutive activity is for increasing a level of intracellular cAMP. In some embodiments, the constitutive activity is for causing melanophore cells to undergo pigment dispersion.

In certain embodiments, the variant of SEQ ID NO:2 is a G protein-coupled receptor having at least about 80% identity to SEQ ID NO:2. In certain embodiments, the variant of SEQ ID NO:2 is a G protein-coupled receptor comprising at least 20 contiguous amino acids of SEQ ID NO:2. In certain embodiments, the variant of SEQ ID NO:2 which is a G protein-coupled receptor is an endogenous G protein-coupled receptor. In certain embodiments, the variant of SEQ ID NO:2 which is a G protein-coupled receptor is a non-endogenous G protein-coupled receptor.

In certain embodiments, the G protein-coupled receptor which has at least about 80% identity to SEQ ID NO: 2 is SEQ ID NO: 2 or an allele thereof. In certain embodiments, the G protein-coupled receptor which has at least about 80% identity to SEQ ID NO: 2 is an allele of SEQ ID NO: 2. In certain embodiments, the G protein-coupled receptor which has at least about 80% identity to SEQ ID NO: 2 is an ortholog of SEQ ID NO: 2. In certain embodiments, the G protein-coupled receptor which has at least about 80% identity to SEQ ID NO: 2 specifically binds (2-Fluoro-4-methanesulfonyl-phenyl)-{6-[4-(3-isopropyl-[1,2,4]oxadiazol-5-yl)-piperidin-1-yl]-5-nitro-pyrimidin-4-yl}-amine. In certain embodiments, the G protein-coupled receptor which has at least about 80% identity to SEQ ID NO: 2 is a receptor for which (2-Fluoro-4-methanesulfonyl-phenyl)-{6-[4-(3-isopropyl-[1,2,4]oxadiazol-5-yl)-piperidin-1-yl]-5-nitro-pyrimidin-4-yl}-amine is an agonist. In some embodiments, the G protein-coupled receptor which has at least about 80% identity to SEQ ID NO: 2 exhibits a detectable level of constitutive activity. In some embodiments, the constitutive activity is for increasing a level of intracellular cAMP. In some embodiments, the constitutive activity is for causing melanophore cells to undergo pigment dispersion.

In certain embodiments, the G protein-coupled receptor which comprises at least 20 contiguous amino acids of SEQ ID NO: 2 is SEQ ID NO: 2 or an allele of SEQ ID NO: 2. In certain embodiments, the G protein-coupled receptor which comprises at least 20 contiguous amino acids of SEQ ID NO: 2 is an allele of SEQ ID NO: 2. In certain embodiments, the G protein-coupled receptor which comprises at least 20 contiguous amino acids of SEQ ID NO: 2 is an ortholog of SEQ ID NO: 2. In certain embodiments, the G protein-coupled receptor which comprises at least 20 contiguous amino acids of SEQ ID NO: 2 specifically binds (2-Fluoro-4-methanesulfonyl-phenyl)-{6-[4-(3-isopropyl-[1,2,4]oxadiazol-5-yl)-piperidin-1-yl]-5-nitro-pyrimidin-4-yl}-amine. In certain embodiments, the G protein-coupled receptor which comprises at least 20 contiguous amino acids of SEQ ID NO: 2 is a receptor for which (2-Fluoro-4-methanesulfonyl-phenyl)-{6-[4-(3-isopropyl-[1,2,4]oxadiazol-5-yl)-piperidin-1-yl]-5-nitro-pyrimidin-4-yl}-amine is an agonist. In some embodiments, the G protein-coupled receptor which comprises at least 20 contiguous amino acids of SEQ ID NO: 2 exhibits a detectable level of constitutive activity. In some embodiments, the constitutive activity is for increasing a level of intracellular cAMP. In some embodiments, the constitutive activity is for causing melanophore cells to undergo pigment dispersion.

In some embodiments, the G protein-coupled receptor is part of a fusion protein comprising a G protein. Techniques for making a GPCR:G fusion construct are well known to the skilled artisan (see, e.g., International Application WO 02/42461).

In certain embodiments, said determining is carried out using a host cell comprising the G protein-coupled receptor. In certain embodiments, the host cell comprises an expression vector, said expression vector comprising a polynucleotide encoding the GPCR. An exemplary suitable expression vector is pCMV. Other suitable expression vectors will be readily apparent to those of ordinary skill in the art, and a wide variety of expression vectors are commercially available (e.g., from Clontech, Palo Alto, Calif.; Stratagene, La Jolla, Calif.; and Invitrogen, Carlsbad, Calif.).

In some embodiments, the host cell is a vertebrate cell. In some embodiments, the host cell is a mammalian cell. In some embodiments, the mammalian host cell is selected from the group consisting of a 293 cell, a 293T cell, a CHO cell, a MCB3901 cell, and a COS-7 cell. In some embodiments, the host cell is a yeast cell. In some embodiments, the host cell is a melanophore cell. Other suitable host cells will be readily apparent to those of ordinary skill in the art, and a wide variety of cell lines are available from the American Type Culture Collection, 10801 University Boulevard, Manassas, Va. 20110-2209.

In certain embodiments, said determining is carried out using membrane comprising the G protein-coupled receptor.

In some embodiments, the test compound is a small molecule. In some embodiments, the test compound is a small molecule, with the proviso that the small molecule is not a polypeptide. In some embodiments, the test compound is a small molecule, with the proviso that the small molecule is not an antibody or an antigen-binding fragment thereof. In some embodiments, the test compound is a small molecule, with the proviso that the small molecule is not a lipid. In some embodiments, the test compound is a small molecule, with the proviso that the small molecule is not a polypeptide or a lipid. In some embodiments, the test compound is a polypeptide. In some embodiments, the test compound is a polypeptide, with the proviso that the polypeptide is not an antibody or an antigen-binding fragment thereof. In some embodiments, the test compound is a lipid. In some embodiments, the test compound is not an antibody or an antigen-binding fragment thereof. In some embodiments, the test compound is an antibody or an antigen-binding fragment thereof.

In some embodiments, the method further comprises the step of optionally determining the structure of the PYY secretagogue, the compound useful for treatment or prevention of a condition modulated by PYY, or the compound useful for a modulation of a PYY-related activity in an individual.

In some embodiments, the method further comprises the step of optionally providing the name or structure of the PYY secretagogue, the compound useful for treatment or prevention of a condition modulated by PYY, or the compound useful for a modulation of a PYY-related activity in an individual.

In some embodiments, said method further comprises the step of optionally producing or synthesizing the PYY secretagogue, the compound useful for treatment or prevention of a condition modulated by PYY, or the compound useful for a modulation of a PYY-related activity in an individual.

In some embodiments, the method further comprises the step of optionally determining the structure of the PYY secretagogue, the compound useful for treatment or prevention of a condition modulated by PYY, or the compound useful for a modulation of a PYY-related activity in an individual.

In some embodiments, the method further comprises the step of optionally providing the name or structure of the PYY secretagogue, the compound useful for treatment or prevention of a condition modulated by PYY, or the compound useful for a modulation of a PYY-related activity in an individual.

In some embodiments, said method further comprises the step of optionally producing or synthesizing the PYY secretagogue, the compound useful for treatment or prevention of a condition modulated by PYY, or the compound useful for a modulation of a PYY-related activity in an individual.

In some embodiments, said method further comprises the step of formulating the PYY secretagogue, the compound useful for treatment or prevention of a condition modulated by PYY, or the compound useful for a modulation of a PYY-related activity in an individual as a pharmaceutical.

In some embodiments, said method further comprises evaluating the bioavailability of the PYY secretagogue, the compound useful for treatment or prevention of a condition modulated by PYY, or the compound useful for a modulation of a PYY-related activity.

In some embodiments, said method further comprises the step of formulating the PYY secretagogue, the compound useful for treatment or prevention of a condition modulated by PYY, or the compound useful for a modulation of a PYY-related activity in an individual into a pharmaceutical composition.

The invention additionally features a process comprising performing a method according to this fourth aspect.

In a fifth aspect, the invention features a method of screening test compounds to identify a PYY secretagogue, a compound for treatment or prevention of a condition modulated by PYY, or a compound for a modulation of a PYY-related activity in an individual, which is characterized by using a G protein-coupled receptor comprising an amino acid sequence selected from the group consisting of:

(a) amino acids 1-335 of SEQ ID NO: 2;

(b) amino acids 2-335 of SEQ ID NO: 2;

(c) an amino acid sequence comprising the amino acid sequence of a polypeptide derived from (a) by substitution, deletion or addition of one or several amino acids in the amino acid sequence defined in (a);

(d) the amino acid sequence of a G protein-coupled receptor encoded by a polynucleotide hybridizing under stringent conditions to the complement of SEQ ID NO: 1;

(e) a variant of SEQ ID NO: 2 when selected from the group consisting of:
  (i) the amino acid sequence of a G protein-coupled receptor having at least about 80% identity to SEQ ID NO: 2; and
  (ii) the amino acid sequence of a G protein-coupled receptor comprising at least 20 contiguous amino acids of SEQ ID NO: 2;

(f) the amino acid sequence of a constitutively active version of a G protein-coupled receptor having SEQ ID NO: 2; and (g) a biologically active fragment of any one of any one of (a) to (f).

In certain embodiments, the G protein-coupled receptor comprises the amino acid sequence of a G protein-coupled receptor having at least about 80% identity to SEQ ID NO: 2.

In certain embodiments, the receptor comprises the amino acid sequence of SEQ ID NO: 2.

In certain embodiments, the variant of SEQ ID NO: 2 is an allele of SEQ ID NO: 2.

In certain embodiments, the variant of SEQ ID NO: 2 is an ortholog of SEQ ID NO: 2. In certain embodiments, the variant of SEQ ID NO: 2 is a mammalian ortholog of SEQ ID NO: 2.

In certain embodiments, the G protein-coupled receptor is recombinant.

In certain embodiments, the method comprises identifying an agonist of the receptor.

In certain embodiments, the method comprises identifying a partial agonist of the receptor.

In some embodiments, said method further comprises the step of formulating the PYY secretagogue, the compound useful for treatment or prevention of a condition modulated by PYY, or the compound useful for a modulation of a PYY-related activity in an individual as a pharmaceutical.

In some embodiments, said method further comprises evaluating the bioavailability of the PYY secretagogue, the compound useful for treatment or prevention of a condition modulated by PYY, or the compound useful for a modulation of a PYY-related activity.

In some embodiments, said method further comprises the step of formulating the PYY secretagogue, the compound useful for treatment or prevention of a condition modulated by PYY, or the compound useful for a modulation of a PYY-related activity in an individual into a pharmaceutical composition.

The invention additionally features a process comprising performing a method according to this fifth aspect.

In a sixth aspect, the invention features a method comprising, having identified a PYY secretagogue, a compound for treatment or prevention of a condition modulated by PYY, or a compound for a modulation of a PYY-related activity in an individual according to the first aspect, the second aspect, the third aspect, the fourth aspect or the fifth aspect, formulating said PYY secretagogue, said compound for treatment or prevention of a condition modulated by PYY, or said compound for a modulation of a PYY-related activity in an individual into a pharmaceutical composition.

In a seventh aspect, the invention features use of a G protein-coupled receptor to screen test compounds as PYY secretagogues, compounds for treatment or prevention of a condition modulated by PYY, or compounds for a modulation of a PYY-related activity in an individual, wherein the G protein-coupled receptor comprises an amino acid sequence selected from the group consisting of:

(a) amino acids 1-335 of SEQ ID NO: 2;
(b) amino acids 2-335 of SEQ ID NO: 2;
(c) an amino acid sequence comprising the amino acid sequence of a polypeptide derived from (a) by substitution, deletion or addition of one or several amino acids in the amino acid sequence defined in (a);
(d) the amino acid sequence of a G protein-coupled receptor encoded by a polynucleotide hybridizing under stringent conditions to the complement of SEQ ID NO: 1;
(e) a variant of SEQ ID NO: 2 when selected from the group consisting of:
  (i) the amino acid sequence of a G protein-coupled receptor having at least about 80% identity to SEQ ID NO: 2; and
  (ii) the amino acid sequence of a G protein-coupled receptor comprising at least 20 contiguous amino acids of SEQ ID NO: 2;
(f) the amino acid sequence of a constitutively active version of a G protein-coupled receptor having SEQ ID NO: 2; and
(g) a biologically active fragment of any one of any one of (a) to (f).

In certain embodiments, the G protein-coupled receptor comprises the amino acid sequence of a G protein-coupled receptor having at least about 80% identity to SEQ ID NO: 2.

In certain embodiments, the receptor comprises the amino acid sequence of SEQ ID NO: 2.

In certain embodiments, the variant of SEQ ID NO: 2 is an allele of SEQ ID NO: 2.

In certain embodiments, the variant of SEQ ID NO: 2 is an ortholog of SEQ ID NO: 2. In certain embodiments, the variant of SEQ ID NO: 2 is a mammalian ortholog of SEQ ID NO: 2.

In certain embodiments, the receptor is recombinant.

In certain embodiments, the test compound is a small molecule.

In certain embodiments, the test compound is a GPR119 agonist.

In certain embodiments, the GPR119 agonist is an agonist of an endogenous GPR119.

In certain embodiments, the GPR119 agonist is an agonist of human GPR119.

In certain embodiments, the GPR119 agonist is a GPR119 partial agonist.

In certain embodiments, the GPR119 agonist is a selective GPR119 agonist.

In certain embodiments, the GPR119 agonist is a small molecule.

In certain embodiments, the GPR119 agonist is orally available.

In certain embodiments, the GPR119 agonist has an $EC_{50}$ value of less than about 10 µM, less than about 1 µM, less than about 100 nM, less than about 75 nM, less than about 50 nM, less than about 25 nM, less than about 15 nM, less than about 10 nM, less than about 5 nM, less than about 4 nM, less than about 3 nM, less than about 2 nM, or less than about 1 nM. In certain embodiments, the GPR119 agonist has an $EC_{50}$ value of less than about 10 µM, less than about 1 µM, less than about 100 nM, less than about 75 nM, less than about 50 nM, less than about 25 nM, less than about 15 nM, less than about 10 nM, less than about 5 nM, less than about 4 nM, less than about 3 nM, less than about 2 nM, or less than about 1 nM at human GPR119 having SEQ ID NO: 2. In certain embodiments, the GPR119 agonist has an $EC_{50}$ value of less than about 10 µM, less than about 1 µM, less than about 100 nM, less than about 75 nM, less than about 50 nM, less than about 25 nM, less than about 15 nM, less than about 10 nM, less than about 5 nM, less than about 4 nM, less than about 3 nM, less than about 2 nM, or less than about 1 nM at human GPR119 having SEQ ID NO: 2 in adenylyl cyclase assay (exemplary adenylyl cyclase assay is provided in Example 9, Example 10 and in Example 11, infra). In certain embodiments, the GPR119 agonist has an $EC_{50}$ value of less than about 10 µM, less than about 1 µM, less than about 100 nM, less than about 75 nM, less than about 50 nM, less than about 25 nM, less than about 15 nM, less than about 10 nM, less than about 5 nM, less than about 4 nM, less than about 3 nM, less than about 2 nM, or less than about 1 nM at human GPR119 having SEQ ID NO: 2 in melanophore assay (exemplary melanophore assay is provided in Example 12, infra).

Exemplary GPR119 agonists are disclosed, e.g., in International Application No. PCT/US2004/001267 (published as WO 04/065380); International Application No. PCT/US2004/005555 (published as WO 04/076413); International Application No. PCT/US2004/022327 (published as WO 05/007647); International Application No. PCT/US2004/022417 (published as WO 05/007658); International Application No. PCT/US2005/019318 (published as WO 2005/121121); International Application No. PCT/GB2004/050046 (published as WO 2005/061489); International Application No. PCT/US06/00567 (published as WO 2006/083491); International Application No. PCT/GB2005/050264 (published as WO 2006/067531); International Application No. PCT/GB2005/050265 (published as WO 2006/067532); International Application No. PCT/GB2005/050266 (published as WO 2006/070208); International Application No. PCT/JP02/09350 (published as WO 03/026661); International Application No. PCT/JP2005/018412 (published as WO 06/040966); International Application No. PCT/JP2005/019000 (published as WO 2006/043490); International Application No. PCT/GB2006/050176 (published as WO 2007/003960); International Application No. PCT/GB2006/050177 (published as WO 2007/003961); International Application No. PCT/GB2006/050178 (published as WO 2007/003962); International Application No. PCT/GB2006/050182 (published as WO 2007/003964); International Application No. PCT/JP02/09350 (published as WO 03/026661); International Application No. PCT/GB2007/050183 (published as WO 2007/116229); International Application No. PCT/GB2007/050190 (published as WO 2007/116230); International Application No. PCT/US2007/073364 (published as WO 2008/008895); International Application No. PCT/EP2007/058991 (published as WO 2008/025798); International Application No. PCT/EP2007/058993 (published as WO 2008/025799); and International Application No. PCT/EP2007/058995 (published as WO 2008/025800).

In an eighth aspect, the invention features a method for identifying PYY secretagogues, compounds useful for treatment or prevention of a condition modulated by PYY, or compounds useful for a modulation of a PYY-related activity in an individual, comprising the steps of:
  (a) contacting a compound which stimulates functionality of a G protein-coupled receptor, wherein said G protein-coupled receptor comprises an amino acid sequence selected from the group consisting of:
    (i) amino acids 1-335 of SEQ ID NO:2;
    (ii) amino acids 2-335 of SEQ ID NO:2;
    (iii) an amino acid sequence comprising the amino acid sequence of a polypeptide derived from (i) by substitution, deletion or addition of one or several amino acids in the amino acid sequence defined in (i);
    (iv) the amino acid sequence of a G protein-coupled receptor encoded by a polynucleotide hybridizing under stringent conditions to the complement of SEQ ID NO:1;
    (v) a variant of SEQ ID NO: 2 when selected from the group consisting of:
      (a') the amino acid sequence of a G protein-coupled receptor having at least about 80% identity to SEQ ID NO: 2; and
      (b') an amino acid sequence of a G protein-coupled receptor comprising at least 20 contiguous amino acids of SEQ ID NO: 2;
    (vi) the amino acid sequence of a constitutively active version of a G protein-coupled receptor having SEQ ID NO: 2; and
    (vii) a biologically active fragment of any one of (i) to (vi);
  in vitro with a vertebrate enteroendocrine cell or with a cell capable of secreting PYY, said compound having been determined or identified by a method according to the first aspect; and
  (b) determining whether the compound stimulates PYY secretion from the vertebrate enteroendocrine cell or from the cell capable of secreting PYY;
wherein the ability of the test compound to stimulate PYY secretion from the vertebrate enteroendocrine cell or from the cell capable of secreting PYY is further indicative of the test compound being a PYY secretagogue, a compound useful for treatment or prevention of a condition modulated by PYY, or a compound useful for a modulation of a PYY-related activity in an individual.

In certain embodiments, the G protein-coupled receptor comprises the amino acid sequence of a G protein-coupled receptor having at least about 80% identity to SEQ ID NO: 2.

In certain embodiments, the receptor comprises the amino acid sequence of SEQ ID NO: 2.

In certain embodiments, the variant of SEQ ID NO: 2 is an allele of SEQ ID NO: 2.

In certain embodiments, the variant of SEQ ID NO: 2 is an ortholog of SEQ ID NO: 2. In certain embodiments, the variant of SEQ ID NO: 2 is a mammalian ortholog of SEQ ID NO: 2.

In certain embodiments, the G protein-coupled receptor is recombinant.

In certain embodiments, the vertebrate enteroendocrine cell is a mammalian enteroendocrine cell. In certain embodiments, the enteroendocrine cell is an L cell. In certain embodiments, the enteroendocrine cell is comprised by or derived from tissue obtained from the small or large intestine. In certain embodiments, the enteroendocrine cell is comprised by or derived from tissue obtained from an L cell-containing region of small or large intestine. In certain embodiments, the enteroendocrine cell is comprised by or derived from duodenum, jejunum, ileum, colon or rectum tissue (see, e.g., Lundberg et al, PNAS USA (1982) 79:4471-4475; Adrian et al, Gastroenterol (1985) 89:1070-1077; Ekblad et al, Peptides (2002) 23:251-261; Ueno et al, Regul Pept (2008) 145:12-16). In certain embodiments, the enteroendocrine cell is an enteroendocrine cell line. In certain embodiments, the cell capable of secreting PYY is a cell comprised by or derived from the islets of Langerhans. In certain embodiments, the cell capable of secreting PYY is a neuronal cell. In certain embodiments, the cell capable of secreting PYY is a recombinant cell engineered to be capable of secreting PYY.

The invention additionally features a method for identifying PYY secretagogues, compounds useful for treatment or prevention of a condition modulated by PYY, or compounds useful for a modulation of a PYY-related activity in an individual, comprising the steps of:
  (a) administering to a vertebrate a compound which stimulates functionality of a G protein-coupled receptor, wherein said G protein-coupled receptor comprises an amino acid sequence selected from the group consisting of:
    (i) amino acids 1-335 of SEQ ID NO:2;
    (ii) amino acids 2-335 of SEQ ID NO:2;
    (iii) an amino acid sequence comprising the amino acid sequence of a polypeptide derived from (i) by substitution, deletion or addition of one or several amino acids in the amino acid sequence defined in (i);
    (iv) the amino acid sequence of a G protein-coupled receptor encoded by a polynucleotide hybridizing under stringent conditions to the complement of SEQ ID NO:1;
    (v) a variant of SEQ ID NO: 2 when selected from the group consisting of:

(a') the amino acid sequence of a G protein-coupled receptor having at least about 80% identity to SEQ ID NO: 2; and
(b') an amino acid sequence of a G protein-coupled receptor comprising at least 20 contiguous amino acids of SEQ ID NO: 2;
(vi) the amino acid sequence of a constitutively active version of a G protein-coupled receptor having SEQ ID NO: 2; and
(vii) a biologically active fragment of any one of (i) to (vi); said compound having been determined or identified by a method according to the first aspect; and
(b) determining whether the compound increases a PYY level in the vertebrate;

wherein the ability of the test compound to increase a PYY level in the vertebrate is further indicative of the test compound being a PYY secretagogue, a compound useful for treatment or prevention of a condition modulated by PYY, or a compound useful for a modulation of a PYY-related activity in an individual.

In certain embodiments, the G protein-coupled receptor comprises the amino acid sequence of a G protein-coupled receptor having at least about 80% identity to SEQ ID NO: 2.

In certain embodiments, the receptor comprises the amino acid sequence of SEQ ID NO: 2.

In certain embodiments, the variant of SEQ ID NO: 2 is an allele of SEQ ID NO: 2.

In certain embodiments, the variant of SEQ ID NO: 2 is an ortholog of SEQ ID NO: 2. In certain embodiments, the variant of SEQ ID NO: 2 is a mammalian ortholog of SEQ ID NO: 2.

In certain embodiments, the G protein-coupled receptor is recombinant.

In certain embodiments, the PYY level is blood or plasma concentration of total PYY. In certain embodiments, the PYY level is blood or plasma concentration of $PYY_{3-36}$.

In certain embodiments, the vertebrate is a mammal. In certain embodiments, the vertebrate is a non-human vertebrate. In certain embodiments, the vertebrate is a non-human mammal. In certain embodiments, the mammal is a non-human mammal.

In certain embodiments, the vertebrate or the mammal is a human. In certain embodiments, the human is a participant in a study reviewed by a governmental agency charged with marketing approval for a drug. In certain embodiments, the study is a clinical trial. In certain embodiments, the governmental agency is the Food and Drug Administration of the United States.

The invention additionally features a method for identifying PYY secretagogues, compounds useful for treatment or prevention of a condition modulated by PYY, or compounds useful for a modulation of a PYY-related activity in an individual, comprising the steps of:
(a) determining whether the compound increases a PYY level in a sample, said sample having been obtained from a vertebrate previously administered with a compound which stimulates functionality of a G protein-coupled receptor, wherein said G protein-coupled receptor comprises an amino acid sequence selected from the group consisting of:
(i) amino acids 1-335 of SEQ ID NO:2;
(ii) amino acids 2-335 of SEQ ID NO:2;
(iii) an amino acid sequence comprising the amino acid sequence of a polypeptide derived from (i) by substitution, deletion or addition of one or several amino acids in the amino acid sequence defined in (i);
(iv) the amino acid sequence of a G protein-coupled receptor encoded by a polynucleotide hybridizing under stringent conditions to the complement of SEQ ID NO:1;
(v) a variant of SEQ ID NO: 2 when selected from the group consisting of:
(a') the amino acid sequence of a G protein-coupled receptor having at least about 80% identity to SEQ ID NO: 2; and
(b') an amino acid sequence of a G protein-coupled receptor comprising at least 20 contiguous amino acids of SEQ ID NO: 2;
(vi) the amino acid sequence of a constitutively active version of a G protein-coupled receptor having SEQ ID NO: 2; and
(vii) a biologically active fragment of any one of (i) to (vi);
said compound having been determined or identified by a method according to the first aspect; and wherein the ability of the test compound to increase a PYY level in the vertebrate is further indicative of the test compound being a PYY secretagogue, a compound useful for treatment or prevention of a condition modulated by PYY, or a compound useful for a modulation of a PYY-related activity in an individual.

In certain embodiments, the G protein-coupled receptor comprises the amino acid sequence of a G protein-coupled receptor having at least about 80% identity to SEQ ID NO: 2.

In certain embodiments, the receptor comprises the amino acid sequence of SEQ ID NO: 2.

In certain embodiments, the variant of SEQ ID NO: 2 is an allele of SEQ ID NO: 2.

In certain embodiments, the variant of SEQ ID NO: 2 is an ortholog of SEQ ID NO: 2. In certain embodiments, the variant of SEQ ID NO: 2 is a mammalian ortholog of SEQ ID NO: 2.

In certain embodiments, the G protein-coupled receptor is recombinant.

In certain embodiments, the vertebrate is a mammal. In certain embodiments, the vertebrate is a non-human vertebrate. In certain embodiments, the vertebrate is a non-human mammal. In certain embodiments, the mammal is a non-human mammal.

In certain embodiments, the vertebrate or the mammal is a human. In certain embodiments, the human is a participant in a study reviewed by a governmental agency charged with marketing approval for a drug. In certain embodiments, the study is a clinical trial. In certain embodiments, the governmental agency is the Food and Drug Administration of the United States.

In some embodiments, a G protein-coupled receptor of the invention is SEQ ID NO:2 or an allele thereof. In some embodiments, a G protein-coupled receptor of the invention is an allele of SEQ ID NO:2. In some embodiments, a G protein-coupled receptor of the invention is an ortholog of SEQ ID NO:2.

In some embodiments, a G protein-coupled receptor of the invention is a G protein-coupled receptor which specifically binds (2-Fluoro-4-methanesulfonyl-phenyl)-{6-[4-(3-isopropyl-[1,2,4]oxadiazol-5-yl)-piperidin-1-yl]-5-nitro-pyrimidin-4-yl}-amine. In some embodiments, a G protein-coupled receptor of the invention is a G protein-coupled receptor for which (2-Fluoro-4-methanesulfonyl-phenyl)-{6-[4-(3-isopropyl-[1,2,4]oxadiazol-5-yl)-piperidin-1-yl]-5-nitro-pyrimidin-4-yl}-amine is a ligand. In some embodiments, a G protein-coupled receptor of the invention is a G protein-coupled receptor for which (2-Fluoro-4-methanesulfonyl-phenyl)-{6-[4-(3-isopropyl-[1,2,4]oxadiazol-5-yl)-piperidin-1-yl]-5-nitro-pyrimidin-4-yl}-amine is an agonist. In some embodiments, a G protein-coupled receptor of the invention exhibits a detectable level of constitutive activity. In some embodiments, the constitutive activity is for increasing a level of intracellular cAMP accumulation. In some embodiments, the constitutive activity is for causing melanophore cells to undergo pigment dispersion.

In certain embodiments, stringent hybridization conditions comprise hybridization at 42° C. in a solution comprising 50% formamide, 5×SSC (1×SSC=150 mM NaCl, 15 mM trisodium citrate), 50 mM sodium phosphate (pH 7.6), 5×Denhardt's solution, 10% dextran sulfate, and 20 µg/ml denatured, sheared salmon sperm DNA, followed by washing at 65° C. in a solution comprising 0.1×SSC. Hybridization techniques are well known to the skilled artisan.

In certain embodiments, the GPCR encoded by a polynucleotide hybridizing under stringent conditions to the complement of SEQ ID NO: 1 is SEQ ID NO:2 or an allele thereof. In certain embodiments, the GPCR encoded by a polynucleotide hybridizing under stringent conditions to the complement of SEQ ID NO: 1 is an allele of SEQ ID NO:2. In certain embodiments, the GPCR encoded by a polynucleotide hybridizing under stringent conditions to the complement of SEQ ID NO: 1 is an ortholog of SEQ ID NO:2. In certain embodiments, the GPCR encoded by a polynucleotide hybridizing under stringent conditions to the complement of SEQ ID NO: 1 specifically binds (2-Fluoro-4-methanesulfonyl-phenyl)-{6-[4-(3-isopropyl-[1,2,4]oxadiazol-5-yl)-piperidin-1-yl]-5-nitro-pyrimidin-4-yl}-amine. In certain embodiments, the GPCR encoded by a polynucleotide hybridizing under stringent conditions to the complement of SEQ ID NO: 1 is a receptor for which (2-Fluoro-4-methane-sulfonyl-phenyl)-{6-[4-(3-isopropyl-[1,2,4]oxadiazol-5-yl)-piperidin-1-yl]-5-nitro-pyrimidin-4-yl}-amine is a ligand. In certain embodiments, the GPCR encoded by a polynucleotide hybridizing under stringent conditions to the complement of SEQ ID NO: 1 is a receptor for which (2-Fluoro-4-methane-sulfonyl-phenyl)-{6-[4-(3-isopropyl-[1,2,4]oxadiazol-5-yl)-piperidin-1-yl]-5-nitro-pyrimidin-4-yl}-amine is an agonist. In some embodiments, the GPCR encoded by a polynucleotide hybridizing under stringent conditions to the complement of SEQ ID NO: 1 exhibits a detectable level of constitutive activity. In some embodiments, the constitutive activity is for increasing a level of intracellular cAMP. In some embodiments, the constitutive activity is for causing melanophore cells to undergo pigment dispersion.

In certain embodiments, the variant of SEQ ID NO:2 is a G protein-coupled receptor having at least about 80% identity to SEQ ID NO:2. In certain embodiments, the variant of SEQ ID NO:2 is a G protein-coupled receptor comprising at least 20 contiguous amino acids of SEQ ID NO:2. In certain embodiments, the variant of SEQ ID NO:2 which is a G protein-coupled receptor is an endogenous G protein-coupled receptor. In certain embodiments, the variant of SEQ ID NO:2 which is a G protein-coupled receptor is a non-endogenous G protein-coupled receptor.

In certain embodiments, the G protein-coupled receptor which has at least about 80% identity to SEQ ID NO: 2 is SEQ ID NO: 2 or an allele thereof. In certain embodiments, the G protein-coupled receptor which has at least about 80% identity to SEQ ID NO: 2 is an allele of SEQ ID NO: 2. In certain embodiments, the G protein-coupled receptor which has at least about 80% identity to SEQ ID NO: 2 is an ortholog of SEQ ID NO: 2. In certain embodiments, the G protein-coupled receptor which has at least about 80% identity to SEQ ID NO: 2 specifically binds (2-Fluoro-4-methanesulfonyl-phenyl)-{6-[4-(3-isopropyl-[1,2,4]oxadiazol-5-yl)-piperidin-1-yl]-5-nitro-pyrimidin-4-yl}-amine. In certain embodiments, the G protein-coupled receptor which has at least about 80% identity to SEQ ID NO: 2 is a receptor for which (2-Fluoro-4-methanesulfonyl-phenyl)-{6-[4-(3-isopropyl-[1,2,4]oxadiazol-5-yl)-piperidin-1-yl]-5-nitro-pyrimidin-4-yl}-amine is an agonist. In some embodiments, the G protein-coupled receptor which has at least about 80% identity to SEQ ID NO: 2 exhibits a detectable level of constitutive activity. In some embodiments, the constitutive activity is for increasing a level of intracellular cAMP. In some embodiments, the constitutive activity is for causing melanophore cells to undergo pigment dispersion.

In certain embodiments, the G protein-coupled receptor which comprises at least 20 contiguous amino acids of SEQ ID NO: 2 is SEQ ID NO: 2 or an allele of SEQ ID NO: 2. In certain embodiments, the G protein-coupled receptor which comprises at least 20 contiguous amino acids of SEQ ID NO: 2 is an allele of SEQ ID NO: 2. In certain embodiments, the G protein-coupled receptor which comprises at least 20 contiguous amino acids of SEQ ID NO: 2 is an ortholog of SEQ ID NO: 2. In certain embodiments, the G protein-coupled receptor which comprises at least 20 contiguous amino acids of SEQ ID NO: 2 specifically binds (2-Fluoro-4-methane-sulfonyl-phenyl)-{6-[4-(3-isopropyl-[1,2,4]oxadiazol-5-yl)-piperidin-1-yl]-5-nitro-pyrimidin-4-yl}-amine. In certain embodiments, the G protein-coupled receptor which comprises at least 20 contiguous amino acids of SEQ ID NO: 2 is a receptor for which (2-Fluoro-4-methanesulfonyl-phenyl)-{6-[4-(3-isopropyl-[1,2,4]oxadiazol-5-yl)-piperidin-1-yl]-5-nitro-pyrimidin-4-yl}-amine is an agonist. In some embodiments, the G protein-coupled receptor which comprises at least 20 contiguous amino acids of SEQ ID NO: 2 exhibits a detectable level of constitutive activity. In some embodiments, the constitutive activity is for increasing a level of intracellular cAMP. In some embodiments, the constitutive activity is for causing melanophore cells to undergo pigment dispersion.

In some embodiments, the G protein-coupled receptor is part of a fusion protein comprising a G protein. Techniques for making a GPCR:G fusion construct are well known to the skilled artisan (see, e.g., International Application WO 02/42461).

In some embodiments, the compound which stimulates functionality of a G protein-coupled receptor is a small molecule. In some embodiments, the compound which stimulates functionality of a G protein-coupled receptor is a small molecule, with the proviso that the small molecule is not a polypeptide. In some embodiments, the compound which stimulates functionality of a G protein-coupled receptor is a small molecule, with the proviso that the small molecule is not an antibody or an antigen-binding fragment thereof. In some embodiments, the compound which stimulates functionality of a G protein-coupled receptor is a small molecule, with the proviso that the small molecule is not a lipid. In some embodiments, the compound which stimulates functionality of a G protein-coupled receptor is a small molecule, with the proviso that the small molecule is not a polypeptide or a lipid. In some embodiments, the compound which stimulates functionality of a G protein-coupled receptor is a polypeptide. In some embodiments, the compound which stimulates functionality of a G protein-coupled receptor is a polypeptide, with the proviso that the polypeptide is not an antibody or an antigen-binding fragment thereof. In some embodiments, the compound which stimulates functionality of a G protein-coupled receptor is a lipid. In some embodiments, the compound which stimulates functionality of a G protein-coupled receptor is not an antibody or an antigen-binding fragment thereof. In some embodiments, the compound which stimulates functionality of a G protein-coupled receptor is an antibody or an antigen-binding fragment thereof.

In some embodiments, the method further comprises the step of optionally determining the structure of the PYY secretagogue, the compound useful for treatment or prevention of a condition modulated by PYY, or the compound useful for a modulation of a PYY-related activity in an individual.

In some embodiments, the method further comprises the step of optionally providing the name or structure of the PYY secretagogue, the compound useful for treatment or prevention of a condition modulated by PYY, or the compound useful for a modulation of a PYY-related activity in an individual.

In some embodiments, said method further comprises the step of optionally producing or synthesizing the PYY secretagogue, the compound useful for treatment or prevention of a condition modulated by PYY, or the compound useful for a modulation of a PYY-related activity in an individual.

In some embodiments, said method further comprises the step of formulating the PYY secretagogue, the compound useful for treatment or prevention of a condition modulated by PYY, or the compound useful for a modulation of a PYY-related activity in an individual as a pharmaceutical.

In some embodiments, said method further comprises evaluating the bioavailability of the PYY secretagogue, the compound useful for treatment or prevention of a condition modulated by PYY, or the compound useful for a modulation of a PYY-related activity.

In some embodiments, said method further comprises the step of formulating the PYY secretagogue, the compound useful for treatment or prevention of a condition modulated by PYY, or the compound useful for a modulation of a PYY-related activity in an individual into a pharmaceutical composition.

The invention additionally features a process comprising performing a method according to this eighth aspect.

In a ninth aspect, the invention features a method for identifying PYY secretagogues, compounds useful for treatment or prevention of a condition modulated by PYY, or compounds useful for a modulation of a PYY-related activity in an individual, comprising the steps of:
(a) contacting a compound in the presence of which less of a complex between a G protein-coupled receptor and an optionally labelled known ligand to the receptor is formed than in the absence of the compound, wherein the G protein-coupled receptor comprises an amino acid sequence selected from the group consisting of:
  (i) amino acids 1-335 of SEQ ID NO:2;
  (ii) amino acids 2-335 of SEQ ID NO:2;
  (iii) an amino acid sequence comprising the amino acid sequence of a polypeptide derived from (i) by substitution, deletion or addition of one or several amino acids in the amino acid sequence defined in (i);
  (iv) the amino acid sequence of a G protein-coupled receptor encoded by a polynucleotide hybridizing under stringent conditions to the complement of SEQ ID NO:1;
  (v) a variant of SEQ ID NO: 2 when selected from the group consisting of:
    (a') the amino acid sequence of a G protein-coupled receptor having at least about 80% identity to SEQ ID NO: 2; and
    (b') the amino acid sequence of a G protein-coupled receptor comprising at least 20 contiguous amino acids of SEQ ID NO: 2;
  (vi) the amino acid sequence of a constitutively active version of a G protein-coupled receptor having SEQ ID NO: 2; and
  (vii) a biologically active fragment of any one of (i) to (vi);
in vitro with a vertebrate enteroendocrine cell or with a cell capable of secreting PYY, said compound having been determined or identified by a method according to the fourth aspect; and
(b) determining whether the compound stimulates PYY secretion from the vertebrate enteroendocrine cell or from the cell capable of secreting PYY;

wherein the ability of the test compound to stimulate PYY secretion from the vertebrate enteroendocrine cell or from the cell capable of secreting PYY is further indicative of the test compound being a PYY secretagogue, a compound useful for treatment or prevention of a condition modulated by PYY, or a compound useful for a modulation of a PYY-related activity in an individual.

In certain embodiments, the G protein-coupled receptor comprises the amino acid sequence of a G protein-coupled receptor having at least about 80% identity to SEQ ID NO: 2.

In certain embodiments, the receptor comprises the amino acid sequence of SEQ ID NO: 2.

In certain embodiments, the variant of SEQ ID NO: 2 is an allele of SEQ ID NO: 2.

In certain embodiments, the variant of SEQ ID NO: 2 is an ortholog of SEQ ID NO: 2. In certain embodiments, the variant of SEQ ID NO: 2 is a mammalian ortholog of SEQ ID NO: 2.

In certain embodiments, the G protein-coupled receptor is recombinant.

In certain embodiments, the vertebrate enteroendocrine cell is a mammalian enteroendocrine cell. In certain embodiments, the enteroendocrine cell is an L cell. In certain embodiments, the enteroendocrine cell is comprised by or derived from tissue obtained from the small or large intestine. In certain embodiments, the enteroendocrine cell is comprised by or derived from tissue obtained from an L cell-containing region of small or large intestine. In certain embodiments, the enteroendocrine cell is comprised by or derived from duodenum, jejunum, ileum, colon or rectum tissue (see, e.g., Lundberg et al, PNAS USA (1982) 79:4471-4475; Adrian et al, Gastroenterol (1985) 89:1070-1077; Ekblad et al, Peptides (2002) 23:251-261; Ueno et al, Regul Pept (2008) 145:12-16). In certain embodiments, the enteroendocrine cell is an enteroendocrine cell line. In certain embodiments, the cell capable of secreting PYY is a cell comprised by or derived from the islets of Langerhans. In certain embodiments, the cell capable of secreting PYY is a neuronal cell. In certain embodiments, the cell capable of secreting PYY is a recombinant cell engineered to be capable of secreting PYY.

The invention additionally features a method for identifying PYY secretagogues, compounds useful for treatment or prevention of a condition modulated by PYY, or compounds useful for a modulation of a PYY-related activity in an individual, comprising the steps of:
(a) administering a compound to a vertebrate, wherein in the presence of said compound less of a complex between a G protein-coupled receptor and an optionally labelled known ligand to the receptor is formed than in the absence of the compound, wherein the G protein-coupled receptor comprises an amino acid sequence selected from the group consisting of:
(i) amino acids 1-335 of SEQ ID NO:2;
(ii) amino acids 2-335 of SEQ ID NO:2;
(iii) an amino acid sequence comprising the amino acid sequence of a polypeptide derived from (i) by substitution, deletion or addition of one or several amino acids in the amino acid sequence in (i);
(iv) the amino acid sequence of a G protein-coupled receptor encoded by a polynucleotide hybridizing under stringent conditions to the complement of SEQ ID NO:1;
(v) a variant of SEQ ID NO: 2 when selected from the group consisting of:
(a') the amino acid sequence of a G protein-coupled receptor having at least about 80% identity to SEQ ID NO: 2; and
(b') the amino acid sequence of a G protein-coupled receptor comprising at least 20 contiguous amino acids of SEQ ID NO: 2;
(vi) the amino acid sequence of a constitutively active version of a G protein-coupled receptor having SEQ ID NO: 2; and
(vii) a biologically active fragment of any one of (i) to (vi);
said compound having been determined or identified by a method according to the fourth aspect; and
(b) determining whether the compound increases a PYY level in the vertebrate;

wherein the ability of the test compound to increase a PYY level in the vertebrate is further indicative of the test compound being a PYY secretagogue, a compound useful for treatment or prevention of a condition modulated by PYY, or a compound useful for a modulation of a PYY-related activity in an individual.

In certain embodiments, the vertebrate is a mammal. In certain embodiments, the vertebrate is a non-human vertebrate. In certain embodiments, the vertebrate is a non-human mammal. In certain embodiments, the mammal is a non-human mammal.

In certain embodiments, the vertebrate or the mammal is a human. In certain embodiments, the human is a participant in a study reviewed by a governmental agency charged with marketing approval for a drug. In certain embodiments, the study is a clinical trial. In certain embodiments, the governmental agency is the Food and Drug Administration of the United States.

The invention additionally features a method for identifying PYY secretagogues, compounds useful for treatment or prevention of a condition modulated by PYY, or compounds useful for a modulation of a PYY-related activity in an individual, comprising the steps of:
(a) determining whether the compound increases a PYY level in a sample, said sample having been obtained from a vertebrate previous administered with a compound in the presence of which less of a complex between a G protein-coupled receptor and an optionally labelled known ligand to the receptor is formed than in the absence of the compound, wherein the G protein-coupled receptor comprises an amino acid sequence selected from the group consisting of:
(i) amino acids 1-335 of SEQ ID NO:2;
(ii) amino acids 2-335 of SEQ ID NO:2;
(iii) an amino acid sequence comprising the amino acid sequence of a polypeptide derived from (i) by substitution, deletion or addition of one or several amino acids in the amino acid sequence defined in (i);
(iv) the amino acid sequence of a G protein-coupled receptor encoded by a polynucleotide hybridizing under stringent conditions stringency to the complement of SEQ ID NO: 1;
(v) a variant of SEQ ID NO: 2 when selected from the group consisting of:
(a') the amino acid sequence of a G protein-coupled receptor having at least about 80% identity to SEQ ID NO: 2; and
(b') the amino acid sequence of a G protein-coupled receptor comprising at least 20 contiguous amino acids of SEQ ID NO: 2;
(vi) the amino acid sequence of a constitutively active version of a G protein-coupled receptor having SEQ ID NO: 2; and
(vii) a biologically active fragment of any one of (i) to (vi);
said compound having been determined or identified by a method according to the fourth aspect; and wherein the ability of the test compound to increase a PYY level in the vertebrate is further indicative of the test compound being a PYY secretagogue, a compound useful for treatment or prevention of a condition modulated by PYY, or a compound useful for a modulation of a PYY-related activity in an individual.

In certain embodiments, the vertebrate is a mammal. In certain embodiments, the vertebrate is a non-human vertebrate. In certain embodiments, the vertebrate is a non-human mammal. In certain embodiments, the mammal is a non-human mammal.

In certain embodiments, the vertebrate or the mammal is a human. In certain embodiments, the human is a participant in a study reviewed by a governmental agency charged with marketing approval for a drug. In certain embodiments, the study is a clinical trial. In certain embodiments, the governmental agency is the Food and Drug Administration of the United States.

In some embodiments, a G protein-coupled receptor of the invention is SEQ ID NO:2 or an allele thereof. In some embodiments, a G protein-coupled receptor of the invention is an allele of SEQ ID NO:2. In some embodiments, a G protein-coupled receptor of the invention is an ortholog of SEQ ID NO:2.

In some embodiments, a G protein-coupled receptor of the invention is a G protein-coupled receptor which specifically binds (2-Fluoro-4-methanesulfonyl-phenyl)-{6-[4-(3-isopropyl-[1,2,4]oxadiazol-5-yl)-piperidin-1-yl]-5-nitro-pyrimidin-4-yl}-amine. In some embodiments, a G protein-coupled receptor of the invention is a G protein-coupled receptor for which (2-Fluoro-4-methanesulfonyl-phenyl)-{6-[4-(3-isopropyl-[1,2,4]oxadiazol-5-yl)-piperidin-1-yl]-5-nitro-pyrimidin-4-yl}-amine is a ligand. In some embodiments, a G protein-coupled receptor of the invention is a G protein-coupled receptor for which (2-Fluoro-4-methanesulfonyl-phenyl)-{6-[4-(3-isopropyl-[1,2,4]oxadiazol-5-yl)-piperidin-1-yl]-5-nitro-pyrimidin-4-yl}-amine is an agonist. In some embodiments, a G protein-coupled receptor of the invention exhibits a detectable level of constitutive activity. In some embodiments, the constitutive activity is for increasing a level of intracellular cAMP accumulation. In some embodiments, the constitutive activity is for causing melanophore cells to undergo pigment dispersion.

In certain embodiments, stringent hybridization conditions comprise hybridization at 42° C. in a solution comprising 50% formamide, 5×SSC (1×SSC=150 mM NaCl, 15 mM trisodium citrate), 50 mM sodium phosphate (pH 7.6), 5×Denhardt's solution, 10% dextran sulfate, and 20 μg/ml denatured, sheared salmon sperm DNA, followed by washing at 65° C. in a solution comprising 0.1×SSC. Hybridization techniques are well known to the skilled artisan.

In certain embodiments, the GPCR encoded by a polynucleotide hybridizing under stringent conditions to the complement of SEQ ID NO: 1 is SEQ ID NO:2 or an allele thereof. In certain embodiments, the GPCR encoded by a polynucleotide hybridizing under stringent conditions to the complement of SEQ ID NO: 1 is an allele of SEQ ID NO:2. In certain embodiments, the GPCR encoded by a polynucleotide hybridizing under stringent conditions to the complement of SEQ ID NO: 1 is an ortholog of SEQ ID NO:2. In certain embodiments, the GPCR encoded by a polynucleotide hybridizing under stringent conditions to the complement of SEQ ID NO: 1 specifically binds (2-Fluoro-4-methanesulfonyl-phenyl)-{6-[4-(3-isopropyl-[1,2,4]oxadiazol-5-yl)-piperidin-1-yl]-5-nitro-pyrimidin-4-yl}-amine. In certain embodiments, the GPCR encoded by a polynucleotide hybridizing under stringent conditions to the complement of SEQ ID NO: 1 is a receptor for which (2-Fluoro-4-methanesulfonyl-phenyl)-{6-[4-(3-isopropyl-[1,2,4]oxadiazol-5-yl)-piperidin-1-yl]-5-nitro-pyrimidin-4-yl}-amine is a ligand. In certain embodiments, the GPCR encoded by a polynucleotide hybridizing under stringent conditions to the complement of SEQ ID NO: 1 is a receptor for which (2-Fluoro-4-methanesulfonyl-phenyl)-{6-[4-(3-isopropyl-[1,2,4]oxadiazol-5-yl)-piperidin-1-yl]-5-nitro-pyrimidin-4-yl}-amine is an agonist. In some embodiments, the GPCR encoded by a polynucleotide hybridizing under stringent conditions to the complement of SEQ ID NO: 1 exhibits a detectable level of constitutive activity. In some embodiments, the constitutive activity is for increasing a level of intracellular cAMP. In some embodiments, the constitutive activity is for causing melanophore cells to undergo pigment dispersion.

In certain embodiments, the variant of SEQ ID NO:2 is a G protein-coupled receptor having at least about 80% identity to SEQ ID NO:2. In certain embodiments, the variant of SEQ ID NO:2 is a G protein-coupled receptor comprising at least 20 contiguous amino acids of SEQ ID NO:2. In certain embodiments, the variant of SEQ ID NO:2 which is a G protein-coupled receptor is an endogenous G protein-coupled receptor. In certain embodiments, the variant of SEQ ID NO:2 which is a G protein-coupled receptor is a non-endogenous G protein-coupled receptor.

In certain embodiments, the G protein-coupled receptor which has at least about 80% identity to SEQ ID NO: 2 is SEQ ID NO: 2 or an allele thereof. In certain embodiments, the G protein-coupled receptor which has at least about 80% identity to SEQ ID NO: 2 is an allele of SEQ ID NO: 2. In certain embodiments, the G protein-coupled receptor which has at least about 80% identity to SEQ ID NO: 2 is an ortholog of SEQ ID NO: 2. In certain embodiments, the G protein-coupled receptor which has at least about 80% identity to SEQ ID NO: 2 specifically binds (2-Fluoro-4-methanesulfonyl-phenyl)-{6-[4-(3-isopropyl-[1,2,4]oxadiazol-5-yl)-piperidin-1-yl]-5-nitro-pyrimidin-4-yl}-amine. In certain embodiments, the G protein-coupled receptor which has at least about 80% identity to SEQ ID NO: 2 is a receptor for which (2-Fluoro-4-methanesulfonyl-phenyl)-{6-[4-(3-isopropyl-[1,2,4]oxadiazol-5-yl)-piperidin-1-yl]-5-nitro-pyrimidin-4-yl}-amine is an agonist. In some embodiments, the G protein-coupled receptor which has at least about 80% identity to SEQ ID NO: 2 exhibits a detectable level of constitutive activity. In some embodiments, the constitutive activity is for increasing a level of intracellular cAMP. In some embodiments, the constitutive activity is for causing melanophore cells to undergo pigment dispersion.

In certain embodiments, the G protein-coupled receptor which comprises at least 20 contiguous amino acids of SEQ ID NO: 2 is SEQ ID NO: 2 or an allele of SEQ ID NO: 2. In certain embodiments, the G protein-coupled receptor which comprises at least 20 contiguous amino acids of SEQ ID NO: 2 is an allele of SEQ ID NO: 2. In certain embodiments, the G protein-coupled receptor which comprises at least 20 contiguous amino acids of SEQ ID NO: 2 is an ortholog of SEQ ID NO: 2. In certain embodiments, the G protein-coupled receptor which comprises at least 20 contiguous amino acids of SEQ ID NO: 2 specifically binds (2-Fluoro-4-methanesulfonyl-phenyl)-{6-[4-(3-isopropyl-[1,2,4]oxadiazol-5-yl)-piperidin-1-yl]-5-nitro-pyrimidin-4-yl}-amine. In certain embodiments, the G protein-coupled receptor which comprises at least 20 contiguous amino acids of SEQ ID NO: 2 is a receptor for which (2-Fluoro-4-methanesulfonyl-phenyl)-{6-[4-(3-isopropyl-[1,2,4]oxadiazol-5-yl)-piperidin-1-yl]-5-nitro-pyrimidin-4-yl}-amine is an agonist. In some embodiments, the G protein-coupled receptor which comprises at least 20 contiguous amino acids of SEQ ID NO: 2 exhibits a detectable level of constitutive activity. In some embodiments, the constitutive activity is for increasing a level of intracellular cAMP. In some embodiments, the constitutive activity is for causing melanophore cells to undergo pigment dispersion.

In some embodiments, the G protein-coupled receptor is part of a fusion protein comprising a G protein. Techniques for making a GPCR:G fusion construct are well known to the skilled artisan (see, e.g., International Application WO 02/42461).

In some embodiments, the compound in the presence of which less of a complex between a G protein-coupled receptor and an optionally labelled known ligand to the receptor is formed than in the absence of the compound is a small molecule. In some embodiments, the compound in the presence of which less of a complex between a G protein-coupled receptor and an optionally labelled known ligand to the receptor is formed than in the absence of the compound is a small molecule, with the proviso that the small molecule is not a polypeptide. In some embodiments, the compound in the presence of which less of a complex between a G protein-coupled receptor and an optionally labelled known ligand to the receptor is formed than in the absence of the compound is a small molecule, with the proviso that the small molecule is not an antibody or an antigen-binding fragment thereof. In some embodiments, the compound in the presence of which less of a complex between a G protein-coupled receptor and an optionally labelled known ligand to the receptor is formed than in the absence of the compound is a small molecule, with the proviso that the small molecule is not a lipid. In some embodiments, the test compound is a small molecule, with the proviso that the small molecule is not a polypeptide or a lipid. In some embodiments, the test compound is a polypeptide. In some embodiments, the compound in the presence of which less of a complex between a G protein-coupled receptor and an optionally labelled known ligand to the receptor is formed than in the absence of the compound is a polypeptide, with the proviso that the polypeptide is not an antibody or an antigen-binding fragment thereof. In some embodiments, the compound in the presence of which less of a complex between a G protein-coupled receptor and an optionally labelled known ligand to the receptor is formed than in the absence of the compound is a lipid. In some embodiments, the compound in the presence of which less of a complex between a G protein-coupled receptor and an optionally labelled known ligand to the receptor is formed than in the absence of the compound is not an antibody or an antigen-binding fragment thereof. In some embodiments, the compound in the presence of which less of a complex between a G protein-coupled receptor and an optionally labelled known ligand to the receptor is formed than in the absence of the compound is an antibody or an antigen-binding fragment thereof.

In certain embodiments, the method is a method for identifying PYY secretagogues.

In certain embodiments, the method is a method for identifying compounds useful for treatment or prevention of a condition modulated by PYY.

In certain embodiments, the method is a method for identifying compounds useful for a modulation of a PYY-related activity in an individual.

In certain embodiments, the ligand for GPR119 is a GPR119 agonist. In certain embodiments, the ligand for GPR119 or the GPR119 agonist is a ligand or agonist of an endogenous vertebrate, mammalian or human GPR119 receptor. In certain embodiments, the ligand for GPR119 or the GPR119 agonist is a ligand or agonist of an endogenous human GPR119 receptor. In certain embodiments, the ligand for GPR119 or the GPR119 agonist is identical to a compound disclosed in, e.g., in International Application No. PCT/US2004/001267 (published as WO 04/065380); International Application No. PCT/US2004/005555 (published as WO 04/076413); International Application No. PCT/US2004/022327 (published as WO 05/007647); International Application No. PCT/US2004/022417 (published as WO 05/007658); International Application No. PCT/US2005/019318 (published as WO 2005/121121); International Application No. PCT/GB2004/050046 (published as WO 2005/061489); International Application No. PCT/US06/00567 (published as WO 2006/083491); International Application No. PCT/GB2005/050264 (published as WO 2006/067531); International Application No. PCT/GB2005/050265 (published as WO 2006/067532); International Application No. PCT/GB2005/050266 (published as WO 2006/070208); International Application No. PCT/JP02/09350 (published as WO 03/026661); International Application No. PCT/JP2005/018412 (published as WO 06/040966); International Application No. PCT/JP2005/019000 (published as WO 2006/043490); International Application No. PCT/GB2006/050176 (published as WO 2007/003960); International Application No. PCT/GB2006/050177 (published as WO 2007/003961); International Application No. PCT/GB2006/050178 (published as WO 2007/003962); International Application No. PCT/GB2006/050182 (published as WO 2007/003964); International Application No. PCT/JP02/09350 (published as WO 03/026661); International Application No. PCT/GB2007/050183 (published as WO 2007/116229); International Application No. PCT/GB2007/050190 (published as WO 2007/116230); International Application No. PCT/US2007/073364 (published as WO 2008/008895); International Application No. PCT/EP2007/058991 (published as WO 2008/025798); International Application No. PCT/EP2007/058993 (published as WO 2008/025799); or International Application No. PCT/EP2007/058995 (published as WO 2008/025800). In certain embodiments, the ligand for GPR119 or the GPR119 agonist is (2-Fluoro-4-methanesulfonyl-phenyl)-{6-[4-(3-isopropyl-[1,2,4]oxadiazol-5-yl)-piperidin-1-yl]-5-nitro-pyrimidin-4-yl}-amine. In certain embodiments, the ligand for GPR119 is an endogenous ligand of an endogenous vertebrate, mammalian, or human GPR119 receptor.

In certain embodiments, the optionally labeled known ligand is a labeled known ligand. In certain embodiments, the labeled known ligand is a radiolabeled known ligand. Techniques for radiolabeling a compound, such as for labeling a known ligand of a G protein-coupled receptor of the invention, are well known to the skilled artisan. See, e.g., International Application WO 04/065380. Also see, e.g., Example 14, infra.

Techniques for detecting the complex between a G protein-coupled receptor and a compound known to be a ligand of the G protein-coupled receptor are well known to the skilled artisan. See, e.g., International Application WO 04/065380. Also see, e.g., Example 15, infra.

In some embodiments, the method further comprises the step of optionally determining the structure of the PYY secretagogue, the compound useful for treatment or prevention of a condition modulated by PYY, or the compound useful for a modulation of a PYY-related activity in an individual.

In some embodiments, the method further comprises the step of optionally providing the name or structure of the PYY secretagogue, the compound useful for treatment or prevention of a condition modulated by PYY, or the compound useful for a modulation of a PYY-related activity in an individual.

In some embodiments, said method further comprises the step of optionally producing or synthesizing the PYY secretagogue, the compound useful for treatment or prevention of a condition modulated by PYY, or the compound useful for a modulation of a PYY-related activity in an individual.

In some embodiments, said method further comprises the step of formulating the PYY secretagogue, the compound useful for treatment or prevention of a condition modulated by PYY, or the compound useful for a modulation of a PYY-related activity in an individual as a pharmaceutical.

In some embodiments, said method further comprises evaluating the bioavailability of the PYY secretagogue, the compound useful for treatment or prevention of a condition modulated by PYY, or the compound useful for a modulation of a PYY-related activity.

In some embodiments, said method further comprises the step of formulating the PYY secretagogue, the compound useful for treatment or prevention of a condition modulated by PYY, or the compound useful for a modulation of a PYY-related activity in an individual into a pharmaceutical composition.

The invention additionally features a process comprising performing a method according to this ninth aspect.

Applicant reserves the right to exclude any one or more candidate compounds from any of the embodiments of the invention. Applicant reserves the right to exclude any one or more modulators from any of the embodiments of the invention. By way of example and not limitation, Applicant reserves the right to exclude any one or more agonists from any of the embodiments of the invention. Applicant reserves the right to exclude any polynucleotide or polypeptide from any of the embodiments of the invention. Applicant additionally reserves the right to exclude any condition modulated by PYY, any bone-related condition, any bone-related condition wherein the bone-related condition is a condition characterized by low bone mass, any bone-related condition wherein the bone-related condition is a bone fracture, any bone-related condition wherein the bone-related condition is a bone disease, any bone-related condition wherein the bone-related condition is enhanced bone healing or bone growth, any metabolic disorder, any angiogenesis-related condition, any ischemia-related condition, any malabsorptive disorder, any convulsive disorder, any cancer, any inflammatory disorder, any inflammatory lung disease, any inflammatory bowel disease, and any modulation of a PYY-related activity in an individual from any of the embodiments of the invention. It is also expressly contemplated that conditions modulated by PYY, bone-related conditions, bone-related conditions wherein the bone-related condition is a condition characterized by low bone mass, bone-related conditions wherein the bone-related condition is a bone fracture, bone-related conditions wherein the bone-related condition is a bone disease, bone-related conditions wherein the bone-related condition is enhanced bone healing or bone growth, metabolic disorders, angiogenesis-related conditions, ischemia-related conditions, malabsorptive disorders, convulsive disorders, cancers, inflammatory disorders, inflammatory lung diseases, inflammatory bowel diseases, and modulations of a PYY-related activity in an individual of the invention can be included in an embodiment either individually or in any combination.

BRIEF DESCRIPTION OF THE DRAWINGS

The invention is illustrated in connection with the figures appended hereto in which:

FIG. 1 shows that GPR119 receptor exhibits constitutive activity for increasing cAMP accumulation in transfected HEK293 cells.

FIG. 2 shows that Compound 1 is an agonist of GPR119 receptor.

FIG. 3 shows an effect of administration of GPR119 agonist on plasma total PYY in wild-type mice.

DETAILED DESCRIPTION OF THE INVENTION

The present invention is based, at least in part, on the surprising discovery by Applicant that administration of a GPR119 agonist to an individual, such as by oral administration, can act to increase a plasma total PYY in the individual. The present invention features methods relating to GPR119 for identifying PYY secretagogues, compounds useful for treatment or prevention of a condition modulated by PYY, and compounds useful for a modulation of a PYY-related activity in an individual. A GPR119 agonist is useful for increasing plasma total PYY in an individual. In certain embodiments, the individual is a human. GPR119 agonists are useful as pharmaceutical agents for treatment or prevention of a condition modulated by PYY and for a modulation of a PYY-related activity in an individual.

The term "ligand", as used herein, shall mean a molecule (e.g., test compound) that specifically binds to a polypeptide, such as GPR119. A ligand may be, for example, a polypeptide, a lipid, a small molecule, an antibody. Compound 1 is an exemplary ligand of GPR119 receptor polypeptide (see, Table A, which sets forth the chemical structure and chemical name of Compound 1). Compound 1 is identical to a compound disclosed in International Patent Application No. PCT/US2004/001267 (published as WO 2004/065380). (2-Fluoro-4-methanesulfonyl-phenyl)-{6-[4-(3-isopropyl-[1,2,4]oxadiazol-5-yl)-piperidin-1-yl]-5-nitro-pyrimidin-4-yl}-amine (see, Table A) is exemplary ligand of GPR119 receptor polypeptide. An endogenous ligand is a ligand that is an endogenous, natural ligand for a native polypeptide, such as GPR119. A ligand may be an "antagonist", "agonist", "partial agonist", or "inverse agonist", or the like.

TABLE A

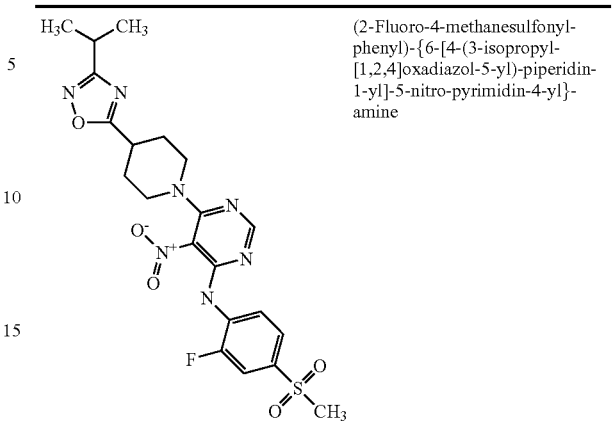

(2-Fluoro-4-methanesulfonyl-phenyl)-{6-[4-(3-isopropyl-[1,2,4]oxadiazol-5-yl)-piperidin-1-yl]-5-nitro-pyrimidin-4-yl}-amine The term "agonist", as used herein, shall mean an agent (e.g., ligand, test compound) that by virtue of binding to a GPCR activates (e.g., stimulates) the GPCR so as to elicit an intracellular response mediated by the GPCR.

The term "partial agonist", as used herein, shall mean an agent (e.g., ligand, test compound) that by virtue of binding to a GPCR activates (e.g., stimulates) the GPCR so as to elicit an intracellular response mediated by the GPCR, albeit to a lesser exent or degree than does a full agonist.

The term "antagonist" shall mean an agent (e.g., ligand, test compound) that binds, and preferably binds competitively, to a GPCR at about the same site as an agonist or partial agonist but which does not activate an intracellular response initiated by the active form of the GPCR, and can thereby inhibit the intracellular response by agonist or partial agonist. An antagonist typically does not diminish the baseline intracellular response in the absence of an agonist or partial agonist.

The term "inverse agonist" shall mean an agent (e.g., ligand, test compound) which binds to a GPCR and which inhibits the baseline intracellular response initiated by the active form of the receptor below the normal base level activity which is observed in the absence of an agonist or partial agonist.

The term "GPR119 agonist," as used herein, refers to a compound that binds to GPR119 receptor and acts as an agonist. Compound 1 is an exemplary GPR119 agonist (see, Table A, which sets forth the chemical structure and chemical name of Compound 1). Compound 1 is identical to a compound disclosed in International Patent Application No. PCT/US2004/001267 (published as WO 2004/065380). (2-Fluoro-4-methanesulfonyl-phenyl)-{6-[4-(3-isopropyl-[1,2,4]oxadiazol-5-yl)-piperidin-1-yl]-5-nitro-pyrimidin-4-yl}-amine is an exemplary GPR119 agonist.

The term "selective GPR119 agonist," as used herein, refers to a GPR119 agonist having selectivity for GPR119 receptor over one or more related receptors, such as corticotrophin-releasing factor-1 (CRF-1) receptor. Compound 1 is an exemplary selective GPR119 agonist (see, Table A, which sets forth the chemical structure and chemical name of Compound 1). Compound 1 is identical to a compound disclosed in International Patent Application No. PCT/US2004/001267 (published as WO 2004/065380). (2-Fluoro-4-methanesulfonyl-phenyl)-{6-[4-(3-isopropyl-[1,2,4]oxadiazol-5-yl)-piperidin-1-yl]-5-nitro-pyrimidin-4-yl}-amine is an exemplary selective GPR119 agonist.

The term "PYY secretagogue" shall mean an agent (e.g., ligand, test compound) that promotes (e.g., stimulates) secretion of PYY in a cell, e.g. an enteroendocrine cell, or that increases a level of total PYY, e.g. a level of blood or plasma total PYY, on administration to an individual such as a vertebrate or a mammal. In certain embodiments, a PYY secretagogue is a compound suitable for increasing a level of total PYY in an individual, for example a level of blood or plasma total PYY.

As used herein, the term "condition modulated by PYY" refers to a condition modulated by $PYY_{1-36}$ or by a fragment thereof that is capable of modulating a G protein-coupled receptor. In certain embodiments, the term "condition modulated by PYY" refers to a condition modulated by $PYY_{3-36}$. In certain embodiments, the term "condition modulated by PYY" refers to a condition modulated by an NPY Y2 receptor (Y2R) agonist. In certain embodiments, the term "condition modulated by PYY" refers to a condition modulated by stimulation of Y2R. In certain embodiments, the term "condition modulated by $PYY_{3-36}$" refers to a condition modulated by a Y2R agonist. In certain embodiments, the term "condition modulated by $PYY_{3-36}$" refers to a condition modulated by stimulation of Y2R.

As used herein, the term "PYY-related activity" refers to an activity for modulating a level of PYY or to an activity associated with PYY. In certain embodiments, the term "PYY-related activity" refers to an activity for increasing a level of PYY or to an activity associated with PYY.

The term "individual," as used herein, refers to a vertebrate, including but not limited to fish (such as commercially farmed fish, pet fish, etc.), amphibians (such as frogs, toads, pet amphibians, etc.), reptiles (such as snakes, lizards, turtles, pet reptiles, etc.), birds (such as chickens, turkeys, pet birds, etc.) and mammals (such as mice, rats, hamsters, rabbits, pigs, dogs, cats, horses, cows, sheep, goats, non-human primates, non-human mammals, pet non-human mammals, humans, etc.). In certain embodiments, the individual is a fish. In certain embodiments, the individual is an amphibian. In certain embodiments, the individual is a reptile. In certain embodiments, the individual is a bird. In certain embodiments, the individual is a turkey. Over the past 25 yr, commercial selection pressure for turkeys with larger breast muscle mass has placed increasing demands on skeletal integrity. The increased breast muscle mass, however, has not been accompanied by compensatory changes in the skeleton, with the result that the turkey industry has experienced an increase in leg problems. Long bone fracture in young adult male turkeys has been reported. (See, e.g., Crespo et al, Poult Sci (2000) 79:602-608.) In certain embodiments, the individual is a mammal. In certain embodiments, the individual is a mouse, a rat, a hamster, a rabbit, a pig, a dog, a cat, a horse, a cow, a sheep, a goat, a non-human primate or a human (which may be included in embodiments of the invention individually or in any combination). In certain embodiments, the individual is a horse. Performance horses, which are horses involved in activities such as racing, pacing and other competitive events, are susceptible to bone fracture. In certain embodiments, the individual is a dog or a cat. In certain embodiments, the individual is a human companion animal (such as a dog, a cat, etc.), a farm animal (such as a cow, a sheep, a goat, a pig, a chicken, etc.), a sports animal (such as a horse, a dog, etc.), a beast of burden (such as a mule, a camel, etc.) or an exotic animal (such as an animal found in a zoo, etc.), which may be included in embodiments of the invention individually or in any combination. In certain embodiments, the individual is a non-human vertebrate. In certain embodiments, the individual is a non-human mammal. In certain embodiments, the individual is a non-human primate (such as a rhesus monkey, a chimpanzee, etc.). In certain embodiments, the individual is a human.

The term "in need of prevention or treatment" as used herein refers to a judgement made by a caregiver (e.g. physician, nurse, nurse practitioner in the case of humans; veterinarian in the case of non-human vertebrates, and in particular embodiment non-human mammals) that an individual requires or will benefit from treatment.

The term "therapeutically effective amount" or "therapeutically effective dose" as used herein refers to the amount of active compound or pharmaceutical agent that elicits the biological or medicinal response in a tissue, system, animal, individual or human that is being sought by a researcher, veterinarian, medical doctor or other clinician, which includes one or more of the following:

(1) Preventing the disease; for example, preventing a disease, condition or disorder in an individual that may be predisposed to the disease, condition or disorder but does not yet experience or display the pathology or symptomatology of the disease, (2) Inhibiting the disease; for example, inhibiting a disease, condition or disorder in an individual that is experiencing or displaying the pathology or symptomatology of the disease, condition or disorder (i.e., arresting further development of the pathology and/or symptomatology), and (3) Ameliorating the disease; for example, ameliorating a disease, condition or disorder in an individual that is experiencing or displaying the pathology or symptomatology of the disease, condition or disorder (i.e., reversing the pathology and/or symptomatology).

The term "therapeutic efficacy" as used herein refers to elicitation of the biological or medicinal response in a tissue, system, animal, individual or human that is being sought by a researcher, veterinarian, medical doctor or other clinician, which includes one or more of the following:

(1) Preventing the disease; for example, preventing a disease, condition or disorder in an individual that may be predisposed to the disease, condition or disorder but does not yet experience or display the pathology or symptomatology of the disease, (2) Inhibiting the disease; for example, inhibiting a disease, condition or disorder in an individual that is experiencing or displaying the pathology or symptomatology of the disease, condition or disorder (i.e., arresting further development of the pathology and/or symptomatology), and (3) Ameliorating the disease; for example, ameliorating a disease, condition or disorder in an individual that is experiencing or displaying the pathology or symptomatology of the disease, condition or disorder (i.e., reversing the pathology and/or symptomatology).

The term "amount that is effective to prevent" refers to that amount of drug that will prevent or reduce the risk of occurrence of the biological or medical event that is sought to be prevented. In many instances, the amount that is effective to prevent is the same as therapeutically effective amount.

The term "peripheral administration" shall mean administration outside of the central nervous system. Peripheral administration does not include direct administration to the brain. Peripheral administration includes, but is not limited to, intravascular, intramuscular, subcutaneous, inhalation, oral, sublingual, enteral, rectal, transdermal, or intra-nasal administration.

The term "composition" shall mean a material comprising at least one component.

The term "active ingredient" shall mean any component that provides pharmacological activity or other direct effect in the diagnosis, cure, mitigation, treatment, or prevention of disease.

The term "pharmaceutical composition" shall mean a composition comprising at least one active ingredient, whereby the composition is amenable to investigation and treatment in a mammal.

By "pharmaceutically acceptable" it is meant that the carrier, vehicle, diluent, excipients, and/or salt must be compatible with the other ingredients of the formulation, and not deleterious to the recipient thereof.

The term "dosage form" shall mean the physical form in which a drug is produced and dispensed, such as a tablet, capsule, or an injectable.

By "bone" is intended the dense, semi-rigid, porous, calcified connective tissue forming the major portion of the skeleton of most vertebrates, comprising a dense organic matrix and an inorganic, mineral component. Bone is any of numerous anatomically distinct structures making up the skeleton of a vertebrate.

The terms "bone mass" and "bone mineral density (BMD)" are used interchangeably herein. BMD in humans is usually measured by a standard radiographic technique, dual energy X-ray absorptiometry (DXA). Of the many techniques developed to assess BMD, DXA is the most highly developed technically and the most thoroughly validated biologically. DXA technology, with suitably adapted software, can also be used to reliably assess BMD in animal studies. DXA is used in the diagnosis of osteoporosis, prognosis (fracture prediction), monitoring the natural history of the disorder, and assessing response to treatment.

The term "low bone mass" as used herein refers to any decrease or reduction in bone mineral density (BMD) in an individual, and includes both osteoporosis and osteopenia as defined in proposals by the World Health Organization (WHO). The WHO has defined normal as a value of BMD within one standard deviation of the young adult reference mean (T-score$\geq$-1). The WHO has defined osteopenia as a value of BMD more than 1 standard deviation below the young adult mean, but less than 2.5 standard deviations below this value (T-score<-1 and >-2.5). The WHO has characterized osteoporosis as a more severe form of osteopenia, and has defined it by value of BMD 2.5 standard deviations or more blow the young adult mean (T-score$\leq$-2.5). (See, e.g., World Health Organization Technical Report Series 921 (2003), Prevention and Management of Osteoporosis, the disclosure of which is herein incorporated by reference in its entirety.) More commonly, osteopenia is defined as a T-score of less than -1 and greater than -2, and osteoporosis is defined as a T-score of less than or equal to -2. In certain embodiments of the present invention, the T-score is measured at the hip with DXA.

The term "osteoporosis" as used herein is defined by a value of BMD 2 standard deviations or more below the young adult reference mean (T-score$\leq$-2) or refers to a diagnosis made by a caregiver (e.g. physician, nurse, nurse practitioner in the case of humans; veterinarian in the case of non-human vertebrates).

Osteoporosis can be classified as either primary or secondary. (See, e.g., World Health Organization Technical Report Series 921 (2003), Prevention and Management of Osteoporosis.) As used herein, the term "osteoporosis" encompasses primary osteoporosis and secondary osteoporosis. In certain embodiments, osteoporosis is primary osteoporosis. In certain embodiments, osteoporosis is secondary osteoporosis.

"Primary osteoporosis" as used herein is associated with menopause (natural, premature, or surgical), aging, or both. It shall be understood that in the present invention, primary osteoporosis associated with menopause (natural, premature, or surgical), primary osteoporosis associated with aging, and primary osteoporosis associated with menopause and aging can be included in embodiments individually or in any combination.

"Secondary osteoporosis" as used herein refers to osteoporosis which is associated not with menopause or aging but rather with medical conditions or with the use of medications or drugs. An increased risk of osteoporosis is associated with a host of medical conditions, including but not limited to endocrine and metabolic disorders, and malignant disease, and with the use of certain medications and drugs, examples of which are well known to those skilled in the art (see, e.g., World Health Organization Technical Report Series 921 (2003), Prevention and Management of Osteoporosis; Williams Textbook of Endocrinology, 10$^{th}$ Edition; the disclosure of which is herein incorporated by reference in its entirety.) Secondary osteoporosis can also be associated with immobilization. A diagnosis of osteoporosis secondary to a medical condition, to use of a medication or drug, or to immobilization can be made by a caregiver (e.g. physician, nurse, nurse practitioner in the case of humans; veterinarian in the case of non-human vertebrates).

By "bone fracture" is intended a complete or incomplete break, rupture or crack of a bone. Diagnosis of fractures normally depends upon clinical examination and radiological findings. In the invention, bone fractures include, but are not limited to, traumatic fractures, long-term fractures, and pathological fractures.

"Traumatic fracture" as used herein shall refer to an immediate fracture which involves a supraliminal trauma with a degree of local violence that exceeds the natural elasticity of the bone. It can be accompanied by simultaneous injury to the soft tissues and very often the skin. A traumatic fracture can be closed (the adjacent soft tissue can be injured but the covering soft parts are largely preserved). A traumatic fracture can be open (the broken ends of the bone are freed by extensive soft tissue injury so that pathogens from outside can enter the wound directly).

"Long-term fracture" as used herein shall refer to a chronic fracture, fatigue fracture, stress fracture or spontaneous fracture type I.

"Pathological fracture" as used herein shall refer to a spontaneous fracture type II. A pathological fracture arises spontaneously, without adequate trauma to account for it. The bone may have been previously damaged, either by a systemic disease (e.g., osteoporosis, osteodystrophy, or Paget's osteitis deformans) or by a local bone lesion (e.g., metastasis, radioosteonecrosis, or bone tumor). See, Adler, Claus-Peter, BONE DISEASES, p. 114 (Springer-Verlag, Germany 2000).

Fractures also include, but are not limited no, oblique torsion fracture, transverse fracture, comminuted fracture, compression fracture, rib fractures, creeping fracture, and fractured femoral neck (Adler, Claus-Peter, BONE DISEASES, Springer-Verlag, Germany (2000)).

As used herein, "bone-related condition" refers to a condition that derives benefit from treatment according to the invention, by increasing bone mass or bone growth or by decreasing loss of bone mass, and includes but is not limited to a condition characterized by low bone mass, a bone fracture, a bone disease, and enhancing bone healing or bone growth. It shall be understood that in the present invention, bone-related conditions that can be treated according to the invention can be included in embodiments individually or in any combination.

As used herein, the term "condition characterized by low bone mass" includes but is not limited to osteopenia, osteoporosis, rheumatoid arthritis, osteoarthritis, periodontal disease, alveolar bone loss, osteotomy bone loss, childhood idiopathic bone loss, curvature of the spine and loss of height. In certain embodiments, osteoporosis is primary osteoporosis. In certain embodiments, osteoporosis is secondary osteoporosis. In certain embodiments, secondary osteoporosis is associated with a medical condition. In certain embodiments, secondary osteoporosis is associated with the use of a medication or drug. In certain embodiments, secondary osteoporosis is associated with immobilization. Conditions characterized by low bone mass also include but are not limited to Paget's disease, bone loss due to metastatic cancer, and osteolytic lesions such as those caused by neoplastic disease, radiotherapy, or chemotherapy. Conditions characterized by low bone mass also include but are not limited to long-term complications of osteoporosis such as curvature of the spine, loss of height and prosthetic surgery. It shall be understood that in the present invention, conditions characterized by low bone mass can be included in embodiments individually or in any combination. (See, e.g., World Health Organization Technical Report Series 921 (2003), Prevention and Management of Osteoporosis; Williams Textbook of Endocrinology, $10^{th}$ Edition, Larsen et al, Eds. (2002), W.B. Saunders Company; and Endocrinology and Metabolism, $4^{th}$ Edition, Felig et al, Eds. (2001), McGraw-Hill Book Company; the disclosure of each of which is herein incorporated by reference in its entirety.)

As used herein, "bone disease" refers to a disorder or condition relating to abnormality of the bone. Bone diseases that can be treated according to the invention, by increasing bone mass or bone growth or decreasing loss of bone mass, include but are not limited to osteopenia, osteoporosis, rheumatoid arthritis, osteoarthritis, periodontal disease, alveolar bone loss, osteotomy bone loss, childhood idiopathic bone loss, curvature of the spine, and loss of height. In certain embodiments, osteoporosis is primary osteoporosis. In certain embodiments, osteoporosis is secondary osteoporosis. In certain embodiments, secondary osteoporosis is associated with a medical conditions. In certain embodiments, secondary osteoporosis is associated with the use of a medication or drug. In certain embodiments, secondary osteoporosis is associated with immobilization. Bone diseases that can be treated according to the invention, by increasing bone mass or bone growth, also include but are not limited to Paget's disease and bone loss due to metastatic cancer. Destructive bone disorders that can be treated according to the invention, by increasing bone mass or growth, include but are not limited to osteoporosis, osteoarthritis, and osteolytic lesions such as those caused by neoplastic disease, radiotherapy, or chemotherapy. It shall be understood that in the present invention, bone diseases that can be treated according to the invention, by increasing bone mass or growth, can be included in embodiments individually or in any combination. (See, e.g., World Health Organization Technical Report Series 921 (2003), Prevention and Management of Osteoporosis; Williams Textbook of Endocrinology, $10^{th}$ Edition, Larsen et al, Eds. (2002), W.B. Saunders Company; and Endocrinology and Metabolism, $4^{th}$ Edition, Felig et al, Eds. (2001), McGraw-Hill Book Company; the disclosure of each of which is herein incorporated by reference in its entirety.)

The present invention also relates to the other conditions that derive benefit from treatment according to the invention, by increasing bone mass or bone growth or decreasing loss of bone mass, including but not limited to enhanced bone healing following facial reconstruction, maxillary reconstruction, mandibular reconstruction, periodontal disease or tooth extraction, enhanced long bone extension, enhanced prosthetic ingrowth and increased bone synostosis.

As used herein, "metabolic disorder" refers to a disorder relating to abnormality of metabolism. Metabolic disorders that can be treated according to the invention include but are not limited to overweight, obesity, hyperphagia, diabetes (inclusive of type 1 diabetes and type 2 diabetes), type 2 diabetes, impaired glucose tolerance, insulin resistance, hyperinsulinemia, dyslipidemia, hypertension and metabolic syndrome. It shall be understood that in the present invention, metabolic disorders that can be treated according to the invention can be included in embodiments individually or in any combination.

The term "metabolic syndrome" as defined herein, and according to the Adult Treatment Panel III (ATP III; National Institutes of Health: Third Report of the National Cholesterol Education Program Expert Panel on Detection, Evaluation, and Treatment of High Blood Cholesterol in Adults (Adult Treatment Panel III), Executive Summary; Bethesda, Md., National Institutes of Health, National Heart, Lung and Blood Institute, 2001 (NIH pub. No 01-3670), occurs when a person meets three or more of five criteria related to obesity, hypertriglyceridemia, low HDL cholesterol, high blood pressure, and high fasting glucose.

The term "obesity," as used herein, is defined as a body mass index (BMI) of 30.0 or greater, in accordance with the WHO classifications of weight [Kopelman, Nature (2000) 404:635-643; the disclosure of which is herein incorporated by reference in its entirety].

"Impaired glucose tolerance" (IGT) as used herein is intended to indicate that condition associated with insulin-resistance that is intermediate between frank, type 2 diabetes and normal glucose tolerance (NGT). IGT is diagnosed by a procedure wherein an affected person's postprandial glucose response is determined to be abnormal as assessed by 2-hour postprandial plasma glucose levels. In this test, a measured amount of glucose is given to the patient and blood glucose levels are measured at regular intervals, usually every half hour for the first two hours and every hour thereafter. In a "normal" or non-IGT individual, glucose levels rise during the first two hours to a level less than 140 mg/dl and then drop rapidly. In an IGT individual, the blood glucose levels are higher and the drop-off level is at a slower rate.

"Insulin resistance" as used herein is intended to encompass the usual diagnosis of insulin resistance made by any of a number of methods, including but not restricted to: the intravenous glucose tolerance test or measurement of the fasting insulin level. It is well known that there is an excellent correlation between the height of the fasting insulin level and the degree of insulin resistance. Therefore, one could use elevated fasting insulin levels as a surrogate marker for insulin resistance for the purpose of identifying which normal glucose tolerance (NGT) individuals have insulin resistance. A diagnosis of insulin resistance can also be made using the euglycemic glucose clamp test.

"Dyslipidemia" is intended herein to encompass disorders comprising any one of elevated level of plasma free fatty acids, elevated level of plasma cholesterol, elevated level of LDL-cholesterol, reduced level of HDL-cholesterol, elevated ratio of total cholesterol to HDL cholesterol, and elevated level of plasma triglycerides.

As used herein, "angiogenesis-related condition" refers to a condition that derives benefit from increased angiogenesis.

Angiogenesis-related conditions that can be treated according to the invention, by increasing angiogenesis, include but are not limited to peripheral arterial disease, wound healing, and ischemia. It shall be understood that in the present invention, angiogenesis-related conditions that can be treated according to the invention can be included in embodiments individually or in any combination.

As used herein, "ischemia" refers to a state of tissue oxygen deprivation or insufficiency.

As used herein, "ischemia-related condition" refers to a condition which relates to ischemia. Ischemia-related conditions that can be treated according to the invention include but are not limited to cerebral ischemia, stroke, ischemic heart disease, myocardial infarction, ischemia-reperfusion injury, post-myocardial infarction remodeling, heart failure, and congestive heart failure. It shall be understood that in the present invention, ischemia-related conditions that can be treated according to the invention can be included in embodiments individually or in any combination. "Stroke" is a cardiovascular disease that affects the blood vessels supplying blood to the brain and is intended herein to include cerebral thrombosis, the most common type of stroke. Cerebral thrombosis occurs when a blood clot (thrombus) forms and blocks blood flow in an artery bring blood to part of the brain. Blood clots usually form in arteries damaged by atherosclerosis.

As used herein, "ischemic heart disease" refers to a disorder caused by lack of oxygen to the tissues of the heart, in which muscles of the heart are affected and the heart cannot pump properly. Ischemic heart disease is the most common cardiomyopathy in the United States.

As used here, "myocardial infarction" refers to the damage or death of an area of heart muscle because of an inadequate supply of oxygen to that are. Myocardial infarctions are often caused by a blood clot that blocks one of the coronary arteries (the blood vessels that bring oxygen to heart muscle). The clot prevents blood and oxygen from reaching that area of the heart, leading to the death of heart cells in that area.

The loss of myocardial tissue due to myocardial infarction results in a sustained excessive hemodynamic burden placed on the ventricle. Ventricular hypertrophy constitutes one of the principle mechanisms by which the heart compensates for an increased load. However, the capacity for this adaptation to sustain cardiac performance in the face of hemodynamic overload is finite and, when chronically maintained, becomes maladaptive. Gradually, the adaptive hypertrophic phenotype transitions to overt heart failure as the enlarged ventricles progressively dilate and contractile function weakens. The natural history of the adaptive and maladaptive response to myocardial infarction in the heart is referred to as "pos-myocardial infaraction remodeling".

"Congestive heart failure" refers to a disorder in which the heart loses its ability to pump blood efficiently. Congestive heart failure becomes more prevalent with advancing age. Ischemic heart disease is the most common cause of congestive heart failure, accounting for 60-70% of all cases. An increased venous pressure greater than 12 mmHg is one of the major Framingham criteria for congestive heart failure, as is a reduction in cardiac output equivalent to a circulation time great than 25 seconds.

As used herein, "malabsorptive disorder" refers to a disorder relating to abnormality of secretion and/or absorption in the intenstinal epithelium. Malabsorptive disorders that can be treated according to the invention include but are not limited to short bowel syndrome, enterocolitis, Crohn's disease, ulcerative colitis, irritable bowel syndrome, cholera and a disorder accompanied by diarrhea. As used herein, the "disorder accompanied by diarrhea" is not particularly limited as long as it is a disease or a symptom accompanied by diarrhea, and it does not matter whether it is an acute disease or a chronic disease. Examples of such a disease or symptom include diarrhea (caused by a parasite, a bacterium, a virus, physical stimulation, dyspepsia, mental disorder, gastrointestinal inflammation or allergy, etc.), irritable bowel syndrome, ulcerative colitis and the like. It is expressly contemplated that each disorder accompanied by diarrhea is a separate embodiment within the scope of the present invention. It shall be understood that in the present invention, malabsorptive disorders that can be treated according to the invention can be included in embodiments individually or in any combination.

As used herein, "convulsive disorder" refers to a disorder of an individual in which the subject suffers from convulsion, e.g., convulsions due to epileptic seizure. Convulsive disorders that can be treated according to the invention include epilepsy and non-epileptic seizures, e.g., convulsions due to administration of a convulsant agent to the individual. It shall be understood that in the present invention, convulsive disorders that can be treated according to the invention can be included in embodiments individually or in any combination.

As used herein, "cancer" refers to a malignant neoplasm. Cancers that can be treated according to the invention include but are not limited to pancreatic cancer, breast cancer, colon cancer, and Barrett's adenocarcinoma. It shall be understood that in the present invention, cancers that can be treated according to the invention can be included in embodiments individually or in any combination.

As used herein, "inflammatory disorder" refers to a disorder relating to abnormality of inflammation. Inflammatory disorders that can be treated according to the invention include but are not limited to atherosclerosis, atherothrombosis, insulin resistance, pancreatitis, restenosis, an inflammatory lung disease, and an inflammatory bowel disease. It shall be understood that in the present invention, inflammatory disorders that can be treated according to the invention can be included in embodiments individually or in any combination.

As used herein, "atherothrombosis" refers to thrombus formation in an atherosclerotic vessel.

As used herein, "inflammatory lung disease" refers to a condition relating to abnormality of inflammation in the lung. Inflammatory lung diseases that can be treated according to the invention include but are not limited to asthma, emphysema and pulmonary arterial hypertension (PAH). PAH is a life-threatening disease characterized by a progressive pulmonary vasculopathy leading to right ventricular hypertrophy; right heart failure occurs if left untreated. PAH shall be understood to encompass the following forms of pulmonary arterial hypertension described in the 2003 World Health Organization (WHO) clinical classification of pulmonary arterial hypertension: idiopathic PAH, familial PAH, PAH associated with other condition, and PAH associated with significant venous or capillary involvement. It shall be understood that in the present invention, inflammatory lung diseases that can be treated according to the invention can be included in embodiments individually or in any combination.

As used herein, the "inflammatory bowel disease" refers to a condition relating to abnormality of inflammation in the bowel. Inflammatory bowel diseases that can be treated according to the invention include but are not limited to Crohn's disease as may be enteritis, enterocolitis, Crohn's disease, granulomatous colitis, ileitis or Crohn's colitis and ulcerative colitis as may be ulcerative colitis, sigmoiditis, pancolitis and ulcerative proctitis. It shall be understood that in the present invention, inflammatory bowel diseases that can be treated according to the invention can be included in embodiments individually or in any combination.

The term "atherosclerosis" as used herein refers to a form of vascular disease characterized by the deposition of atheromatous plaques containing cholesterol and lipids on the innermost layer of the walls of large and medium-sized arteries.

"Alzheimer's disease" is a progressive neurodegenerative disease characterized by significant loss of function in more than one cognitive domain and often accompanied by changes in behavior or personality. Alzheimer's disease is the most common cause of dementia. The beta-amyloid peptide (Aβ) is believed to play a central role in the pathology of Alzheimer's disease.

"Mild cognitive impairment" (MCI) is a state of cognitive impairment, most often of memory only, that is not severe enough to significantly impact occupational or social functioning. However, many people with MCI progress to Alzheimer's disease, at a rate of 10-15% per year and up to 60% within five years. Growing evidence shows that Alzheimer's disease pathology begins much earlier than the development of symptoms severe enough to allow a diagnosis of Alzheimer's criteria. In 2001, the American Academy of Neurology (AAN) published clinical practice parameters for the detection of MCI that will increase awareness, diagnosis, and treatment of both MCI and mild forms of Alzheimer's disease.

As used herein, "prion-associated disease" is intended to include but not be limited to bovine spongiform encephalopathy, Creutzfeldt-Jakob disease, kuru, Gerstmann-Straussler-Scheinker syndrome, and fatal familial insomnia (Collins et al, Lancet (2004) 363:51-61).

As used herein, "excitotoxic injury" refers to neuronal cell damage or neuronal cell death caused resulting from substance-induced paroxysmal overactivity, e.g. glutamate-induced paroxysmal activity.

"Parkinson's disease" is a chronic, progressive neurodegenerative disorder characterized by motor symptoms such as tremor, bradykinesia, muscle rigidity, gait dysfunction, and postural instability. Researchers have identified degeneration of dopaminergic neurons in the *substantia nigra* as the primary pathophysiological mechanism of Parkinson's disease.

"Adiponectin" is a plasma protein secreted by adipocytes and comprised of an N-terminally disposed collagen-like region and a C-terminal globular region. Reduced levels of adiponectin have been associated with a number of metabolic-related disorders, including atherosclerosis, coronary heart disease, stroke, insulin resistance and type 2 diabetes. The serum adiponectin level for women has been reported to be higher than that for men, for example 13.5 μg/ml versus 7.2 μg/ml in one study (Yamamoto et al, Clin Sci (London) (2002) 103:137-142).

The term "endogenous" shall mean a material that an individual (for example, and not limitation, a human) naturally produces. By contrast, "non-endogenous" shall mean that which is not naturally produced by an individual (for example, and not limitation, a human).

The term "biologically active fragment" of a G protein-coupled receptor shall mean a fragment of the GPCR having structural and biochemical functions of a naturally occurring GPCR. In certain embodiments, the biologically active fragment couples to a G protein. In certain embodiments, the biologically active fragment binds to a known ligand of the GPCR.

The term "primer" is used herein to denote a specific nucleotide sequence which is complementary to a target nucleotide sequence and used to hybridize to the target nucleotide sequence. A primer serves as an initiation point for nucleotide polymerization catalyzed by DNA polymerase, RNA polymerase, or reverse transcriptase.

The term "expression vector" shall mean a DNA sequence that is required for the transcription of cloned DNA and translation of the transcribed mRNA in an appropriate host cell recombinant for the expression vector. An appropriately constructed expression vector should contain an origin of replication for autonomous replication in host cells, selectable markers, a limited number of useful restriction enzyme sites, a potential for high copy number, and active promoters. The cloned DNA to be transcribed is operably linked to a constitutively or conditionally active promoter within the expression vector.

The term "host cell" shall mean a cell capable of having a vector incorporated therein. In the present context, the vector will typically contain nucleic acid encoding a GPCR or GPCR fusion protein in operable connection with a suitable promoter sequence to permit expression of the GPCR or GPCR fusion protein to occur. In particular embodiment, the host cell is a eukaryotic host cell. In certain embodiments, the eukaryotic host cell is a mammalian host cell. In certain embodiments, the eukaryotic host cell is a yeast host cell. In certain embodiments, the eukaryotic host cell is a melanophore host cell.

The term "contact" or "contacting" shall mean bringing at least two moieties together.

The terms "modulate" or "modify" shall be taken to refer to an increase or decrease in the amount, quality, or effect of a particular activity, function or molecule or, when in reference to a condition, shall be taken to refer to a change in the status of said condition. By way of illustration and not limitation, agonists, partial agonists, inverse agonists, and antagonists of a G protein-coupled receptor are modulators of the receptor.

The term "small molecule" shall be taken to mean a compound having a molecular weight of less than about 10,000 grams per mole, including a peptide, peptidomimetic, amino acid, amino acid analogue, polynucleotide, polynucleotide analogue, nucleotide, nucleotide analogue, organic compound or inorganic compound (i.e. including a heterorganic compound or organometallic compound), and salts, esters and other pharmaceutically acceptable forms thereof. In certain embodiments, small molecules are organic or inorganic compounds having a molecular weight of less than about 5,000 grams per mole. In certain embodiments, small molecules are organic or inorganic compounds having molecular weight of less than about 1,000 grams per mole. In certain embodiments, small molecules are organic or inorganic compounds having a molecular weight of less than about 800 grams per mole. In certain embodiments, small molecules are organic or inorganic compounds having a molecular weight of less than about 600 grams per mole. In certain embodiments, small molecules are organic or inorganic compounds having a molecular weight of less than about 500 grams per mole.

Amino acid abbreviations used herein are set out in Table B:

TABLE B

| ALANINE | ALA | A |
|---|---|---|
| ARGININE | ARG | R |
| ASPARAGINE | ASN | N |
| ASPARTIC ACID | ASP | D |
| CYSTEINE | CYS | C |
| GLUTAMIC ACID | GLU | E |
| GLUTAMINE | GLN | Q |
| GLYCINE | GLY | G |
| HISTIDINE | HIS | H |

TABLE B-continued

| | | |
|---|---|---|
| ISOLEUCINE | ILE | I |
| LEUCINE | LEU | L |
| LYSINE | LYS | K |
| METHIONINE | MET | M |
| PHENYLALANINE | PHE | F |
| PROLINE | PRO | P |
| SERINE | SER | S |
| THREONINE | THR | T |
| TRYPTOPHAN | TRP | W |
| TYROSINE | TYR | Y |
| VALINE | VAL | V |

The term "polypeptide" shall refer to a polymer of amino acids without regard to the length of the polymer. Thus, peptides, oligopeptides, and proteins are included within the definition of polypeptide. This term also does not specify or exclude post-expression modifications of polypeptides. For example, polypeptides that include the covalent attachment of glycosyl groups, acetyl groups, phosphate groups, lipid groups and the like are expressly encompassed by the term polypeptide.

The term "polynucleotide" shall refer to RNA, DNA, or RNA/DNA hybrid sequence of more than one nucleotide in either single chain or duplex form. The polynucleotides of the invention may be prepared by any known method, including synthetic, recombinant, ex vivo generation, or a combination thereof, as well as utilizing any purification methods known in the art.

The term "antibody" is intended herein to encompass monoclonal antibody and polyclonal antibody.

The term "second messenger" shall mean an intracellular response produced as a result of receptor activation. A second messenger can include, for example, inositol 1,4,5-triphosphate ($IP_3$), diacylglycerol (DAG), cyclic AMP (cAMP), cyclic GMP (cGMP), MAP kinase activity, MAPK/ERK kinase kinase-1 (MEKK1) activity, and $Ca^{2+}$. Second messenger response can be measured for a determination of receptor activation.

The term "receptor functionality" shall refer to the normal operation of a receptor to receive a stimulus and moderate an effect in the cell, including, but not limited to regulating gene transcription, regulating the influx or efflux of ions, effecting a catalytic reaction, and/or modulating activity through G-proteins, such as eliciting a second messenger response.

The term "stimulate" or "stimulating," in relationship to the term "response" or "functionality of the receptor" shall mean that a response or a functionality of the receptor is increased in the presence of a compound as opposed to in the absence of the compound.

The term "inhibit" or "inhibiting," in relationship to the term "response" or "functionality of the receptor" shall mean that a response a functionality of the receptor is decreased or prevented in the presence of a compound as opposed to in the absence of the compound.

The term "compound efficacy" shall mean a measurement of the ability of a compound to inhibit or stimulate receptor functionality, as opposed to receptor binding affinity.

The term "test compound," used interchangeably herein with "candidate compound," shall mean a molecule (for example, and not limitation, a chemical compound) which is amenable to a screening technique.

The term "constitutively active" in relationship to a G protein-coupled receptor shall mean that the G protein-coupled receptor exhibits agonist-independent activity.

The term "directly identifying" or "directly identified", in relationship to the phrase "test compound," shall mean the screening of a compound against a G protein-coupled receptor in the absence of a known ligand (e.g., a known agonist) to the G protein-coupled receptor.

Where a range of values is provided, it is understood that each intervening value, to the tenth of the lower limit unless the context clearly indicates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

A. Introduction

The order of the following sections is set forth for presentational efficiency and is not intended, nor should be construed, as a limitation on the disclosure or the claims to follow.

B. Receptor Expression

1. GPCR Polypeptides of Interest

A GPCR of the invention may comprise an amino acid sequence selected from the group consisting of:
(a) amino acids 1-335 of SEQ ID NO: 2;
(b) amino acids 2-335 of SEQ ID NO: 2;
(c) an amino acid sequence comprising the amino acid sequence of a polypeptide derived from (a) by substitution, deletion or addition of one or several amino acids in the amino acid sequence defined in (a);
(d) the amino acid sequence of a G protein-coupled receptor encoded by a polynucleotide hybridizing under stringent conditions to the complement of SEQ ID NO: 1;
(e) a variant of SEQ ID NO: 2 when selected from the group consisting of:
  (i) the amino acid sequence of a G protein-coupled receptor having at least about 80% identity to SEQ ID NO: 2; and
  (ii) the amino acid sequence of a G protein-coupled receptor comprising at least 20 contiguous amino acids of SEQ ID NO: 2;
(f) the amino acid sequence of a constitutively active version of a G protein-coupled receptor having SEQ ID NO: 2; and
(g) a biologically active fragment of any one of any one of (a) to (f).

In certain embodiments, a GPCR of the invention comprises the amino acid sequence of SEQ ID NO: 2. In some embodiments, a GPCR of the invention is an allele of SEQ ID NO:2. In some embodiments, a GPCR of the invention is an ortholog of SEQ ID NO:2.

In some embodiments, a GPCR of the invention is recombinant. In some embodiments, the recombinant GPCR is recombinant human GPR119.

In certain embodiments, a GPCR that may be used in the subject methods exhibits a detectable level of constitutive activity.

In some embodiments, a GPCR of the invention is endogenous. In some embodiments, a GPCR of the invention is a mammalian GPR119. In some embodiments, a GPCR of the invention that is endogenous is a mammalian GPR119.

By way of illustration and not limitation, deletion of an N-terminal methionine residue is envisioned to provide a biologically active fragment that may be used in the subject invention. In certain embodiments, a biologically active fragment of the invention is a fragment optionally fused at its N-terminus to a peptide comprising an N-terminal methionine residue and an HA epitope tag (from hemagglutinin influenza virus) that specifically binds Compound 1. In certain embodiments, a biologically active fragment of the invention is a fragment optionally fused at its N-terminus to a peptide comprising an N-terminal methionine residue and an HA epitope tag (from hemagglutinin influenza virus) that specifically binds (2-Fluoro-4-methanesulfonyl-phenyl)-{6-[4-(3-isopropyl-[1,2,4]oxadiazol-5-yl)-piperidin-1-yl]-5-nitro-pyrimidin-4-yl}-amine. In certain embodiments, a biologically active fragment of the invention is a fragment optionally fused at its N-terminus to a peptide comprising an N-terminal methionine residue and an HA epitope tag that specifically binds (2-Fluoro-4-methanesulfonyl-phenyl)-{6-[4-(3-isopropyl-[1,2,4]oxadiazol-5-yl)-piperidin-1-yl]-5-nitro-pyrimidin-4-yl}-amine with an $IC_{50}$ value in receptor binding assay according to Example 15, infra, of less than about 50 µM, less than about 25 µM, less than about 10 µM, less than about 5 µM, less than about 1 µM, less than about 500 nM, less than about 100 nM, or less than about 50 nM. In certain embodiments, a biologically active fragment of the invention is a fragment optionally fused at its N-terminus to a peptide comprising an N-terminal methionine residue and an HA epitope tag that specifically binds (2-Fluoro-4-methanesulfonyl-phenyl)-{6-[4-(3-isopropyl-[1,2,4]oxadiazol-5-yl)-piperidin-1-yl]-5-nitro-pyrimidin-4-yl}-amine with an $IC_{50}$ value in receptor binding assay according to Example 15, infra, of less than about 10 µM, less than about 5 µM, less than about 1 µM, less than about 500 nM, less than about 100 nM, or less than about 50 nM. In certain embodiments, a biologically active fragment of the invention is a fragment optionally fused at its N-terminus to a peptide comprising an N-terminal methionine residue and an HA epitope tag for which (2-Fluoro-4-methanesulfonyl-phenyl)-{6-[4-(3-isopropyl-[1,2,4]oxadiazol-5-yl)-piperidin-1-yl]-5-nitro-pyrimidin-4-yl}-amine is an agonist having an $EC_{50}$ value at said fragment optionally fused at its N-terminus to said peptide in whole cell adenylyl cyclase assay according to Example 10 or in HTR® assay according to Example 11, infra, of less than about 5 µM, less than about 1 µM, less than about 100 nM, less than about 50 nM, less than about 25 nM, less than about 10 nM, less than about 5 nM, or less than about 1 nM. In certain embodiments, a biologically active fragment of the invention is a fragment optionally fused at its N-terminus to a peptide comprising an N-terminal methionine residue and an HA epitope tag for which (2-Fluoro-4-methanesulfonyl-phenyl)-{6-[4-(3-isopropyl-[1,2,4]oxadiazol-5-yl)-piperidin-1-yl]-5-nitro-pyrimidin-4-yl}-amine is an agonist having an $EC_{50}$ value at said fragment optionally fused at its N-terminus to said peptide in whole cell adenylyl cyclase assay according to Example 10 or in HTRF® assay according to Example 11, infra, of less than about 100 nM, less than about 50 nM, less than about 25 nM, less than about 10 nM, less than about 5 nM, or less than about 1 nM. In some embodiments, a biologically active fragment of the invention is a fragment optionally fused at its N-terminus to a peptide comprising an N-terminal methionine residue and an HA epitope tag that exhibits a detectable level of constitutive activity. In some embodiments, the constitutive activity is for increasing a level of intracellular cAMP. In some embodiments, the constitutive activity is for causing melanophore cells to undergo pigment dispersion. In certain embodiments, the fragment is fused at its N-terminus to a peptide consisting essentially of an N-terminal methionine residue and an HA epitope tag. Techniques for fusing a peptide comprising or consisting essentially of an N-terminal methionine residue and an HA epitope tag to the N-terminus of a polypeptide fragment are well known in the art and can be obtained commercially (e.g., Clontech, Mountain View, Calif.).

An allelic variant of human GPR119 of SEQ ID NO: 2 is envisioned to be within the scope of the invention. Human GPR119 is envisioned to be within the scope of the invention.

A variant which is a vertebrate ortholog of human GPR119 of SEQ ID NO: 2 is envisioned to be within the scope of the invention. A variant which is a mammalian ortholog of human GPR119 of SEQ ID NO: 2 is envisioned to be within the scope of the invention. By way of illustration and not limitation, mouse GPR119 (e.g., GenBank® Accession No. AY288423), rat GPR119 (GenBank® Accession No. AAN95195), hamster GPR119, dog GPR119, and non-human primate GPR119 are envisioned to be within the scope of the invention.

In certain embodiments, the variant of SEQ ID NO: 2 is a GPCR.

A variant of SEQ ID NO: 2 having at least about 80%, at least about 85%, at least about 90%, at least about 95%, at least about 96%, at least about 97%, at least about 98%, or at least about 99% identity to SEQ ID NO: 2 is envisioned to be within the scope of the invention. In certain embodiments, the variant of SEQ ID NO: 2 having at least about 80%, at least about 85%, at least about 90%, at least about 95%, at least about 96%, at least about 97%, at least about 98%, or at least about 99% identity to SEQ ID NO: 2 is a GPCR. In some embodiments, the variant of SEQ ID NO: 2 is an endogenous GPCR. In some embodiments, the variant of SEQ ID NO: 2 is a non-endogenous GPCR. In some embodiments, the variant of SEQ ID NO: 2 that is an endogenous GPCR is a mammalian GPCR. In certain embodiments, the variant of SEQ ID NO: 2 specifically binds Compound 1. In certain embodiments, the variant of SEQ ID NO: 2 specifically binds (2-Fluoro-4-methanesulfonyl-phenyl)-{6-[4-(3-isopropyl-[1,2,4]oxadiazol-5-yl)-piperidin-1-yl]-5-nitro-pyrimidin-4-yl}-amine. In certain embodiments, the variant of SEQ ID NO: 2 specifically binds (2-Fluoro-4-methanesulfonyl-phenyl)-{6-[4-(3-isopropyl-[1,2,4]oxadiazol-5-yl)-piperidin-1-yl]-5-nitro-pyrimidin-4-yl}-amine with an $IC_{50}$ value in receptor binding assay according to Example 15, infra, of less than about 50 µM, less than about 25 µM, less than about 10 µM, less than about 5 µM, less than about 1 µM, less than about 500 nM, less than about 100 nM, or less than about 50 nM. In certain embodiments, the variant of SEQ ID NO: 2 specifically binds (2-Fluoro-4-methanesulfonyl-phenyl)-{6-[4-(3-isopropyl-[1,2,4]oxadiazol-5-yl)-piperidin-1-yl]-5-nitro-pyrimidin-4-yl}-amine with an $IC_{50}$ value in receptor binding assay according to Example 15, infra, of less than about 10 µM, less than about 5 µM, less than about 1 µM, less than about 500 nM, less than about 100 nM, or less than about 50 nM. In certain embodiments, the variant of SEQ ID NO: 2 is a receptor for which (2-Fluoro-4-methanesulfonyl-phenyl)-{6-[4-(3-isopropyl-[1,2,4]oxadiazol-5-yl)-piperidin-1-yl]-5-nitro-pyrimidin-4-yl}-amine is an agonist having an $EC_{50}$ value at said receptor in whole cell adenylyl cyclase assay according to Example 10 or in HTRF® assay according to Example 11, infra, of less than about 5 µM, less than about 1 µM, less than about 100 nM, less than about 50 nM, less than about 25 nM, less than about 10 nM, less than about 5 nM, or less than about 1 nM. In certain embodiments, the variant of SEQ ID NO: 2 is a receptor for which (2-Fluoro-4-methanesulfonyl-phenyl)-{6-[4-(3-isopropyl-[1,2,4]oxadiazol-5-yl)-piperidin-1-yl]-5-nitro-pyrimidin-4-yl}-amine is an agonist having an $EC_{50}$ value at said receptor in whole cell adenylyl cyclase assay according to Example 10 or in HTRF® assay according to Example 11, infra, of less than about 100 nM, less than about 50 nM, less than about 25 nM, less than about 10 nM, less than about 5 nM, or less than about 1 nM. In some embodiments, the variant of SEQ ID NO: 2 exhibits a detectable level of constitutive activity. In some embodiments, the constitutive activity is for increasing a level of intracellular cAMP. In some embodiments, the constitutive activity is for causing melanophore cells to undergo pigment dispersion. Percent identity can be determined conventionally using known computer programs.

In certain embodiments, a variant GPCR that may be used in the subject methods has an amino acid sequence having at least about 80%, at least about 85%, at least about 90%, at least about 95%, of at least about 96%, at least about 97%, at least about 98%, or at least about 99% identity to SEQ ID NO: 2. By a variant GPCR having, for example, 95% "identity" to SEQ ID NO: 2 is meant that the amino acid sequence of the variant is identical to amino acids 1-335 of SEQ ID NO: 2 except that it may include up to five amino acid alterations per each 100 amino acids of SEQ ID NO: 2. Thus, to obtain for example an amino acid sequence having at least 95% identity to the amino acid sequence of SEQ ID NO: 2, up to 5% (5 of 100) of the amino acid residues in the sequence may be inserted, deleted, or substituted with another amino acid compared with amino acids 1-335 of SEQ ID NO: 2. These alternations may occur at the amino or carboxy termini or anywhere between those terminal positions, interspersed either subjectly among residues in the sequence or in one or more contiguous groups within the sequence.

In certain embodiments, a variant G protein-coupled receptor that may be used in the subject methods is a G protein-coupled receptor having an amino acid sequence derived from SEQ ID NO: 2 by deletion, substitution, and/or addition of one or several amino acids. In certain embodiments, a variant G protein-coupled receptor that may be used in the subject methods is a G protein-coupled receptor having an amino acid sequence derived from SEQ ID NO: 2 by no more than 10 conservative amino acid substitutions and/or no more than 3 non-conservative amino acid substitutions in the amino acid sequence of SEQ ID NO: 2. In certain embodiments, arginine, lysine and histidine may conservatively substitute for each other; glutamic acid and aspartic acid may conservatively substitute for each other; glutamine and asparagine may conservatively substitute for each other; leucine, isoleucine and valine may conservatively substitute for each other; phenylalanine, tryptophan and tyrosine may conservatively substitute for each other; and glycine, alanine, serine, threonine and methionine may conservatively substitute for each other. The amino acid substitutions, amino acid deletions, and amino acid additions may be at any position (e.g., the C- or N-terminus, or at internal positions). In some embodiments, the variant is an endogenous G protein-coupled receptor. In some embodiments, the variant is an endogenous vertebrate G protein-coupled receptor. In some embodiments, the variant is an endogenous mammalian G protein-coupled receptor. In some embodiments, the variant is an endogenous human G protein-coupled receptor. In some embodiments, the variant is a non-endogenous G protein-coupled receptor. In some embodiments, the variant exhibits a detectable level of constitutive activity. In some embodiments, the constitutive activity is for increasing intracellular cAMP. In some embodiments, the constitutive activity is for causing melanophore cells to undergo pigment dispersion. In certain embodiments, said G protein-coupled receptor having an amino acid sequence derived from SEQ ID NO: 2 is a G protein-coupled receptor for which Compound 1 is a ligand. In certain embodiments, said G protein-coupled receptor having an amino acid sequence derived from SEQ ID NO: 2 is a G protein-coupled receptor for which (2-Fluoro-4-methane-sulfonyl-phenyl)-{6-[4-(3-isopropyl-[1,2,4]oxadiazol-5-yl)-piperidin-1-yl]-5-nitro-pyrimidin-4-yl}-amine is a ligand having an $IC_{50}$ value in receptor binding assay according to Example 15, infra, of less than about 50 µM, less than about 25 µM, less than about 10 µM, less than about 5 µM, less than about 1 µM, less than about 500 nM, less than about 100 nM, or less than about 50 nM. In certain embodiments, said G protein-coupled receptor having an amino acid sequence derived from SEQ ID NO: 2 is a G protein-coupled receptor for which Compound 1 is an agonist. In certain embodiments, said G protein-coupled receptor having an amino acid sequence derived from SEQ ID NO: 2 is a G protein-coupled receptor for which (2-Fluoro-4-methanesulfonyl-phenyl)-{6-[4-(3-isopropyl-[1,2,4]oxadiazol-5-yl)-piperidin-1-yl]-5-nitro-pyrimidin-4-yl}-amine is an agonist having an $EC_{50}$ value in whole cell adenylyl cyclase assay according to Example 10 or in HTR® assay according to Example 11, infra, of less than about 5 µM, less than about 1 µM, less than about 100 nM, less than about 50 nM, less than about 25 nM, less than about 10 nM, less than about 5 nM, or less than about 1 nM.

A variant of SEQ ID NO: 2 that is a G protein-coupled receptor comprising at least 20, at least 30, at least 40, at least 50, at least 75, or at least 100 contiguous amino acids of SEQ ID NO: 2 is envisioned to be within the scope of the invention. In certain embodiments, the variant of SEQ ID NO: 2 comprising at least 20, at least 30, at least 40, at least 50, at least 75, or at least 100 contiguous amino acids of SEQ ID NO: 2 is a GPCR. In some embodiments, the variant of SEQ ID NO: 2 is an endogenous GPCR. In some embodiments, the variant of SEQ ID NO: 2 is a non-endogenous GPCR. In some embodiments, the variant of SEQ ID NO: 2 that is an endogenous GPCR is a mammalian GPCR. In certain embodiments, the variant of SEQ ID NO: 2 specifically binds Compound 1. In certain embodiments, the variant of SEQ ID NO: 2 specifically binds (2-Fluoro-4-methanesulfonyl-phenyl)-{6-[4-(3-isopropyl-[1,2,4]oxadiazol-5-yl)-piperidin-1-yl]-5-nitro-pyrimidin-4-yl}-amine. In certain embodiments, the variant of SEQ ID NO: 2 specifically binds (2-Fluoro-4-methanesulfonyl-phenyl)-{6-[4-(3-isopropyl-[1,2,4]oxadiazol-5-yl)-piperidin-1-yl]-5-nitro-pyrimidin-4-yl}-amine with an $IC_{50}$ value in receptor binding assay according to Example 15, infra, of less than about 50 µM, less than about 25 µM, less than about 10 µM, less than about 5 µM, less than about 1 µM, less than about 500 nM, less than about 100 nM, or less than about 50 nM. In certain embodiments, the variant of SEQ ID NO: 2 specifically binds (2-Fluoro-4-methanesulfonyl-phenyl)-{6-[4-(3-isopropyl-[1,2,4]oxadiazol-5-yl)-piperidin-1-yl]-5-nitro-pyrimidin-4-yl}-amine with an $IC_{50}$ value in receptor binding assay according to Example 15, infra, of less than about 10 µM, less than about 5 µM, less than about 1 µM, less than about 500 nM, less than about 100 nM, or less than about 50 nM. In certain embodiments, the variant of SEQ ID NO: 2 is a receptor for which (2-Fluoro-4-methanesulfonyl-phenyl)-{6-[4-(3-isopropyl-[1,2,4]oxadiazol-5-yl)-piperidin-1-yl]-5-nitro-pyrimidin-4-yl}-amine is an agonist having an $EC_{50}$ value at said receptor in whole cell adenylyl cyclase assay according to Example 10 or in HTRF® assay according to Example 11, infra, of less than about 5 µM, less than about 1 µM, less than about 100 nM, less than about 50 nM, less than about 25 nM, less than about 10 nM, less than about 5 nM, or less than about 1 nM. In certain embodiments, the variant of SEQ ID NO: 2 is a receptor for which (2-Fluoro-4-methanesulfonyl-phenyl)-{6-[4-(3-isopropyl-[1,2,4]oxadiazol-5-yl)-piperidin-1-yl]-5-nitro-pyrimidin-4-yl}-amine is an agonist having an $EC_{50}$ value at said receptor in whole cell adenylyl cyclase assay according to Example 10 or in HTRF® assay according to Example 11, infra, of less than about 100 nM, less than about 50 nM, less than about 25 nM, less than about 10 nM, less than about 5 nM, or less than about 1 nM. In some embodiments, the variant of SEQ ID NO: 2 exhibits a detectable level of constitutive activity. In some embodiments, the constitutive activity is for increasing a level of intracellular cAMP. In some embodiments, the constitutive activity is for causing melanophore cells to undergo pigment dispersion. In some embodiments, the G protein-coupled receptor comprising at least 20, at least 30, at least 40, at least 50, at least 75, or at least 100 contiguous amino acids of SEQ ID NO: 2 exhibits a detectable level of constitutive activity. In some embodiments, the constitutive activity is for increasing a level of intracellular cAMP. In some embodiments, the constitutive activity is for causing melanophore cells to undergo pigment dispersion.

In some embodiments, a variant GPCR that may be used in the subject methods is a GPCR encoded by a polynucleotide hybridizing under stringent conditions to the complement of SEQ ID NO: 1. In some embodiments, the GPCR encoded by a polynucleotide hybridizing under stringent conditions to the complement of SEQ ID NO: 1 is an endogenous GPCR. In some embodiments, the GPCR encoded by a polynucleotide hybridizing under stringent conditions to the complement of SEQ ID NO: 1 is a non-endogenous GPCR. In some embodiments, the GPCR encoded by a polynucleotide hybridizing under stringent conditions to the complement of SEQ ID NO: 1 and that is an endogenous GPCR is a mammalian endogenous GPCR. In certain embodiments, the GPCR encoded by a polynucleotide hybridizing under stringent conditions to the complement of SEQ ID NO: 1 is SEQ ID NO:2 or an allele thereof. In certain embodiments, the GPCR encoded by a polynucleotide hybridizing under stringent conditions to the complement of SEQ ID NO: 1 is an allele of SEQ ID NO:2. In certain embodiments, the GPCR encoded by a polynucleotide hybridizing under stringent conditions to the complement of SEQ ID NO: 1 is an ortholog of SEQ ID NO:2. In certain embodiments, the GPCR encoded by a polynucleotide hybridizing under stringent conditions to the complement of SEQ ID NO: 1 specifically binds Compound 1. In certain embodiments, the GPCR encoded by a polynucleotide hybridizing under stringent conditions to the complement of SEQ ID NO: 1 specifically binds (2-Fluoro-4-methanesulfonyl-phenyl)-{6-[4-(3-isopropyl-[1,2,4]oxadiazol-5-yl)-piperidin-1-yl]-5-nitro-pyrimidin-4-yl}-amine. In certain embodiments, the GPCR encoded by a polynucleotide hybridizing under stringent conditions to the complement of SEQ ID NO: 1 specifically binds (2-Fluoro-4-methanesulfonyl-phenyl)-{6-[4-(3-isopropyl-[1,2,4]oxadiazol-5-yl)-piperidin-1-yl]-5-nitro-pyrimidin-4-yl}-amine with an $IC_{50}$ value in receptor binding assay according to Example 15, infra, of less than about 50 µM, less than about 25 µM, less than about 10 µM, less than about 5 µM, less than about 1 µM, less than about 500 nM, less than about 100 nM, or less than about 50 nM. In certain embodiments, the GPCR encoded by a polynucleotide hybridizing under stringent conditions to the complement of SEQ ID NO: 1 specifically binds (2-Fluoro-4-methanesulfonyl-phenyl)-{6-[4-(3-isopropyl-[1,2,4]oxadiazol-5-yl)-piperidin-1-yl]-5-nitro-pyrimidin-4-yl}-amine with $IC_{50}$ value in receptor binding assay according to Example 15, infra, of less than about 10 µM, less than about 5 µM, less than about 1 µM, less than about 500 nM, less than about 100 nM, or less than about 50 nM. In certain embodiments, the GPCR encoded by a polynucleotide hybridizing under stringent conditions to the complement of SEQ ID NO: 1 is a receptor for which (2-Fluoro-4-methanesulfonyl-phenyl)-{6-[4-(3-isopropyl-[1,2,4]oxadiazol-5-yl)-piperidin-1-yl]-5-nitro-pyrimidin-4-yl}-amine is an agonist having an $EC_{50}$ value at said receptor in whole cell adenylyl cyclase assay according to Example 10 or in HTRF® assay according to Example 11, infra, of less than about 5 µM, less than about 1 µM, less than about 100 nM, less than about 50 nM, less than about 25 nM, less than about 10 nM, less than about 5 nM, or less than about 1 nM. In certain embodiments, the GPCR encoded by a polynucleotide hybridizing under stringent conditions to the complement of SEQ ID NO: 1 is a receptor for which (2-Fluoro-4-methanesulfonyl-phenyl)-{6-[4-(3-isopropyl-[1,2,4]oxadiazol-5-yl)-piperidin-1-yl]-5-nitro-pyrimidin-4-yl}-amine is an agonist having an $EC_{50}$ value at said receptor in whole cell adenylyl cyclase assay according to Example 10 or in HTRF® assay according to Example 11, infra, of less than about 100 nM, less than about 50 nM, less than about 25 nM, less than about 10 nM, less than about 5 nM, or less than about 1 nM. In some embodiments, the GPCR encoded by a polynucleotide hybridizing under stringent conditions to the complement of SEQ ID NO: 1 exhibits a detectable level of constitutive activity. In some embodiments, the constitutive activity is for increasing a level of intracellular cAMP. In some embodiments, the constitutive activity is for causing melanophore cells to undergo pigment dispersion.

Hybridization techniques are well known to the skilled artisan. In some embodiments, stringent hybridization conditions include overnight incubation at 42° C. in a solution comprising: 50% formamide, 5×SSC (1×SSC=150 mM NaCl, 15 mM trisodium citrate), 50 mM sodium phosphate (pH 7.6), 5×Denhardt's solution, 10% dextran sulfate, and 20 µg/ml denatured, sheared salmon sperm DNA; followed by washing the filter in 0.1×SSC at about 65° C. In some embodiments, stringent hybridization conditions include overnight incubation at 42° C. in a solution comprising: 50% formamide, 5×SSC (1×SSC=150 mM NaCl, 15 mM trisodium citrate), 50 mM sodium phosphate (pH 7.6), 5×Denhardt's solution, 10% dextran sulfate, and 20 µg/ml denatured, sheared salmon sperm DNA; followed by a wash in 0.1×SSC/0.1% SDS (sodium dodecyl sulfate) or in 0.2×SSC/0.1% SDS at about 50° C., at about 55° C., at about 60° C. or at about 65° C. In some embodiments, said stringent conditions comprise washing at 65° C. with 0.1×SSC. In some embodiments, said stringent conditions comprise washing at about 50° C., at about 55° C., at about 60° C., or at about 65° with 0.1×SSC/0.1SDS or with 0.2×SSC/0.1% SDS.

In some embodiments, a GPCR that may be used in the subject methods is a non-endogenous, constitutively activated receptor comprising the amino acid sequence of SEQ ID NO: 2, wherein the leucine at amino acid position 224 of SEQ ID NO: 2 is substituted with an amino acid other than leucine. In some embodiments, the amino acid other than leucine is lysine. In some embodiments, the amino acid other than leucine is alanine. In some embodiments, the amino acid other than leucine is arginine. In some embodiments, the amino acid other than leucine is histidine. In some embodiments, the constitutive activity is for increasing a level of intracellular cAMP. In some embodiments, the constitutive activity is for causing melanophore cells to undergo pigment dispersion.

In certain embodiments, a GPCR of the invention comprises a constitutively active version of a G protein-coupled receptor having SEQ ID NO: 2. In some embodiments, the constitutively active version of the receptor is an endogenous constitutively active version having SEQ ID NO: 2. In some embodiments, the constitutively active version of the receptor is a non-endogenous constitutively active version having a mutation positioned at amino acid position 224 of SEQ ID NO: 2. In some embodiments, the mutated residue has been mutated to a residue other than leucine. In some embodiments, the mutated residue has been mutated to a lysine residue. In some embodiments, the mutated residue has been mutated to an alanine residue. In some embodiments, the mutated residue has been mutated to an arginine residue. In some embodiments, the mutated residue has been mutated to a histidine residue. In some embodiments, the constitutive activity is for increasing a level of intracellular cAMP. In some embodiments, the constitutive activity is for causing melanophore cells to undergo pigment dispersion.

In certain embodiments, a GPCR of the invention forms part of a fusion protein with a G protein.

a. Sequence Identity

In certain embodiments, percent identity is evaluated using the Basic Local Alignment Search Tool ("BLAST"), which is well known in the art [See, e.g., Karlin and Altschul, Proc Natl Acad Sci USA (1990) 87:2264-2268; Altschul et al., J Mol Biol (1990) 215:403-410; Altschul et all, Nature Genetics (1993) 3:266-272; and Altschul et al., Nucleic Acids Res (1997) 25:3389-3402; the disclosure of each of which is herein incorporated by reference in its entirety]. The BLAST programs may be used with the default parameters or with modified parameters provided by the user. Preferably, the parameters are default parameters.

In certain embodiments, a preferred method for determining the best overall match between a query sequence (e.g., the amino acid sequence of SEQ ID NO:2) and a sequence to be interrogated, also referred to as a global sequence alignment, can be determined using the FASTDB computer program based on the algorithm of Brutlag et al. (Comp App Biosci (1990) 6:237-245; the disclosure of which is herein incorporated by reference in its entirety). In a sequence alignment the query and interrogated sequences are both amino acid sequences. The results of said global sequence alignment is in percent identity. Preferred parameters used in a FASTDB amino acid alignment are: Matrix=PAM 0, k-tuple=2, Mismatch Penalty=1, Joining Penalty=20, Randomization Group=25, Length=0, Cutoff Score=1, Window Size=sequence length, Gap Penalty=5, Gap Size Penalty=0.05, Window Size=247 or the length of the interrogated amino acid sequence, whichever is shorter. If the interrogated sequence is shorter than the query sequence due to N- or C-terminal deletions, not because of internal deletions, the results, in percent identity, must be manually corrected because the FASTDB program does not account for N- and C-terminal truncations of the interrogated sequence when calculating global percent identity. For interrogated sequences truncated at the N- and C-termini, relative to the query sequence, the percent identity is corrected by calculating the number of residues of the query sequence that are N- and C-terminal of the interrogated sequence, that are not matched/aligned with a corresponding interrogated sequence residue, as a percent of the total bases of the query sequence. Whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of the present invention. Only residues to the N- and C-termini of the interrogated sequence, which are not matched/aligned with the query sequence, are considered for the purposes of manually adjusting the percent identity score. That is, only query amino acid residues outside the farthest N- and C-terminal residues of the interrogated sequence.

For example, a 90 amino acid residue interrogated sequence is aligned with a 100-residue query sequence to determine percent identity. The deletion occurs at the N-terminus of the interrogated sequence and therefore, the FASTDB alignment does not match/align with the first residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched, the final percent identity would be 90%. In another example, a 90-residue interrogated sequence is compared with a 100-residue query sequence. This time the deletions are internal so there are no residues at the N- or C-termini of the interrogated sequence, which are not matched/aligned with the query. In this case, the percent identity calculated by FASTDB is not manually corrected. Once again, only residue positions outside the N- and C-terminal ends of the subject sequence, as displayed in the FASTDB alignment, which are not matched/aligned with the query sequence are manually corrected. No other corrections are made for the purposes of the present invention.

b. Fusion Proteins

In certain embodiments, a polypeptide of interest is a fusion protein, and may contain, for example, an affinity tag domain or a reporter domain. Suitable affinity tags include any amino acid sequence that may be specifically bound to another moiety, usually another polypeptide, most usually an antibody. Suitable affinity tags include epitope tags, for example, the V5 tag, the FLAG tag, the HA tag (from hemagglutinin influenza virus), the myc tag, and the like, as is known in the art. Suitable affinity tags also include domains for which, binding substrates are known, e.g., HIS, GST and MBP tags, as is known in the art, and domains from other proteins for which specific binding partners, e.g., antibodies, particularly monoclonal antibodies, are available. Suitable affinity tags also include any protein-protein interaction domain, such as a IgG Fc region, which may be specifically bound and detected using a suitable binding partner, e.g. the IgG Fc receptor. It is expressly contemplated that such a fusion protein may contain a heterologous N-terminal domain (e.g., an epitope tag) fused in-frame with a GPCR that has had its N-terminal methionine residue either deleted or substituted with an alternative amino acid.

Suitable reporter domains include any domain that can report the presence of a polypeptide. While it is recognized that an affinity tag may be used to report the presence of a polypeptide using, e.g., a labeled antibody that specifically binds to the tag, light emitting reporter domains are more usually used. Suitable light emitting reporter domains include luciferase (from, e.g., firefly, *Vargula*, *Renilla reniformis* or *Renilla muelleri*), or light emitting variants thereof. Other suitable reporter domains include fluorescent proteins, (from e.g., jellyfish, corals and other coelenterates as such those from *Aequoria*, *Renilla*, *Ptilosarcus*, *Stylatula* species), or light emitting variants thereof. Light emitting variants of these reporter proteins are very well known in the art and may be brighter, dimmer, or have different excitation and/or emission spectra, as compared to a native reporter protein. For example, some variants are altered such that they no longer appear green, and may appear blue, cyan, yellow, enhanced yellow red (termed BFP, CFP, YFP eYFP and RFP, respectively) or have other emission spectra, as is known in the art. Other suitable reporter domains include domains that can report the presence of a polypeptide through a biochemical or color change, such as β-galactosidase, β-glucuronidase, chloramphenicol acetyl transferase, and secreted embryonic alkaline phosphatase.

Also as is known in the art, an affinity tags or a reporter domain may be present at any position in a polypeptide of interest. However, in most embodiments, they are present at the C- or N-terminal end of a polypeptide of interest.

2. Nucleic Acids Encoding GPCR Polypeptides of Interest

Since the genetic code and recombinant techniques for manipulating nucleic acid are known, and the amino acid sequences of GPCR polypeptides of interest described as above, the design and production of nucleic acids encoding a GPCR polypeptide of interest is well within the skill of an artisan. In certain embodiments, standard recombinant DNA technology (Ausubel, et al, *Short Protocols in Molecular Biology*, 3rd ed., Wiley & Sons, 1995; Sambrook, et al., *Molecular Cloning: A Laboratory Manual*, Second Edition, (1989) Cold Spring Harbor, N.Y.) methods are used. For example, GPCR coding sequences may be isolated from a library of GPCR coding sequence using any one or a combination of a variety of recombinant methods that do not need to be described herein. Subsequent substitution, deletion, and/or addition of nucleotides in the nucleic acid sequence encoding a protein may also be done using standard recombinant DNA techniques. For example, site directed mutagenesis and subcloning may be used to introduce/delete/substitute nucleic acid residues in a polynucleotide encoding a polypeptide of interest. In other embodiments, PCR may be used. Nucleic acids encoding a polypeptide of interest may also be made by chemical synthesis entirely from oligonucleotides (e.g., Cello et al., Science (2002) 297:1016-8). In some embodiments, the codons of the nucleic acids encoding polypeptides of interest are optimized for expression in cells of a particular species, particularly a mammalian, e.g., mouse, rat, hamster, non-human primate, or human, species. In some embodiments, the codons of the nucleic acids encoding polypeptides of interest are optimized for expression in cells of a particular species, particularly an amphibian species.

a. Vectors

The invention further provides vectors (also referred to as "constructs") comprising a subject nucleic acid. In many embodiments of the invention, the subject nucleic acid sequences will be expressed in a host after the sequences have been operably linked to an expression control sequence, including, e.g. a promoter. The subject nucleic acids are also typically placed in an expression vector that can replicate in a host cell either as an episome or as an integral part of the host chromosomal DNA. Commonly, expression vectors will contain selection markers, e.g., tetracycline or neomycin, to permit detection of those cells transformed with the desired DNA sequences (see, e.g., U.S. Pat. No. 4,704,362, which is incorporated herein by reference). Vectors, including single and dual expression cassette vectors are well known in the art (Ausubel, et al, *Short Protocols in Molecular Biology*, 3rd ed., Wiley & Sons, 1995; Sambrook, et al., *Molecular Cloning: A Laboratory Manual*, Second Edition, (1989) Cold Spring Harbor, N.Y.). Suitable vectors include viral vectors, plasmids, cosmids, artificial chromosomes (human artificial chromosomes, bacterial artificial chromosomes, yeast artificial chromosomes, etc.), mini-chromosomes, and the like. Retroviral, adenoviral and adeno-associated viral vectors may be used.

A variety of expression vectors are available to those in the art for purposes of producing a polypeptide of interest in a cell and include expression vectors which are commercially available (e.g., from Invitrogen, Carlsbad, Calif.; Clontech, Mountain View, Calif.; Stratagene, La Jolla, Calif.). Commercially available expression vectors include, by way of non-limiting example, CMV promoter-based vectors. One suitable expression vector is pCMV. The expression vector may be adenoviral. An exemplary adenoviral vector may be purchased as AdEasy™ from Qbiogene (Carlsbad, Calif.) (He T C et al, Proc Natl Acad Sci USA (1998) 95:2509-2514; and U.S. Pat. No. 5,922,576; the disclosure of each of which is herein incorporated by reference in its entirety). Other suitable expression vectors will be readily apparent to those of ordinary skill in the art.

The subject nucleic acids usually comprise an single open reading frame encoding a subject polypeptide of interest, however, in certain embodiments, since the host cell for expression of the polypeptide of interest may be a eukaryotic cell, e.g., a mammalian cell, such as a human cell, the open reading frame may be interrupted by introns. Subject nucleic acid are typically part of a transcriptional unit which may contain, in addition to the subject nucleic acid 3' and 5' untranslated regions (UTRs) which may direct RNA stability, translational efficiency, etc. The subject nucleic acid may also be part of an expression cassette which contains, in addition to the subject nucleic acid a promoter, which directs the transcription and expression of a polypeptide of interest, and a transcriptional terminator.

Eukaryotic promoters can be any promoter that is functional in a eukaryotic host cell, including viral promoters and promoters derived from eukaryotic genes. Exemplary eukaryotic promoters include, but are not limited to, the following: the promoter of the mouse metallothionein I gene sequence (Hamer et al., J. Mol. Appl. Gen. 1:273-288, 1982); the TK promoter of Herpes virus (McKnight, Cell 31:355-365, 1982); the SV40 early promoter (Benoist et al., Nature (London) 290:304-310, 1981); the yeast gal1 gene sequence promoter (Johnston et al., Proc. Natl. Acad. Sci. (USA) 79:6971-6975, 1982); Silver et al., Proc. Natl. Acad. Sci. (USA) 81:5951-59SS, 1984), the CMV promoter, the EF-1 promoter, Ecdysone-responsive promoter(s), tetracycline-responsive promoter, and the like. Viral promoters may be of particular interest as they are generally particularly strong promoters. In certain embodiments, a promoter is used that is a promoter of the target pathogen. Promoters for use in the present invention are selected such that they are functional in the cell type (and/or animal) into which they are being introduced. In certain embodiments, the promoter is a CMV promoter.

In certain embodiments, a subject vector may also provide for expression of a selectable marker. Suitable vectors and selectable markers are well known in the art and discussed in Ausubel, et al, (Short Protocols in Molecular Biology, 3rd ed., Wiley & Sons, 1995) and Sambrook, et al, (Molecular Cloning: A Laboratory Manual, Third Edition, (2001) Cold Spring Harbor, N.Y.). A variety of different genes have been employed as selectable markers, and the particular gene employed in the subject vectors as a selectable marker is chosen primarily as a matter of convenience. Known selectable marker genes include: the thymidine kinase gene, the dihydrofolate reductase gene, the xanthine-guanine phosphoribosyl transferase gene, CAD, the adenosine deaminase gene, the asparagine synthetase gene, the antibiotic resistance genes, e.g. tetr, ampr, Cmr or cat, kanr or neor (aminoglycoside phosphotransferase genes), the hygromycin B phosphotransferase gene, and the like. As mentioned above, polypeptides of interest may be fusion proteins that contain an affinity domain and/or a reporter domain. Methods for making fusions between a reporter or tag and a GPCR, for example, at the C- or N-terminus of the GPCR, are well within the skill of one of skill in the art (e.g. McLean et al, Mol. Pharma. Mol Pharmacol. 1999 56:1182-91; Ramsay et al., Br. J. Pharmacology, 2001, 315-323) and will not be described any further. It is expressly contemplated that such a fusion protein may contain a heterologous N-terminal domain (e.g., an epitope tag) fused in-frame with a GPCR that has had its N-terminal methionine residue either deleted or substituted with an alternative amino acid. It is appreciated that a polypeptide of interest may first be made from a native polypeptide and then operably linked to a suitable reporter/tag as described above.

The subject nucleic acids may also contain restriction sites, multiple cloning sites, primer binding sites, ligatable ends, recombination sites etc., usually in order to facilitate the construction of a nucleic acid encoding a polypeptide of interest.

b. Host Cells

The invention further provides host cells comprising a vector comprising a subject nucleic acid. Suitable host cells include prokaryotic, e.g., bacterial cells (for example *E. coli*), as well as eukaryotic cells e.g. an animal cell (for example an insect, mammal, fish, amphibian, bird or reptile cell), a plant cell (for example a maize or *Arabidopsis* cell), or a fungal cell (for example a *S. cerevisiae* cell). In certain embodiments, any cell suitable for expression of a polypeptide of interest-encoding nucleic acid may be used as a host cell. Usually, an animal host cell line is used, examples of which are as follows: monkey kidney cells (COS cells), monkey kidney CVI cells transformed by SV40 (COS-7, ATCC CRL 165 1); human embryonic kidney cells (HEK-293 ["293"], Graham et al. J. Gen Virol. 36:59 (1977)); HEK-293T ["293T"] cells; baby hamster kidney cells (BHK, ATCC CCL 10); chinese hamster ovary-cells (CHO, Urlaub and Chasin, Proc. Natl. Acad. Sci. (USA) 77:4216, (1980); Syrian golden hamster cells MCB3901 (ATCC CRL-9595); mouse sertoli cells (TM4, Mather, Biol. Reprod. 23:243-251 (1980)); monkey kidney cells (CVI ATCC CCL 70); african green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (hep G2, HB 8065); mouse mammary tumor (MMT 060562, ATCC CCL 51); TRI cells (Mather et al., Annals N.Y. Acad. Sci 383:44-68 (1982)); NIH/3T3 cells (ATCC CRL-1658); and mouse L cells (ATCC CCL-1). In certain embodiments, melanophores are used. Melanophores are skin cells found in lower vertebrates. Relevant materials and methods will be followed according to the disclosure of U.S. Pat. No. 5,462,856 and U.S. Pat. No. 6,051,386. These patent disclosures are herein incorporated by reference in their entirety.

Additional cell lines will become apparent to those of ordinary skill in the art, and a wide variety of cell lines are available from the American Type Culture Collection, 10801 University Boulevard, Manassas, Va. 20110-2209.

C. Screening of Candidate Compounds

1. Generic GPCR Screening Assay Techniques

When a G protein receptor becomes active, it binds to a G protein (e.g., Gq, Gs, Gi, Gz, Go) and stimulates the binding of GTP to the G protein. The G protein then acts as a GTPase and slowly hydrolyzes the GTP to GDP, whereby the receptor, under normal conditions, becomes deactivated. However, activated receptors continue to exchange GDP to GTP. A non-hydrolyzable analog of GTP, [$^{35}$S]GTPγS, can be used to monitor enhanced binding to membranes which express activated receptors. It is reported that [$^{35}$S]GTPγS can be used to monitor G protein coupling to membranes in the absence and presence of ligand. An example of this monitoring, among other examples well-known and available to those in the art, was reported by Traynor and Nahorski in 1995. A preferred use of this assay system is for initial screening of candidate compounds because the system is generically applicable to all G protein-coupled receptors regardless of the particular G protein that interacts with the intracellular domain of the receptor.

2. Specific GPCR Screening Assay Techniques

Once candidate compounds are identified using the "generic" G protein-coupled receptor assay (i.e., an assay to select compounds that are agonists or inverse agonists), in some embodiments further screening to confirm that the compounds have interacted at the receptor site is preferred. For example, a compound identified by the "generic" assay may not bind to the receptor, but may instead merely "uncouple" the G protein from the intracellular domain.

a. Gs, Gz and Gi.

Gs stimulates the enzyme adenylyl cyclase. Gi (and Gz and Go), on the other hand, inhibit adenylyl cyclase. Adenylyl cyclase catalyzes the conversion of ATP to cAMP; thus, activated GPCRs that couple the Gs protein are associated with increased cellular levels of cAMP. On the other hand, activated GPCRs that couple Gi (or Gz, Go) protein are associated with decreased cellular levels of cAMP. See, generally, "Indirect Mechanisms of Synaptic Transmission," Chpt. 8, *From Neuron To Brain* ($3^{rd}$ Ed.) Nichols, J. G. et al eds. Sinauer Associates, Inc. (1992). Thus, assays that detect cAMP can be utilized to determine if a candidate compound is, e.g., an inverse agonist to the receptor (i.e., such a compound would decrease the levels of cAMP). A variety of approaches known in the art for measuring cAMP can be utilized; in some embodiments a preferred approach relies upon the use of anti-cAMP antibodies in an ELISA-based format. Another type of assay that can be utilized is a whole cell second messenger reporter system assay. Promoters on genes drive the expression of the proteins that a particular gene encodes. Cyclic AMP drives gene expression by promoting the binding of a cAMP-responsive DNA binding protein or transcription factor (CREB) that then binds to the promoter at specific sites called cAMP response elements and drives the expression of the gene. Reporter systems can be constructed which have a promoter containing multiple cAMP response elements before the reporter gene, e.g., β-galactosidase or luciferase. Thus, an activated Gs-linked receptor causes the accumulation of cAMP that then activates the gene and expression of the reporter protein. The reporter protein such as β-galactosidase or luciferase can then be detected using standard biochemical assays (Chen et al. 1995).

b. Go and Gq.

Gq and Go are associated with activation of the enzyme phospholipase C, which in turn hydrolyzes the phospholipid $PIP_2$, releasing two intracellular messengers: diacylglycerol (DAG) and inositol 1,4,5-triphosphate (IP3). Increased accumulation of $IP_3$ is associated with activation of Gq- and Go-associated receptors. See, generally, "Indirect Mechanisms of Synaptic Transmission," Chpt. 8, *From Neuron To Brain* ($3^{rd}$ Ed.) Nichols, J. G. et al eds. Sinauer Associates, Inc. (1992). Assays that detect $IP_3$ accumulation can be utilized to determine if a candidate compound is, e.g., an inverse agonist to a Gq- or Go-associated receptor (i.e., such a compound would decrease the levels of IP3). Gq-associated receptors can also been examined using an API reporter assay in that Gq-dependent phospholipase C causes activation of genes containing API elements; thus, activated Gq-associated receptors will evidence an increase in the expression of such genes, whereby inverse agonists thereto will evidence a decrease in such expression, and agonists will evidence an increase in such expression. Commercially available assays for such detection are available.

3. GPCR Fusion Protein

The use of an endogenous, constitutively active GPCR or a non-endogenous, constitutively activated GPCR, for use in screening of candidate compounds for the direct identification of inverse agonists or agonists provides an interesting screening challenge in that, by definition, the receptor is active even in the absence of an endogenous ligand bound thereto. Thus, in order to differentiate between, e.g., the non-endogenous receptor in the presence of a candidate compound and the non-endogenous receptor in the absence of that compound, with an aim of such a differentiation to allow for an understanding as to whether such compound may be an inverse agonist or agonist or have no affect on such a receptor, in some embodiments it is preferred that an approach be utilized that can enhance such differentiation. In some embodiments, a preferred approach is the use of a GPCR Fusion Protein.

Generally, once it is determined that a non-endogenous GPCR has been constitutively activated using the assay techniques set forth above (as well as others known to the art-skilled), it is possible to determine the predominant G protein that couples with the endogenous GPCR. Coupling of the G protein to the GPCR provides a signaling pathway that can be assessed. In some embodiments it is preferred that screening take place using a mammalian or a melanophore expression system, as such a system will be expected to have endogenous G protein therein. Thus, by definition, in such a system, the non-endogenous, constitutively activated GPCR will continuously signal. In some embodiments it is preferred that this signal be enhanced such that in the presence of, e.g., an inverse agonist to the receptor, it is more likely that it will be able to more readily differentiate, particularly in the context of screening, between the receptor when it is contacted with the inverse agonist.

The GPCR Fusion Protein is intended to enhance the efficacy of G protein coupling with the GPCR. The GPCR Fusion Protein may be preferred for screening with either an endogenous, constitutively active GPCR or a non-endogenous, constitutively activated GPCR because such an approach increases the signal that is generated in such screening techniques. This is important in facilitating a significant "signal to noise" ratio; such a significant ratio is preferred for the screening of candidate compounds as disclosed herein.

The construction of a construct useful for expression of a GPCR Fusion Protein is within the purview of those having ordinary skill in the art. Commercially available expression vectors and systems offer a variety of approaches that can fit the particular needs of an investigator. Important criteria in the construction of such a GPCR Fusion Protein construct include but are not limited to, that the GPCR sequence and the G protein sequence both be in-frame (preferably, the sequence for the endogenous GPCR is upstream of the G protein sequence), and that the "stop" codon of the GPCR be deleted or replaced such that upon expression of the GPCR, the G protein can also be expressed. The GPCR can be linked directly to the G protein, or there can be spacer residues between the two (preferably, no more than about 12, although this number can be readily ascertained by one of ordinary skill in the art). Based upon convenience, it is preferred to use a spacer. In some embodiments, it is preferred that the G protein that couples to the non-endogenous GPCR will have been identified prior to the creation of the GPCR Fusion Protein construct.

As noted above, activated GPCRs that couple to Gi, Gz and Go are expected to inhibit the formation of cAMP making assays based upon these types of GPCRs challenging (i.e., the cAMP signal decreases upon activation, thus making the direct identification of, e.g., agonists (which would further decrease this signal) challenging). As will be disclosed herein, it has been ascertained that for these types of receptors, it is possible to create a GPCR Fusion Protein that is not based upon the GPCR's endogenous G protein, in an effort to establish a viable cyclase-based assay. Thus, for example, an endogenous Gi coupled receptor can be fused to a Gs protein—such a fusion construct, upon expression, "drives" or "forces" the endogenous GPCR to couple with, e.g., Gs rather than the "natural" Gi protein, such that a cyclase-based assay can be established. Thus, for Gi, Gz and Go coupled receptors, in some embodiments it is preferred that when a GPCR Fusion Protein is used and the assay is based upon detection of adenylyl cyclase activity, that the fusion construct be established with Gs (or an equivalent G protein that stimulates the formation of the enzyme adenylyl cyclase).

TABLE C

| G protein | Effect of cAMP Production upon Activation of GPCR (i.e., constitutive activation or agonist binding) | Effect of $IP_3$ Accumulation upon Activation of GPCR (i.e., constitutive activation or agonist binding) | Effect of cAMP Production upon contact with an Inverse Agonist | Effect on $IP_3$ Accumulation upon contact with an Inverse Agonist |
|---|---|---|---|---|
| Gs | Increase | N/A | Decrease | N/A |
| Gi | Decrease | N/A | Increase | N/A |
| Gz | Decrease | N/A | Increase | N/A |
| Go | Decrease | Increase | Increase | Decrease |
| Gq | N/A | Increase | N/A | Decrease |

Equally effective is a G Protein Fusion construct that utilizes a Gq Protein fused with a Gs, Gi, Gz or Go Protein. In some embodiments a preferred fusion construct can be accomplished with a Gq Protein wherein the first six (6) amino acids of the G-protein α-subunit ("Gαq") is deleted and the last five (5) amino acids at the C-terminal end of Gαq is replaced with the corresponding amino acids of the Gα of the G protein of interest. For example, a fusion construct can have a Gq (6 amino acid deletion) fused with a Gi Protein, resulting in a "Gq/Gi Fusion Construct". This fusion construct will force the endogenous Gi coupled receptor to couple to its non-endogenous G protein, Gq, such that the second messenger, for example, inositol triphosphate or diacylglycerol, can be measured in lieu of cAMP production.

4. Co-Transfection of a Target Gi Coupled GPCR with a Signal-Enhancer Gs Coupled GPCR (cAMP Based Assays)

A Gi coupled receptor is known to inhibit adenylyl cyclase, and, therefore, decreases the level of cAMP production, which can make the assessment of cAMP levels challenging. In certain embodiments, an effective technique in measuring the decrease in production of cAMP as an indication of activation of a receptor that predominantly couples Gi upon activation can be accomplished by co-transfecting a signal enhancer, e.g., a non-endogenous, constitutively activated receptor that predominantly couples with Gs upon activation (e.g., TSHR-A6231; see infra), with the Gi linked GPCR. As is apparent, activation of a Gs coupled receptor can be determined based upon an increase in production of cAMP. Activation of a Gi coupled receptor leads to a decrease in production cAMP. Thus, the co-transfection approach is intended to advantageously exploit these "opposite" affects. For example, co-transfection of a non-endogenous, constitutively activated Gs coupled receptor (the "signal enhancer") with expression vector alone provides a baseline cAMP signal (i.e., although the Gi coupled receptor will decrease cAMP levels, this "decrease" will be relative to the substantial increase in cAMP levels established by constitutively activated Gs coupled signal enhancer). By then co-transfecting the signal enhancer with the "target receptor", an inverse agonist of the Gi coupled target receptor will increase the measured cAMP signal, while an agonist of the Gi coupled target receptor will decrease this signal.

Candidate compounds that are directly identified using this approach should be assessed independently to ensure that these do not target the signal enhancing receptor (this can be done prior to or after screening against the co-transfected receptors).

Composition/Formulation and Methods of Treatment

A compound of the invention, e.g. a GPR119 agonist, a PYY secretagogue, a compound useful for treatment or prevention of a condition modulated by PYY, or a compound useful for a modulation of a PYY-related activity in an individual, can be formulated into pharmaceutical compositions and medicaments for use in accordance with the present invention using techniques well known in the art. Proper formulation is dependent on the route of administration chosen. In certain embodiments, said administration is to a non-human vertebrate or to a non-human mammal.

As relates to therapies of the present invention, namely therapies relating to a GPR119 agonist, the compounds according to the invention can be administered in any suitable way. Suitable routes of administration include oral, nasal, rectal, transmucosal, transdermal, or intestinal administration, parenteral delivery, including intramuscular, subcutaneous, intramedullary injections, as well as intrathecal, direct intraventricular, intravenous, intraperitoneal, intranasal, intrapulmonary (inhaled) or intraocular injections using methods known in the art. Other suitable routes of administration are aerosol and depot formulation. Sustained release formulations, particularly depot, of the invented medicaments are expressly contemplated. In certain preferred embodiments, the compounds according to the present invention are administered orally. The compounds according to the present invention can be made up in solid or liquid form, such as tablets, capsules, powders, syrups, elixirs and the like, aerosols, sterile solutions, suspensions or emulsions, and the like. In certain embodiments, the GPR119 agonist is administered orally.

In certain preferred embodiments, the compounds according to the present invention, e.g. GPR119 agonists, are administered orally. In certain preferred embodiments, the compounds according to the present invention, e.g. GPR119 agonists, are administered in a manner that allows for stimulation of PYY secretion in gut enteroendocrine cells. In certain preferred embodiments, the compounds according to the present invention, e.g. GPR119 agonists, are administered orally in a manner that allows for stimulation of PYY secretion in gut enteroendocrine cells.

In certain preferred embodiments, the compounds according to the present invention, e.g. PYY secretagogues, compounds useful for treatment or prevention of a condition modulated by PYY, or compounds useful for a modulation of a PYY-related activity in an individual, are administered orally. In certain preferred embodiments, the compounds according to the present invention, e.g. GPR119 agonists, are administered in a manner that allows for stimulation of PYY secretion in gut enteroendocrine cells. In certain preferred embodiments, the compounds according to the present invention, e.g. GPR119 agonists, are administered orally in a manner that allows for stimulation of PYY secretion in gut enteroendocrine cells.

Formulations for oral administration may be in the form of aqueous solutions and suspensions, in addition to solid tablet and capsule formulations. The aqueous solutions and suspensions may be prepared from sterile powders or granules. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants are well and widely known in the art.

Pharmaceutical compositions of the GPR119 agonist may be prepared by methods well known in the art, e.g., by means of conventional mixing, dissolving, granulation, dragee-making, levigating, emulsifying, encapsulating, entrapping, lyophilizing processes or spray drying.

Pharmaceutical compositions for use in accordance with the present invention may be formulated in conventional manner using one or more physiologically acceptable carriers comprising excipients and auxiliaries which facilitate processing of the active compounds into preparations which can be used pharmaceutically. Suitable pharmaceutically acceptable carriers are available to those in the art (see, e.g., Remington: The Science and Practice of Pharmacy, (Gennaro et al., eds.), $20^{th}$ Edition, 2000, Lippincott Williams & Wilkins; and Handbook of Pharmaceutical Excipients (Rowe et al., eds), $4^{th}$ Edition, 2003, Pharmaceutical Press; the disclosure of each of which is herein incorporated by reference in its entirety). Proper formulation is dependent upon the route of administration chosen. The term "carrier" material or "excipient" material herein means any substance, not itself a therapeutic agent, used as a carrier and/or diluent and/or adjuvant, or vehicle for delivery of a therapeutic agent to a subject or added to a pharmaceutical composition to improve its handling or storage properties or to permit or facilitate formation of a dose unit of the composition into a discrete article such as a capsule or tablet suitable for oral admininstration. Excipients can include, by way of illustration and not limitation, diluents, disintegrants, binding agents, adhesives, wetting agents, polymers, lubricants, glidants, substances added to mask or counteract a disagreeable taste or odor, flavors, dyes, fragrances, and substances added to improved appearance of the composition. Acceptable excipients include stearic acid, magnesium stearate, magnesium oxide, sodium and calcium salts of phosphoric and sulfuric acids, magnesium carbonate, talc, gelatin, acacia gum, sodium alginate, pectin, dextrin, mannitol, sorbitol, lactose, sucrose, starches, gelatin, cellulosic materials, such as cellulose esters of alkanoic acids and cellulose alkyl esters, low melting wax cocoa butter or powder, polymers, such as polyvinyl-pyrrolidone, polyvinyl alcohol, and polytheylene glycols, and other pharmaceutically acceptable materials. The components of the pharmaceutical composition can be encapsulated or tableted for convenient administration.

Pharmaceutically acceptable refers to those properties and/or substances which are acceptable to the patient from a pharmacological/toxicological point of view and to the manufacturing pharmaceutical chemist from a physical/chemical point of view regarding composition, formulation, stability, patient acceptance and bioavailability.

Dragee cores are provided with suitable coatings. For this purpose, concentrated sugar solutions may be used which may optionally contain gum Arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical compositions which can be used orally include push-fit capsules made of gelatin, as well as soft, sealed capsules made of gelatin and a plasticizer, such as glycerol or sorbitol. The push-fit capsules can contain the active ingredients in admixture with a filler such as lactose, a binder such as starch, and/or a lubricant such as talc or magnesium stearate and, optionally, stabilizers. In soft capsules, the active compounds may be dissolved or suspended in suitable liquids, such as fatty oils, liquid paraffin, liquid polyethylene glycols, cremophor, capmul, medium or long chain mono-, di- or triglycerides. Stabilizers may be added in these formulations, also.

Additionally, a GPR119 agonist may be delivered using a sustained-release system. Various sustained-release materials have been established and are well known to those skilled in the art. Sustained-release tablets or capsules are particularly preferred. For example, a time delay material such as glyceryl monostearate or glyceryl distearate may be employed. The dosage form may also be coated by the techniques described in the U.S. Pat. Nos. 4,256,108, 4,166,452, and 4,265,874 to form osmotic therapeutic tablets for controlled release.

It is expressly contemplated that therapies of the present invention, namely therapies relating to a GPR119 agonist, may be administered or provided alone or in combination with one or more other pharmaceutically or physiologically acceptable compound. In one aspect of the present invention, the other pharmaceutically or physiologically acceptable compound is not a GPR119 agonist. In one aspect of the present invention, the other pharmaceutically or physiologically acceptable compound is a pharmaceutical agent selected from the group consisting of calcium, vitamin D, estrogen, tibolone, selective estrogen receptor modulator (SERM; e.g., raloxifene, tamoxifen), biphosphonate (e.g., etidronate, alendronate, risedronate), calcitonin, 1α-hydroxylated metabolite of vitamin D, fluoride, thiazide, anabolic steroid, ipriflavone, vitamin K, parathyroid hormone (PTH), strontium, statin, osteoprotererin, EP4 receptor selective agonist, cannabinoid receptor type 2 (CB2) selective agonist, and p38 MAP kinase inhibitor. (See, e.g., World Health Organization Technical Report Series 921 (2003), Prevention and Management of Osteoporosis.)

In one aspect, the present invention features a composition comprising or consisting essentially of an amount of a GPR119 agonist according to the present invention. In one aspect, the present invention features a pharmaceutical composition comprising or consisting essentially of an amount of a GPR119 agonist according to the present invention and at least one pharmaceutically acceptable carrier.

In one aspect, the present invention features a composition comprising or consisting essentially of an amount of a GPR119 agonist according to the present invention. In one aspect, the present invention features a pharmaceutical composition comprising or consisting essentially of an amount of a GPR119 agonist according to the present invention and at least one pharmaceutically acceptable carrier. The present invention also relates to a dosage form of the composition or of the pharmaceutical composition wherein the GPR119 agonist, the PYY secretagogue, the compound useful for treatment or prevention of a condition modulated by PYY, or the compound useful for a modulation of a PYY-related activity in an individual is in an amount sufficient to increase a PYY level in an individual, such as a plasma total PYY level or a plasma $PYY_{3-36}$ level. The present invention also relates to a dosage form of the composition or of the pharmaceutical composition wherein the GPR119 agonist is in an amount sufficient to give an effect in treating or preventing a condition characterized by low bone mass, such as osteoporosis, and/or in increasing bone mass in an individual.

In one aspect, the present invention features a composition comprising or consisting essentially of an amount of a GPR119 agonist according to the present invention. In one aspect, the present invention features a pharmaceutical composition comprising or consisting essentially of an amount of a GPR119 agonist according to the present invention and at least one pharmaceutically acceptable carrier. The present invention also relates to a dosage form of the composition or of the pharmaceutical composition wherein the GPR119 agonist is in an amount sufficient to give an effect in increasing a PYY level in an individual. The present invention also relates to a dosage form of the composition or of the pharmaceutical composition wherein the GPR119 agonist is in an amount sufficient to give an effect in increasing a total PYY (inclusive of $PYY_{1-36}$ and $PYY_{3-36}$) level in an individual. The present invention also relates to a dosage form of the composition or of the pharmaceutical composition wherein the GPR119 agonist is in an amount sufficient to give an effect in increasing a $PYY_{3-36}$ level in an individual.

Pharmaceutical compositions suitable for use in the present invention include compositions wherein the active ingredients are contained in an amount to achieve their intended purpose. In some embodiments, a pharmaceutical composition of the present invention is understood to be useful for treatment or prevention of a condition modulated by PYY. Conditions modulated by PYY are according to the present invention. In some embodiments, a pharmaceutical composition of the present invention is understood to be useful for increasing a PYY level in an individual. As relates to the present invention, determination of the amount of a GPR119 agonist sufficient to achieve an intended purpose according to the invention is well within the capability of those skilled in the art, especially in light of the detailed disclosure provided herein.

The data obtained from animal studies, including but not limited to studies using mice, rats, rabbits, pigs, and non-human primates, can be used in formulating a range of dosage for use in humans. In general, one skilled in the art understands how to extrapolate in vivo data obtained in an animal model system to another, such as a human. In some circumstances, these extrapolations may merely be based on the weight of the animal model in comparison to another, such as a human; in other circumstances, these extrapolations are not simply based on weights but rather incorporate a variety of factors. Representative factors include the type, age, weight, sex, diet and medical condition of the patient, the severity of the disease, the route of administration, pharmacological considerations such as the activity, efficacy, pharmacokinetic and toxicology profiles of the particular compound employed, whether a drug delivery system is utilized, on whether an acute or chronic disease state is being treated or prophylaxis is conducted or on whether further active compounds are administered in addition to the compounds of the present invention and as part of a drug combination. The dosage regimen for treating a disease condition with the compounds and/or compositions of this invention is selected in accordance with a variety factors as cited above. Thus, the actual dosage regimen employed may vary widely and therefore may deviate from a preferred dosage regimen and one skilled in the art will recognize that dosage and dosage regimen outside these typical ranges can be tested and, where appropriate, may be used in the methods of this invention.

An exemplary animal model system is the rat ovariectomy (OVX) bone loss model. The ovariectomized rat is an excellent preclinical animal model that correctly emulates the important clinical feature of the estrogen depleted human skeleton and the response of therapeutic agents. In this model, a therapeutic efficacy is achieved when the bone loss associated with ovariectomy is partially or completely prevented. (See, e.g., Bollag et al, Mol Cell Endocrinol (2001) 177:35-41; and Jee et al, J Musculoskel Neuron Interact (2001) 1:193-207.) In certain embodiments, therapeutic efficacy is achieved when the bone loss associated with ovariectomy is at least about 10% prevented, at least about 20% prevented, at least about 30% prevented, at least about 40% prevented, at least about 50% prevented, at least about 60% prevented, at least about 70% prevented, at least about 75% prevented, at least about 80% prevented, at least about 85% prevented, at least about 90% prevented, at least about 95% prevented, or 100% prevented.

An additional exemplary animal model system is increase of a blood PYY level after glucose challenge in mice. In certain embodiments, the blood PYY level is a plasma PYY level. In certain embodiments, the PYY level is a glucose-independent PYY level. In certain embodiments, the PYY level is a glucose-dependent PYY level. In certain embodiments, the PYY is total PYY, inclusive of $PYY_{1-36}$ and $PYY_{3-36}$. In certain embodiments, the PYY is $PYY_{3-36}$. Kits for measuring total PYY or $PYY_{3-36}$ in rodents or humans are commercially available, such as from Phoenix Pharmaceuticals, Inc. (Burlingame, Calif.). Also, $PYY_{1-36}$ and $PYY_{3-36}$ can be independently measured by biochemical means (Eberlein et al, Peptides (1989) 10:797-803; Grandt et al, Regul Pept (1994) 51:151-159; Cruze et al, Peptides (2007) 28:269-280). In certain embodiments, a PYY-related activity of the invention is a $PYY_{3-36}$-related activity. In certain embodiments, therapeutic efficacy is achieved when a blood or plasma PYY level is increased by at least about 10%, at least about 25%, at least about 50%, at least about 100%, at least about 150%, at least about 200%, at least about 300%, at least about 400%, at least about 500%, at least about 600%, at least about 700%, at least about 800%, at least about 900%, or at least about 1000%.

It is expressly contemplated that a GPR119 agonist can be administered on a daily or regular basis to achieve an increased level of PYY in an individual. In certain embodiments, a GPR119 agonist is administered on a daily or regular basis to achieve an increased blood (e.g., plasma) level of PYY in an individual. In certain embodiments, a GPR119 agonist is administered on a daily or regular basis to achieve an increased blood (e.g., plasma) level of PYY in an individual that is at least about 10%, at least about 25%, at least about 50%, at least about 100%, at least about 150%, at least about 200%, at least about 300%, at least about 400%, at least about 500%, at least about 600%, at least about 700%, at least about 800%, at least about 900%, or at least about 1000% a normal blood (e.g., plasma) level of PYY (e.g., a normal pre-meal plasma PYY level (e.g., plasma total PYY level) or a plasma PYY level (e.g., a plasma total PYY level) between the normal pre-meal and post-meal plasma PYY levels) in an individual or the blood (e.g., plasma) level of PYY (e.g., plasma total PYY) in the individual prior to treatment. It is noted that these ranges of increased blood (e.g., plasma) level of PYY (e.g., plasma total PYY) are exemplary ranges and are not meant to be limiting to the invention.

It is expressly contemplated that a GPR119 agonist can be administered on a daily or regular basis to achieve an increased level of PYY in an individual. In certain embodiments, a GPR119 agonist is administered on a daily or regular basis to achieve an increased blood (e.g., plasma) level of PYY in an individual. In certain embodiments, a GPR119 agonist is administered on a daily or regular basis to achieve an increased blood (e.g., plasma) level of PYY in an individual within a concentration range of 0.1 ng/ml to 10 ng/ml or 100 ng/ml, 0.2 ng/ml to 10 ng/ml or 100 ng/ml, 0.3 ng/ml to 10 ng/ml or 100 ng/ml, 0.4 ng/ml to 10 ng/ml or 100 ng/ml, 0.5 ng/ml to 10 ng/ml or 100 ng/ml, 0.6 ng/ml to 10 ng/ml or 100 ng/ml, 0.7 ng/ml to 10 ng/ml or 100 ng/ml, 0.8 ng/ml to 10 ng/ml or 100 ng/ml, 0.9 ng/ml to 10 ng/ml or 100 ng/ml, 1 ng/ml to 10 ng/ml or 100 ng/ml, 2 ng/ml to 10 ng/ml or 100 ng/ml, 3 ng/ml to 10 ng/ml or 100 ng/ml, or 5 ng/ml to 10 ng/ml or 100 ng/ml. It is noted that these ranges of blood (e.g., plasma) PYY concentration (e.g., plasma total PYY concentration) are exemplary ranges and are not meant to be limiting to the invention.

Dosage amount and interval may be adjusted in order to provide an intended therapeutic effect. It will be appreciated that the exact dosage of a GPR119 agonist in accordance with the present invention will vary depending on the GPR119 agonist, its potency, the mode of administration, the age and weight of the patient and the severity of the condition to be treated. The exact formulation, route of administration and dosage can be chosen by the individual physician in view of the patient's condition. By way of illustration and not limitation, an amount of a GPR119 agonist in accordance with the present invention is an amount less than about 0.001 mg/kg body weight, less than about 0.005 mg/kg body weight, less than about 0.01 mg/kg body weight, less than about 0.05 mg/kg body weight, less than about 0.1 mg/kg body weight, less than about 0.5 mg/kg body weight, less than about 1 mg/kg body weight, less than about 5 mg/kg body weight, less than about 10 mg/kg body weight, less than about 50 mg/kg body weight, or less than about 100 mg/kg body weight.

A preferred dosage range for the amount of a compound of the invention (e.g. a GPR119 agonist, a PYY secretagogue, a compound useful for treatment or prevention of a condition modulated by PYY, or a compound useful for a modulation of a PYY-related activity in an individual), which can be administered on a daily or regular basis to achieve desired results is 0.1-100 mg/kg body mass. Other preferred dosage range is 0.1-30 mg/kg body mass. Other preferred dosage range is 0.1-10 mg/kg body mass. Other preferred dosage range is 0.1-3.0 mg/kg body mass. Exemplary preferred dosage is selected from the group consisting of 0.1 mg/kg, 0.3 mg/kg, 1.0 mg/kg, 3.0 mg/kg, 10 mg/kg, 30 mg/kg and 100 mg/kg. Of course, these daily dosages can be delivered or administered in small amounts periodically during the course of a day. It is noted that these dosage ranges are only preferred ranges and are not meant to be limiting to the invention. It is noted that these dosages are only preferred dosages and are not meant to be limiting to the invention.

Dosage amount and interval may be adjusted individually to provide plasma levels of a GPR119 agonist according to the present invention which achieve an intended therapeutic effect. Dosage intervals can also be determined using the value for a selected range of GPR119 agonist concentration so as to achieve the intended therapeutic effect. A GPR119 agonist should be administered using a regimen that maintains plasma levels within the selected range of GPR119 agonist concentration for 10-90% of the time, preferably between 30-99% of the time, and most preferably between 50-90% of the time. In cases of local administration or selective uptake, the range of GPR119 agonist concentration providing the intended therapeutic effect may not be related to plasma concentration.

The amount of composition administered will, of course, be dependent on the individual being treated, on the individual's weight, the severity of the affliction, the manner of administration, and the judgement of the prescribing physician.

In one aspect, the present invention accordingly features a method of treating or preventing a condition characterized by low bone mass, such as osteoporosis, or of increasing bone mass comprising administering to an individual in need thereof a therapeutically effective amount of a composition comprising or consisting essentially of an amount of a GPR119 agonist according to the present invention. In certain embodiments, the composition is a pharmaceutical composition.

In one aspect, the present invention relates to a method of treating or preventing a condition characterized by low bone mass, such as osteoporosis, or of increasing bone mass comprising administering to an individual in need thereof a therapeutically effective amount of a composition comprising or consisting essentially of an amount of a GPR119 agonist according to the present invention. In a related aspect, the present invention features said method wherein the GPR119 agonist is administered in an amount sufficient to give an effect in increasing a PYY level in the individual. In certain embodiments, the composition is a pharmaceutical composition.

Therapies of the present invention, such as therapies relating to a GPR119 agonist, are useful in treatment or prevention of a condition modulated by PYY.

In certain embodiments, the condition modulated by PYY is a bone-related condition.

In certain embodiments, the bone-related condition is a condition characterized by low bone mass. In certain embodiments, the condition characterized by low bone mass is selected from the group consisting of osteopenia, osteoporosis, rheumatoid arthritis, osteoarthritis, periodontal disease, alveolar bone loss, osteotomy bone loss, childhood idiopathic bone loss, Paget's disease, bone loss due to metastatic cancer, osteolytic lesions, curvature of the spine, and loss of height.

In certain embodiments, the bone-related condition is a bone fracture. In certain embodiments, the bone fracture is selected from the group consisting of a traumatic bone fracture, a long-term bone fracture, and an osteoporotic bone fracture.

In certain embodiments, the bone-related condition is a bone disease. In certain embodiments, the bone disease is selected from the group consisting of osteopenia, osteoporosis, rheumatoid arthritis, osteoarthritis, periodontal disease, alveolar bone loss, osteotomy bone loss, childhood idiopathic bone loss, Paget's disease, bone loss due to metastatic cancer, osteolytic lesions, curvature of the spine, and loss of height.

In certain embodiments, the bone-related condition is enhanced bone healing or bone growth, wherein said enhanced bone healing or bone growth is selected from the group consisting of enhanced bone healing following facial reconstruction, maxillary reconstruction, mandibular reconstruction, periodontal disease or tooth extraction, enhanced long bone extension, enhanced prosthetic ingrowth, and increased bone synostosis.

In certain embodiments, the condition modulated by PYY is a metabolic disorder.

In certain embodiments, the metabolic disorder is selected from the group consisting of overweight, obesity, hyperphagia, diabetes (inclusive of type 1 diabetes and type 2 diabetes), type 1 diabetes, type 2 diabetes, impaired glucose tolerance, insulin resistance, hyperinsulinemia, dyslipidemia, hypertension and metabolic syndrome.

In certain embodiments, the condition modulated by PYY is an angiogenesis-related condition.

In certain embodiments, the angiogeneisis-related condition is selected from the group consisting of peripheral arterial disease, wound healing and ischemia.

In certain embodiments, the condition modulated by PYY is an ischemia-related condition.

In certain embodiments, the ischemia-related condition is selected from the group consisting of cerebral ischemia, stroke, ischemic heart disease, myocardial infarction, ischemia-reperfusion injury, post-myocardial infarction remodeling, heart failure, and congestive heart failure.

In certain embodiments, the condition modulated by PYY is a malabsorptive disorder.

In certain embodiments, the malabsorptive disorder is selected from the group consisting of short bowel syndrome, enterocolitis, Crohn's disease, ulcerative colitis, irritable bowel syndrome, cholera, and a disorder accompanied by diarrhea.

In certain embodiments, the condition modulated by PYY is a convulsive disorder.

In certain embodiments, the convulsive disorder is epilepsy.

In certain embodiments, the condition modulated by PYY is a cancer.

In certain embodiments, the cancer is selected from the group consisting of pancreatic cancer, breast cancer, colon cancer, and Barrett's adenocarcinoma.

In certain embodiments, the condition modulated by PYY is an inflammatory disorder.

In certain embodiments, the inflammatory disorder is selected from the group consisting of atherosclerosis, atherothrombosis, psoriasis, psoriatic arthritis, rheumatoid arthritis, osteoarthritis, insulin resistance, diabetes (inclusive of type 1 diabetes and type 2 diabetes), type 1 diabetes, type 2 diabetes, metabolic syndrome, obesity, lower than normal HDL-cholesterol, hypertension, hyperlipidemia, ischemic heart disease, myocardial infarction, congestive heart failure, osteoporosis, higher than normal osteoclastogenesis, pancreatitis, interstitial nephritis, acute transplant rejection, chronic hepatitis, hepatic steatosis, multiple sclerosis, systemic lupus erythematosus (SLE), restenosis, ischemia-reperfusion injury, allergic inflammation, Parkinson's disease, prion-associated disease, excitotoxic injury, Alzheimer's disease, mild cognitive impairment (MCI), disseminated intravascular coagulation, septic shock, an inflammatory lung disease, and an inflammatory bowel disease. In certain embodiments, the inflammatory lung disease is selected from the group consisting of asthma, emphysema, interstitial lung disease, idiopathic pulmonary fibrosis, bronchiolitis obliterans syndrome, chronic obstructive pulmonary disease (COPD), and pulmonary arterial hypertension. In certain embodiments, the inflammatory bowel disease is selected from the group consisting of enteritis, enterocolitis, Crohn's disease, granulomatous colitis, ileitis, Crohn's colitis, ulcerative colitis, sigmoiditis, pancolitis, and ulcerative proctitis.

In certain embodiments, the inflammatory disorder is selected from the group consisting of atherosclerosis, atherothrombosis, insulin resistance, pancreatitis, restenosis, an inflammatory lung disease, and an inflammatory bowel disease. In certain embodiments, the inflammatory lung disease is selected from the group consisting of asthma, emphysema, and pulmonary arterial hypertension. In certain embodiments, the inflammatory bowel disease is selected from the group consisting of enteritis, enterocolitis, Crohn's disease, granulomatous colitis, ileitis, Crohn's colitis, ulcerative colitis, sigmoiditis, pancolitis, and ulcerative proctitis.

Conditions characterized by low bone mass include but are not limited to osteopenia, osteoporosis, rheumatoid arthritis, osteoarthritis, periodontal disease, alveolar bone loss, osteotomy bone loss, childhood idiopathic bone loss, Paget's disease, bone loss due to metastatic cancer, osteolytic lesions, curvature of the spine, and loss of height. In certain embodiments, the condition characterized by low bone mass is osteoporosis. In certain embodiments, the condition characterized by low bone mass is osteoporosis. In certain embodiments, osteoporosis is primary osteoporosis. In certain embodiments, osteoporosis is secondary osteoporosis. Conditions characterized by low bone mass also include but are not limited to long-term complications of osteoporosis such as curvature of the spine, loss of height and prosthetic surgery. It is understood that conditions characterized by low bone mass can be included in embodiments individually or in any combination. In certain embodiments, the condition characterized by low bone mass is primary osteoporosis.

In certain embodiments, the individual in need of increased bone mass has a bone mineral density (BMD) of greater than 1 (T-score<−1), greater than or equal to 1.5 (T-score≦−1.5), greater than or equal to 2 (T-score≦−2) or greater than or equal to 2.5 (T-score≦−2.5) standard deviations below the young adult reference mean. In certain embodiments, the individual in need of increased bone mass is in need of treatment of bone fracture. In certain embodiments, the individual in need of treatment of a bone fracture has a traumatic bone fracture, a long-term bone fracture, or an osteoporotic bone fracture. In certain embodiments, the individual is in need of treatment for a bone disease. In certain embodiments, the individual in need of treatment for a bone disease has osteopenia, osteoporosis, rheumatoid arthritis, osteoarthritis, periodontal disease, alveolar bone loss, osteotomy bone loss, childhood idiopathic bone loss, Paget's disease, bone loss due to metastatic cancer, osteolytic lesions, curvature of the spine, or loss of height. In certain embodiments, the individual in need of treatment for a bone disease has osteoporosis. In certain embodiments, osteoporosis is primary osteoporosis. In certain embodiments, osteoporosis is secondary osteoporosis. Destructive bone disorders that can be treated according to the invention include but are not limited to osteoporosis, osteoarthritis, and osteolytic lesions such as those caused by neoplastic disease, radiotherapy, or chemotherapy. In certain embodiments, osteoporosis is primary osteoporosis. In certain embodiments, osteoporosis is secondary osteoporosis.

Therapies of the present invention, such as therapies relating to a GPR119 agonist are additionally useful in enhancing bone healing following facial reconstruction, maxillary reconstruction, mandibular reconstruction, periodontal disease or tooth extraction, enhancing long bone extension, enhancing prosthetic ingrowth or increasing bone synostosis in an individual.

Therapies of the present invention, such as therapies relating to a GPR119 agonist, are useful in a modulation of a PYY-related activity in an individual. In certain embodiments, the modulation of a PYY-related activity is selected from the group consisting of:
(a) increasing plasma PYY;
(b) increasing bone mass;
(c) decreasing loss of bone mass;
(d) increasing bone formation;
(e) decreasing food uptake;
(f) decreasing body weight;
(g) increasing satiety;
(h) increasing glucose disposal;
(i) decreasing plasma glucose;
(j) increasing angiogenesis;
(k) decreasing secretion in intestinal epithelium;
(l) increasing absorption in intestinal epithelium; and
(m) increasing plasma adiponectin In certain embodiments, the individual is a vertebrate. In certain embodiments, the individual that is a vertebrate is a fish, an amphibian, a reptile, a bird or a mammal. In certain embodiments, the individual or vertebrate is a mammal. In certain embodiments, the individual or vertebrate that is a mammal is a mouse, a rat, a hamster, a rabbit, a pig, a dog, a cat, a horse, a cow, a sheep, a goat, a non-human mammal, a non-human primate or a human. In certain embodiments, the individual is a human. In certain embodiments, the human is a post-menopausal woman or a man over the age of 50.

Without further elaboration, it is believed that one skilled in the art can, using the preceding description, practice the present invention to its fullest extent. The foregoing detailed description is given for clearness of understanding only, and no unnecessary limitation should be understood therefrom, as modifications within the scope of the invention may become apparent to those skilled in the art.

Throughout this application, various publications, patents and patent applications are cited. The disclosures of these publications, patents and patent applications referenced in this application are herein incorporated by reference in their entirety into the present disclosure. Citation herein by Applicant of a publication, patent, or patent application is not an admission by Applicant of said publication, patent, or patent application as prior art.

EXAMPLES

Without further elaboration, it is believed that one skilled in the art can, using the preceding description, practice the present invention to its fullest extent. The following detailed examples are to be construed as merely illustrative, and not limitations of the preceding disclosure in any way whatsoever. Those skilled in the art will promptly recognize appropriate variations from the procedures.

Example 1

GPR119 Receptor Exhibits Constitutive Activity for Increasing cAMP Accumulation in Transfected HEK293 Cells GPR119 receptor was shown to exhibit constitutive activity in cAMP assay. cAMP measurements were done with a Flash Plate adenylyl cyclase kit (NEN Life Science Products, Boston, Mass.) according to the supplier's protocol. Briefly, HEK293 cells were transfected with either empty vector DNA ("Vector") or human GPR119 receptor expression plasmid DNA ("GPR119") using Lipofectamine (Invitrogen, Carlsbad, Calif.). After 24 h, transfected cells were harvested in GIBCO (Gaithersburg, Md.) cell dissociation buffer (Catalog no. 13151-014) and resuspended in assay buffer (50% 1×PBS/50% stimulation buffer). Incubation was carried out with $10^5$ cells per well for 60 min at room temperature. After another 2-h incubation with tracer in detection buffer, plates were counted in a Wallac (Gaithersburg, Md.) MicroBeta scintillation counter. Values of cAMP per well were extrapolated from a standard cAMP curve that was included on each assay plate. Results are presented in FIG. 1. From the results shown in FIG. 1, it is apparent that GPR119 receptor exhibits constitutive activity for increasing cAMP accumulation in transfected HEK293 cells.

Example 2

Compound 1 is an Agonist of GPR119 Receptor as Evidenced, E.G., by Stimulation of cAMP Accumulation in GPR119-Transfected HEK293 Cells Compound 1 (2-Fluoro-4-methanesulfonyl-phenyl)-{6-[4-(3-isopropyl-[1,2,4]oxadiazol-5-yl)-piperidin-1-yl]-5-nitro-pyrimidin-4-yl}-amine) was shown to be an agonist of GPR119 receptor in cAMP assay. cAMP measurements were done with a Flash Plate adenylyl cyclase kit (NEN Life Science Products, Boston, Mass.) according to the supplier's protocol. Briefly, HEK293 cells were transfected with either empty vector DNA ("Vector") or human GPR119 receptor expression plasmid DNA ("GPR119") using Lipofectamine (Invitrogen, Carlsbad, Calif.). After 24 h, transfected cells were harvested in GIBCO (Gaithersburg, Md.) cell dissociation buffer (Catalog no. 13151-014) and resuspended in assay buffer (50% 1×PBS/50% stimulation buffer). Compound 1 was incubated with $10^5$ cells per well for 60 min at room temperature. After another 2-h incubation with tracer in detection buffer, plates were counted in a Wallac (Gaithersburg, Md.) MicroBeta scintillation counter. Values of cAMP per well were extrapolated from a standard cAMP curve that was included on each assay plate. Results are presented in FIG. 2. From the results shown in FIG. 2, it is apparent that Compound 1 is an agonist of GPR119 receptor.

Example 3

Effect of Administration of GPR119 Agonist on Plasma PYY in Wild-Type Mice

C57BL/6 male mice (approximately 8 weeks of age; obtained from Harlan, Indianapolis, Ind.) were fasted for 18 hours, and randomly assigned into eight groups with n=6 for each group. Mice were administered per orally with vehicle (80% polyethylene glycol 400/10% Tween 80/10% ethanol) or with a GPR119 agonist (Compound 1; (2-Fluoro-4-methanesulfonyl-phenyl)-{6-[4-(3-isopropyl-[1,2,4]oxadiazol-5-yl)-piperidin-1-yl]-5-nitro-pyrimidin-4-yl}-amine) at 10 mg/kg, as indicated in FIG. 3. Thirty minutes after treatment, a glucose bolus at 3 g/kg was delivered per orally, and blood was collected at 0 minute (no glucose bolus), 2 minutes, 5 minutes, and 10 minutes after glucose bolus. Plasma total PYY (inclusive of $PYY_{1-36}$ and $PYY_{3-36}$) levels were determined by using a PYY EIA kit purchased from Phoenix Pharmaceuticals, Inc. (Peptide YY (PYY) (Rat, Mouse, Porcine, Canine) EIA kit, Catalog No. EK-059-03) according to instructions provided in the kit. From the results shown in FIG. 3, it is apparent that administration of the GPR119 agonist (Compound 1) increased plasma total PYY in the mice. From the results shown in FIG. 3, it is apparent that the GPR119 agonist (Compound 1) stimulated plasma total PYY in the mice. Compound 1 is identical to a compound disclosed in International Patent Application No. PCT/US2004/001267 (published as WO 2004/065380).

Example 4

Effect of Administration of GPR119 Agonist on Plasma PYY IN GPR119-Deficient (Knockout) Mice Compared to Wild-Type Mice GPR119-deficient male mice (Chu et al, Endocrinology (2007) 148:2601-2609) and wild-type littermates are fasted for 18 hours. Mice are administered per orally with vehicle (80% polyethylene glycol 400/10% ethanol/10% Tween 80) or with a GPR119 agonist in accordance with the present invention (Compound 1; (2-Fluoro-4-methanesulfonyl-phenyl)-{6-[4-(3-isopropyl-[1,2,4]-5-yl)-piperidin-1-yl]-5-nitro-pyrimidin-4-yl}-amine) at 20 mg/kg. Thirty minutes after treatment, blood (100 microliter) is collected via retro orbital vein of the eye (time 0 minutes) followed by a glucose bolus at 3g/kg (per orally). Five minutes after delivering glucose, another blood sample (100 microliter) is collected (time 5 minutes). Plasma are collected after centrifugation and plasma total PYY levels are determined by using PYY EIA kit purchased from Phoenix Pharmaceuticals, Inc. (Peptide YY (PYY) (Rat, Mouse, Porcine, Canine) EIA kit, Catalog No. EK-059-03) according to instructions provided in the kit. It can be further shown that functional GPR119 receptor is necessary for the administered GPR119 agonist to increase plasma total PYY in the mice. Compound 1 can be shown to stimulate plasma total PYY in the wild-type mice but not in the GPR119-deficient mice. Compound 1 is identical to a compound disclosed in International Patent Application No. PCT/US2004/001267 (published as WO 2004/065380).

Example 5

Effect of Administration of GPR119 Agonist on Bone Mass in Ovariectomized Rats

A GPR119 agonist in accordance with the present invention can be shown to be effective in treating or preventing a condition characterized by low bone mass, such as osteoporosis, and/or in increasing bone mass in an individual using the in vivo ovariectomized (OVX) rat model described below (see, e.g., Bollag et al, Mol Cell Endocrinol (2001) 177:35-41).

Twenty virgin female OVX and 20 virgin non-OVX Sprague-Dawley rats (150-175 g), age 8 weeks, are purchased from Harlan Sprague-Dawley, Inc. (Indianapolis, Ind.). Animals are fed ad libitum on a normal commercial pellet diet, Teklab Rodent diet (1.46% calcium), with free access to water. The rats are randomly divided into four weight-matched experimental groups and selected to receive per orally vehicle or a GPR119 agonist in accordance with the present invention. Treatment is continued on a daily basis for 6 weeks.

1. Control. Ten non-OVX rats are administered per orally vehicle.

2. Control+Treatment. Ten non-OVX rats are administered per orally GPR119 agonist.

3. OVX. Ten OVX rats are administered per orally vehicle.

4. OVX+Treatment. Ten OVX rats are administered per orally GPR119 agonist.

The rats are weighed daily and length measured at baseline and again at 6 weeks. Dual energy X-ray absorptiometry (DXA) using a Hologic QDR 1000/W (Waltham, Mass.) is performed on all animals prior to initiation of treatment and at 6 weeks, and data is analyzed using the software Rat Whole Body version 5.53. Bone mineral density (BMD) is determined at the spine.

The percent change in vertebral bone density after 6 weeks of treatment is determined. It is shown that administration of a GPR119 agonist attenuates the negative effects of ovariectomy on vertebral bone density. Attenuation of the negative effects of ovariectomy on vertebral bone density is indicative of the treatment having efficacy in treating or preventing a condition characterized by low bone mass, such as osteoporosis, and/or in increasing bone mass in an individual.

Example 6

Effect of Administration of GPR119 Agonist on Bone Fracture Healing

A GPR119 agonist in accordance with the present invention can be shown to be effective in treatment of bone fracture using the in vivo assay described below.

Fracture Technique

Sprague-Dawley rats at 3 months of age are anesthetized with Ketamine. A 1 cm incision is made on the anteromedial aspect of the proximal part of the right tibia or femur. The following describes the tibial surgical technique. The incision is carried through to the bone, and a 1 mm hole is drilled 4 mm proximal to the distal aspect of the tibial tuberosity 2 mm medial to the anterior ridge. Intramedullary nailing is performed with a 0.8 mm stainless steel tube (maximum load 36.3 N, maximum stiffness 61.8 N/mm, tested under the same conditions as the bones). No reaming of the medullary canal is performed. A standardized closed fracture is produced 2 mm above the tibiofibular junction by three-point bending using specially designed adjustable forceps with blunt jaws. To minimize soft tissue damage, care is taken not to displace the fracture. The skin is closed with monofilament nylon sutures. The operation is performed under sterile conditions. Radiographs of all fractures are taken immediately after nailing, and rats with fractures outside the specified diaphyseal area or with displaced nails are excluded. The remaining animals are divided randomly into the following groups with 10-12 animals per each subgroup per time point for testing the fracture healing. The rats are administered on a daily basis per orally with vehicle or with a GPR119 agonist. The GPR119 agonist is used at an amount between 0.001 mg/kg body weight and 100 mg/kg body weight. Treatment is continued for 10, 20, 40 and 80 days.

At 10, 20, 40 and 80 days, 10-12 rats from each group are anesthetized with Ketamine and sacrificed by exsanguination. Both tibiofibular bones are removed by dissection and all soft tissue is stripped. Bones from 5-6 rats for each group are stored in 70% ethanol for histological analysis, and bones from another 5-6 rats for each group are stored in a buffered Ringer's solution (+4° C., pH 7.4) for radiographs and biomechanical testing which is performed.

Histological Analysis

The methods for histological analysis of fractured bone have been previously published by Mosekilde and Bak (Bone (1993) 14:19-27). Briefly, the fracture site is sawed 8 mm to each side of the fracture line, embedded undecalcified in methymethacrylate, and cut frontals sections on a Reichert-Jung Polycut microtome in 8 μm thick. Masson-Trichome stained mid-frontal sections (including both tibia and fibula) are used for visualization of the cellular and tissue response to fracture healing with and without treatment. Sirius red stained sections are used to demonstrate the characteristics of the callus structure and to differentiate between woven bone and lamellar bone at the fracture site. The following measurements are performed: (1) fracture gap-measured as the shortest distance between the cortical bone ends in the fracture, (2) callus length and callus diameter, (3) total bone volume area of callus, (4) bony tissue per tissue area inside the callus area, (5) fibrous tissue in the callus, and (6) cartilage area in the callus.

Biomechanical Analysis

The methods for biomechanical analysis have been previously published by Bak and Andreassen (Calcif Tissue Int (1989) 45:292-297). Briefly, radiographs of all fractures are taken prior to the biomechanical test. The mechanical properties of the healing fractures are analyzed by a destructive three- or four-point bending procedure. Maximum load, stiffness, energy at maximum load, deflection at maximum load, and maximum stress are determined.

Example 7

Full-Length Cloning of Endogenous Human GPR119

Polynucleotide encoding endogenous human GPR119 was cloned by PCR using the GPR119 specific primers 5'-GTC-CTGCCACTTCGAGAC<u>ATG</u>G-3' (SEQ ID NO:3; sense, <u>ATG</u> as initiation codon) 5'-GAAACTTCTCTGCCCTTAC-CGTC-3' (SEQ ID NO:4; antisense, 3' of stop codon) and human genomic DNA as template. TaqPlus Precision™ DNA polymerase (Stratagene) was used for amplification by the following cycle with step 2 to step 4 repeated 35 times: 94° C., 3 minutes; 94° C., 1 minute; 58° C., 1 minute; 72° C., 2 minutes; 72° C., 10 minutes. A 1.0 Kb PCR fragment of predicted size was isolated and cloned into the pCRII-TOPO™ vector (Invitrogen) and completely sequenced using the 17 DNA sequenase kit (Amersham). See, SEQ ID NO:1 for nucleic acid sequence and SEQ ID NO:2 for the deduced amino acid sequence.

Example 8

Receptor Expression

Although a variety of cells are available to the art for the expression of G protein-coupled receptors, it is most preferred that eukaryotic cells be utilized. In certain embodiments, mammalian cells or melanophores are utilized. The following are illustrative; those of ordinary skill in the art are credited with the ability to determine those techniques that are preferentially beneficial for the needs of the artisan. See, e.g., Example 12, infra, as it relates to melanophores.

a. Transient Transfection

On day one, $6 \times 10^6$/10 cm dish of 293 cells are plated out. On day two, two reaction tubes are prepared (the proportions to follow for each tube are per plate): tube A is prepared by mixing 4 μg DNA (e.g., pCMV vector; pCMV vector with receptor cDNA, etc.) in 0.5 ml serum free DMEM (Gibco BRL); tube B is prepared by mixing 24 μl lipofectamine (Gibco BRL) in 0.5 ml serum free DMEM. Tubes A and B are admixed by inversions (several times), followed by incubation at room temperature for 30-45 min. The admixture is referred to as the "transfection mixture". Plated 293 cells are washed with 1×PBS, followed by addition of 5 ml serum free DMEM. 1 ml of the transfection mixture is added to the cells, followed by incubation for 4 hrs at 37° C./5% $CO_2$. The transfection mixture is removed by aspiration, followed by the addition of 10 ml of DMEM/10% Fetal Bovine Serum. Cells are incubated at 37° C./5% $CO_2$. After 48hr incubation, cells are harvested and utilized for analysis.

b. Stable Cell Lines

Approximately 12×10$^6$ 293 cells are plated on a 15 cm tissue culture plate. Grown in DME High Glucose Medium containing ten percent fetal bovine serum and one percent sodium pyruvate, L-glutamine, and antibiotics. Twenty-four hours following plating of 293 cells (or to ~80% confluency), the cells are transfected using 12 µg of DNA (e.g., pCMV-neo$^r$ vector with receptor cDNA). The 12 µg of DNA is combined with 60 µl of lipofectamine and 2 ml of DME High Glucose Medium without serum. The medium is aspirated from the plates and the cells are washed once with medium without serum. The DNA, lipofectamine, and medium mixture are added to the plate along with 10 ml of medium without serum. Following incubation at 37° C. for four to five hours, the medium is aspirated and 25 ml of medium containing serum is added. Twenty-four hours following transfection, the medium is aspirated again, and fresh medium with serum is added. Forty-eight hours following transfection, the medium is aspirated and medium with serum is added containing geneticin (G418 drug) at a final concentration of approximately 12×10$^6$ 293 cells are plated on a 15 cm tissue culture plate. Grown in DME High Glucose Medium containing ten percent fetal bovine serum and one percent sodium pyruvate, L-glutamine, and antibiotics. Twenty-four hours following plating of 293 cells (or to ~80% confluency), the cells are transfected using 12 µg of DNA (e.g., pCMV vector with receptor cDNA). The 12 µg of DNA is combined with 60 µl of lipofectamine and 2 ml of DME High Glucose Medium without serum. The medium is aspirated from the plates and the cells are washed once with medium without serum. The DNA, lipofectamine, and medium mixture are added to the plate along with 10 ml of medium without serum. Following incubation at 37° C. for four to five hours, the medium is aspirated and 25 ml of medium containing serum is added. Twenty-four hours following transfection, the medium is aspirated again, and fresh medium with serum is added. Forty-eight hours following transfection, the medium is aspirated and medium with serum is added containing geneticin (G418 drug) at a final concentration of 500 µg/ml. The transfected cells now undergo selection for positively transfected cells containing the G418 resistance gene. The medium is replaced every four to five days as selection occurs. During selection, cells are grown to create stable pools, or split for stable clonal selection.

Example 9

Assays for Screening Candidate Compounds as, e.g., GPR119 Agonists

A variety of approaches are available for screening candidate compounds as, e.g., GPR119 agonists. The following are illustrative; those of ordinary skill in the art are credited with the ability to determine those techniques that are preferentially beneficial for the needs of the artisan. Assays for screening compounds as agonists of a G protein-coupled receptor are well known to the skilled artisan (see, e.g., International Application WO 02/42461).

1. Membrane Binding Assays: [$^{35}$S]GTPγS Assay

When a G protein-coupled receptor is in its active state, either as a result of ligand binding or constitutive activation, the receptor couples to a G protein and stimulates the release of GDP and subsequent binding of GTP to the G protein. The alpha subunit of the G protein-receptor complex acts as a GTPase and slowly hydrolyzes the GTP to GDP, at which point the receptor normally is deactivated. Activated receptors continue to exchange GDP for GTP. The non-hydrolyzable GTP analog, [$^{35}$S]GTPγS, can be utilized to demonstrate enhanced binding of [$^{35}$S]GTPγS to membranes expressing activated receptors. The advantage of using [$^{35}$S]GTPγS binding to measure activation is that: (a) it is generically applicable to all G protein-coupled receptors; (b) it is proximal at the membrane surface making it less likely to pick-up molecules which affect the intracellular cascade.

The assay utilizes the ability of G protein coupled receptors to stimulate [$^{35}$S]GTPγS binding to membranes expressing the relevant receptors. The assay is generic and has application to drug discovery at all G protein-coupled receptors.

Membrane Preparation

In some embodiments, membranes comprising a G protein-coupled receptor of the invention and for use in the identification of candidate compounds as, e.g., agonists of the receptor, are preferably prepared as follows:

a. Materials

"Membrane Scrape Buffer" is comprised of 20 mM HEPES and 10 mM EDTA, pH 7.4; "Membrane Wash Buffer" is comprised of 20 mM HEPES and 0.1 mM EDTA, pH 7.4; "Binding Buffer" is comprised of 20 mM HEPES, 100 mM NaCl, and 10 mM $MgCl_2$, pH 7.4.

b. Procedure

All materials will be kept on ice throughout the procedure. Firstly, the media will be aspirated from a confluent monolayer of cells, followed by rinse with 10 ml cold PBS, followed by aspiration. Thereafter, 5 ml of Membrane Scrape Buffer will be added to scrape cells; this will be followed by transfer of cellular extract into 50 ml centrifuge tubes (centrifuged at 20,000 rpm for 17 minutes at 4° C.). Thereafter, the supernatant will be aspirated and the pellet will be resuspended in 30 ml Membrane Wash Buffer followed by centrifuge at 20,000 rpm for 17 minutes at 4° C. The supernatant will then be aspirated and the pellet resuspended in Binding Buffer. This will then be homogenized using a Brinkman Polytron™ homogenizer (15-20 second bursts until the all material is in suspension). This is referred to herein as "Membrane Protein".

Bradford Protein Assay

Following the homogenization, protein concentration of the membranes will be determined using the Bradford Protein Assay (protein can be diluted to about 1.5 mg/ml, aliquoted and frozen (−80° C.) for later use; when frozen, protocol for use will be as follows: on the day of the assay, frozen Membrane Protein is thawed at room temperature, followed by vortex and then homogenized with a Polytron at about 12×1,000 rpm for about 5-10 seconds; it is noted that for multiple preparations, the homogenizer should be thoroughly cleaned between homogenization of different preparations).

a. Materials

Binding Buffer (as per above); Bradford Dye Reagent; Bradford Protein Standard will be utilized, following manufacturer instructions (Biorad, cat. no. 500-0006).

b. Procedure

Duplicate tubes will be prepared, one including the membrane, and one as a control "blank". Each contained 800 µl Binding Buffer. Thereafter, 10 µl of Bradford Protein Standard (1 mg/ml) will be added to each tube, and 10 µl of membrane Protein will then be added to just one tube (not the blank). Thereafter, 200 µl of Bradford Dye Reagent will be added to each tube, followed by vortex of each. After five (5) minutes, the tubes will be re-vortexed and the material therein will be transferred to cuvettes. The cuvettes will then be read using a CECIL 3041 spectrophotometer, at wavelength 595.

Identification Assay a. Materials

GDP Buffer consists of 37.5 ml Binding Buffer and 2 mg GDP (Sigma, cat. no. G-7127), followed by a series of dilutions in Binding Buffer to obtain 0.2 µM GDP (final concentration of GDP in each well was 0.1 µM GDP); each well comprising a candidate compound, has a final volume of 200 µl consisting of 100 µl GDP Buffer (final concentration, 0.1 µM GDP), 50 µl Membrane Protein in Binding Buffer, and 50 µl [$^{35}$S]GTPγS (0.6 nM) in Binding Buffer (2.5 µl [$^{35}$S]GTPγS per 10 ml Binding Buffer).

b. Procedure

Candidate compounds will be preferably screened using a 96-well plate format (these can be frozen at −80° C.). Membrane Protein (or membranes with expression vector excluding the Target GPCR, as control), will be homogenized briefly until in suspension. Protein concentration will then be determined using the Bradford Protein Assay set forth above. Membrane Protein (and control) will then be diluted to 0.25 mg/ml in Binding Buffer (final assay concentration, 12.5 µg/well). Thereafter, 100 µl GDP Buffer was added to each well of a Wallac Scintistrip™ (Wallac). A 5 µl pin-tool will then be used to transfer 5 µl of a candidate compound into such well (i.e., 5 µl in total assay volume of 200 µl is a 1:40 ratio such that the final screening concentration of the candidate compound is 10 µM). Again, to avoid contamination, after each transfer step the pin tool should be rinsed in three reservoirs comprising water (1×), ethanol (1×) and water (2×)—excess liquid should be shaken from the tool after each rinse and dried with paper and kimwipes. Thereafter, 50 µl of Membrane Protein will be added to each well (a control well comprising membranes without the Target GPCR was also utilized), and pre-incubated for 5-10 minutes at room temperature. Thereafter, 50 µl of [$^{35}$S]GTPγS (0.6 nM) in Binding Buffer will be added to each well, followed by incubation on a shaker for 60 minutes at room temperature (again, in this example, plates were covered with foil). The assay will then be stopped by spinning of the plates at 4000 RPM for 15 minutes at 22° C. The plates will then be aspirated with an 8 channel manifold and sealed with plate covers. The plates will then be read on a Wallac 1450 using setting "Prot. #37" (as per manufacturer's instructions).

2. Adenylyl Cyclase Assay

A Flash Plate™ Adenylyl Cyclase kit (New England Nuclear; Cat. No. SMP004A) designed for cell-based assays can be modified for use with crude plasma membranes. The Flash Plate wells can contain a scintillant coating which also contains a specific antibody recognizing cAMP. The cAMP generated in the wells can be quantitated by a direct competition for binding of radioactive cAMP tracer to the cAMP antibody. The following serves as a brief protocol for the measurement of changes in cAMP levels in cells that express the receptors.

In certain embodiments, a modified Flash Plate™ Adenylyl Cyclase kit (New England Nuclear; Cat. No. SMP004A) is utilized for identification of candidate compounds as, e.g., GPR119 agonists in accordance with the following protocol.

Cells transfected with a G protein-coupled receptor of the invention are harvested approximately three days after transfection. Membranes are prepared by homogenization of suspended cells in buffer containing 20 mM HEPES, pH 7.4 and 10 mM MgCl$_2$. Homogenization is performed on ice using a Brinkman Polytron™ for approximately 10 seconds. The resulting homogenate is centrifuged at 49,000×g for 15 minutes at 4° C. The resulting pellet is then resuspended in buffer containing 20 mM HEPES, pH 7.4 and 0.1 mM EDTA, homogenized for 10 seconds, followed by centrifugation at 49,000×g for 15 minutes at 4° C. The resulting pellet is then stored at −80° C. until utilized. On the day of direct identification screening, the membrane pellet is slowly thawed at room temperature, resuspended in buffer containing 20 mM HEPES, pH 7.4 and 10 mM MgCl$_2$, to yield a final protein concentration of 0.60 mg/ml (the resuspended membranes are placed on ice until use).

cAMP standards and Detection Buffer (comprising 2 µCi of tracer ([$^{125}$I]cAMP (100 µl) to 11 ml Detection Buffer)) are prepared and maintained in accordance with the manufacturer's instructions. Assay Buffer was prepared fresh for screening and contained 20 mM HEPES, pH 7.4, 10 mM MgCl$_2$, 20 mM phospocreatine (Sigma), 0.1 units/ml creatine phosphokinase (Sigma), 50 µM GTP (Sigma), and 0.2 mM ATP (Sigma); Assay Buffer was then stored on ice until utilized.

Candidate compounds are added, preferably, to e.g. 96-well plate wells (3 µl/well; 12 µM final assay concentration), together with 40 µl Membrane Protein (30 µg/well) and 50 µl of Assay Buffer. This admixture was then incubated for 30 minutes at room temperature, with gentle shaking.

Following the incubation, 100 µl of Detection Buffer is added to each well, followed by incubation for 2-24 hours. Plates are then counted in a Wallac MicroBeta™ plate reader using "Prot. #31" (as per manufacturer's instructions).

3. CRE-Luc Reporter Assay 293 and 293T cells are plated-out on 96 well plates at a density of 2×10$^4$ cells per well and were transfected using Lipofectamine Reagent (BRL) the following day according to manufacturer instructions. A DNA/lipid mixture is prepared for each 6-well transfection as follows: 260 ng of plasmid DNA in 100 µl of DMEM is gently mixed with 2 µl of lipid in 100 µl of DMEM (the 260 ng of plasmid DNA consists of 200 ng of a 8×CRE-Luc reporter plasmid, 50 ng of pCMV comprising a G protein-coupled receptor of the invention or pCMV alone, and 10 ng of a GPRS expression plasmid (GPRS in pcDNA3 (Invitrogen)). The 8×CRE-Luc reporter plasmid was prepared as follows: vector SRIF-β-gal was obtained by cloning the rat somatostatin promoter (−71/+51) at BglV-HindIII site in the pβgal-Basic Vector (Clontech). Eight (8) copies of cAMP response element were obtained by PCR from an adenovirus template AdpCF126CCRE8 [see, Suzuki et al., Hum Gene Ther (1996) 7:1883-1893; the disclosure of which is herein incorporated by reference in its entirety) and cloned into the SRIF-β-gal vector at the Kpn-BglV site, resulting in the 8×CRE-β-gal reporter vector. The 8×CRE-Luc reporter plasmid was generated by replacing the beta-galactosidase gene in the 8×CRE-β-gal reporter vector with the luciferase gene obtained from the pGL3-basic vector (Promega) at the HindIII-BamHI site. Following 30 min. incubation at room temperature, the DNA/lipid mixture is diluted with 400 µl of DMEM and 100 µl of the diluted mixture is added to each well. 100 µl of DMEM with 10% FCS are added to each well after a 4 hr incubation in a cell culture incubator. The following day the transfected cells are changed with 200 µl/well of DMEM with 10% FCS. Eight (8)

hours later, the wells are changed to 100 µl/well of DMEM without phenol red, after one wash with PBS. Luciferase activity is measured the next day using the LucLite™ reporter gene assay kit (Packard) following manufacturer instructions and read on a 1450 MicroBeta™ scintillation and luminescence counter (Wallac).

Example 10

Whole Cell Adenylyl Cyclase Assay for, e.g., GPR119 Agonist Activity

Cyclic AMP measurements are done with a Flash Plate™ Adenylyl Cyclase kit (New England Nuclear) according to the supplier's protocol. HEK293 cells are plated in 15-cm tissue culture dish at $12 \times 10^6$ cells per dish in regular growth medium (DME/10% FBS). On the next day, 10 µg of either empty vector DNA or expression plasmid DNA are transfected into cells with lipofectamine (Invitrogen, Carlsbad, Calif.) according to manufacturer's protocol. After 24 hours in culture, transfected cells are harvested in GIBCO cell dissociation buffer (Cat #13151-014), pelleted by centrifugation for 5 minutes at 1,100 rpm, and carefully re-suspended into an appropriate volume of Assay Buffer (50% 1×PBS and 50% Stimulation Buffer) to give a final cell count at $2 \times 10^6$ cells/mil. Test compounds are prepared in 50 µl Assay Buffer at desired assay concentration where indicated, and pipetted into wells of the 96-well Flash Plate. The cell suspension prepared above was then added (50 µl per well). After an incubation time of 60 minutes at room temperature, 100 µl of Detection Mix containing tracer [$^{125}$I]-cAMP is then added to the wells. Plates are incubated for additional 2 hours followed by counting in a Wallac MicroBeta scintillation counter. Values of cAMP/well are extrapolated from a standard cAMP curve which is included on each assay plate.

An increase in cAMP level in GPR119-transfected HEK293 cells over that in HEK293 cells transfected with empty vector is indicative of a test compound being a compound that stimulates GPR119 receptor functionality.

Example 11

Homogeneous Time-Resolved Fluorescence (HTRF®) Assay for Direct cAMP Measurement Compounds are screened for compounds which stimulate GPR119 receptor, e.g. for agonists of GPR119 receptor, using HTRF® assay for direct cAMP measurement (Gabriel et al, ASSAY and Drug Development Technologies, 1:291-303, 2003) and recombinant CHO-K1 cells stably transfected with GPR119 receptor. Compounds are screened for agonists of GPR119 receptor using HTRF® assay for direct cAMP measurement (Gabriel et al, ASSAY and Drug Development Technologies, 1:291-303, 2003) and recombinant CHO-K1 cells stably transfected with GPR119 receptor. CHO-K1 cells are obtained from ATCC (Manassas, Va.; Catalog # CCL-61). An agonist of GPR119 receptor is detected in HTRF® assay for direct cAMP measurement as a compound which increases cAMP concentration. HTRF® assay also is used to determine $EC_{50}$ values for GPR119 receptor agonists.

Principle of the assay: HTRF® assay kit is purchased from Cisbio-US, Inc. (Bedford, Mass.; Catalog #62AM4PEC). The HTRF® assay supported by the kit is a competitive immunoassay between endogenous cAMP produced by the CHO-K1 cells and tracer cAMP labeled with the dye d2. The tracer binding is visualized by a monoclonal anti-cAMP antibody labeled with Cryptate. The specific signal (i.e., fluorescence resonance energy transfer, FRET) is inversely proportional to the concentration of unlabeled cAMP in the standard or sample.

Standard curve: The fluorescence ratio (665 nm/1620 nm) of the standards (0.17 to 712 nM cAMP) included in the assay is calculated and used to generate a cAMP standard curve according to the kit manufacturer's instructions. The fluorescence ratio of the samples (test compound or compound buffer) is calculated and used to deduce respective cAMP concentrations by reference to the cAMP standard curve.

Setup of the assay: HTRF® assay is carried out using a two-step protocol essentially according to the kit manufacturer's instructions, in 20 µl total volume per well in 384-well plate format (ProxiPlates; PerkinElmer, Fremont, Calif.; catalog #6008280). To each of the experimental wells is transferred 3000 recombinant CHO-K1 cells in 5 µl assay buffer (phosphate buffered saline containing calcium chloride and magnesium chloride (Invitrogen, Carlsbad, Calif.; catalog #14040) supplemented with IBMX (100 µM) and rolipram (10 µM) (phosphodiesterase inhibitors; Sigma-Aldrich, St. Louis, Mo.; catalog #15879 and catalog # R6520, respectively) and 0.1% bovine serum albumin (BSA) fraction V (Sigma-Aldrich; catalog # A3059)), followed by test compound in 5 µl assay buffer or 5 µl assay buffer. The plate is then incubated at room temperature for 1 hour. To each well is then added 5 µl cAMP-d2 conjugate in lysis buffer and 5 µl Cryptate conjugate in lysis buffer according to the kit manufacturer's instructions. The plate is then further incubated at room temperature for 1 hour, after which the assay plate is read.

Assay readout: HTRF® readout is accomplished using a PHERAstar (BMG LABTECH Inc., Durham, N.C.) or EnVision™ (PerkinElmer, Fremont Calif.) microplate reader.

Example 12

Melanophore Assay for, e.g., GPR119 Agonist Activity

Melanophores are maintained in culture as reported by Potenza et al [Pigment Cell Research (1992) 5:372-378] and transfected with an expression vector encoding a GPR119 receptor (GPR119; e.g., human GPR119, GenBank Accession No. AAP72125 and alleles thereof) using electroporation. Following electroporation, the transfected cells are plated into 96 well plates for the assay. The cells are then allowed to grow for 48 hours in order to both recover from the electroporation procedure and attain maximal receptor expression levels.

On the assay day, the growth medium on the cells is replaced with serum-free buffer containing 10 nM melatonin. The melatonin acts via an endogenous Gi-coupled GPCR in the melanophores to lower intracellular cAMP levels. In response to lowered cAMP levels, the melanophores translocate their pigment to the center of the cell. The net effect of this is a significant decrease in the absorbance reading of the cell monolayer in the well, measured at 600-650 nM.

After a 1-hour incubation in melatonin, the cells become completely pigment-aggregated. At this point a baseline absorbance reading is collected. Serial dilutions of test compounds are then added to the plate, and compounds having GPR119 agonist activity produce increases in intracellular cAMP levels. In response to these increased cAMP levels, the melanophores translocate their pigment back into the cell periphery. After one hour, stimulated cells are fully pigment-dispersed. The cell monolayer in the dispersed state absorbs much more light in the 600-650 nm range. The measured increase in absorbance compared to the baseline reading allows one to quantitate the degree of receptor stimulation and plot a dose-response curve.

Materials and methods relating to melanophore assay are found in U.S. Pat. Nos. 5,462,856 and 6,051,386, the disclosure of each of which is herein incorporated by reference in its entirety.

An increase in pigment dispersion in GPR119-transfected melanophores over that in melanophores transfected with empty vector is indicative of a test compound being a compound that stimulates GPR119 receptor functionality.

Other assays for identifying a compound as a GPR119 agonist will be readily apparent to the skilled artisan (see, e.g., Example 9, supra).

Example 13

Yeast Reporter Assay for, e.g., GPR119 Agonist Activity

The yeast cell-based reporter assays have previously been described in the literature (e.g., see Miret et al, J Biol Chem (2002) 277:6881-6887; Campbell et al, Bioorg Med Chem Lett (1999) 9:2413-2418; King et al, Science (1990) 250:121-123; WO 99/14344; WO 00/12704; and U.S. Pat. No. 6,100,042). Briefly, yeast cells have been engineered such that the endogenous yeast G-alpha (GPA1) has been deleted and replaced with G-protein chimeras constructed using multiple techniques. Additionally, the endogenous yeast alpha-cell GPCR, Ste3 has been deleted to allow for a homologous expression of a mammalian GPCR of choice. In the yeast, elements of the pheromone signaling transduction pathway, which are conserved in eukaryotic cells (for example, the mitogen-activated protein kinase pathway), drive the expression of Fus1. By placing β-galactosidase (LacZ) under the control of the Fus1 promoter (Fus1p), a system has been developed whereby receptor activation leads to an enzymatic readout.

Yeast cells are transformed by an adaptation of the lithium acetate method described by Agatep et al (Agatep et al, 1998, Transformation of Saccharomyces cerevisiae by the lithium acetate/single-stranded carrier DNA/polyethylene glycol (LiAc/ss-DNA/PEG) protocol. Technical Tips Online, Trends Journals, Elsevier). Briefly, yeast cells are grown overnight on yeast tryptone plates (YT). Carrier single-stranded DNA (10 μg), 2 μg of each of two Fus1p-LacZ reporter plasmids (one with URA selection marker and one with TRP), 2 μg of GPR119 (e.g., human receptor) in yeast expression vector (2 μg origin of replication) and a lithium acetate/polyethylene glycol/TE buffer is pipetted into an Eppendorf tube. The yeast expression plasmid containing the receptor/no receptor control has a LEU marker. Yeast cells are inoculated into this mixture and the reaction proceeds at 30° C. for 60 min. The yeast cells are then heat-shocked at 42° C. for 15 min. The cells are then washed and spread on selection plates. The selection plates are synthetic defined yeast media minus LEU, URA and TRP (SD-LUT). After incubating at 30° C. for 2-3 days, colonies that grow on the selection plates are then tested in the LacZ assay.

In order to perform fluorimetric enzyme assays for β-galactosidase, yeast cells carrying the subject GPR119 receptor are grown overnight in liquid SD-LUT medium to an unsaturated concentration (i.e. the cells are still dividing and have not yet reached stationary phase). They are diluted in fresh medium to an optimal assay concentration and 90 μl of yeast cells are added to 96-well black polystyrene plates (Costar). Test compounds, dissolved in DMSO and diluted in a 10% DMSO solution to 10× concentration, are added to the plates and the plates placed at 30° C. for 4 h. After 4 h, the substrate for the β-galactosidase is added to each well. In these experiments, Fluorescein di (β-D-galactopyranoside) is used (FDG), a substrate for the enzyme that releases fluorescein, allowing a fluorimetric read-out. 20 μl per well of 500 μM FDG/2.5% Triton X100 is added (the detergent is necessary to render the cells permeable). After incubation of the cells with the substrate for 60 min, 20 μl per well of 1M sodium carbonate is added to terminate the reaction and enhance the fluorescent signal. The plates are then read in a fluorimeter at 485/535 nm.

An increase in fluorescent signal in GPR119-transformed yeast cells over that in yeast cells transformed with empty vector is indicative of a test compound being a compound that stimulates GPR119 receptor functionality (e.g., a compound that is an agonist or partial agonist of GPR119). In certain embodiments, compounds of the invention give an increase in fluorescent signal above that of the background signal (the signal obtained in the presence of vehicle alone).

Example 14

Radiolabeled Compound

In certain embodiments, a compound known to be a ligand of a G protein-coupled receptor of the invention is radiolabeled. A radiolabeled compound as described herein can be used in a screening assay to identify/evaluate compounds. In general terms, a newly synthesized or identified compound (i.e., test compound) can be evaluated for its ability to reduce binding of the radiolabeled known ligand to the receptor, by its ability to reduce formation of the complex between the radiolabeled known ligand and the receptor. Suitable radionuclides that may be incorporated in compounds of the present invention include but are not limited to $^3$H (also written as T), $^{11}$C, $^{14}$C, $^{18}$F, $^{125}$I, $^{82}$Br, $^{123}$I, $^{124}$I, $^{125}$I, $^{131}$I, $^{75}$Br, $^{76}$Br, $^{15}$O, $^{13}$N, $^{35}$S and $^{77}$Br. Compounds that incorporate $^3$H, $^{14}$C, $^{125}$I, $^{131}$I, $^{35}$S or $^{82}$Br will generally be most useful.

It is understood that a "radiolabelled" compound" is a compound that has incorporated at least one radionuclide. In some embodiments, the radionuclide is selected from the group consisting of $^3$H, $^{14}$C, 125I, $^{35}$S and $^{82}$Br. In some embodiments, the radionuclide $^3$H or $^{14}$C. Moreover, it should be understood that all of the atoms represented in the compounds known to be ligands of a G protein-coupled receptor of the invention can be either the most commonly occurring isotope of such atoms or the more scarce radioisotope or nonradioactive isotope.

Synthetic methods for incorporating radioisotopes into organic compounds including those applicable to those compounds known to be ligands of a G protein-coupled receptor of the invention are well known in the art and include incorporating activity levels of tritium into target molecules include: A. Catalytic Reduction with Tritium Gas—This procedure normally yields high specific activity products and requires halogenated or unsaturated precursors. B. Reduction with Sodium Borohydride [$^3$H]—This procedure is rather inexpensive and requires precursors containing reducible functional groups such as aldehydes, ketones, lactones, esters, and the like. C. Reduction with Lithium Aluminum Hydride [$^3$H ]—This procedure offers products at almost theoretical specific activities. It also requires precursors containing reducible functional groups such as aldehydes, ketones, lactones, esters, and the like. D. Tritium Gas Exposure Labeling—This procedure involves exposing precursors containing exchangeable protons to tritium gas in the presence of a suitable catalyst. E. N-Methylation using Methyl Iodide [$^3$H]—This procedure is usually employed to prepare O-methyl or N-methyl ($^3$H) products by treating appropriate precursors with high specific activity methyl iodide ($^3$H). This method in general allows for high specific activity, such as about 80-87 Ci/mmol.

Synthetic methods for incorporating activity levels of $^{125}$I into target molecules include: A. Sandmeyer and like reactions—This procedure transforms an aryl or heteroaryl amine into a diazonium salt, such as a tetrafluoroborate salt, and subsequently to $^{125}$I labelled compound using Na $^{125}$I. A represented procedure was reported by Zhu, D.-G. and co-workers in *J. Org. Chem.* 2002, 67, 943-948. B. Ortho $^{125}$Iodination of phenols—This procedure allows for the incorporation of $^{125}$I at the ortho position of a phenol as reported by Collier, T. L. and co-workers in *J. Labelled Compd Radiopharm.* 1999, 42, S264-S266. C. Aryl and heteroaryl bromide exchange with $^{125}$I—This method is generally a two step process. The first step is the conversion of the aryl or heteroaryl bromide to the corresponding tri-alkyltin intermediate using for example, a Pd catalyzed reaction (i.e. Pd(Ph$_3$P)$_4$] or through an aryl or heteroaryl lithium, in the presence of a tri-alkyltinhalide or hexaalkylditin [e.g., (CH$_3$)$_3$SnSn(CH$_3$)$_3$). A represented procedure was reported by Bas, M.-D. and co-workers in *J. Labelled Compd Radiopharm.* 2001, 44, S280-S282.

The foregoing techniques are intended to be illustrative and not limiting. Other techniques for radiolabeling a compound known to be a ligand of a G protein-coupled receptor of the invention are well known to the skilled artisan.

Example 15

Receptor Binding Assay

A test compound can be evaluated for its ability to reduce formation of the complex between a compound known to be a ligand of a G protein-coupled receptor of the invention and the receptor. In certain embodiments, the known ligand is radiolabeled. The radiolabeled known ligand can be used in a screening assay to identify/evaluate compounds. In general terms, a newly synthesized or identified compound (i.e., test compound) can be evaluated for its ability to reduce binding of the radiolabeled known ligand to the receptor, by its ability to reduce formation of the complex between the radiolabeled known ligand and the receptor.

A level of specific binding of the radiolabeled known ligand in the presence of the test compound less than a level of specific binding of the radiolabeled known ligand in the absence of the test compound is indicative of less of the complex between said radiolabeled known ligand and said receptor being formed in the presence of the test compound than in the absence of the test compound.

Assay Protocol for Detecting the Complex Between a Compound Known to be a Ligand of a G Protein-Coupled Receptor of the Invention and the Receptor A. Preparation of the Receptor 293 cells are transiently transfected with 10 ug expression vector comprising a polynucleotide encoding a G protein-coupled receptor of the invention using 60 ul Lipofectamine (per 15-cm dish). The transiently transfected cells are grown in the dish for 24 hours (75% confluency) with a media change and removed with 10 ml/dish of Hepes-EDTA buffer (20 mM Hepes+10 mM EDTA, pH 7.4). The cells are then centrifuged in a Beckman Coulter centrifuge for 20 minutes, 17,000 rpm (JA-25.50 rotor). Subsequently, the pellet is resuspended in 20 mM Hepes+1 mM EDTA, pH 7.4 and homogenized with a 50-ml Dounce homogenizer and again centrifuged. After removing the supernatant, the pellets are stored at −80° C., until used in binding assay. When used in the assay, membranes are thawed on ice for 20 minutes and then 10 mL of incubation buffer (20 mM Hepes, 1 mM MgCl$_2$, 100 mM NaCl, pH 7.4) added. The membranes are then vortexed to resuspend the crude membrane pellet and homogenized with a Brinkmann PT-3100 Polytron homogenizer for 15 seconds at setting 6. The concentration of membrane protein is determined using the BRL Bradford protein assay.

B. Binding Assay

For total binding, a total volume of 50 ul of appropriately diluted membranes (diluted in assay buffer containing 50 mM Tris HCl (pH 7.4), 10 mM MgCl$_2$, and 1 mM EDTA; 5-50 ug protein) is added to 96-well polyproylene microtiter plates followed by addition of 100 ul of assay buffer and 50 ul of a radiolabeled known ligand. For nonspecific binding, 50 ul of assay buffer is added instead of 100 ul and an additional 50 ul of 10 uM said known ligand which is not radiolabeled is added before 50 ul of said radiolabeled known ligand is added. Plates are then incubated at room temperature for 60-120 minutes. The binding reaction is terminated by filtering assay plates through a Microplate Devices GF/C Unifilter filtration plate with a Brandell 96-well plate harvestor followed by washing with cold 50 mM Tris HCl, pH 7.4 containing 0.9% NaCl. Then, the bottom of the filtration plate are sealed, 50 ul of Optiphase Supermix is added to each well, the top of the plates are sealed, and plates are counted in a Trilux MicroBeta scintillation counter. For determining whether less of the complex between said radiolabeled known ligand and said receptor is formed in the presence of a test compound, instead of adding 100 ul of assay buffer, 100 ul of appropriately diluted said test compound is added to appropriate wells followed by addition of 50 ul of said radiolabeled known ligand.

C. Calculations

The test compounds are initially assayed at 10, 1 and 0.1 μM and then at a range of concentrations chosen such that the middle dose would cause about 50% inhibition of binding of the radiolabeled known ligand (i.e., IC$_{50}$). Specific binding in the absence of test compound (B$_O$) is the difference of total binding (B$_T$) minus non-specific binding (NSB) and similarly specific binding (in the presence of test compound) (B) is the difference of displacement binding (B$_D$) minus non-specific binding (NSB). IC$_{50}$ is determined from an inhibition response curve, logit-log plot of % B/B$_O$ vs concentration of test compound.

K$_i$ is calculated by the Cheng and Prustoff transformation:

$$K_i = IC_{50}/(1+[L]/K_D)$$

where [L] is the concentration of radiolabeled known ligand used in the assay and K$_D$ is the dissociation constant of the radiolabeled known ligand determined independently under the same binding conditions.

Example 16

Effect of GPR119 Agonist on PYY Secretion in Enteroendocrine Cell or in Cells in Tissue Derived from an L Cell-Containing Region of Intestine or in Cells Capable of Secreting PYY A GPR119 agonist in accordance with the present invention can be shown to stimulate PYY secretion in an enteroendocrine cell, e.g. an enteroendocrine cell line, or in cells such as enteroendocrine cells in tissue derived from an L cell-containing region of intestine [e.g., duodenum, jejunum, ileum, colon or rectum tissue; see, e.g., Lundberg et al, PNAS USA (1982) 79:4471-4475; Adrian et al, Gastroenterol (1985) 89:1070-1077; Ekblad et al, Peptides (2002) 23:251-261; Ueno et al, Regul Pept (2008) 145:12-16)] or in cells capable of secreting PYY using the in vitro assay described here. Enteroendocrine cells or cells such as enteroendocrine cells in tissue derived from an L cell-containing region of intestine are plated in 24-well plates on day one in complete culture medium (DMEM/10% FBS). On day two the culture medium is replaced with a low glucose medium (DMEM/3 mM Glucose/10% FBS). On day three cells are washed twice with 1×PBS. The washed cells are stimulated with vehicle or with GPR119 agonist at various concentrations (e.g., in the range of 1 nM to 20 uM) or with forskolin (1 uM) as a positive control in serum free DMEM with 15 mM glucose for one hour at 37° C. and 5% $CO_2$ in a tissue culture incubator. The supernatants are then collected and clarified by centrifugation at 500 g and 4° C. for 5 minutes. Total PYY released into the supernatant is determined using a PYY EIA kit purchased from Phoenix Pharmaceuticals, Inc. (PeptideYY (PYY) (Rat, Mouse, Porcine, Canine) EIA kit, Catalog No. EK-059-03) according to instructions provided in the kit.

It is expressly contemplated that cells capable of secreting PYY include but are not limited to an enteroendocrine cell, as may be an enteroendorine cell line, a cell such as may be an enteroendocrine cell in tissue derived from an L cell-containing region of intestine, an alpha cell of the islets of Langerhans, a cell line derived from the islets of Langerhans such as may be RINm5F (Bargsten, Arch Histol Cytol (2004) 67:79-94), a cell such as a neuronal cell as may be in tissue from the medulla oblongata, a neuronal cell line, and a recombinant cell.

Example 17

In Vivo Effects of a GPR119 Agonist on Atherogenesis in Mice

Male apoE$^{-/-}$ mice (Jackson Laboratory, Bar Harbor, Me.) are fed a normal chow. The apolipoprotein E-deficient (apoE$^{-/-}$) mouse is an established animal model of atherosclerosis, developing extensive atherosclerotic lesions on a chow diet [Zhang et al, Science (1992) 258:468-471]. At the age of 12 weeks, a GPR119 agonist or vehicle alone is administered per daily oral administration. A preferred dose of the GPR119 agonist is 0.1-100 mg/kg. Other preferred dose is selected from the group consisting of 0.1 mg/kg, 0.3 mg/kg, 1.0 mg/kg, 3.0 mg/kg, 10 mg/kg, 30 mg/kg and 100 mg/kg.

The mice are anesthetized with an intraperitoneal injection of pentobarbital (50 mg/kg), and the hearts, which contain the aoritic sinus and aortic arch, are harvested 14 days after the administration of the GPR119 agonist. Hearts are also harvested from unmanipulated mice at the start of the experiment. Ten mice are used for each of the three experimental groups.

The frozen cross-sections (10 µM thick) of aortic sinus embedded in Optimal Cutting Temperature (OCT; Sakura Finetechnical Co., Ltd) compound after overnight fixation in 10% formalin are mounted on slides. For the analysis of plaque size, 3 sections (100 µM apart) from each mouse were stained with Oil Red O. The lesion size and the diameter of lipid droplets in the lesions are quantified with an image analyzing computer software, and the mean values are determined. The mean value for the group administered with the GPR119 agonist is compared with the mean value for the group administered with vehicle alone.

Data are presented as means±SEM and are analyzed by Student's t test or the Mann-Whitney U test, depending on their distribution pattern. A value of $P<0.05$ is considered statistically significant. See, e.g., Okamoto et al, Circulation (2002) 106:2767-2770.

These results can demonstrate that the GPR119 agonist is an inhibitor of atherogenesis.

It is expressly contemplated that in other embodiment a GPR119 agonist can be shown to be an inhibitor of atherogenesis in the ApoE$^{-/-}$ mice using a non-invasive in vivo technique [see, e.g., Fayad et al, Circulation (1998) 98:1541-1547]. It is expressly contemplated that in other embodiment, administration of the agonist is other than oral, for example that administration of the agonist is intraperitoneal or intravenous. It is expressly contemplated that in other embodiment, treatment begins other than at 12 weeks of age, either earlier or later than at 12 weeks of age. It is expressly contemplated that in other embodiment treatment continues for less than or more than 14 days. It is expressly contemplated that administration may be other than daily.

Example 18

In Vivo Effects of a GPR119 Agonist on Chronic Inflammatory Arthritis in Mice

Both male and female MRL-lpr mice (Jackson Laboratory, Bar Harbor, Me.) are used at 13-14 weeks of age. MRL-lpr mice spontaneously develop a chronic inflammatory arthritis with similar characteristics to human rheumatoid arthritis including cell infiltration, pannus formation, bone and cartilage breakdown, and the presence of serum rheumatoid factor. The disease normally develops towards the end of the animal's life span; however, injection with complete Freund's adjuvant (CFA) initiates early onset and increases the severity of arthritis [Rakay et al, J Immunol (1993) 151:5081-5087].

On Day 0 of each experiment, all groups of mice are injected with CFA intradermally into a thoracic and an inguinal site with 0.05 ml CFA supplemented to 10 mg/ml with heat inactivated *Mycobacterium tuberculosis* H37 Ra (Difco, Detroit, Mich.). Immediately, a GPR119 agonist or vehicle alone is administered per daily oral administration. A preferred dose of the GPR119 agonist is 0.1-100 mg/kg. Other preferred dose is selected from the group consisting of 0.1 mg/kg, 0.3 mg/kg, 1.0 mg/kg, 3.0 mg/kg, 10 mg/kg, 30 mg/kg and 100 mg/kg.

Treatment is continued for 30 days. For quantifying swelling, ankle widths are measured with a micrometer. The statistical comparison of paired sets of ankle width measurements is carried out using the Student's t test.

Histopathological Analysis

At day 30 after CFA priming, the hind paws are fixed in buffered formalin. After decalcification in 10% formic acid for 48 hours, the tissues are processed for paraffin embedding. Serial sections of the tarso-metatarsal joints are cut to a thickness of 5 mm and stained with hematoxylin and eosin. Sections are examined by an individual without knowledge of the experimental protocol. A minimum of 10 sections/joint are assessed and scored to provide a semiquantitative measure of subsynovial inflammation (0, normal; 1 focal inflammatory infiltrates; 2, inflammatory infiltrate that dominates the cellular histology), synovial hyperplasia (0, normal; 1, a continuous, minimum three-layer thick, synovial lining seen in one joint; 2, minimum three-layer thick, synovial lining detected in several joints), pannus formation and cartilage erosion (0, normal; 1, pannus partially covered cartilage surfaces without evident cartilage loss; 2, pannus connected to evident cartilage loss), bone destruction (0, normal; 1, detectable destruction of bone by the pannus or osteoclast activity; 2, the pannus or osteoclast activity has destroyed a significant part of the bone), and finally, overall pathology is the overall assessment derived by the summation of the values for these criteria [see, e.g., Gong et al, J Exp Med (1997) 186:131-137]. Statistical analysis of the histopathology indices is done using the Student's t test.

These results can demonstrate that the GPR119 agonist is an inhibitor of a chronic inflammatory arthritis, for example that the GPR119 agonist is an inhibitor of rheumatoid arthritis.

It is expressly contemplated that in other embodiment, administration of the agonist is other than oral, for example that administration of the agonist is intraperitoneal or intravenous. It is expressly contemplated that in other embodiment, treatment begins other than at 13-14 weeks of age, either earlier or later than at 13-14 weeks of age. It is expressly contemplated that in other embodiment treatment continues for less than or more than 30 days. It is expressly contemplated that administration may be other than daily.

Example 19

Reduction of Colon Injury of Animal Model for Inflammatory Bowel Disease

A GPR119 agonist can be shown to confer protection from inflammatory bowel disease using the animal model essentially as described in WO 03/105763.

Methods

Animal Preparation:

10-11 weeks old male HSD rats, ranging 250-300 grams, are housed in a 12:12 light:dark cycle, and allowed ad libitum access to a standard rodent diet (Taklad L M 485, Madison, Wis.) and water. The animals are fasted for 24 hours before the experiment.

Procedure:

A simple and reproducible rat model of chronic colonic inflammation has been previously described by Morris et al (Gastroenterology (1989) 96:795-803). It exhibits a relatively long duration of inflammation and ulceration, affording an opportunity to study the pathophysiology of colonic inflammatory disease in a specifically controlled fasion, and to evaluate new treatments potentially applicable to inflammatory bowel disease in humans.

Rats are anesthetized with 3% isofluorane and placed on a regulated heating pad set at 37° C. A gavage needle is inserted rectally into the colon 7 cm. The hapten trinitrobenzenesulfonic acid (TNBS) dissolved in 50% ethanol (v/v) is delivered into the lumen of the colon through the gavage needle at a dose of 30 mg/kg, in a total volume of 0.4-0.6 mL. Control groups receive saline solution (NaCl 0.9%) intracolonically.

Four days after induction of colitis, the colon is resected from anesthetized rats, which are then euthanized by decapitation. Weights of excised colon and spleen are measured, and the colon photographed for scoring of gross morphologic damage according to the a rating scale (0=no damage, 1=localized hyperemia but no ulcers, 2=linear ulcers with no significant inflammation, 3=linear ulcer with inflammation at one site, 4=two or more sites of ulceration and/or inflammation, 5=two or more major sites of inflammation and ulceration or one major site of inflammation and ulceration extending >1 cm along the length of the colon) before division into 3 parts. The segment of colon 1 cm from the cecum is fixed in 10% formalin. Other segments are immediately frozen on dry ice.

Inflammation is defined as regions of hyperemia and bowel wall thickening. Colons are observed independently by several observers blinded to experimental treatment.

For this assay, 5 treatment groups are set up as follows:

Group A (n=3). intracolonic saline with oral treatment of saline;

Group B (n=8). oral treatment of saline prior to induction of colitis by 30 mg/kg TNBS;

Group C (n=10). Experimental group-oral treatment of GPR119 agonist (at a dose of, e.g., 30 mg/kg) twice daily for 2 days before, 2 days after, and 30 min before induction of colitis by 30 mg/kg TNBS.

Group D (n=9). Positive control-intramuscular injection of Depo-Medrol 600 µg/kg 60 min prior to induction of colitis by 30 mg/kg TNBS;

Group E (n=10). Positive control, 5-amino salicylic acid (Sigma) suspension at 200 mg/kg intracolonic administration in 0.5 mL saline, 60 min before induction of colitis and daily thereafter.

A preferred dose of the GPR119 agonist is 0.1-100 mg/kg. Other preferred dose is selected from the group consisting of 0.1 mg/kg, 0.3 mg/kg, 1.0 mg/kg, 3.0 mg/kg, 10 mg/kg, 30 mg/kg and 100 mg/kg.

It is expressly contemplated that in other embodiment, administration of the agonist is other than oral, for example that administration of the agonist is subcutaneous or intravenous.

Example 20

Effect of GPR119 Agonist on Kainate Seizures in Mice

A GPR119 agonist can be shown to confer protection from kainate seizures in mice using the animal model essentially as described in Woldbye et al (Neurobiology of Disease (2005) 20:760-772).

Male NMRI mice (Taconic M&B, DK; 23-30 g) are administered per orally with GPR119 agonist at doses of, e.g., 0.2, 1, 10, 20 or 30 mg/kg (n=7-8) in vehicle containing 0.05% bovine serum albumin in 10 mM phosphate-buffered saline (PBS, 0.13 M NaCl, 7 mM $Na_2HPO_4$, 3 mM $NaH_2PO_4$). A control group receives only vehicle by oral administration (n=28). Five minutes later, all animals receive a subcutaneous injection of kainate dissolved in isotonic saline and adjusted to pH 7.4 (30 mg/kg; #2020, Ocean Produce International, Canada); seizure severity is scored according to a modified rating scale of Marsh et al (PNAS USA (1999) 96:13518-13523): 0=no seizure activity, 1=staring or facial movements, 2=head nodding or isolated twitches, 3=motor seizure with forelimb colonus, 4=motor seizure with rearing, 5=motor seizure with loss of posture or status epilepticus (at least 10 min of continuous motor seizure activity), 6=death. The seizure score and latencies to first motor seizure (when scored as at least 3) and motor seizure with loss of posture are determined for each treatment group by an observed blinded to the identity of the mice.

A preferred dose of the GPR119 agonist is 0.1-100 mg/kg. Other preferred dose is selected from the group consisting of 0.1 mg/kg, 0.3 mg/kg, 1.0 mg/kg, 3.0 mg/kg, 10 mg/kg, 30 mg/kg and 100 mg/kg.

It is expressly contemplated that in other embodiment, administration of the agonist is other than oral, for example that administration of the agonist is intraperitoneal or intravenous. It is expressly contemplated that the subcutaneous injection of kainate may alternatively be carried out at a time after administration of the GPR119 agonist which is greater than 5 minutes.

Example 21

Effect of GPR119 Agonist on Food Intake in Lean Mice

A GPR119 agonist can be shown to decrease food intake using lean fasted-refed mice essentially as described in Ortiz et al (JPET (2007) 323:692-700).

Lean C57BL/6 mice (Taconic Farms, Germantown, N.Y.) are acclimated for a minimum of a week with controlled temperature and humidity on a 12-h light/dark cycle. Mice are housed in pairs in cages with a grid floor with food and water (standard chow pellet diet) continuously available. A study includes 20 mice per treatment group. The mice are fasted overnight (18 h) with water available during the dark phase, and they are dosed orally with GPR119 agonist (at a dose of, e.g., 30 mg/kg) in USP saline or only vehicle. Preweighed food is provided 30 min after dosing, and cumulative food intake is measured over 72 h (e.g., at 1 h, at 2h, at 4 h, at 24 h, at 48 h, and at 72 h).

A preferred dose of the GPR119 agonist is 0.1-100 mg/kg. Other preferred dose is selected from the group consisting of 0.1 mg/kg, 0.3 mg/kg, 1.0 mg/kg, 3.0 mg/kg, 10 mg/kg, 30 mg/kg and 100 mg/kg.

It is expressly contemplated that in other embodiment, administration of the agonist is other than oral, for example that administration of the agonist is intraperitoneal or intravenous.

Example 22

Effect of GPR119 Agonist on Body Weight and Plasma Adiponectin in Diet-Induced Obese (DIO) Mice A GPR119 agonist can be shown to provide a reduction in body weight and an increase in plasma adiponectin using the diet-induced obese (DIO) mouse essentially as described in Ortiz et al (JPET (2007) 323:692-700).

Male C57BL/6 mice (Taconic Farms) are fed a high-fat diet containing 45% calories from fat (rodent diet D12451; Research Diets, Inc., New Brunswick, N.J.) for 20 to 22 weeks, and they have an average body weight over about 5 SDs greater than mice fed a standard chow pellet diet (5% calories from fat). A study includes 10 mice per treatment group. Mice are kept in standard animal rooms under controlled temperature and humidity and a 12/12-h light dark cycle. Water and food are continuously available. Animals are adapted to the grid floors for 4 days, and they are dosed with vehicle (USP saline) for a further 4 days before recording of 2 days of baseline body weight and 24-h food and water consumption. Mice are assigned to treatment groups based upon their body weight such that the initial mean and standard error of the mean of body weight is similar. Animals are administered GPR119 agonist (at a dose of, e.g., 30 mg/kg) in USP saline or only vehicle orally every day before the dark phase, and body weight and food and water consumption are measured. Animals are dosed daily for 40 days.

Blood is collected on day 40 by retro-orbital bleeding for adiponectin analysis; plasma adiponectin is measured using a Mouse Adiponectin ELISA kit (Catalog No. EZMADP-60K; Millipore Corp., Billerica, Mass.) according to manufacturer's instructions.

A preferred dose of the GPR119 agonist is 0.1-100 mg/kg. Other preferred dose is selected from the group consisting of 0.1 mg/kg, 0.3 mg/kg, 1.0 mg/kg, 3.0 mg/kg, 10 mg/kg, 30 mg/kg and 100 mg/kg.

It is expressly contemplated that in other embodiment, administration of the agonist is other than oral, for example that administration of the agonist is subcutaneous or intravenous.

Example 23

Effect of GPR119 Agonist on Plasma Glucose, Plasma Insulin, and Glucose Disoposal in Diet-Induced Obese (DIO) Mice A GPR119 agonist can be shown to provide favorable improvements in metabolic parameters of diet-induced obese (DIO) mice associated with risk for type 2 diabetes, such as glucose disposal (to increase glucose disposal in fasted mice, e.g. glucose disposal following an OGTT), plasma glucose level (to decrease blood glucose in fed mice), and plasma insulin level (to increase plasma insulin in fasted mice), essentially as described in Ortiz et al (JPET (2007) 323:692-700).

Male C57BL/6 mice (Taconic Farms) are fed a high-fat diet containing 45% calories from fat (rodent diet D12451; Research Diets, Inc., New Brunswick, N.J.) for 20 to 22 weeks, and they have an average body weight over 5 SDs greater than mice fed a standard chow pellet diet (5% calories from fat). A study includes 10 mice per treatment group. Mice are kept in standard animal rooms under controlled temperature and humidity and a 12/12-h light dark cycle. Water and food are continuously available. Animals are adapted to the grid floors for 4 days, and they are dosed with vehicle (USP saline) for a further 4 days before recording of 2 days of baseline body weight and 24-h food and water consumption. Mice are assigned to treatment groups based upon their body weight such that the initial mean and standard error of the mean of body weight is similar.

Animals are orally administered GPR119 agonist (at a dose of, e.g., 30 mg/kg) in USP saline or only vehicle every day before the dark phase. Animals are dosed daily for 11 days. Blood samples are collected from the tail of fed mice and analyzed with an Ascensia glucose meter (Bayer Healthcare, Tarrytown, N.Y.) on day 10 of treatment. Food is removed 5 h into the feeding phase, and the animals are fasted for 14 h before blood collection using retro-orbital bleeding for insulin analysis. Oral glucose tolerance test (OGTT) is performed 2 h after retro-orbital bleeding following oral administration of 2 g/kg glucose, and tail blood glucose is measured at 30-min intervals for 3 h. Insulin is measured by enzyme-linked immunosorbent assay (EIA) (Alpco Diagnostics, Windham, N.H.).

A preferred dose of the GPR119 agonist is 0.1-100 mg/kg. Other preferred dose is selected from the group consisting of 0.1 mg/kg, 0.3 mg/kg, 1.0 mg/kg, 3.0 mg/kg, 10 mg/kg, 30 mg/kg and 100 mg/kg.

It is expressly contemplated that in other embodiment, administration of the agonist is other than oral, for example that administration of the agonist is subcutaneous or intravenous. It is expressly contemplated in other embodiment, that intraperitoneal glucose tolerance test (IPGTT) is performed 2 h after retro-orbital bleeding following intraperitoneal administration of 2 g/kg glucose.

Example 24

Effect of GPR119 Agonist on Collateral-Dependent Blood flow in a Rat Model of Peripheral Arterial Insufficiency A GPR119 agonist can be shown to increase collateral-dependent blood flow using a rat model of acute onset peripheral arterial insufficiency that is characteristic of the large vessel occlusive disease that often presents with symptoms of intermittent claudication, essentially as described in Cruze et al (Peptides (2007) 28:269-280).

Peripheral arterial insufficiency is established in adult male Sprague Dawley rats (325-350 g; Taconic Farms, Inc.) with bilateral occlusion of the femoral arteries distal to the inguinal ligament. In the same surgical procedure, a catheter connected to a 14 days osmotic pump (Alzet®) is inserted into the iliac artery for infusion near the site of collateral expansion for systemic delivery of vascular growth factor-A (residues 1-165) (VEGF$_{165}$) at a dose of 15 µg/kg/day; GPR 19 agonist (at a dose of, e.g., 30 mg/kg) and vehicle alone (phosphate buffered saline, 10% sodium citrate, 1.6% glycerol, 0.008% Tween 20) are administered per daily oral administration. All agents are supplied and administered in a manner blinded to the investigators. Blood flow is measured on day 16 to eliminate any acute effects of GPR 19 agonist or VEGF$_{165}$ on blood flow. Muscle blood flow is determined in a blinded manner, utilizing radiolabeled microspheres during treadmill running, as described in Yang et al (Am J Physiol Heart Circ Phys (2000) 278:H1966-H1973). The dose of VEGF$_{165}$ used (15 µg/kg/day) yields a near-maximal increase in collateral-dependent blood flow in this model (Cruze et al, Peptides (2007) 28:269-280).

A preferred dose of the GPR 19 agonist is 0.1-100 mg/kg. Other preferred dose is selected from the group consisting of 0.1 mg/kg, 0.3 mg/kg, 1.0 mg/kg, 3.0 mg/kg, 10 mg/kg, 30 mg/kg and 100 mg/kg.

It is expressly contemplated that in other embodiment, administration of the agonist is other than oral, for example that administration of the agonist is by intravenous infusion at a dose of, e.g., 30 mg/kg/day. A preferred infusion dose of the GPR 19 agonist is 0.1-100 mg/kg/day. Other preferred infusion dose is selected from the group consisting of 0.1 mg/kg/day, 0.3 mg/kg/day, 1.0 mg/kg/day, 3.0 mg/kg/day, 10 mg/kg/day, 30 mg/kg/day and 100 mg/kg/day.

Example 25

Effect of GPR119 Agonist on Vasoactive Intestinal Peptide (VIP)-Induced Jejunal Secretions in In Vivo Rat Model A GPR119 agonist can be shown to decrease secretion in intestinal epithelium using an in vivo rat model of vasoactive intestinal peptide (VIP)-induced jejunal secretions, essentially as described by Balasubramaniam et al (J Med Chem (2000) 43:3420-3427) and Souli et al (Peptides (1997) 18:551-557). Balasubramaniam et al (J Med Chem (2000) 43:3420-3427) also describe analogues of PYY having activity in this assay.

Male Wistar rats (Charles River Laboratories, Inc., Wilmington, Mass.) are anesthetized, and a saphenous vein is cannulated to infuse drugs. The abdomen is opened, a jejunal loop (~20 cm long) is delimited by two ligatures. At time zero, 2 mL of 0.9% saline prewarmed to 37° C. is instilled into the jejunal loop. The loop is then returned into the abdomen and closed. VIP (30 µg/kg/hour) is infused through the saphenous vein at the rate of 2.5 mL/hour for 30 minutes starting at time zero. GPR119 agonist (at a dose of, e.g., 30 mg/kg) or saline (controls) are orally administered as bolus doses 15 min before starting VIP infusions. At the end of the experiment rats are sacrificed, and the jejunal loop excised. The loop is then measured and weighed before and after removing the instilled fluid. The net water flux expressed as µL/cm/30 min is calculated using the formula (F-E-2000)/L, where F and E are the weights (mg) of the loop before and after emptying the remaining fluid, L is the length of the loop in cm, and 2000 is the volume in µL of the fluid instilled initially. Net absorption is indicated by a negative value and net secretion by a positive value. Each dose is investigated in 6-8 animals.

A preferred dose of the GPR119 agonist is 0.1-100 mg/kg. Other preferred dose is selected from the group consisting of 0.1 mg/kg, 0.3 mg/kg, 1.0 mg/kg, 3.0 mg/kg, 10 mg/kg, 30 mg/kg and 100 mg/kg.

It is expressly contemplated that in other embodiment, administration of the agonist is other than oral, for example that administration of the agonist is subcutaneous or intravenous.

Example 26

Effect of GPR119 Agonist on Intestinal Absorption in In Vivo Dog Model

A GPR119 agonist can be shown to increase absorption in intestinal epithelium using an in vivo dog model, essentially as described by Balasubramaniam et al (J Med Chem (2000) 43:3420-3427). Balasubramaniam et al (J Med Chem (2000) 43:3420-3427) also describe analogues of PYY having activity in this assay.

In vivo effects of GPR119 agonist on water and electrolyte absorption by the jejunum, ileu, and colon under basal conditions are investigated in awake dogs with jejunal, ileal and/or colonal Thirty-Vella loops essentially as described in greater detail in Bilchik et al (Gastroenterology (1993) 105: 1441-1448) and Bilchik et al (Am J Surg (1994) 167:570-574). Each experiment consists of a 90-min basal period followed by a 150-min experimental period. The small bowel segment is perfused through the proximal cannula at 2 mL/min using a roller pump. The perfusate, pH 7.4 maintained at 37° C., contained (in nmol/L) 140 Na$^+$, 5.2 K$^+$, 119.8Cl$^-$, 25 HCO$_3$, 1.2 Ca$^{2+}$, 1.2 Mg$^{2+}$, 2.4 HPO$_2^{4-}$, 0.4 H$_2$PO$_4^-$, 10 glucose and 10 µC [$^{14}$C]poly(ethylene glycol) in 5 g/L poly(ethylene glycol). After a 20-min washout period, perfusate is collected every 15 min for determination of Na$^+$, Cl$^-$ and water contents.

GPR119 agonist is administered per orally at a dose of, e.g., 30 mg/kg at time zero.

A preferred dose of the GPR119 agonist is 0.1-100 mg/kg. Other preferred dose is selected from the group consisting of 0.1 mg/kg, 0.3 mg/kg, 1.0 mg/kg, 3.0 mg/kg, 10 mg/kg, 30 mg/kg and 100 mg/kg.

It is expressly contemplated that in other embodiment, administration of the agonist is other than oral, for example that administration of the agonist is by intraluminal infusion at a dose of, e.g., 30 mg/kg/hour starting at time zero. A preferred infusion dose of the GPR119 agonist is 0.1-100 mg/kg/hour. Other preferred infusion dose is selected from the group consisting of 0.1 mg/kg/hour, 0.3 mg/kg/hour, 1.0 mg/kg/hour, 3.0 mg/kg/hour, 10 mg/kg/hour, 30 mg/kg/hour and 100 mg/kg/hour.

Example 27

Inhibition of Diarrhea of Castor Oil-Induced Defecation and Diarrheal Symptom in Mice A GPR119 agonist can be shown to inhibit diarrheal symptom using a castor oil-induced defecation and diarrheal symptom mouse model essentially as described in EP 1902730.

C57BL/6 mice are used. Mice are individually housed in cages with a floor mat in an animal room with a controlled environment (temperature: 23° C., relative humidity: 55%, light hours: from 7:00 till 19:00) with ad libitum access to rodent chow (CE-2, Nippon CLEA) and drinking water.

GPR119 agonist (at a dose of, e.g., 30 mg/kg), conventional antidiarrheal agent Ioperamide (1 mg/kg), conventional antidiarrheal agent atropine (10 mg/kg), or only vehicle are administered per oral administration, intraperitoneal administration, intraperitoneal administration, and oral administration, respectively, to the mice, and at 15 minutes after the administration, castor oil (0.3 mammal) is orally administered to the mice. The fecal weight and diarrhea score (normal: 0, soft feces: 1, watery feces: 2) is measured in a time-dependent manner (1, 2, and 4 hours after administration). At the same time, the same measurement is carried out for mice to which only a vehicle is administered and castor oil is not administered.

A preferred dose of the GPR119 agonist is 0.1-100 mg/kg. Other preferred dose is selected from the group consisting of 0.1 mg/kg, 0.3 mg/kg, 1.0 mg/kg, 3.0 mg/kg, 10 mg/kg, 30 mg/kg and 100 mg/kg.

It is expressly contemplated that in other embodiment, administration of the agonist is other than oral, for example that administration of the agonist is intraperitoneal or intravenous.

Example 28

Oral Bioavailability

Physicochemico analytical approaches for directly assessing oral bioavailability of a compound of the invention, such as a GPR119 agonist, a PYY secretagogue, a compound useful for treatment or prevention of a condition modulated by PYY, or a compound useful for a modulation of a PYY-related activity, are well known to those of ordinary skill in the art and may be used (see, e.g., without limitation: Wong P C et al., Cardiovasc Drug Rev (2002) 20:137-52; and Buchan P et al., Headache (2002) Suppl 2:S54-62; the disclosure of each of which is hereby incorporated by reference in its entirety). By way of further illustration and not limitation, said alternative analytical approaches may comprise liquid chromatography-tandem mass spectrometry (Chavez-Eng C M et al., J ChromatogrB Analyt Technol Biomed Life Sci (2002) 767:117-29; Jetter A et al., Clin Pharmacol Ther (2002) 71:21-9; Zimmerman J J et al., J Clin Pharmacol (1999) 39:1155-61; and Barrish A et al., Rapid Commun Mass Spectrom (1996) 10:1033-7; the disclosure of each of which is hereby incorporated by reference in its entirety). Recently, positron emission tomography (PET) has been successfully used to obtain direct measurements of drug distribution, including oral bioavailability, in the mammalian body following oral administration of the drug (Gulyas et al., Eur J Nucl Med Mol Imaging (2002) 29:1031-8; the disclosure of which is hereby incorporated by reference in its entirety).

While the foregoing specification teaches the principles of the present invention, with examples provided for the purpose of illustration, it will be understood that the practice of the invention encompasses all of the usual variations, adaptions, or modifications, as come within the scope of the following claims and its equivalents.

What is claimed is:

1. A method for identifying a peptide YY (PYY) secretagogue, comprising:
   (a) contacting in vitro a test compound with a host cell or with a membrane of a host cell comprising a G protein-coupled receptor (GPCR) wherein the GPCR comprises an amino acid sequence selected from the group consisting of:
      (i) amino acids 1-335 of SEQ ID NO:2; and
      (ii) an amino acid sequence of a GPCR encoded by the nucleotide sequence set forth in SEQ ID NO:1;
   (b) determining the ability of the test compound to stimulate functionality of the GPCR;
   (c) administering a compound which stimulates functionality of the GPCR in step (b) to a vertebrate; and
   (d) determining whether the compound increases a PYY level in the vertebrate,
   wherein the ability of the test compound to increase a PYY level in the vertebrate is indicative of the test compound being a PYY secretagogue.

2. The method of claim 1, wherein the vertebrate is a human.

3. The method of claim 1, wherein the GPCR in step (a) is recombinant.

4. The method of claim 1, wherein the host cell comprises an expression vector, the expression vector comprising a polynucleotide encoding the GPCR.

5. The method of claim 1, wherein the determining the ability of the test compound to stimulate functionality of the GPCR is through the measurement of the level of a second messenger.

6. The method of claim 5, wherein the second messenger is selected from the group consisting of cyclic AMP (cAMP), cyclic GMP (cGMP), inositol 1,4,5-triphosphate (IP3), diacylglycerol (DAG), MAP kinase activity, MAPK/ERK kinase kinase-1 (MEKK1) activity, and Ca2+.

7. The method of claim 6, wherein the second messenger is cAMP.

8. The method of claim 1, wherein the determining the ability of the test compound to stimulate functionality of the GPCR is through the use of a Melanophore assay, through the measurement of GTPγS binding to a membrane comprising the GPCR, or through a reporter assay.

9. The method of claim 1, wherein the host cell is a mammalian host cell, a yeast host cell, or a melanophore host cell.

10. The method of claim 1, wherein the GPCR comprises the amino acid sequence of SEQ ID NO:2.

11. A method for identifying a PYY secretagogue, comprising:
   (a) administering a G protein coupled receptor 119 (GPR119) agonist to a vertebrate; and
   (b) determining whether the GPR119 agonist increases a PYY level in the vertebrate,
   wherein the ability of the GPR119 agonist to increase a PYY level in the vertebrate is indicative of the GPR119 agonist being a PYY secretagogue.

12. The method of claim 11, wherein the vertebrate is a human.

13. The method of claim 11, wherein the GPR119 agonist is an agonist of human GPR119.

14. The method of claim 11, wherein the GPR119 agonist is a selective GPR119 agonist.

15. The method of claim 11, wherein the GPR119 agonist has an EC50 of less than 10 μM for elevating cAMP in GPR119 transfected cells.

16. The method of claim 11, wherein the GPR119 agonist is a small molecule.

17. The method of claim 11, wherein the GPR119 agonist is orally bioavailable.

18. The method of claim 11, wherein the GPR119 agonist: (i) is a selective GPR119 agonist; (ii) has an EC50 of less than 10 μM for elevating cAMP in GPR119 transfected cells; (iii) is a small molecule; and (iv) is orally bioavailable.

19. A method for identifying a PYY secretagogue, comprising:
   (a) contacting in vitro a GPCR with a ligand for the GPCR in the presence or absence of a test compound, wherein a ligand for the GPCR is a ligand for GPR119 and wherein the GPCR comprises an amino acid sequence selected from the group consisting of:

(i) amino acids 1-335 of SEQ ID NO:2; and
(ii) an amino acid sequence of a GPCR encoded by the nucleotide sequence set forth in SEQ ID NO:1;
(b) detecting the complex between the ligand and the GPCR;
(c) determining whether less of the complex is formed in the presence of the test compound than in the absence of the test compound;
(d) administering a compound in the presence of which less of the complex is formed in step (c) to a vertebrate; and
(e) determining whether the compound increases a PYY level in the vertebrate,
wherein the ability of the test compound to increase a PYY level in the vertebrate is indicative of the test compound being a PYY secretagogue.

20. The method of claim 19, wherein the vertebrate is a human.

21. The method of claim 19, wherein the GPCR comprises the amino acid sequence set forth in SEQ ID NO:2.

22. The method of claim 19, wherein the ligand is labeled.

23. The method of claim 19, wherein the ligand is radiolabeled.

24. The method of claim 14, wherein the GPR119 agonist has a selectivity for GPR119 over corticotrophin releasing factor-1 (CRF-1) receptor of at least 100-fold.

25. The method of claim 11, wherein the GPR119 agonist has an EC50 of less than 1 µM for elevating cAMP in GPR119 transfected cells.

26. The method of claim 11, wherein the GPR119 agonist has an EC50 of less than 100 nM for elevating cAMP in GPR119 transfected cells.

27. The method of claim 11, wherein the GPR119 agonist has an EC50 of less than 100 nM for elevating cAMP in GPR119 transfected cells and is orally bioavailable.

* * * * *